(12) United States Patent
Wolleb et al.

(10) Patent No.: US 10,249,827 B2
(45) Date of Patent: Apr. 2, 2019

(54) AZADIBENZOFURANS FOR ELECTRONIC APPLICATIONS

(71) Applicant: UDC Ireland Limited, Dublin (IE)

(72) Inventors: Annemarie Wolleb, Fehren (CH); Thomas Schaefer, Liestal (CH); Heinz Wolleb, Fehren (CH); Ute Heinemeyer, Neustadt (DE); Nicolle Langer, Lampertheim (DE); Christian Lennartz, Schifferstadt (DE); Gerhard Wagenblast, Wachenheim (DE); Soichi Watanabe, Seoul (KR); Flavio Luiz Benedito, Ludwigshafen (DE); Heinz Hottinger, Ettingen (CH); Oliver Dosenbach, Bad Bellingen (DE)

(73) Assignee: UDC Ireland Limited, Dublin (IE)

( * ) Notice: Subject to any disclaimer, the term of this patent is extended or adjusted under 35 U.S.C. 154(b) by 520 days.

(21) Appl. No.: 14/427,134

(22) PCT Filed: Sep. 18, 2013

(86) PCT No.: PCT/EP2013/069403
§ 371 (c)(1),
(2) Date: Mar. 10, 2015

(87) PCT Pub. No.: WO2014/044722
PCT Pub. Date: Mar. 27, 2014

(65) Prior Publication Data
US 2015/0243907 A1 Aug. 27, 2015

Related U.S. Application Data

(60) Provisional application No. 61/703,289, filed on Sep. 20, 2012.

(30) Foreign Application Priority Data

Sep. 20, 2012 (EP) .................................... 12185230

(51) Int. Cl.
| | | |
|---|---|---|
| *H01L 51/00* | (2006.01) | |
| *C07D 487/04* | (2006.01) | |
| *C07F 7/08* | (2006.01) | |
| *C09K 11/06* | (2006.01) | |

(Continued)

(52) U.S. Cl.
CPC ........ *H01L 51/0072* (2013.01); *C07D 209/86* (2013.01); *C07D 405/04* (2013.01); *C07D 405/14* (2013.01); *C07D 487/04* (2013.01); *C07D 491/048* (2013.01); *C07D 491/147* (2013.01); *C07D 519/00* (2013.01); *C07F 7/0814* (2013.01); *C09B 57/00* (2013.01); *C09B 57/008* (2013.01); *C09K 11/025* (2013.01); *C09K 11/06* (2013.01); *H01L 51/0071* (2013.01); *H01L 51/0094* (2013.01); *C09K 2211/1007* (2013.01); *C09K 2211/1011* (2013.01); *C09K 2211/1029* (2013.01); *C09K 2211/1033* (2013.01); *C09K 2211/1048* (2013.01); *C09K 2211/1059* (2013.01); *C09K 2211/1088* (2013.01); *C09K 2211/185* (2013.01); *H01L 51/0054* (2013.01); *H01L 51/0058* (2013.01); *H01L 51/0073* (2013.01); *H01L 51/0085* (2013.01); *H01L 51/5012* (2013.01); *H01L 51/5016* (2013.01); *H01L 51/5056* (2013.01); *H01L 51/5088* (2013.01); *H01L 51/5092* (2013.01); *H01L 51/5206* (2013.01); *H01L 2251/308* (2013.01); *Y02E 10/549* (2013.01); *Y02P 70/521* (2015.11)

(58) Field of Classification Search
None
See application file for complete search history.

(56) References Cited

U.S. PATENT DOCUMENTS

| | | | |
|---|---|---|---|
| 3,663,559 A | 5/1972 | Derijckere et al. | |
| 3,669,969 A * | 6/1972 | Lunn .................. | C07D 235/24 514/885 |

(Continued)

FOREIGN PATENT DOCUMENTS

| | | |
|---|---|---|
| CN | 102203977 | 9/2011 |
| CN | 102234286 | 11/2011 |

(Continued)

OTHER PUBLICATIONS

Krug et al. "Discovery of 4-Benzylamino-Substituted alpha-Carbolines as a Novel Class of Receptor Tyrosine Kinase Inhibitors" ChemMedChem 2011, 6, 63-72.*

(Continued)

*Primary Examiner* — Robert S Loewe
(74) *Attorney, Agent, or Firm* — Riverside Law LLP

(57) ABSTRACT

The present invention relates to compounds of formula (I), which are characterized in that they substituted by benzimidazo[1,2-a]benzimidazo-5-yl and/or benzimidazo[1,2-a]benzimidazo-2,5-ylene groups and in that at least one of the substituents $B^1$, $B^2$, $B^3$, $B^4$, $B^5$, $B^6$, $B^7$ and $B^8$ represents N; a process for their production and their use in electronic devices, especially electroluminescent devices. When used as host material for phosphorescent emitters in electroluminescent devices, the compounds of formula I may provide improved efficiency, stability, manufacturability, or spectral characteristics of electroluminescent devices.

(I)

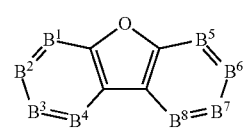

20 Claims, No Drawings

(51) Int. Cl.
*C09B 57/00* (2006.01)
*C07D 405/14* (2006.01)
*C07D 405/04* (2006.01)
*C07D 491/048* (2006.01)
*C07D 491/147* (2006.01)
*C07D 519/00* (2006.01)
*C07D 209/86* (2006.01)
*C09K 11/02* (2006.01)
*H01L 51/50* (2006.01)
*H01L 51/52* (2006.01)

(56) References Cited

U.S. PATENT DOCUMENTS

| | | | |
|---|---|---|---|
| 3,706,747 A | 12/1972 | DeAngelis et al. | |
| 6,551,723 B1* | 4/2003 | Okada | H01L 51/004 313/504 |
| 6,687,266 B1 | 2/2004 | Ma et al. | |
| 6,921,915 B2 | 7/2005 | Takiguchi et al. | |
| 9,502,664 B2* | 11/2016 | Schaefer | C07D 487/04 |
| 9,620,724 B2* | 4/2017 | Schaefer | H01L 51/0072 |
| 2001/0015432 A1 | 8/2001 | Igarashi | |
| 2001/0019782 A1 | 9/2001 | Igarashi et al. | |
| 2002/0024293 A1 | 2/2002 | Igarashi et al. | |
| 2002/0048689 A1 | 4/2002 | Igarashi et al. | |
| 2002/0055014 A1 | 5/2002 | Okada et al. | |
| 2002/0094453 A1 | 7/2002 | Takiguchi et al. | |
| 2005/0064576 A1 | 3/2005 | Fennell | |
| 2006/0008670 A1 | 1/2006 | Lin et al. | |
| 2007/0190359 A1 | 8/2007 | Knowles et al. | |
| 2008/0220265 A1 | 9/2008 | Xia et al. | |
| 2008/0265216 A1 | 10/2008 | Hartmann et al. | |
| 2009/0039776 A1 | 2/2009 | Yamada et al. | |
| 2009/0134784 A1 | 5/2009 | Lin et al. | |
| 2009/0153034 A1 | 6/2009 | Lin et al. | |
| 2010/0102709 A1 | 4/2010 | Zeika et al. | |
| 2010/0187984 A1 | 7/2010 | Lin et al. | |
| 2010/0244004 A1 | 9/2010 | Xia et al. | |
| 2010/0244006 A1* | 9/2010 | Ise | C07D 487/04 257/40 |
| 2011/0057559 A1 | 3/2011 | Xia et al. | |
| 2011/0189127 A1 | 8/2011 | Venkatraman et al. | |
| 2011/0210316 A1 | 9/2011 | Kadoma et al. | |
| 2011/0215309 A1 | 9/2011 | D'Andrade et al. | |
| 2011/0227049 A1 | 9/2011 | Xia et al. | |
| 2011/0233528 A1 | 9/2011 | Levermore et al. | |
| 2011/0248246 A1 | 10/2011 | Ogita | |
| 2011/0275762 A1 | 11/2011 | Cmiljanovic et al. | |
| 2012/0241681 A1* | 9/2012 | Schaefer | C07D 487/04 252/500 |
| 2012/0261654 A1 | 10/2012 | Yasukawa et al. | |
| 2012/0292600 A1 | 11/2012 | Kottas et al. | |
| 2012/0305894 A1 | 12/2012 | Kim et al. | |
| 2013/0092922 A1* | 4/2013 | Stoessel | C07D 235/00 257/40 |

FOREIGN PATENT DOCUMENTS

| | | |
|---|---|---|
| CN | 102341401 | 2/2012 |
| CN | 103517906 | 1/2014 |
| CN | 103917542 | 7/2014 |
| CN | 104395316 | 3/2015 |
| DE | 10 2010 024 542 A1 | 12/2011 |
| EP | 1 191 612 A2 | 3/2002 |
| EP | 1 191 613 A2 | 3/2002 |
| EP | 1 211 257 A2 | 6/2002 |
| EP | 1 786 050 A1 | 5/2007 |
| EP | 1 837 927 A1 | 9/2007 |
| EP | 1 885 818 A1 | 2/2008 |
| EP | 1 837 926 B1 | 5/2008 |
| EP | 1 988 587 A1 | 11/2008 |
| EP | 2 180 029 A1 | 4/2010 |
| EP | 2 246 862 A1 | 11/2010 |
| EP | 2 401 254 A1 | 1/2012 |
| EP | 2527334 | 11/2012 |
| EP | 2 551 933 A1 | 1/2013 |
| EP | 2711363 A1 | 3/2014 |
| GB | 1300928 | 12/1972 |
| JP | H01-203387 | 8/1989 |
| JP | 2002-284862 A | 10/2002 |
| JP | 2002284862 | 10/2002 |
| JP | 2007-123392 A | 5/2007 |
| JP | 2008-74939 A | 4/2008 |
| JP | 2011-84531 A | 4/2011 |
| JP | 2011184362 | 9/2011 |
| JP | 2011524359 | 9/2011 |
| JP | 2012502485 | 1/2012 |
| JP | 2012508223 | 4/2012 |
| JP | 2012515216 | 7/2012 |
| JP | 6034196 | 6/2014 |
| JP | 2014501544 | 6/2014 |
| JP | 2014515014 | 6/2014 |
| JP | 2014540428 | 2/2015 |
| JP | 2015504422 | 2/2015 |
| JP | 2015520944 | 7/2015 |
| JP | 2015529639 | 10/2015 |
| TW | 201247839 | 12/2012 |
| TW | 201336846 | 9/2013 |
| WO | WO 99/47474 A1 | 9/1999 |
| WO | WO 00/70655 A2 | 11/2000 |
| WO | WO 01/41512 A1 | 6/2001 |
| WO | WO 02/02714 A2 | 1/2002 |
| WO | WO 02/15645 A1 | 2/2002 |
| WO | WO 02/060910 A1 | 8/2002 |
| WO | WO 2005/019373 A2 | 3/2005 |
| WO | WO 2005/113704 A2 | 12/2005 |
| WO | WO 2006/014599 A2 | 2/2006 |
| WO | WO 2006/056418 A2 | 6/2006 |
| WO | WO 2006/067074 A1 | 6/2006 |
| WO | WO 2006/098460 A1 | 9/2006 |
| WO | WO 2006/100298 A1 | 9/2006 |
| WO | WO 2006/115301 A1 | 11/2006 |
| WO | WO 2006/121811 A1 | 11/2006 |
| WO | WO 2006/128800 A1 | 12/2006 |
| WO | WO 2007/095118 A2 | 8/2007 |
| WO | WO 2007/101820 A1 | 9/2007 |
| WO | WO 2007/115970 A1 | 10/2007 |
| WO | WO 2007/115981 A1 | 10/2007 |
| WO | WO 2008/000727 A1 | 1/2008 |
| WO | WO 2008/034758 A2 | 3/2008 |
| WO | WO 2008/156879 A1 | 12/2008 |
| WO | WO 2009/003898 A1 | 1/2009 |
| WO | WO 2009/003919 A1 | 1/2009 |
| WO | 2009035668 | 3/2009 |
| WO | WO 2009/050281 A1 | 4/2009 |
| WO | WO 2009/050290 A1 | 4/2009 |
| WO | WO 2009/060757 A1 | 5/2009 |
| WO | WO 2009/060780 A1 | 5/2009 |
| WO | WO 2009/073245 A1 | 6/2009 |
| WO | WO 2010/027583 A1 | 3/2010 |
| WO | WO 2010/028151 A1 | 3/2010 |
| WO | WO 2010/028262 A1 | 3/2010 |
| WO | WO 2010/056669 A1 | 5/2010 |
| WO | WO 2010/068876 A1 | 6/2010 |
| WO | 2010083359 | 7/2010 |
| WO | WO 2010/079051 A1 | 7/2010 |
| WO | WO 2010/086089 A1 | 8/2010 |
| WO | WO 2010/090077 A1 | 8/2010 |
| WO | WO 2010/097433 A1 | 9/2010 |
| WO | WO 2010/118029 A1 | 10/2010 |
| WO | WO 2010/129323 A1 | 11/2010 |
| WO | WO 2010/132236 A1 | 11/2010 |
| WO | 2011021038 | 2/2011 |
| WO | 2011034518 | 3/2011 |
| WO | WO 2011051404 A1 | 5/2011 |
| WO | WO 2011/073149 A1 | 6/2011 |
| WO | WO 2011/090535 A1 | 7/2011 |
| WO | WO 2011/106344 A1 | 9/2011 |
| WO | WO 2011/109042 A1 | 9/2011 |
| WO | WO 2011/137072 A1 | 11/2011 |
| WO | WO 2011/157779 A1 | 12/2011 |
| WO | WO 2011/157790 A1 | 12/2011 |
| WO | WO 2011/160757 A1 | 12/2011 |

| WO | WO 2012/008881 A1 | 1/2012 |
| --- | --- | --- |
| WO | WO 2012/014621 A1 | 2/2012 |
| WO | WO 2012/048266 A1 | 4/2012 |
| WO | WO 2012/053627 A1 | 4/2012 |
| WO | WO 2012/090967 A1 | 7/2012 |
| WO | 2012102967 | 8/2012 |
| WO | WO 2012/111462 A1 | 8/2012 |
| WO | WO 2012/115034 A1 | 8/2012 |
| WO | WO 2012/121936 A2 | 9/2012 |
| WO | WO 2012/130709 A1 | 10/2012 |
| WO | WO 2012/147397 A1 | 11/2012 |
| WO | WO 2012/166608 A1 | 12/2012 |
| WO | WO 2012/170461 A1 | 12/2012 |
| WO | WO 2012/170463 A1 | 12/2012 |
| WO | WO 2012/170571 A1 | 12/2012 |
| WO | WO 2012/172482 A1 | 12/2012 |
| WO | WO 2013/068376 A1 | 5/2013 |
| WO | WO 2014/009317 A1 | 1/2014 |

OTHER PUBLICATIONS

International Search Report dated Feb. 4, 2014 in PCT/EP2013/069403.

Martin Krug, et al., "Discovery and selectivity-profiling of 4-benzylamino 1-aza-9-oxafluorene derivatives as lead structures for IGF-1R inhibitors" Bioorganic & Medicinal Chemistry Letters, vol. 20, 2010, pp. 6915-6919.

Shunsaku Shiotani, et al., "Furopyridines. X [1]. Synthesis of Tricyclic Heterocycles, Furo [2,3-b:4,5-c'], Furo [2,3-b:4,5-c']-, Furo [2,3-c:4,5-c']- and Furo [3,2-c:4,5-c']dipyridine" J. Heterocyclic Chem., vol. 27, XP002716145, 1990, pp. 637-642.

Examination Report dated Jul. 14, 2017; Notification of Reasons for Refusal for Japanese Patent Application No. 2015-532398; 5 pages.

Search Report by Registered Searching Organization dated Jun. 22, 2017; Japanese Patent Application No. 2015-532398; 16 pages.

Supplemental Search Report for Chinese Patent Application No. 201380048768X dated Aug. 30, 2016; 1 page.

The First Office Action for Chinese Patent Application No. 201380048768.X; Title: Azadibenzofurans for electronic applications; Patentee: UDC Ireland Co., Ltd.; 7 pages.

Patent Search for Chinese Patent Application No. 201380048768X dated Jan. 18, 2016; 1 page.

Bratt et al., 1980, "Polyhalogenoaromatic compounds. Part 41. Photochemical dehalogenation and arylation reactions of polyhalogenoaromatic and polyhalogenoheteroaromatic compounds," Journal of the Chemical Society, Perkin Transactions 1:648-656.

International Search Report dated Feb. 4, 2014 in PCT/EP2013/069403 (3 pages).

* cited by examiner

AZADIBENZOFURANS FOR ELECTRONIC APPLICATIONS

CROSS REFERENCE TO RELATED APPLICATIONS

The present application is a 35 U.S.C. § 371 national stage patent application of International patent application PCT/EP2013/069403, filed on Sep. 18, 2013, published as WO/2014/044722 on Mar. 27, 2014, the text of which is incorporated by reference, and claims the benefit of the filing date of U.S. provisional application No. 61/703,289, filed on Sep. 20, 2012, and European application no. 12185230.5, filed on Sep. 20, 2012, the text of each of which is also incorporated by reference.

DESCRIPTION

The present invention relates to compounds of formula I, a process for their production and their use in electronic devices, especially electroluminescent devices. When used as hole transport material in electroluminescent devices, the compounds of formula I may provide improved efficiency, stability, manufacturability, or spectral characteristics of electroluminescent devices.

Khan, Misbahul Ain; Ribeiro, Vera Lucia Teixeira, Pakistan Journal of Scientific and Industrial Research 43 (2000) 168-170 describes the synthesis of benzimidazo[1,2-a]benzimadozoles

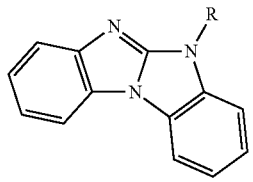

(R=H, Me, Et) by trialkyl phosphite-induced deoxygenation and thermolysis of 1-(o-nitrophenyl)- and 1-(o-azidophenyl)benzimidazoles.

Pedro Molina et al. Tetrahedron (1994) 10029-10036 reports that aza Wittig-type reaction of bis(iminophosphoranes), derived from bis(2-aminophenyl)amine with two equivalents of isocyanate directly provided benzimidazo[1,2-a]benzimidazole derivatives.

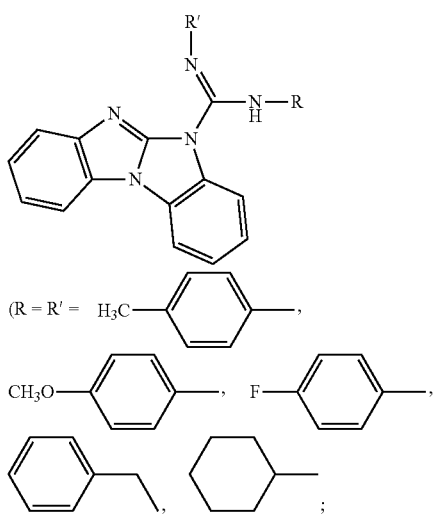

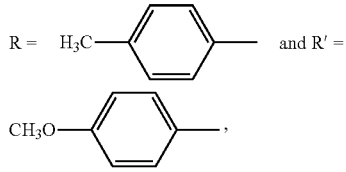

R=isopropyl and R'=ethyl)

Kolesnikova, I. V.; Zhurnal Organicheskoi Khimii 25 (1989) 1689-95 describes the synthesis of 5H-benzimidazo[1,2-a]benzimidazole 1,2,3,4,7,8,9,10-octafluoro-5-(2,3,4,5,6-pentafluorophenyl).

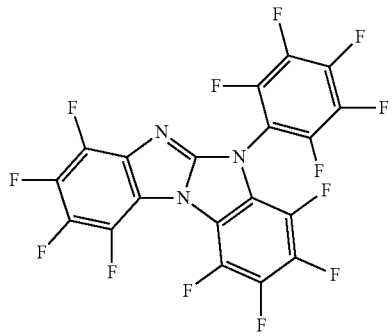 [SMILES: Fc1c(F)c(F)c(-n2c3c(F)c(F)c(F)c(F)c3n3c4c(F)c(F)c(F)c(F)c4nc23)c(F)c1F]

Achour, Reddouane; Zniber, Rachid, Bulletin des Societes Chimiques Belges 96 (1987) 787-92 describes the synthesis of benzimidazobenzimidazoles

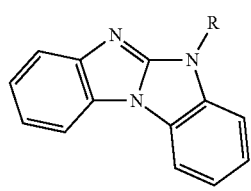

(R=H, —CH(CH$_3$)$_2$) which were prepared from benzimidazolinone derivatives.

Hubert, Andre J.; Reimlinger, Hans, Chemische Berichte 103 (1970) 2828-35 describes the synthesis of benzimidazobenzimidazoles

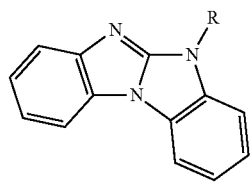

(R=H, CH$_3$,

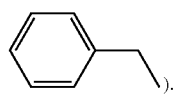

).

WO2011160757 relates to an electronic device comprising an anode, cathode and at least one organic layer which contains a compound of formulae
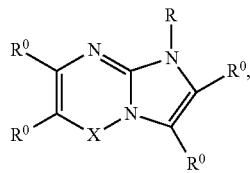
(I)
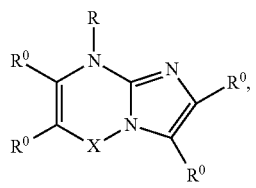
(II)
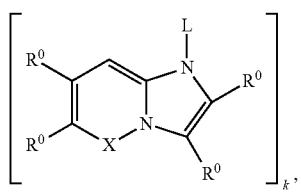
(III)
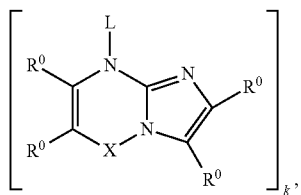
(IV)
wherein X may be a single bond and L may be a divalent group. The following 4H-Imidazo[1,2-a]imidazole compounds are explicitly disclosed:
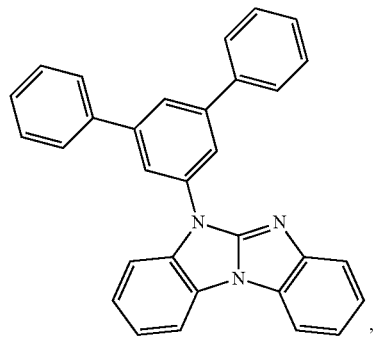,
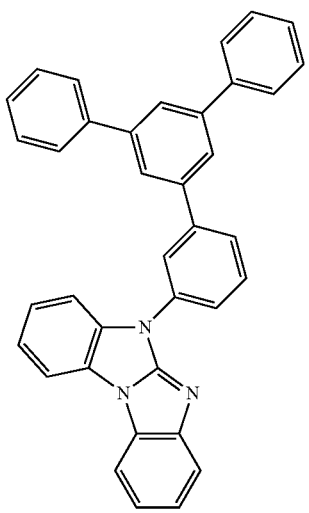,
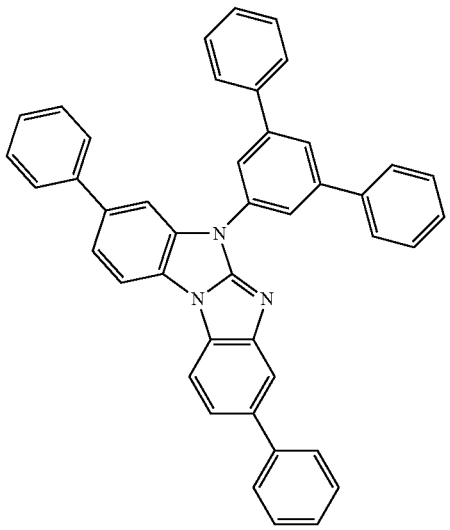,
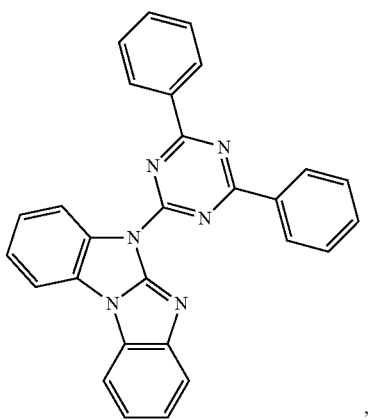, -continued

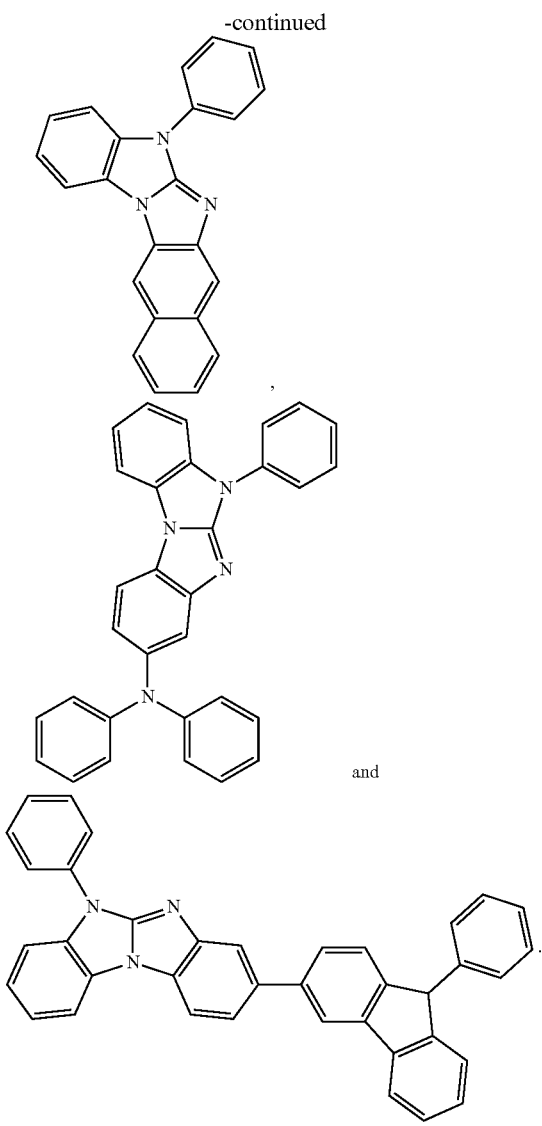

X. Wang et al. Org. Lett. 14 (2012) 452-455 discloses a highly efficient copper-catalyzed synthesis for compounds of formula

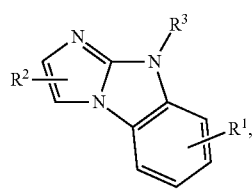

wherein compounds of formula

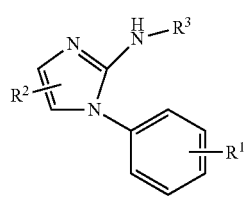

are reacted in the presence of copper acetate (Cu(OAc)$_2$)/ PPh$_3$/1,10-phenathroline/sodium acetate and oxygen in m-xylene (1 atm) at elevated temperature [published on web: Dec. 29, 2011]. Among others the following compounds can be prepared by the described synthesis method:

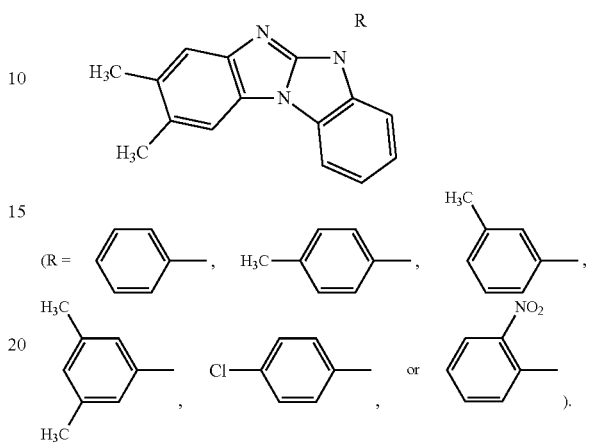

WO2012/130709 relates to 4H-Imidazo[1,2-a]imidazoles,

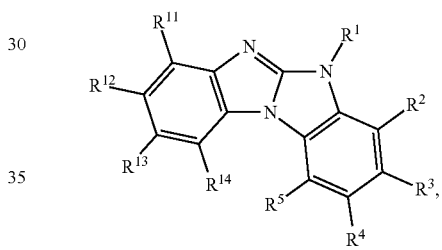

such as, for example,

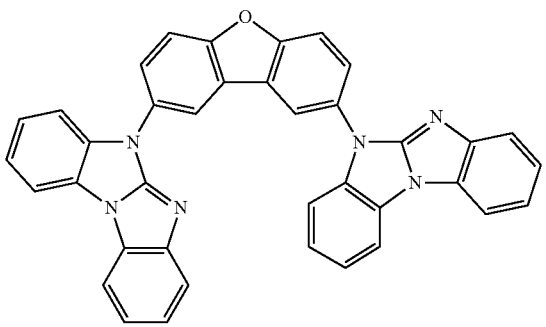 [SMILES: c1ccc2c(c1)nc1n(-c3ccc4oc5ccc(-n6c7ccccc7n7c8ccccc8nc67)cc5c4c3)c3ccccc3n21]

a process for their production and their use in electronic devices, especially electroluminescent devices.

WO2013/068376 describes 4H-imidazo[1,2-a]imidazoles of formula

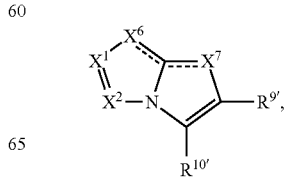

wherein $X^6$ is —N= and $X^7$ is —NR$^6$—, or $X^7$ is =N— and $X^6$ is —NR$^6$—, R$^6$ is a group of formula

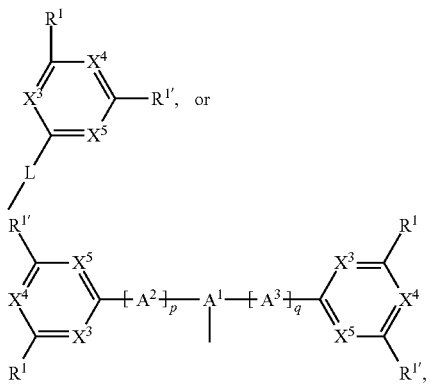

such as, for example,

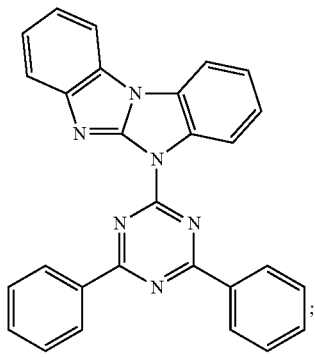 [SMILES: c1ccc(-c2nc(-c3ccccc3)nc(-n3c4ccccc4n4c5ccccc5nc34)n2)cc1]

a process for their production and their use in electronic devices, especially electroluminescent devices.

PCT/EP2013/064395 relates to compounds of formula

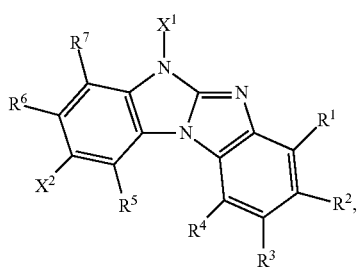

(I)

a process for their production and their use in electronic devices, especially electroluminescent devices. The 2,5-disubstituted benzimidazo[1,2-a]benzimidazole derivatives are suitable hole transporting materials, or host materials for phosphorescent emitters.

US20090134784 provides carbazole-containing compounds. In particular, the compounds are oligocarbazole-containing compounds having an unsymmetrical structure. The compounds may be substituted by azadibenzofuranyl and are useful as hosts in the emissive layer of organic light emitting devices.

WO2010028262 relates to white phosphorescent organic light emitting devices. The following compound

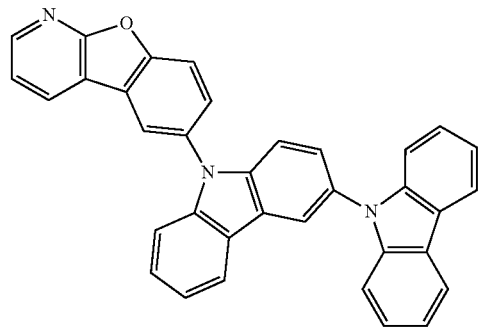 [SMILES: c1cnc2oc3ccc(-n4c5ccccc5c5cc(-n6c7ccccc7c7ccccc76)ccc54)cc3c2c1]

is used as host and exciton blocking material.

US20100187984 discloses a process for making an aza-dibenzothiophene compound or an aza-dibenzofuran compound, comprising:
treating an acetic acid solution of an amino-arylthio pyridine intermediate having the formula

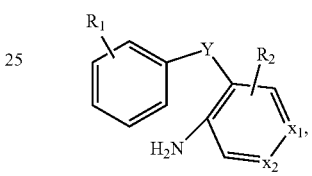

wherein one of $X_1$ and $X_2$ is nitrogen and the other of $X_1$ and $X_2$ is carbon and wherein Y is S or O, with tBuONO to produce an aza complex having the formula

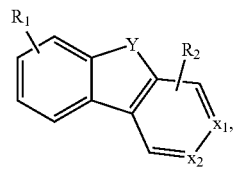

wherein $R_1$ and $R_2$ may represent mono, di, tri, or tetra substitutions; wherein $R_1$ is selected from the group consisting of hydrogen, alkyl, aryl, heteroaryl and halide; and wherein $R_2$ is selected from the group consisting of hydrogen, alkyl, aryl and halide. The aza-dibenzothiophene and aza-dibenzofuran compounds disclosed in US20100187984 are used as hosts in OLEDs.

In addition, reference is made to WO2012090967, WO2011137072, WO2010090077, WO2009060780, WO2009060757, JP2011084531 and JP2008074939 with respect to azadibenzofuranyl substituted compounds and their use in OLEDs.

None of the above references disclose benzimidazo[1,2-a]benzimidazo-5-yl substituted aza-dibenzofuran compounds.

Notwithstanding these developments, there remains a need for organic light emitting devices comprising new hole transport materials to provide improved efficiency, stability, manufacturability, and/or spectral characteristics of electroluminescent devices.

Accordingly, it is an object of the present invention, with respect to the aforementioned prior art, to provide further materials suitable for use in OLEDs and further applications in organic electronics. More particularly, it should be possible to provide hole transport materials, electron/exciton blocker materials and matrix materials for use in OLEDs. The materials should be suitable especially for OLEDs which comprise at least one phosphorescence emitter, especially at least one green emitter or at least one blue emitter. Furthermore, the materials should be suitable for providing OLEDs which ensure good efficiencies, good operative lifetimes and a high stability to thermal stress, and a low use and operating voltage of the OLEDs.

Certain aza-dibenzofuran derivatives substituted with a benzimidazo[1,2-a]benzimidazo-5-yl group and/or a benzimidazo[1,2-a]benzimidazo-2,5-ylene group are found to be suitable for use in organo-electroluminescent devices. In particular, said derivatives are suitable hole transporting materials, or host materials for phosphorescent emitters with good efficiency and durability.

Said object has been solved by compounds of the formula

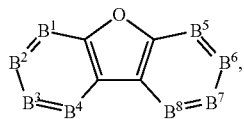

(I)

wherein
$B^1$ is N, or $CR^{81}$,
$B^2$ is N, or $CR^{82}$,
$B^3$ is N, or $CR^{83}$,
$B^4$ is N, or $CR^{84}$,
$B^5$ is N, or $CR^{85}$,
$B^6$ is N, or $CR^{86}$,
$B^7$ is N, or $CR^{87}$,
$B^8$ is N, or $CR^{88}$,
$R^{81}$, $R^{82}$, $R^{83}$, $R^{84}$, $R^{85}$, $R^{86}$, $R^{87}$ and $R^{88}$ are independently of each other H, a $C_1$-$C_{25}$alkyl group, which can optionally be substituted by E and or interrupted by D; a $C_6$-$C_{24}$aryl group, which can optionally be substituted by G, a $C_2$-$C_{30}$heteroaryl group, which can optionally be substituted by G; or a group of formula -$(A^1)_o$-$(A^2)_p$-$(A^3)_q$-$(A^4)_r$-$R^{16}$,
o is 0, or 1, p is 0, or 1, q is 0, or 1, r is 0, or 1,
$A^1$, $A^2$, $A^3$ and $A^4$ are independently of each other a $C_6$-$C_{24}$arylen group, which can optionally be substituted by G, or a $C_2$-$C_{30}$heteroarylen group, which can optionally be substituted by G;
$R^{16}$ is —$NR^{10}R^{11}$, or —$Si(R^{12})(R^{13})(R^{14})$, a $C_6$-$C_{24}$aryl group, which can optionally be substituted by G; or a $C_2$-$C_{30}$heteroaryl group, which can optionally be substituted by G;
$R^{10}$ and $R^{11}$ are independently of each other a $C_6$-$C_{24}$aryl group, which can optionally be substituted by G; or a $C_2$-$C_{30}$heteroaryl group, which can optionally be substituted by G;
$R^{12}$, $R^{13}$ and $R^{14}$ are independently of each other a $C_1$-$C_{25}$alkyl group, which can optionally be substituted by E and or interrupted by D; $C_6$-$C_{24}$aryl group, which can optionally be substituted by G; or a $C_2$-$C_{30}$heteroaryl group, which can optionally be substituted by G;
D is —CO—, —COO—, —S—, —SO—, —$SO_2$—, —O—, —$NR^{65}$—, —$SiR^{70}R^{71}$—, —$POR^{72}$—, —$CR^{63}$=$CR^{64}$—, or —C≡C—,
E is —$OR^{69}$, —$SR^{69}$, —$NR^{65}R^{66}$, —$COR^{68}$, —$COOR^{67}$, —$CONR^{65}R^{66}$, —CN, or F,
G is E, or a $C_1$-$C_{18}$alkyl group, a $C_6$-$C_{24}$aryl group, a $C_6$-$C_{24}$aryl group, which is substituted by F, $C_1$-$C_{18}$alkyl, or $C_1$-$C_{18}$alkyl which is interrupted by O; a $C_2$-$C_{30}$heteroaryl group, or a $C_2$-$C_{30}$heteroaryl group, which is substituted by F, $C_1$-$C_{18}$alkyl, or $C_1$-$C_{18}$alkyl which is interrupted by O;
$R^{63}$ and $R^{64}$ are independently of each other H, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;
$R^{65}$ and $R^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; or
$R^{65}$ and $R^{66}$ together form a five or six membered ring,
$R^{67}$ is a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—,
$R^{68}$ is H; a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—,
$R^{69}$ is a $C_6$-$C_{18}$aryl; a $C_6$-$C_{18}$aryl, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—,
$R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and
$R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl,
with the proviso that
at least one of the substituents $B^1$, $B^2$, $B^3$, $B^4$, $B^5$, $B^6$, $B^7$ and $B^8$ represents N;
not more than two of the groups $B^1$, $B^2$, $B^3$ and $B^4$ represent N; and
not more than two of the groups $B^5$, $B^6$, $B^7$ and $B^8$ represent N; and
with the further proviso that at least one of the substituents $R^{81}$, $R^{82}$, $R^{83}$, $R^{84}$, $R^{85}$, $R^{86}$, $R^{87}$ and $R^{88}$ represent a group of formula -$(A^1)_o$-$(A^2)_p$-$(A^3)_q$-$(A^4)_r$-$R^{16}$, wherein $R^{16}$ represents a benzimidazo[1,2-a]benzimidazo-5-yl group, which can optionally be substituted by G;
and/or at least one of the groups $A^1$, $A^2$, $A^3$ and $A^4$ represents a benzimidazo[1,2-a]benzimidazo-2,5-ylene group, which can optionally be substituted by G.

Certain compounds of the present invention have a LUMO-Level of 2.0-2.5 eV and show, when used as host in combination with phosphorescent emitters, excellent power efficiencies, in particular. electroluminescent (EL) devices comprising the compounds of the present invention exhibit reduced drive voltage while maintaining excellent luminance properties.

The compounds of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices, such as, for example, organic light-emitting diodes (OLEDs).

Accordingly, a further subject of the present invention is directed to an electronic device, comprising a compound according to the present invention. The electronic device is preferably an electroluminescent device.

The compounds of formula I can in principal be used in any layer of an EL device, but are preferably used as host, hole transport and electron blocking material. Particularly, the compounds of formula I are used as host material for blue light emitting phosphorescent emitters.

Hence, a further subject of the present invention is directed to an hole transport layer, comprising a compound of formula I according to the present invention.

A further subject of the present invention is directed to an emitting layer, comprising a compound of formula I according to the present invention. In said embodiment a compound of formula I is preferably used as host material in combination with a phosphorescent emitter.

The compounds of formula I have preferably a molecular weight below 1500 g/mol.

A further subject of the present invention is directed to an electron blocking layer, comprising a compound of formula I according to the present invention.

D is preferably —CO—, —COO—, —S—, —SO—, —SO$_2$—, —O—, —NR$^{65}$—, wherein R$^{65}$ is C$_1$-C$_{18}$alkyl, such as methyl, ethyl, n-propyl, iso-propyl, n-butyl, isobutyl, or sec-butyl, or C$_6$-C$_{18}$aryl, such as phenyl, tolyl, naphthyl, or biphenylyl, or C$_2$-C$_{30}$heteroaryl, such as, for example, benzimidazo[1,2-a]benzimidazo-5-yl

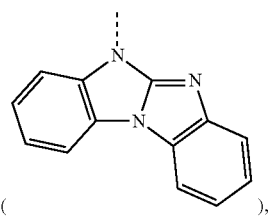

benzimidazo[1,2-a]benzimidazo-2-yl

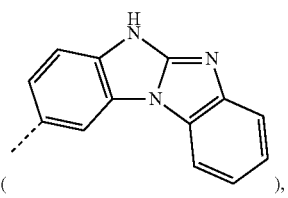

carbazolyl, dibenzofuranyl, which can be unsubstituted or substituted especially by C$_6$-C$_{10}$aryl, or C$_6$-C$_{10}$aryl, which is substituted by C$_1$-C$_4$alkyl; or C$_2$-C$_{14}$heteroaryl.

E is preferably —OR$^{69}$; —SR$^{69}$; —NR$^{65}$R$^{65}$; —COR$^{68}$; —COOR$^{67}$; —CONR$^{65}$R$^{65}$; or —CN; wherein R$^{65}$, R$^{67}$, R$^{68}$ and R$^{69}$ are independently of each other C$_1$-C$_{18}$alkyl, such as methyl, ethyl, n-propyl, iso-propyl, n-butyl, isobutyl, sec-butyl, hexyl, octyl, or 2-ethyl-hexyl, or C$_6$-C$_{14}$aryl, such as phenyl, tolyl, naphthyl, or biphenylyl.

Among the compounds of formula (I) compounds of formula

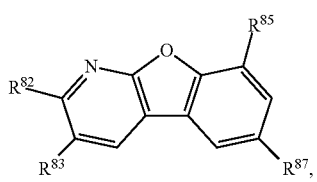

(I')

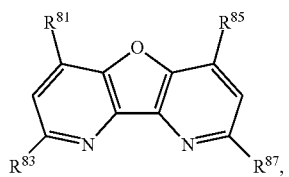

(I″)

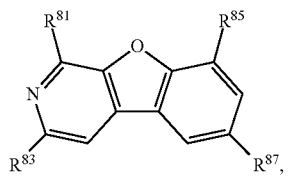

(I‴)

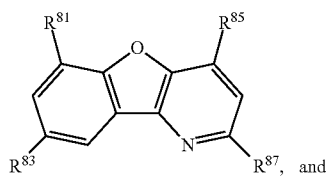

(I⁗)

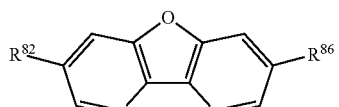

and (I″″″, = Io)

are preferred, where R$^{81}$, R$^{82}$, R$^{83}$, R$^{85}$, R$^{86}$ and R$^{87}$ have the (preferred) meanings given above and below, respectively.

In a preferred embodiment the present invention is directed to compounds of formula

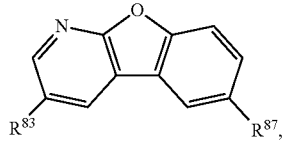

(Ia)

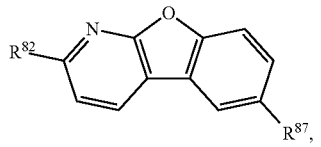

(Ib)

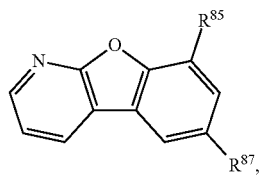

(Ic)

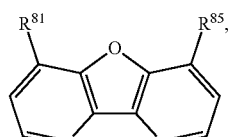

(Id)

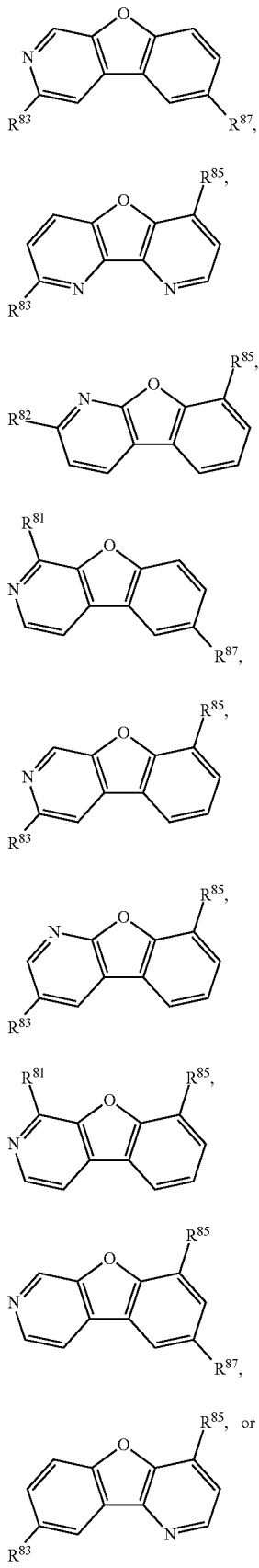

wherein $R^{81}$, $R^{82}$, $R^{83}$, $R^{85}$, $R^{86}$ and $R^{87}$ are as defined above.

Compounds of formula (Ia), (Ib), (Ic), (Id), (Ie), (If), (Ii), (Ij), (Il) and (In) are preferred. Compounds of formula (Ia), (Ib), (Ic), (Id), (Ie), (If), (Ij) and (In) are especially preferred.

$R^{16'}$ ($R^{16}$) may be a $C_6$-$C_{24}$aryl group, which can optionally be substituted by G, or a $C_2$-$C_{30}$heteroaryl group, which can optionally be substituted by G.

The $C_6$-$C_{24}$aryl group, which optionally can be substituted by G, is typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted.

The $C_2$-$C_{30}$heteroaryl group $R^{16'}$ ($R^{16}$), which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated m-electrons such as 9H-pyrido[2,3-b]indolyl, benzofuro[2,3-b]pyridyl, benzothiopheno[2,3-b]pyridyl, 9H-pyrido[2,3-c]indolyl, benzofuro[2,3-c]pyridyl, benzothiopheno[2,3-c]pyridyl, furo[3,2-b:4,5-b']dipyridyl, pyrrolo[3,2-b:4,5-b']dipyridyl, thieno[3,2-b:4,5-b']dipyridyl, thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, benzimidazo[1,2-a]benzimidazo-5-yl, benzimidazo[1,2-a]benzimidazo-2-yl, carbazolyl, or phenoxazinyl, which can be unsubstituted or substituted.

The $C_6$-$C_{24}$aryl and $C_2$-$C_{30}$heteroaryl groups may be substituted by G.

G has the same preferences as E, or is $C_1$-$C_{18}$alkyl, such as methyl, ethyl, n-propyl, iso-propyl, n-butyl, isobutyl, sec-butyl, hexyl, octyl, or 2-ethyl-hexyl, or is $C_1$-$C_{18}$perfluoroalkyl, such, for example, —$CF_3$.

Preferred $C_2$-$C_{30}$heteroaryl groups are pyridyl, triazinyl, pyrimidinyl, especially 9H-pyrido[2,3-b]indolyl, benzofuro[2,3-b]pyridyl, benzothiopheno[2,3-b]pyridyl, 9H-pyrido[2,3-c]indolyl, benzofuro[2,3-c]pyridyl, benzothiopheno[2,3-c]pyridyl, furo[3,2-b:4,5-b']dipyridyl, pyrrolo[3,2-b:4,5-b']dipyridyl, thieno[3,2-b:4,5-b']dipyridyl, benzimidazo[1,2-a]benzimidazo-5-yl

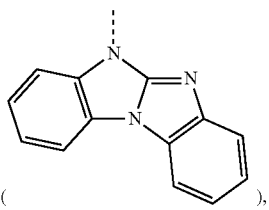

benzimidazo[1,2-a]benzimidazo-2-yl

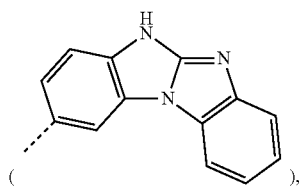

carbazolyl, dibenzofuranyl, and dibenzothiophenyl, which can be unsubstituted or substituted especially by $C_6$-$C_{10}$aryl, or $C_6$-$C_{10}$aryl, which is substituted by $C_1$-$C_4$alkyl; or $C_2$-$C_{14}$heteroaryl.

$R^{16}$ is a group of the formula

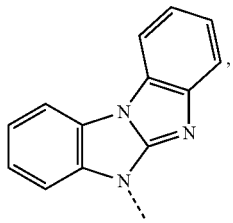

or $R^{16}$ has the meaning of $R^{16'}$, if at least one of the groups $A^1$, $A^2$, $A^3$ and $A^4$ represent a group of formula

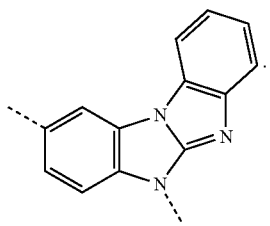

$R^{16'}$ is preferably H, or a group of the formula —Si($R^{12}$)($R^{13}$)($R^{14}$), especially

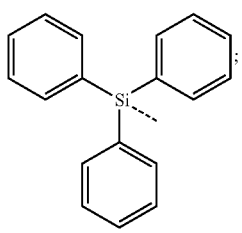 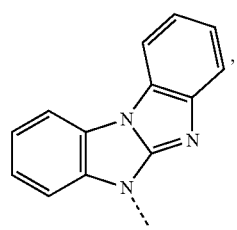

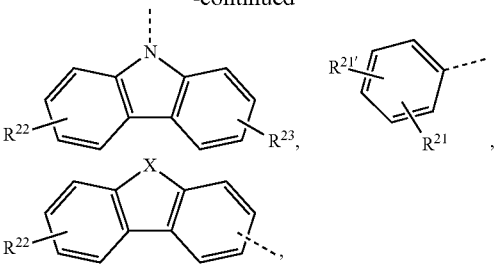

especially

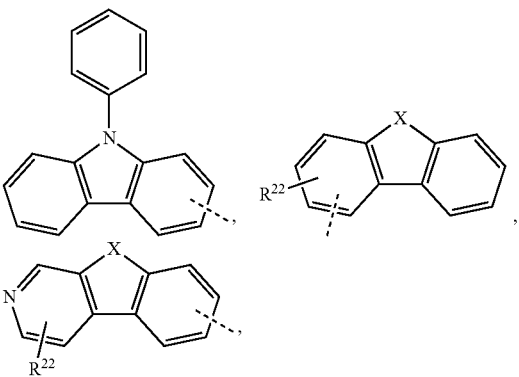

especially

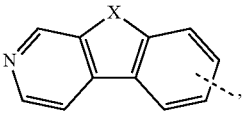

very especially

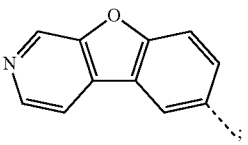

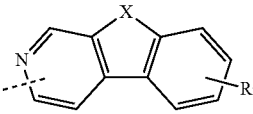

especially

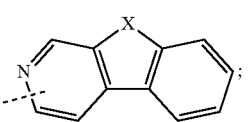

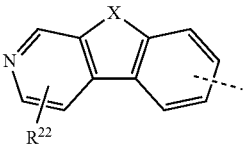

-continued

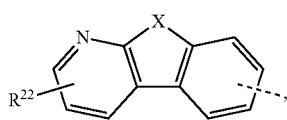

especially

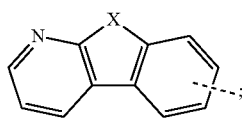

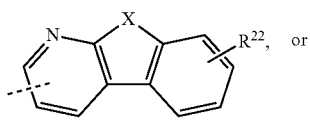

especially

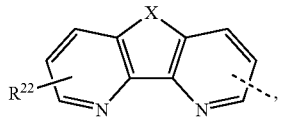

$R^{12}$, $R^{13}$ and $R^{14}$ are independently of each other a phenyl group, which can optionally be substituted by one, or more $C_1$-$C_{18}$alkyl groups;

$R^{21}$ and $R^{21'}$ are independently of each other H, a phenyl group, or a $C_1$-$C_{18}$alkyl group;

$R^{22}$ and $R^{23}$ are independently of each other H, or a group of the formula

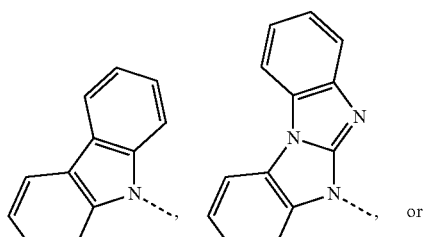

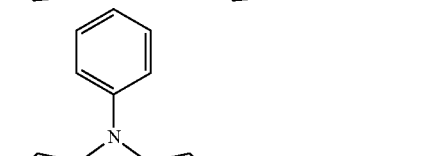

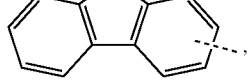

especially

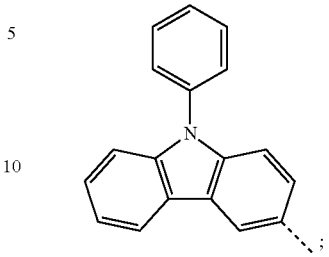

X is O, S, or $NR^{24}$, $R^{24}$ is a $C_6$-$C_{24}$aryl group, or a $C_2$-$C_{30}$heteroaryl group, which can optionally be substituted by G, wherein G is as defined in above; and $R^{89}$ is H, a group of formula especially

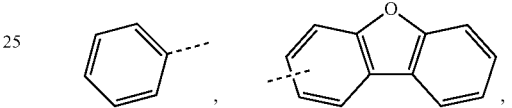

especially

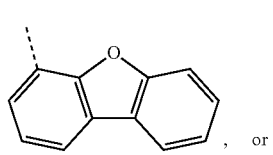

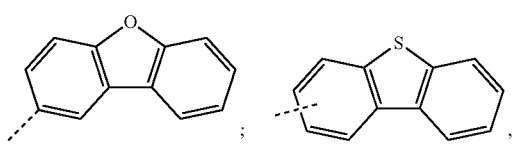

especially

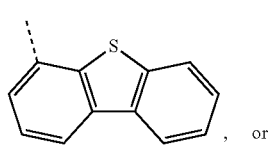

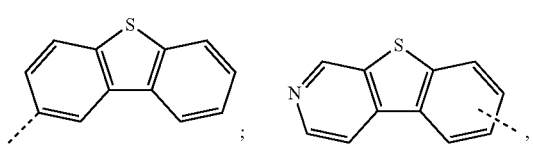

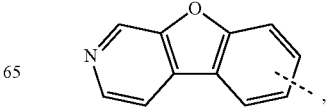

especially

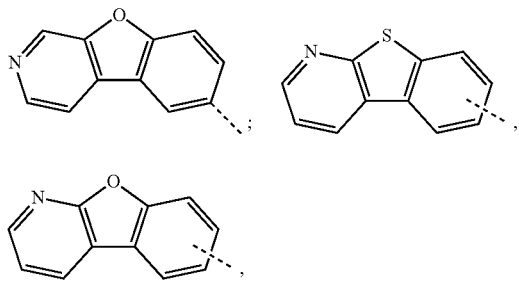

especially

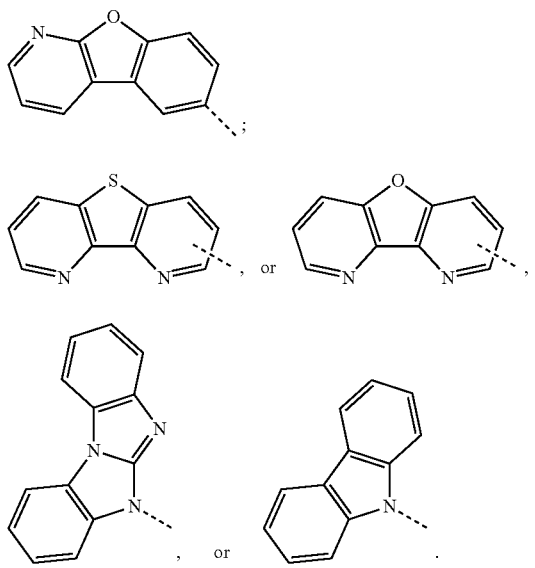

A¹, A², A³ and A⁴ are independently of each other a $C_6$-$C_{24}$arylen group, which can optionally be substituted by G, or a $C_2$-$C_{30}$heteroarylen group, which can optionally be substituted by G. The $C_6$-$C_{24}$arylen groups A¹, A², A³ and A⁴ which optionally can be substituted by G, are typically phenylene, 4-methylphenylene, 4-methoxyphenylene, naphthylene, especially 1-naphthylene, or 2-naphthylene, biphenylylene, terphenylylene, pyrenylene, 2- or 9-fluorenylene, phenanthrylene, or anthrylene, which may be unsubstituted or substituted.

The $C_2$-$C_{30}$heteroarylen groups A¹, A², A³ and A⁴, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated-electrons such as benzofuro[2,3-b]pyridylene

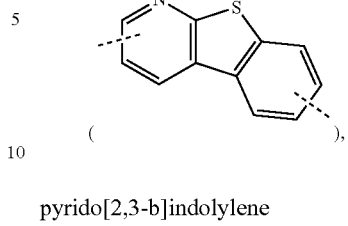

benzothiopheno[2,3-b]pyridylene

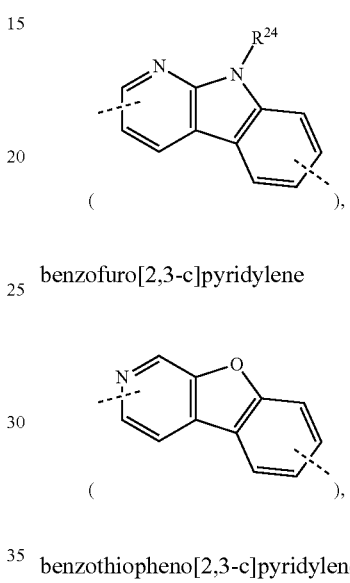

pyrido[2,3-b]indolylene benzofuro[2,3-c]pyridylene benzothiopheno[2,3-c]pyridylene

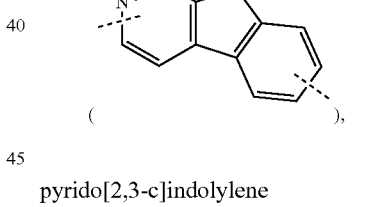

pyrido[2,3-c]indolylene

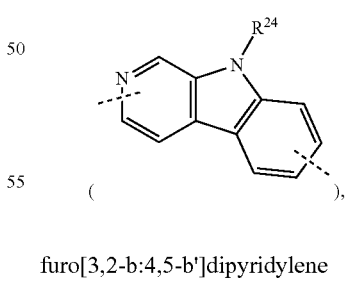

furo[3,2-b:4,5-b']dipyridylene

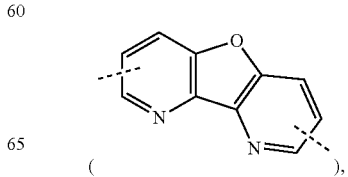

thieno[3,2-b:4,5-b']dipyridylene

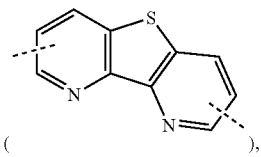

pyrrolo[3,2-b:4,5-b']dipyridylene

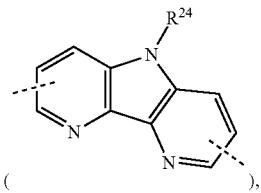

thienylene, benzothiophenylene, thianthrenylene, furylene, furfurylene, 2H-pyranylene, benzofuranylene, isobenzofuranylene, dibenzofuranylene

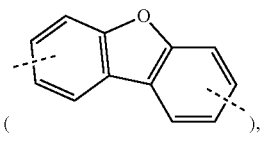

dibenzothiophenylene

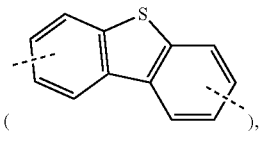

phenoxythienylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, chinolylene, isochinolylene, phthalazinylene, naphthyridinylene, chinoxalinylene, chinazolinylene, cinnolinylene, pteridinylene, carbolinylene, benzotriazolylene, benzoxazolylene, phenanthridinylene, acridinylene, pyrimidinylene, phenanthrolinylene, phenazinylene, isothiazolylene, phenothiazinylene, isoxazolylene, furazanylene, carbazolylene

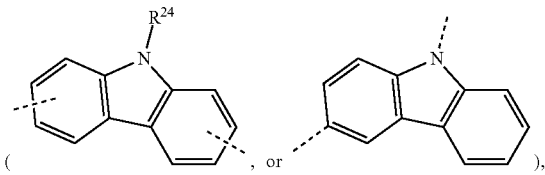

benzimidazo[1,2-a]benzimidazo-2,5-ylene

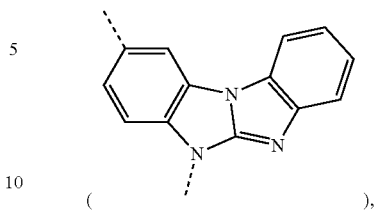

or phenoxazinylene, which can be unsubstituted or substituted.

Preferred $C_6$-$C_{24}$arylen groups are 1,3-phenylene, 3,3'-biphenylylene, 3,3'-m-terphenylene, 2- or 9-fluorenylene, phenanthrylene, which may be unsubstituted or substituted, especially by $C_6$-$C_{10}$aryl, $C_6$-$C_{10}$aryl which is substituted by $C_1$-$C_4$alkyl; or $C_2$-$C_{14}$heteroaryl.

Preferred $C_2$-$C_{30}$heteroarylen groups are pyridylene, triazinylene, pyrimidinylene, especially benzofuro[2,3-b]pyridylene, benzothiopheno[2,3-b]pyridylene, pyrido[2,3-b]indolylene, benzofuro[2,3-c]pyridylene, benzothiopheno[2,3-c]pyridylene, pyrido[2,3-c]indolylene furo[3,2-b:4,5-b']dipyridylene, thieno[3,2-b:4,5-b']dipyridylene, pyrrolo[3,2-b:4,5-b']dipyridylene, dibenzofuranylene, dibenzothiophenylene, carbazolylene and benzimidazo[1,2-a]benzimidazo-2,5-ylene, which can be unsubstituted or substituted, especially by $C_6$-$C_{10}$aryl, $C_6$-$C_{10}$aryl which is substituted by $C_1$-$C_4$alkyl; or $C_2$-$C_{14}$heteroaryl.

Benzimidazo[1,2-a]benzimidazo-5-yl, benzimidazo[1,2-a]benzimidazo-2-yl, carbazolyl and dibenzofuranyl are examples of a $C_2$-$C_{14}$heteroaryl group. Phenyl, 1-naphthyl and 2-naphthyl are examples of a $C_6$-$C_{10}$aryl group.

The $C_6$-$C_{24}$arylen and $C_2$-$C_{30}$heteroarylen groups may be substituted by G.

$A^1$, $A^2$, $A^3$ and $A^4$ are preferably a group of the formula

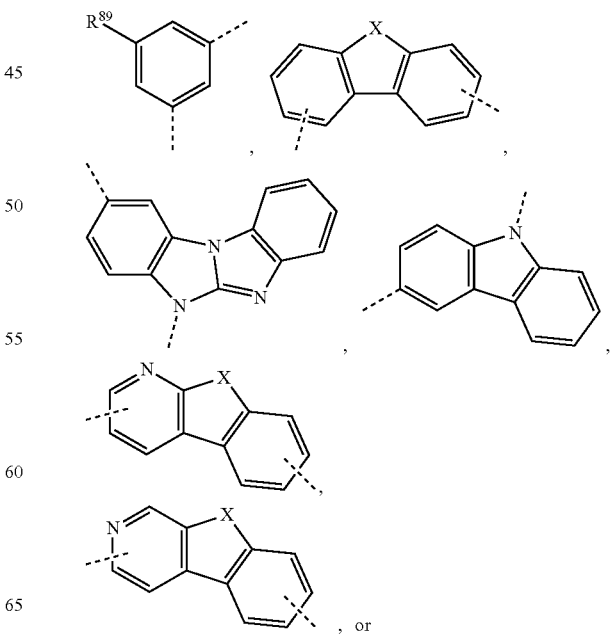

, or

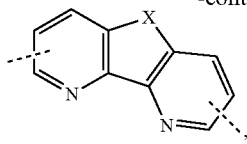

wherein $R^{89}$ and X are as defined below. X is preferably O.

The aza-dibenzofuran derivatives of the present invention are characterized in that they are substituted with at least one benzimidazo[1,2-a]benzimidazo-5-yl group and/or at least one benzimidazo[1,2-a]benzimidazo-2,5-ylene group.

In particular, the aza-dibenzofuran derivatives of the present invention are characterized in that at least one of the substituents $R^{81}$, $R^{82}$, $R^{83}$, $R^{84}$, $R^{85}$, $R^{86}$, $R^{87}$ and $R^{88}$ is a group of formula $-(A^1)_o-(A^2)_p-(A^3)_q-(A^4)_r-R^{16}$, wherein $R^{16}$ is a group of the formula

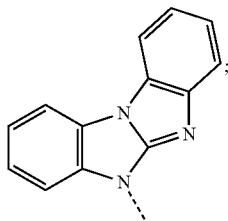

and/or at least one of the substituents $R^{81}$, $R^{82}$, $R^{83}$, $R^{84}$, $R^{85}$, $R^{86}$, $R^{87}$ and $R^{88}$ is a group of formula $-(A^1)_o-(A^2)_p-(A^3)_q-(A^4)_r-R^{16'}$, wherein at least one of the groups $A^1$, $A^2$, $A^3$ and $A^4$ represent a group of formula

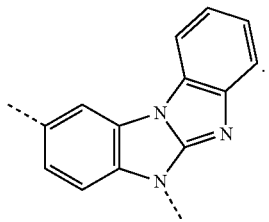

In a preferred embodiment the present invention is directed to compounds of formula (Ia), (Ib), (Ic), (Id), (Ie), (If), (Ig), (Ih), (Ii), (Ij), (Ik), (Il), (Im), (In) and (Io), wherein in the compounds of formula (Ia)
$R^{83}$ is a group of the formula $-(A^1)_o-(A^2)_p-(A^3)_q-(A^4)_r-R^{16}$; and
$R^{87}$ is H, or a group of the formula $-(A^1)_o-(A^2)_p-(A^3)_q-(A^4)_r-R^{16'}$; or
$R^{83}$ is H, or a group of the formula $-(A^1)_o-(A^2)_p-(A^3)_q-(A^4)_r-R^{16'}$; and
$R^{87}$ is a group of the formula $-(A^1)_o-(A^2)_p-(A^3)_q-(A^4)_r-R^{16}$;
in the compounds of formula (Ib)
$R^{82}$ is a group of the formula $-(A^1)_o-(A^2)_p-(A^3)_q-(A^4)_r-R^{16}$; and
$R^{87}$ is H, or a group of the formula $-(A^1)_o-(A^2)_p-(A^3)_q-(A^4)_r-R^{16'}$; or
$R^{82}$ is H, or a group of the formula $-(A^1)_o-(A^2)_p-(A^3)_q-(A^4)_r-R^{16'}$; and
$R^{87}$ is a group of the formula $-(A^1)_o-(A^2)_p-(A^3)_q-(A^4)_r-R^{16}$;
in the compounds of formula (Ic)
$R^{85}$ is a group of the formula $-(A^1)_o-(A^2)_p-(A^3)_q-(A^4)_r-R^{16}$; and
$R^{87}$ is H, or a group of the formula $-(A^1)_o-(A^2)_p-(A^3)_q-(A^4)_r-R^{16'}$; or
$R^{85}$ is H, or a group of the formula $-(A^1)_o-(A^2)_p-(A^3)_q-(A^4)_r-R^{16'}$; and
$R^{87}$ is a group of the formula $-(A^1)_o-(A^2)_p-(A^3)_q-(A^4)_r-R^{16}$;
in the compounds of formula (Id)
$R^{81}$ is a group of the formula $-(A^1)_o-(A^2)_p-(A^3)_q-(A^4)_r-R^{16}$; and
$R^{85}$ is H, or a group of the formula $-(A^1)_o-(A^2)_p-(A^3)_q-(A^4)_r-R^{16'}$; or
$R^{81}$ is H, or a group of the formula $-(A^1)_o-(A^2)_p-(A^3)_q-(A^4)_r-R^{16'}$; and
$R^{85}$ is a group of the formula $-(A^1)_o-(A^2)_p-(A^3)_q-(A^4)_r-R^{16}$;
in the compounds of formula (Ie)
$R^{83}$ is a group of the formula $-(A^1)_o-(A^2)_p-(A^3)_q-(A^4)_r-R^{16}$; and
$R^{87}$ is H, or a group of the formula $-(A^1)_o-(A^2)_p-(A^3)_q-(A^4)_r-R^{16'}$; or
$R^{83}$ is H, or a group of the formula $-(A^1)_o-(A^2)_p-(A^3)_q-(A^4)_r-R^{16'}$; and
$R^{87}$ is a group of the formula $-(A^1)_o-(A^2)_p-(A^3)_q-(A^4)_r-R^{16}$;
in the compounds of formula (If)
$R^{83}$ is a group of the formula $-(A^1)_o-(A^2)_p-(A^3)_q-(A^4)_r-R^{16}$; and
$R^{85}$ is H, or a group of the formula $-(A^1)_o-(A^2)_p-(A^3)_q-(A^4)_r-R^{16'}$; or
$R^{83}$ is H, or a group of the formula $-(A^1)_o-(A^2)_p-(A^3)_q-(A^4)_r-R^{16'}$; and
$R^{85}$ is a group of the formula $-(A^1)_o-(A^2)_p-(A^3)_q-(A^4)_r-R^{16}$;
in the compounds of formula (Ig)
$R^{82}$ is a group of the formula $-(A^1)_o-(A^2)_p-(A^3)_q-(A^4)_r-R^{16}$; and
$R^{85}$ is H, or a group of the formula $-(A^1)_o-(A^2)_p-(A^3)_q-(A^4)_r-R^{16'}$; or
$R^{82}$ is H, or a group of the formula $-(A^1)_o-(A^2)_p-(A^3)_q-(A^4)_r-R^{16'}$; and
$R^{85}$ is a group of the formula $-(A^1)_o-(A^2)_p-(A^3)_q-(A^4)_r-R^{16}$;
in the compounds of formula (Ih)
$R^{81}$ is a group of the formula $-(A^1)_o-(A^2)_p-(A^3)_q-(A^4)_r-R^{16}$; and
$R^{87}$ is H, or a group of the formula $-(A^1)_o-(A^2)_p-(A^3)_q-(A^4)_r-R^{16'}$; or
$R^{81}$ is H, or a group of the formula $-(A^1)_o-(A^2)_p-(A^3)_q-(A^4)_r-R^{16'}$; and
$R^{87}$ is a group of the formula $-(A^1)_o-(A^2)_p-(A^3)_q-(A^4)_r-R^{16}$;
in the compounds of formula (Ii)
$R^{83}$ is a group of the formula $-(A^1)_o-(A^2)_p-(A^3)_q-(A^4)_r-R^{16}$; and
$R^{85}$ is H, or a group of the formula $-(A^1)_o-(A^2)_p-(A^3)_q-(A^4)_r-R^{16'}$; or
$R^{83}$ is H, or a group of the formula $-(A^1)_o-(A^2)_p-(A^3)_q-(A^4)_r-R^{16'}$; and
$R^{85}$ is a group of the formula $-(A^1)_o-(A^2)_p-(A^3)_q-(A^4)_r-R^{16}$;
in the compounds of formula (Ij)
$R^{83}$ is a group of the formula $-(A^1)_o-(A^2)_p-(A^3)_q-(A^4)_r-R^{16}$; and
$R^{85}$ is H, or a group of the formula $-(A^1)_o-(A^2)_p-(A^3)_q-(A^4)_r-R^{16'}$; or
$R^{83}$ is H, or a group of the formula $-(A^1)_o-(A^2)_p-(A^3)_q-(A^4)_r-R^{16'}$; and
$R^{85}$ is a group of the formula $-(A^1)_o-(A^2)_p-(A^3)_q-(A^4)_r-R^{16}$;
in the compounds of formula (Ik)
$R^{81}$ is a group of the formula $-(A^1)_o-(A^2)_p-(A^3)_q-(A^4)_r-R^{16}$; and
$R^{85}$ is H, or a group of the formula $-(A^1)_o-(A^2)_p-(A^3)_q-(A^4)_r-R^{16'}$; or $R^{81}$ is H, or a group of the formula $-(A^1)_o-(A^2)_p-(A^3)_q-(A^4)_r-R^{16'}$; and $R^{85}$ is a group of the formula $-(A^1)_o-(A^2)_p-(A^3)_q-(A^4)_r-R^{16}$;

in the compounds of formula (Il)

$R^{85}$ is a group of the formula $-(A^1)_o-(A^2)_p-(A^3)_q-(A^4)_r-R^{16}$; and $R^{87}$ is H, or a group of the formula $-(A^1)_o-(A^2)_p-(A^3)_q-(A^4)_r-R^{16'}$; or $R^{85}$ is H, or a group of the formula $-(A^1)_o-(A^2)_p-(A^3)_q-(A^4)_r-R^{16'}$; and $R^{87}$ is a group of the formula $-(A^1)_o-(A^2)_p-(A^3)_q-(A^4)_r-R^{16}$;

in the compounds of formula (Im)

$R^{83}$ is a group of the formula $-(A^1)_o-(A^2)_p-(A^3)_q-(A^4)_r-R^{16}$; and $R^{85}$ is H, or a group of the formula $-(A^1)_o-(A^2)_p-(A^3)_q-(A^4)_r-R^{16'}$; or $R^{83}$ is H, or a group of the formula $-(A^1)_o-(A^2)_p-(A^3)_q-(A^4)_r-R^{16'}$; and $R^{85}$ is a group of the formula $-(A^1)_o-(A^2)_p-(A^3)_q-(A^4)_r-R^{16}$;

in the compounds of formula (In)

$R^{83}$ is a group of the formula $-(A^1)_o-(A^2)_p-(A^3)_q-(A^4)_r-R^{16}$; and $R^{87}$ is H, or a group of the formula $-(A^1)_o-(A^2)_p-(A^3)_q-(A^4)_r-R^{16'}$; or $R^{83}$ is H, or a group of the formula $-(A^1)_o-(A^2)_p-(A^3)_q-(A^4)_r-R^{16'}$; and $R^{87}$ is a group of the formula $-(A^1)_o-(A^2)_p-(A^3)_q-(A^4)_r-R^{16}$.

o is 0, or 1, p is 0, or 1, q is 0, or 1, r is 0, or 1;

in the compounds of formula (Io)

$R^{82}$ is a group of the formula $-(A^1)_o-(A^2)_p-(A^3)_q-(A^4)_r-R^{16}$; and $R^{86}$ is H, or a group of the formula $-(A^1)_o-(A^2)_p-(A^3)_q-(A^4)_r-R^{16'}$; or $R^{82}$ is H, or a group of the formula $-(A^1)_o-(A^2)_p-(A^3)_q-(A^4)_r-R^{16'}$; and $R^{86}$ is a group of the formula $-(A^1)_o-(A^2)_p-(A^3)_q-(A^4)_r-R^{16}$;

$A^1$, $A^2$, $A^3$ and $A^4$ are independently of each other a group of the formula

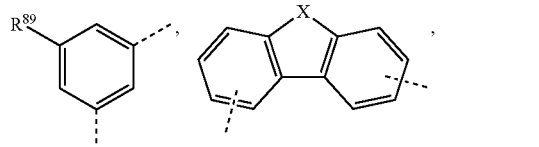,

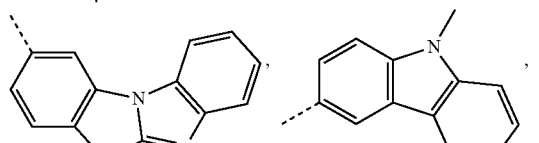,

,

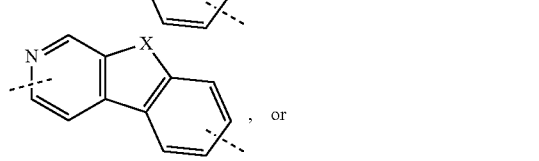, or

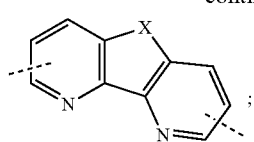;

$R^{16}$ is a group of the formula

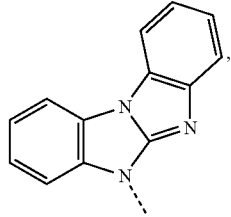, or $R^{16}$ has the meaning of $R^{16'}$, if at least one of the groups $A^1$, $A^2$, $A^3$ and $A^4$ represent a group of formula

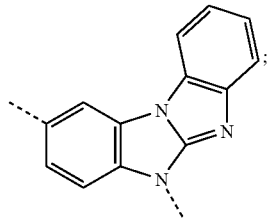;

$R^{16'}$ is H, or a group of the formula $-Si(R^{12})(R^{13})(R^{14})$,

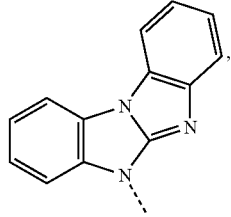,

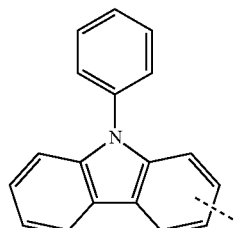,

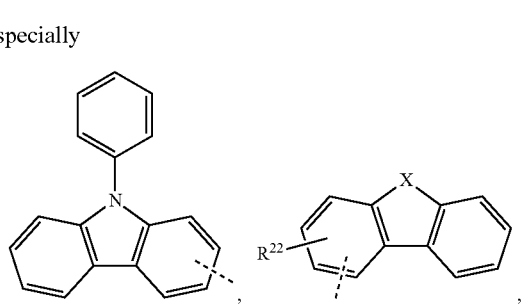

especially

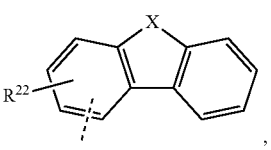

-continued

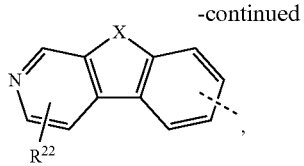

especially

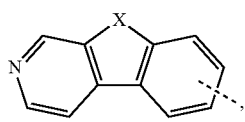

very especially

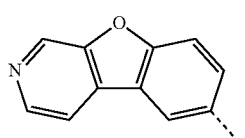

;

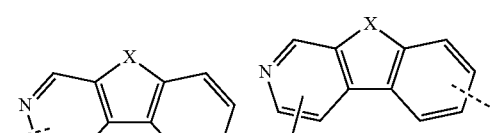

especially

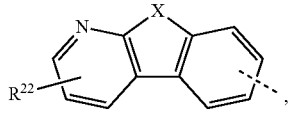

;

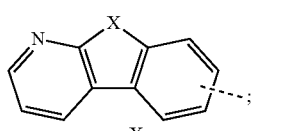

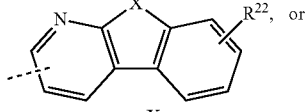

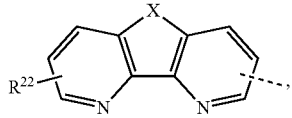

especially

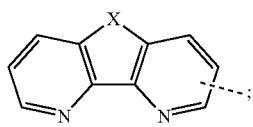

;

$R^{12}$, $R^{13}$ and $R^{14}$ are independently of each other a phenyl group, which can optionally be substituted by one, or more alkyl groups, especially $C_1$-$C_{18}$alkyl groups;

$R^{21}$ and $R^{21'}$ are independently of each other H, a phenyl group, or a $C_1$-$C_{18}$alkyl group;

$R^{22}$ and $R^{23}$ are independently of each other H, or a group of the formula

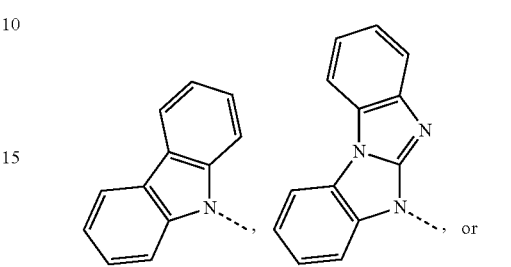

especially

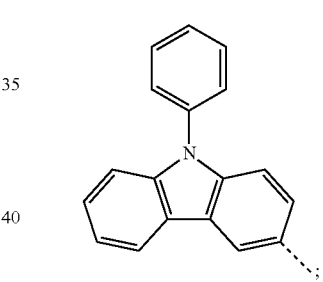

;

X is O, S, or $NR^{24}$, $R^{24}$ is a $C_6$-$C_{24}$aryl group, or a $C_2$-$C_{30}$heteroaryl group, which can optionally be substituted by G, wherein G is as defined in above; and $R^{89}$ is H, a group of formula especially

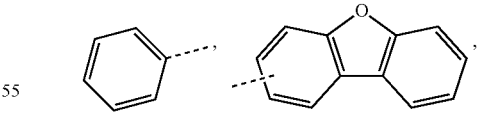

especially

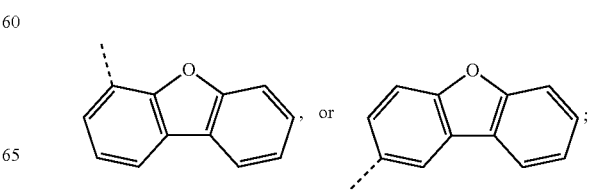

;

-continued
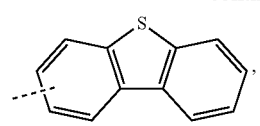
especially
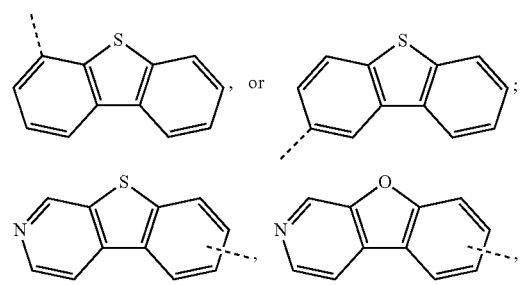
especially
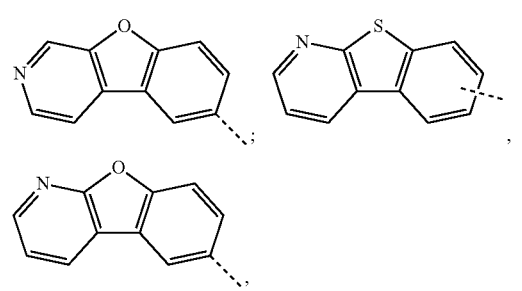
especially
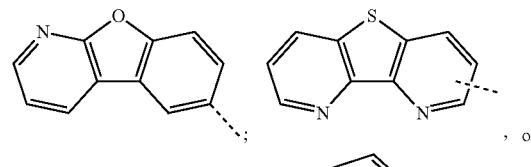, or
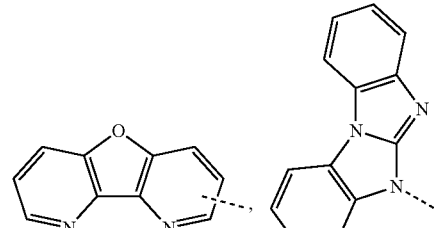, or
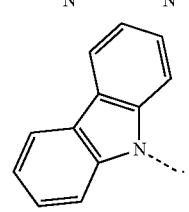
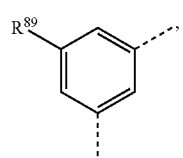 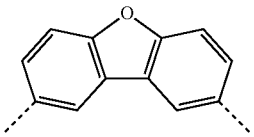
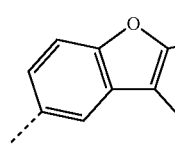 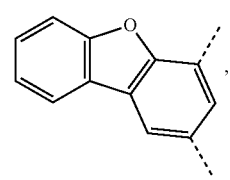
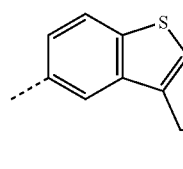 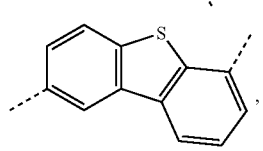
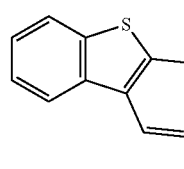 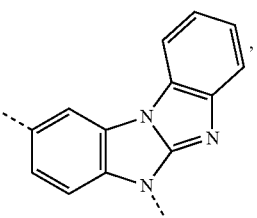
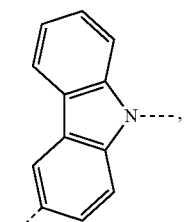 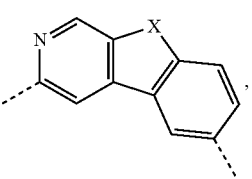
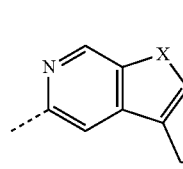 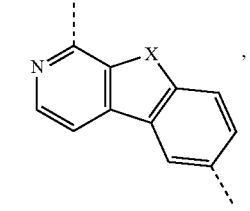
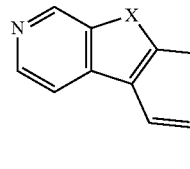 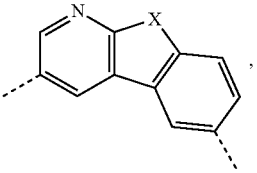
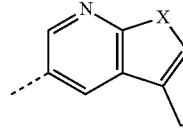 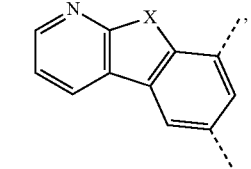
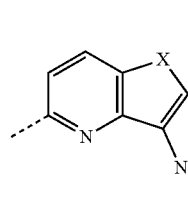 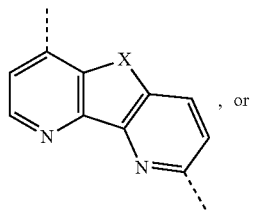, or
More preferred, $A^1$, $A^2$, $A^3$ and $A^4$ are independently of each other a group of the formula

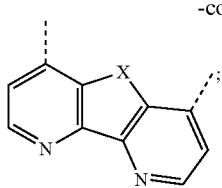
$R^{16}$ is a group of the formula
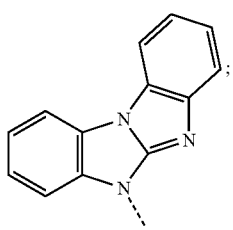
or $R^{16}$ has the meaning of $R^{16'}$, if at least one of the groups $A^1$, $A^2$, $A^3$ and $A^4$ represent a group of formula
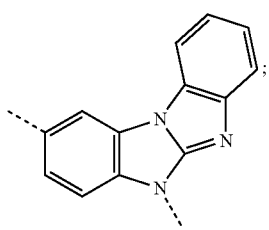
$R^{16'}$ is H, or a group of the formula
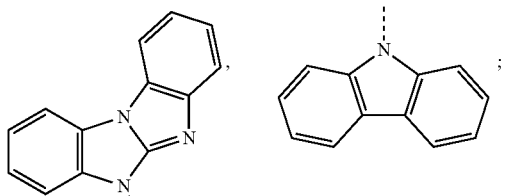
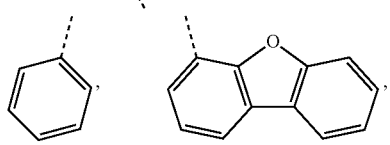
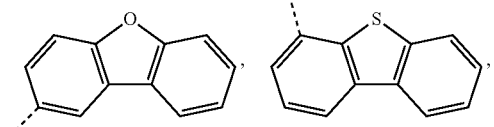
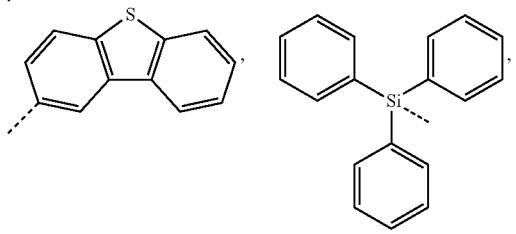
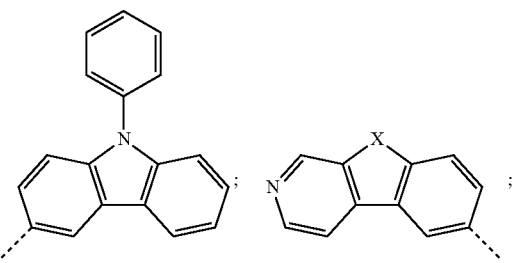
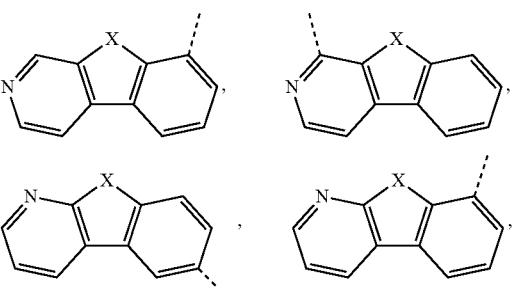
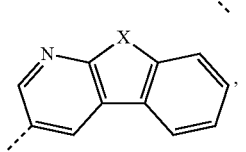
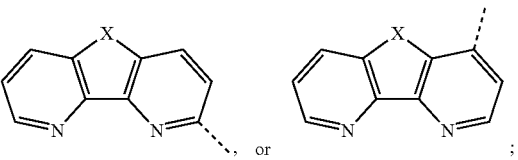
and $R^{89}$ is H, a group of formula
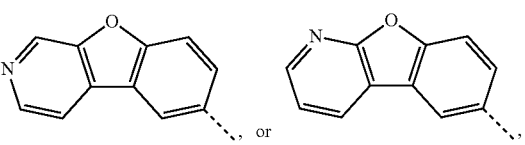
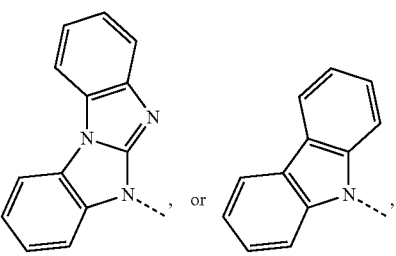
wherein X is O, S, or $NR^{24}$,
wherein $R^{24}$ is
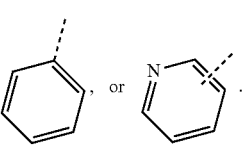

$R^{24}$ is preferably
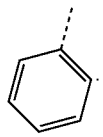
X is preferably O.
The group of the formula $-(A^1)_o-(A^2)_p-(A^3)_q-(A^4)_r-R^{16}$ is preferably a group of formula
(XIIa)
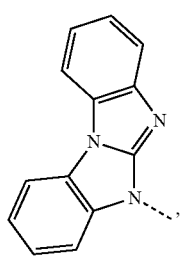
(XIIb)
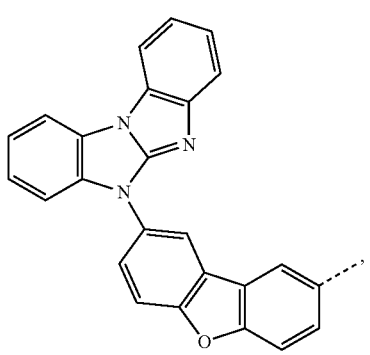
(XIIc)
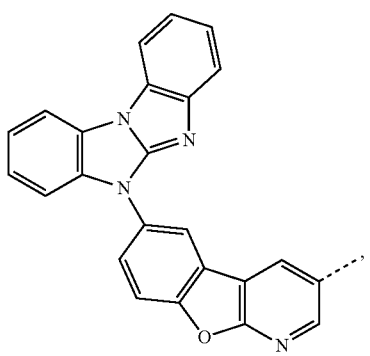
(XIId)
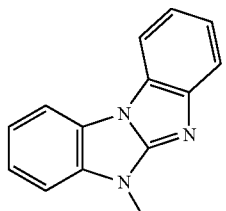
(XIIe)
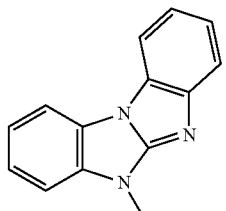
(XIIf)
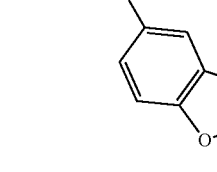
(XIIg)
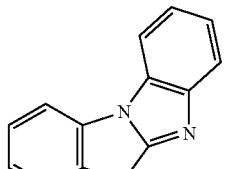
(XIIh)
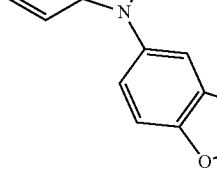
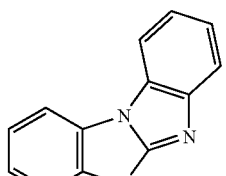
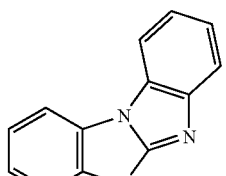
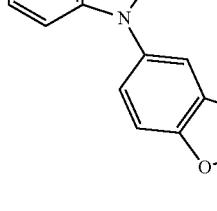

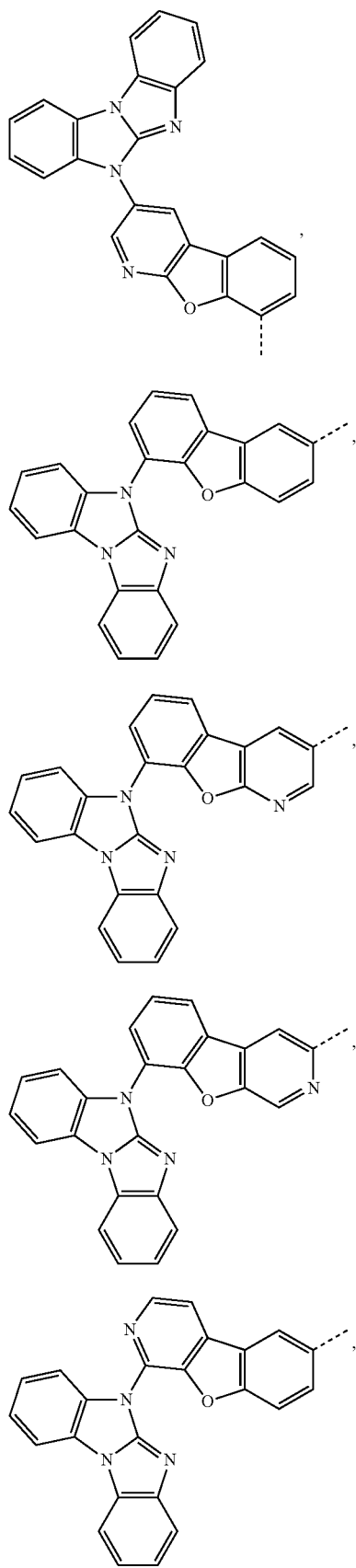
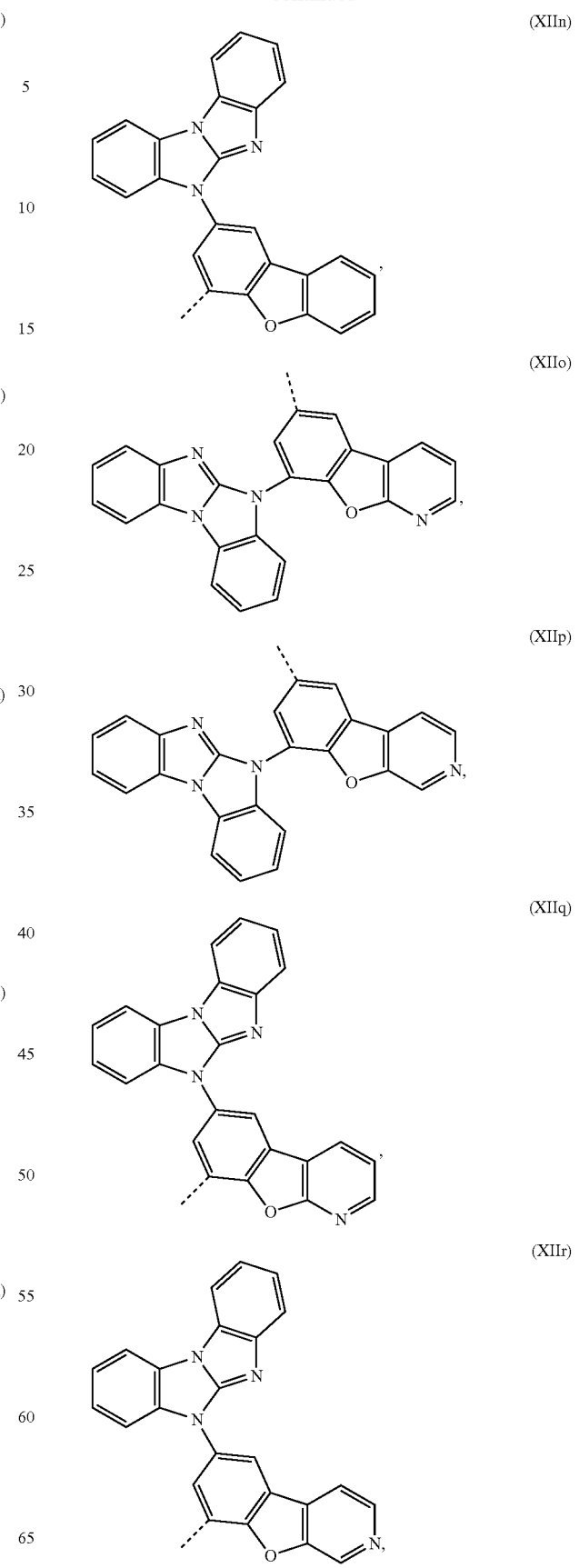

(XIIs)
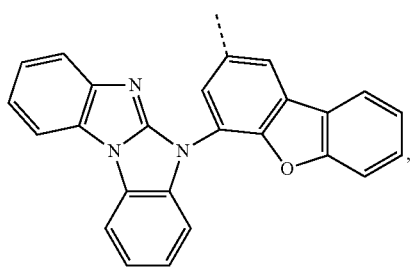
(XIIt)
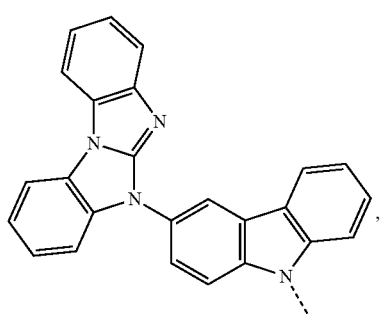
(XIIu)
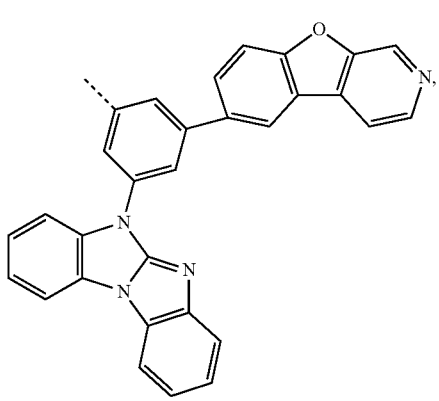
(XIIv)
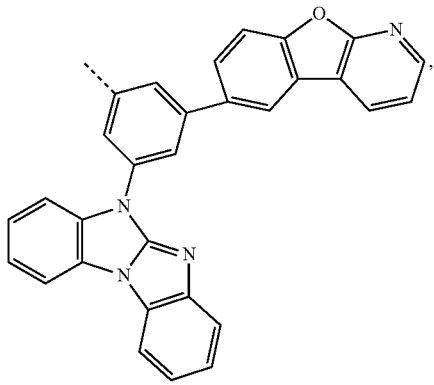
(XIIw)
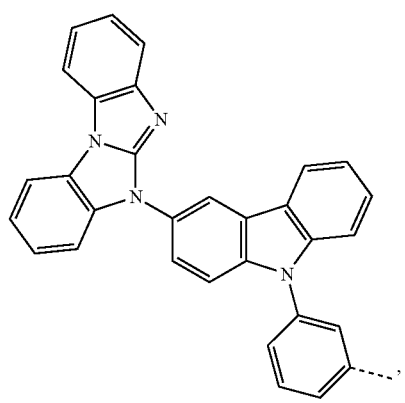
(XIIx)
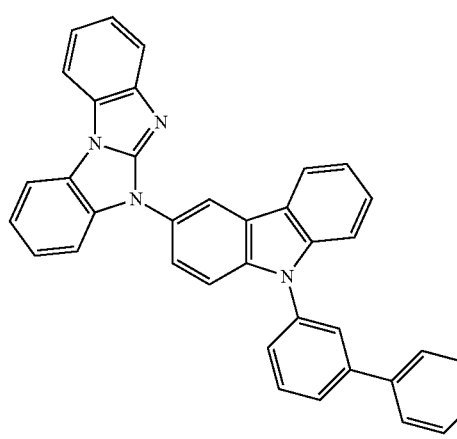
(XIIy)
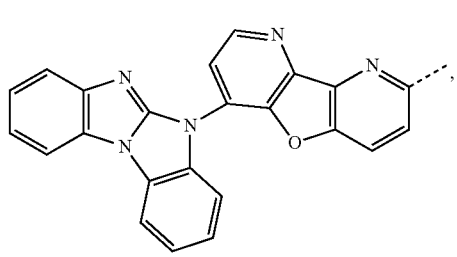
(XIIz)
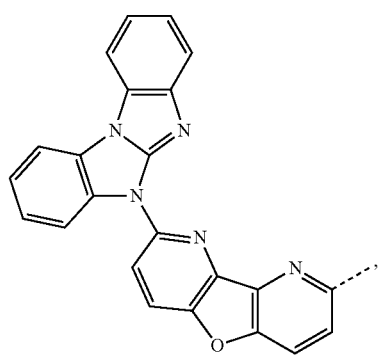

(XIIIa)
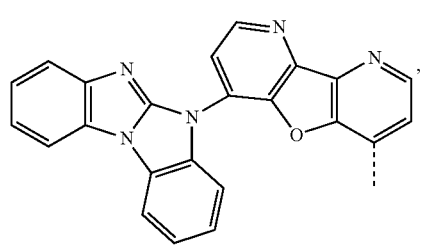

(XIIIb)
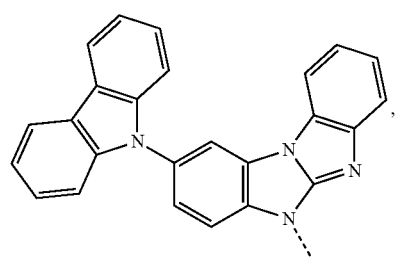

(XIIIc)
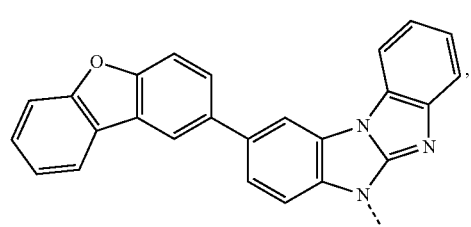

(XIIId)
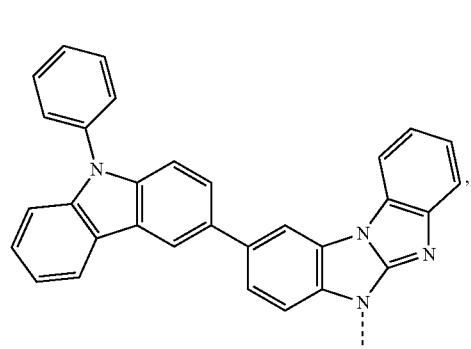

(XIIIe)
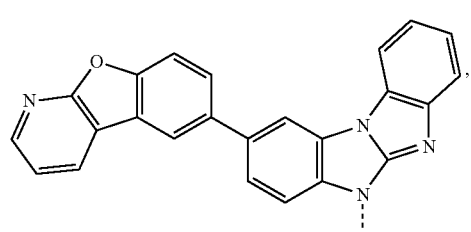

(XIIIf)
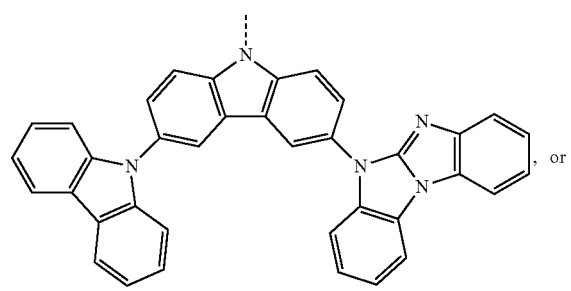, or (XIIIg)
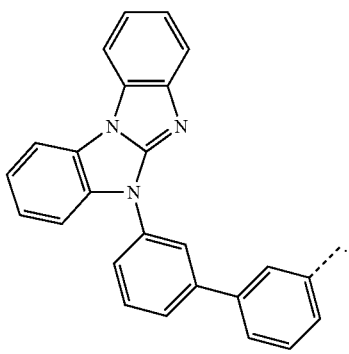

The group of the formula -(A$^1$)$_o$-(A$^2$)$_p$-(A$^3$)$_q$-(A$^4$)$_r$-R$^{16'}$ is preferably H, or a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf), or (IIIg), as defined above; or a group of formula (XIVa)
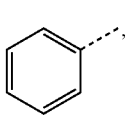

(XIVb)
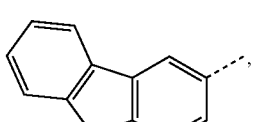

(XIVc)
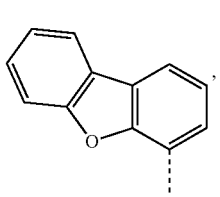

(XIVd)
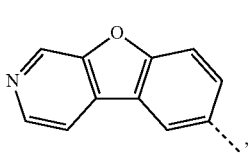

(XIVe)
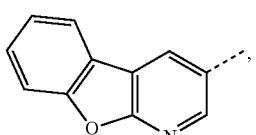

(XIVf)
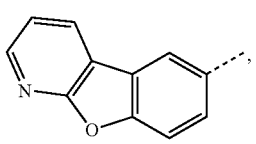

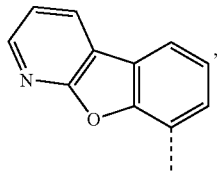 (XIVg)
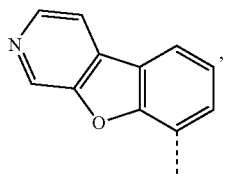 (XIVh)
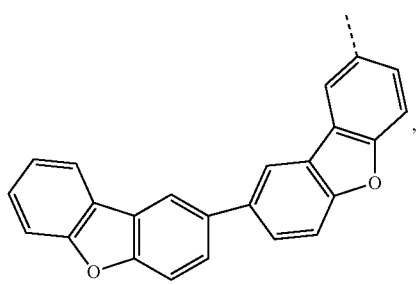 (XIVi)
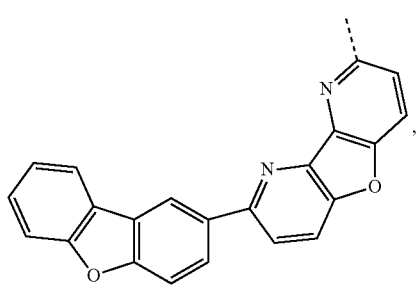 (XIVj)
 (XIVk)
 (XIVl)
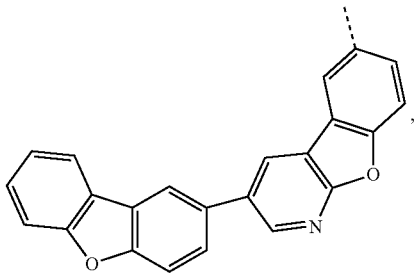 (XIVm)
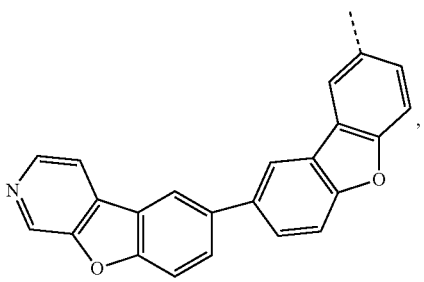 (XIVn)
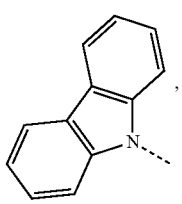 (XIVo)
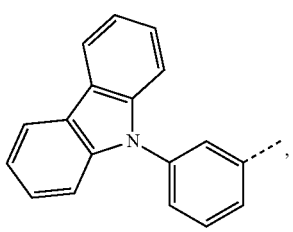 (XIVp)
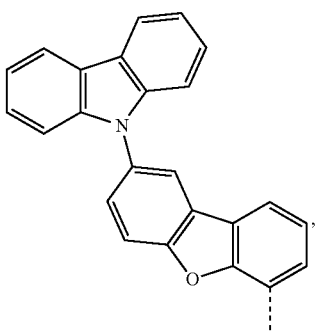 (XIVq)

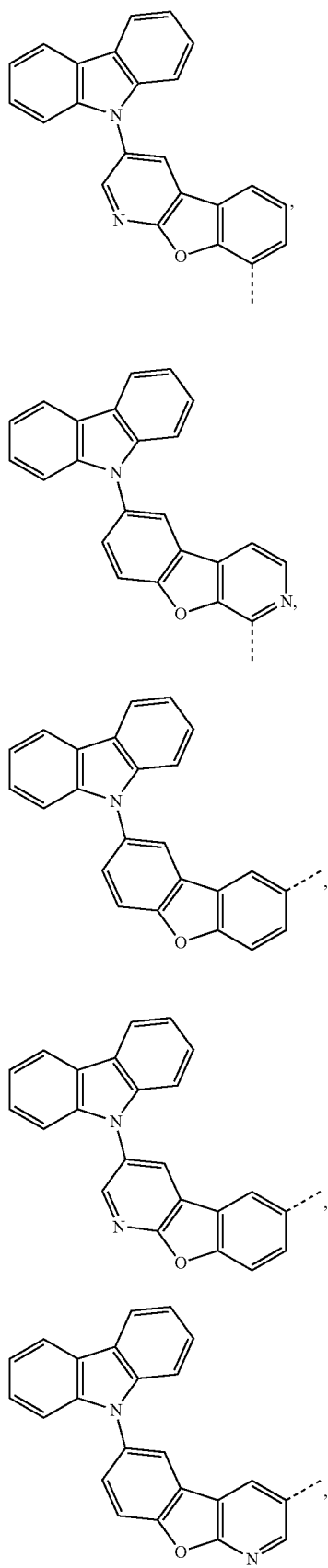
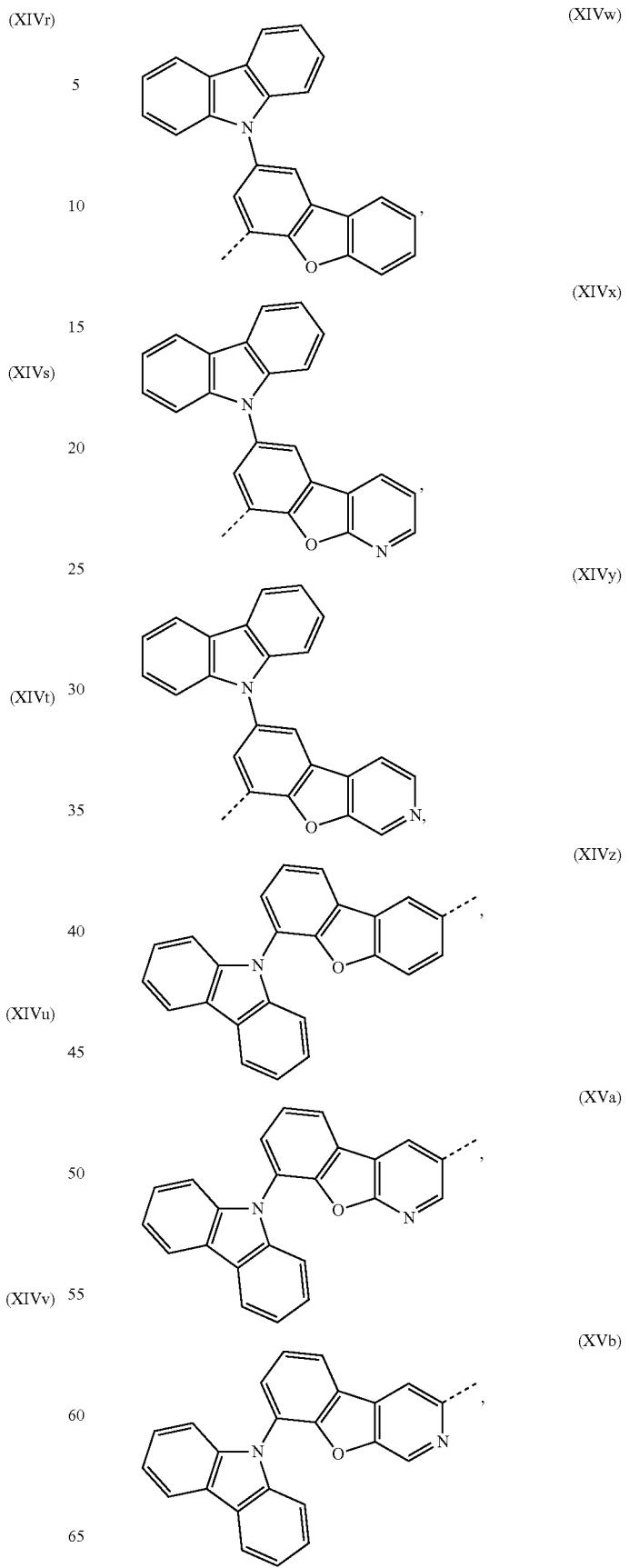

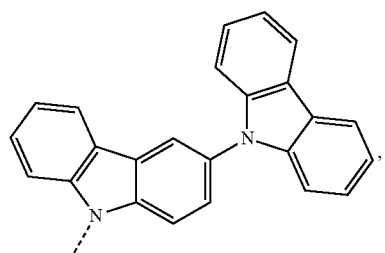
(XVc)
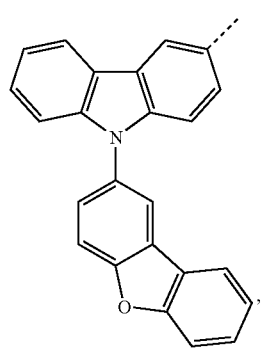
(XVd)
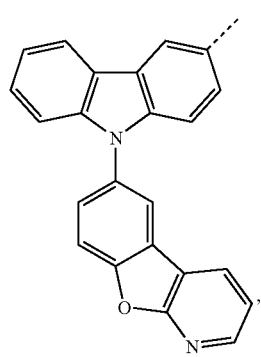
(XVe)
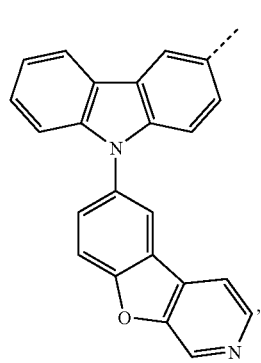
(XVf)
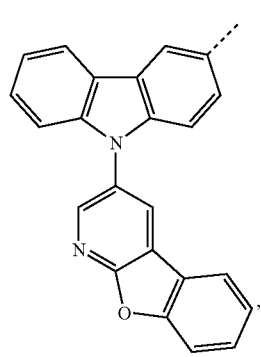
(XVg)
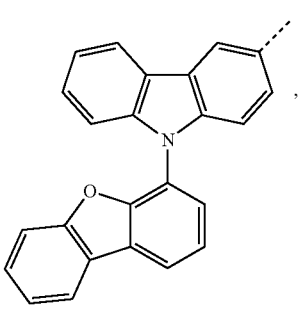
(XVh)

(XVi)
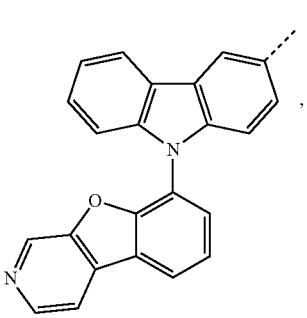
(XVj)
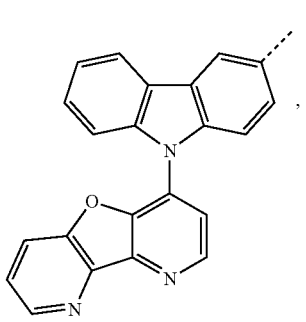
(XVk)
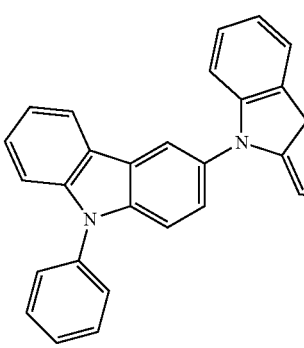
(XVl)

(XVm)
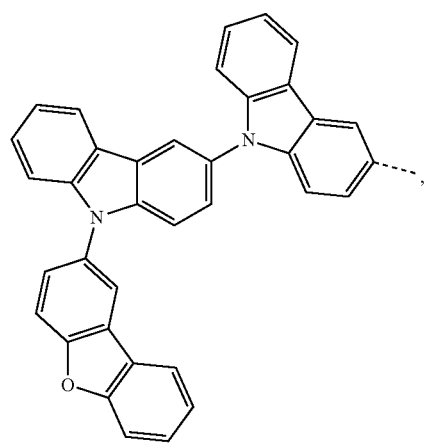
(XVn)
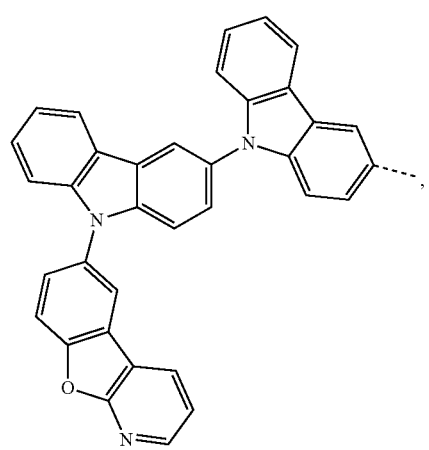
(XVo)
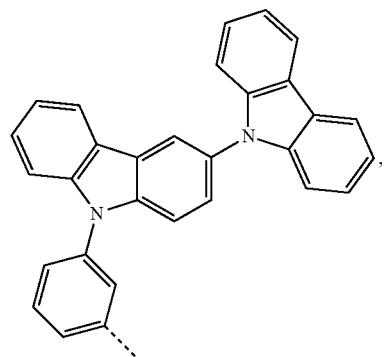
(XVp)
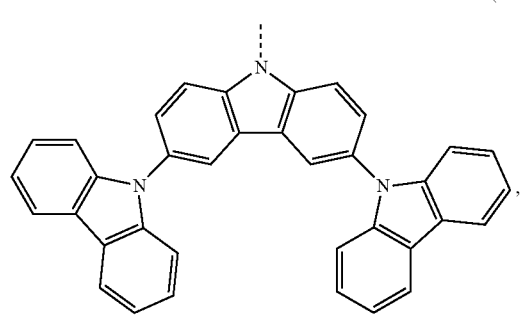
(XVq)
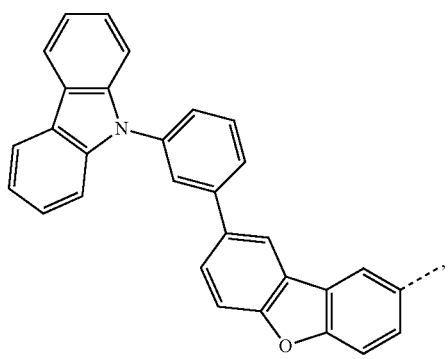
(XVr)
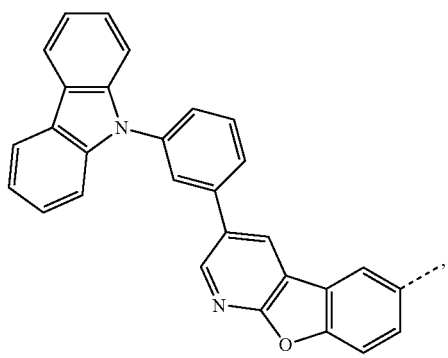
(XVs)
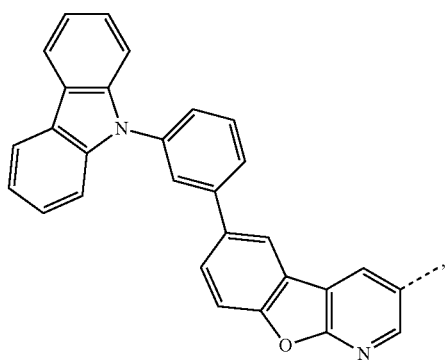
(XVt)
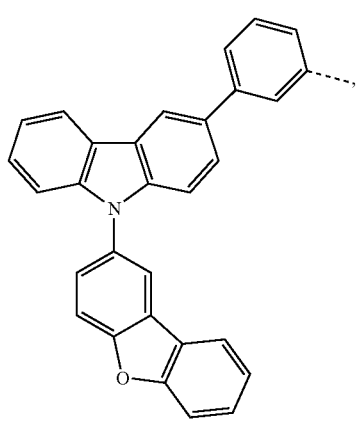

(XVu)
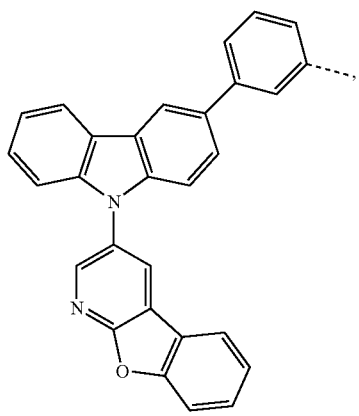

(XVv)
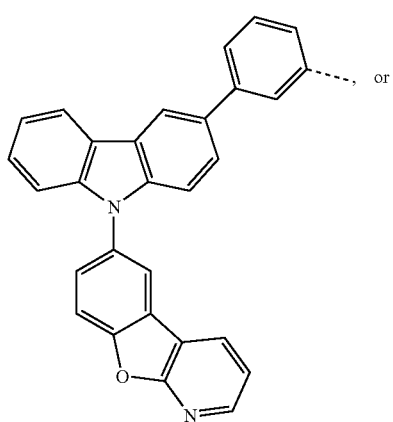
, or (XVw)
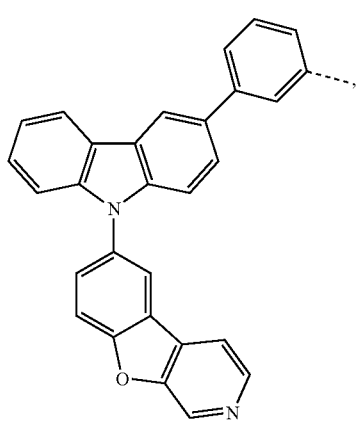

(XVx)
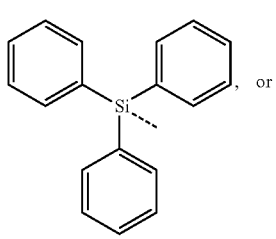
, or (XVy)
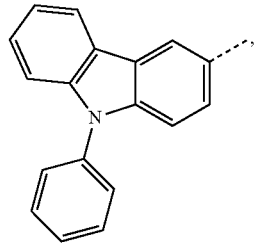

(XVz)
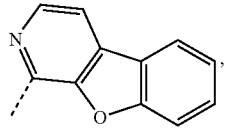

(XVIa)
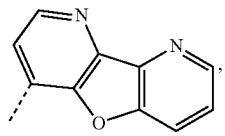

(XVIb)
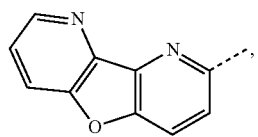

(XVIc)
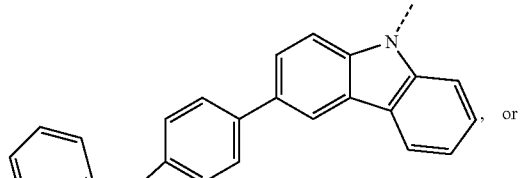
, or (XVId)
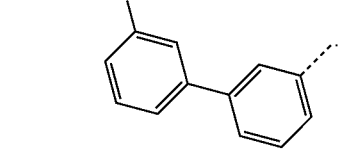

In a preferred embodiment the present invention is directed to compounds of formula (Ia), wherein $R^{83}$ is a group of formula (XIIa), (XIIb), (XIIc), (XIId), (XIIe), (XIIf), (XIIg), (XIIh), (XIIi), (XIIj), (XIIk), (XIII), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{87}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv) (XIIw), (XIIx), (XIIy), (XIIz), (XIIIa), (XIIIb), (XIIIc), (XIIId), (XIIIe), (XIIIf)

or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above; or a compound of formula (Ia), wherein $R^{87}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{83}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above.

In said embodiment compounds of formula (Ia), wherein $R^{83}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{87}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; or compounds of formula (Ia), wherein $R^{87}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{83}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; are more preferred.

In a preferred embodiment the present invention is directed to compounds of formula (Ib), wherein $R^{82}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{87}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above; or compounds of formula (Ib), wherein $R^{87}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{82}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above.

In said embodiment compounds of formula (Ib), wherein $R^{82}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{87}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; or compounds of formula (Ib), wherein $R^{87}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{82}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; are more preferred.

In a preferred embodiment the present invention is directed to compounds of formula (Ic), wherein $R^{85}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{87}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above; or compounds of formula (Ic), wherein $R^{87}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above; and $R^{85}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above.

In said embodiment compounds of formula (Ic), wherein $R^{85}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{87}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; or compounds of formula (Ic), wherein $R^{87}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{85}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; are more preferred.

In a preferred embodiment the present invention is directed to compounds of formula (Id), wherein $R^{81}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{85}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above; or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above; or compounds of formula (Id), wherein $R^{85}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above; and $R^{81}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above.

In said embodiment compounds of formula (Id), wherein $R^{81}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{85}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; or compounds of formula (Id), wherein $R^{85}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{81}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; are more preferred.

In a preferred embodiment the present invention is directed to compounds of formula (Ie), wherein $R^{83}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{87}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above; or compounds of formula (Ie), wherein $R^{87}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{83}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above.

In said embodiment compounds of formula (Ie), wherein $R^{83}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (IIIg) as defined above, and $R^{87}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; or compounds of formula (Ie), wherein $R^{87}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{83}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; are more preferred.

In a preferred embodiment the present invention is directed to compounds of formula (If), wherein $R^{83}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{85}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above; or compounds of formula (If), wherein $R^{85}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{83}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv) (XIIw), (XIIx), (XIIy), (XIIz), (XIIIa), (XIIIb), (XIIIc), (XIIId), (XIIIe), (XIIIf)

or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above.

In said embodiment compounds of formula (If), wherein $R^{83}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (IIIg) as defined above, and $R^{85}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (IIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; or compounds of formula (If), wherein $R^{85}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{83}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; are more preferred.

In a preferred embodiment the present invention is directed to compounds of formula (Ij), wherein $R^{83}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{85}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above; or compounds of formula (Ij), wherein $R^{85}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{83}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above.

In said embodiment compounds of formula compounds of formula (Ij), wherein $R^{83}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{85}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (IIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; or compounds of formula (Ij), wherein $R^{85}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{83}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; are more preferred.

In a preferred embodiment the present invention is directed to compounds of formula (Il), wherein $R^{85}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{87}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv) (XIIw), (XIIx), (XIIy), (XIIz), (XIIIa), (XIIIb), (XIIIc), (XIIId), (XIIIe), (XIIIf)

or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above; or compounds of formula (II), wherein $R^{87}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{85}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above.

In a preferred embodiment the present invention is directed to compounds of formula (In), wherein $R^{83}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as above, and $R^{87}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above; or compounds of formula (In), wherein $R^{87}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{83}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId) as defined above.

In said embodiment compounds of formula (In), wherein $R^{83}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (IIIg) as defined above, and $R^{87}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (IIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; or compounds of formula (In), wherein $R^{87}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{83}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; are more preferred.

Examples of preferred compounds are compounds A-1 to A-65, B-1 to B-8, C-1 to C-65, D-1 to D-8, E-1 to E-65, F-1 to F-65 and G-1 shown in claim 9.

In a particularly preferred embodiment the present invention is directed to compounds of formula (Ia), wherein $R^{83}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{87}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; or to compounds of formula (Ia), wherein $R^{87}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{83}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; such as, for example, compound (A-4).

In another particularly preferred embodiment the present invention is directed to compounds of formula (Ie), wherein $R^{83}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{87}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; or to compounds of formula (Ie), wherein $R^{87}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, and $R^{83}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg) as defined above, or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId) as defined above; such as, for example, compound

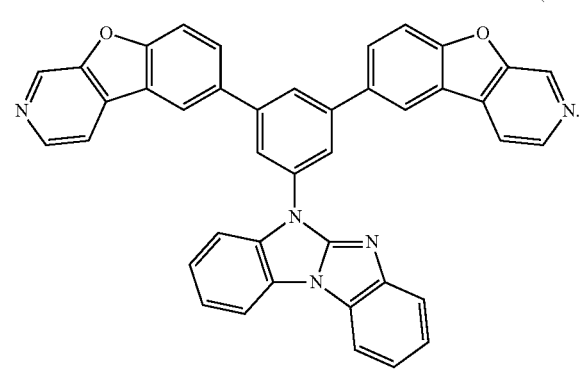

(E-57)

Compounds, such as, for example, (E-57) can advantageously be used as host and/or hole transport material.

Compounds, such as, for example,

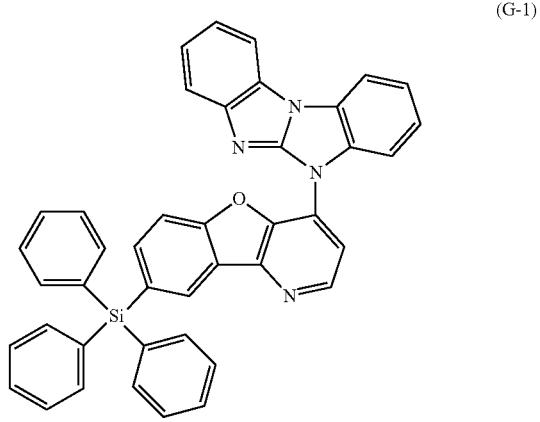 [SMILES: c1ccc([Si](c2ccccc2)(c2ccccc2)c2ccc3oc4c(-n5c6ccccc6n6c7ccccc7nc56)ccnc4c3c2)cc1]

(G-1)

are particularly suitable as electron transport material.

Halogen is fluorine, chlorine, bromine and iodine.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

$C_1$-$C_{18}$perfluoroalkyl, especially $C_1$-$C_4$perfluoroalkyl, is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

The term "cycloalkyl group" is typically $C_4$-$C_{18}$cycloalkyl, especially $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted.

$C_6$-$C_{24}$aryl ($C_6$-$C_{18}$aryl), which optionally can be substituted, is typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted. Phenyl, 1-naphthyl and 2-naphthyl are examples of a $C_6$-$C_{10}$aryl group.

$C_2$-$C_{30}$heteroaryl represents a ring with five to seven ring atoms or a condensed ring system, wherein nitrogen, oxygen or sulfur are the possible hetero atoms, and is typically a heterocyclic group with five to 30 atoms having at least six conjugated π-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazoyl, 5-benzimidazo[1,2-a]benzimidazoyl, carbazolyl, or phenoxazinyl, which can be unsubstituted or substituted. Benzimidazo[1,2-a]benzimidazo-5-yl, benzimidazo[1,2-a]benzimidazo-2-yl, carbazolyl and dibenzofuranyl are examples of a $C_2$-$C_{14}$heteroaryl group.

$C_6$-$C_{24}$arylen groups, which optionally can be substituted by G, are typically phenylene, 4-methylphenylene, 4-methoxyphenylene, naphthylene, especially 1-naphthylene, or 2-naphthylene, biphenylylene, terphenylylene, pyrenylene, 2- or 9-fluorenylene, phenanthrylene, or anthrylene, which may be unsubstituted or substituted. Preferred $C_6$-$C_{24}$arylen groups are 1,3-phenylene, 3,3'-biphenylylene, 3,3'-m-terphenylylene, 2- or 9-fluorenylene, phenanthrylene, which may be unsubstituted or substituted.

$C_2$-$C_{30}$heteroarylen groups, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated-electrons such as thienylene, benzothiophenylene, dibenzothiophenylene, thianthrenylene, furylene, furfurylene, 2H-pyranylene, benzofuranylene, isobenzofuranylene, dibenzofuranylene, phenoxythienylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, chinolylene, isochinolylene, phthalazinylene, naphthyridinylene, chinoxalinylene, chinazolinylene, cinnolinylene, pteridinylene, carbolinylene, benzotriazolylene, benzoxazolylene, phenanthridinylene, acridinylene, pyrimidinylene, phenanthrolinylene, phenazinylene, isothiazolinylene, phenothiazinylene, isoxazolylene, furazanylene, carbazolylene, benzimidazo[1,2-a]benzimidazo-2,5-ylene, or phenoxazinylene, which can be unsubstituted or substituted. Preferred $C_2$-$C_{30}$heteroarylen groups are pyridylene, triazinylene, pyrimidinylene, carbazolylene, dibenzofuranylene and benzimidazo[1,2-a]benzimidazo-2,5-ylene

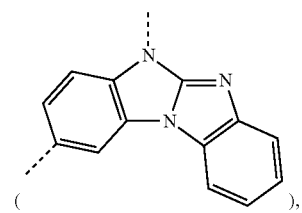

( ), which can be unsubstituted or substituted, especially by $C_6$-$C_{18}$aryl, $C_6$-$C_{18}$aryl which is substituted by $C_1$-$C_4$alkyl; or $C_2$-$C_{14}$heteroaryl.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, or a cyano group. The $C_6$-$C_{24}$aryl ($C_6$-$C_{18}$aryl) and $C_2$-$C_{30}$heteroaryl groups are preferably substituted by one, or more $C_1$-$C_8$alkyl groups.

If a substituent occurs more than one time in a group, it can be different in each occurrence.

The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$)$C_4H_9$), $CH_2$—CH(OR$^{y'}$)—$CH_2$—O—$R^y$, where $R^y$ is $C_5$-$C_{12}$cycloalkyl, phenyl, $C_7$-$C_{15}$phenylalkyl, and $R^{y'}$ embraces the same definitions as $R^y$ or is H; $C_1$-$C_8$alkylene-COO—$R^z$, e.g. $CH_2COOR^z$, $CH(CH_3)CO$-OR$^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above;

$CH_2CH_2$—O—CO—CH=$CH_2$; $CH_2CH(OH)CH_2$—O—CO—C($CH_3$)=$CH_2$.

The synthesis of

is described, for example, in Achour, Reddouane; Zniber, Rachid, Bulletin des Societes Chimiques Belges 96 (1987) 787-92.

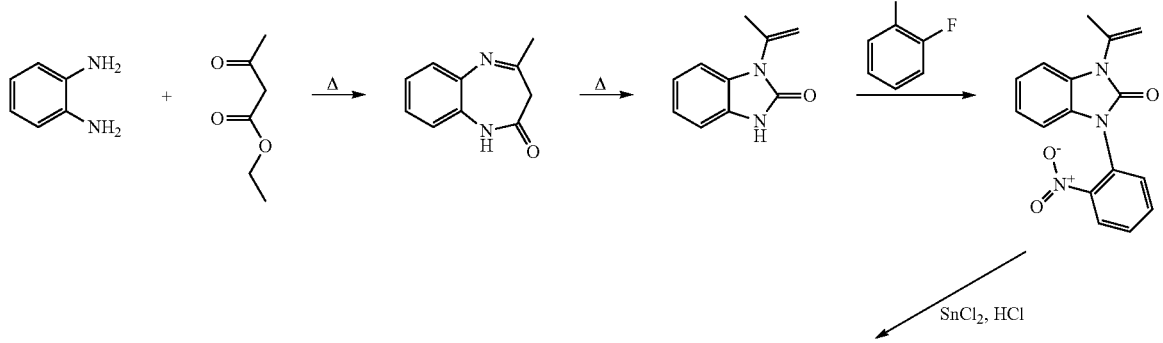

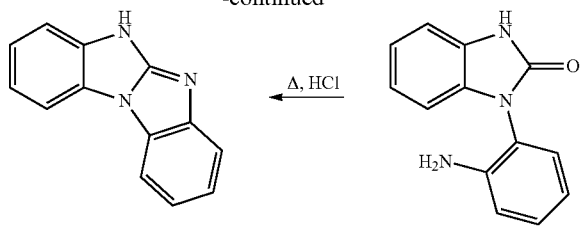

Suitable base skeletons of the formula

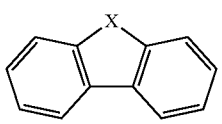

are either commercially available (especially in the cases when X is S, O, NH), or can be obtained by processes known to those skilled in the art. Reference is made to WO2010079051 and EP1885818.

The halogenation can be performed by methods known to those skilled in the art. Preference is given to brominating or iodinating in the 3 and 6 positions (dibromination) or in the 3 or 6 positions (monobromination) of the base skeleton of the formula (II) 2,8 positions (dibenzofuran and dibenzothiophene) or 3,6 positions (carbazole).

Optionally substituted dibenzofurans, dibenzothiophenes and carbazoles can be dibrominated in the 2,8 positions (dibenzofuran and dibenzothiophene) or 3,6 positions (carbazole) with bromine or NBS in glacial acetic acid or in chloroform. For example, the bromination with $Br_2$ can be effected in glacial acetic acid or chloroform at low temperatures, e.g. 0° C. Suitable processes are described, for example, in M. Park, J. R. Buck, C. J. Rizzo, Tetrahedron, 54 (1998) 12707-12714 for X=NPh, and in W. Yang et al., J. Mater. Chem. 13 (2003) 1351 for X=S. In addition, 3,6-dibromocarbazole, 3,6-dibromo-9-phenylcarbazole, 2,8-dibromodibenzothiophene, 2,8-dibromodibenzofuran, 2-bromocarbazole, 3-bromodibenzothiophene, 3-bromodibenzofuran, 3-bromocarbazole, 2-bromodibenzothiophene and 2-bromodibenzofuran are commercially available.

Monobromination in the 4 position of dibenzofuran (and analogously for dibenzothiophene) is described, for example, in J. Am. Chem. Soc. 1984, 106, 7150. Dibenzofuran (dibenzothiophene) can be monobrominated in the 3 position by a sequence known to those skilled in the art, comprising a nitration, reduction and subsequent Sandmeyer reaction.

Monobromination in the 2 position of dibenzofuran or dibenzothiophene and monobromination in the 3 position of carbazole are effected analogously to the dibromination, with the exception that only one equivalent of bromine or NBS is added.

Alternatively, it is also possible to utilize iodinated dibenzofurans, dibenzothiophenes and carbazoles. The preparation is described, inter alia, in Tetrahedron. Lett. 47 (2006) 6957-6960, Eur. J. Inorg. Chem. 24 (2005) 4976-4984, J. Heterocyclic Chem. 39 (2002) 933-941, J. Am. Chem. Soc. 124 (2002) 11900-11907, J. Heterocyclic Chem, 38 (2001) 77-87.

For the nucleophilic substitution, Cl- or F-substituted dibenzofurans, dibenzothiophenes and carbazoles are required. The chlorination is described, inter alia, in J. Heterocyclic Chemistry, 34 (1997) 891-900, Org. Lett., 6 (2004) 3501-3504; J. Chem. Soc. [Section] C: Organic, 16 (1971) 2775-7, Tetrahedron Lett. 25 (1984) 5363-6, J. Org. Chem. 69 (2004) 8177-8182. The fluorination is described in J. Org. Chem. 63 (1998) 878-880 and J. Chem. Soc., Perkin Trans. 2, 5 (2002) 953-957.

The introduction of the group

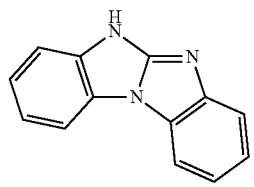 [SMILES: c1ccc2c(c1)nc1[nH]c3ccccc3n12]

is performed in the presence of a base. Suitable bases are known to those skilled in the art and are preferably selected from the group consisting of alkali metal and alkaline earth metal hydroxides such as NaOH, KOH, $Ca(OH)_2$, alkali metal hydrides such as NaH, KH, alkali metal amides such as $NaNH_2$, alkali metal or alkaline earth metal carbonates such as $K_2CO_3$ or $Cs_2CO_3$, and alkali metal alkoxides such as NaOMe, NaOEt. In addition, mixtures of the aforementioned bases are suitable. Particular preference is given to NaOH, KOH, NaH or $K_2CO_3$.

Heteroarylation can be effected, for example, by copper-catalyzed coupling of

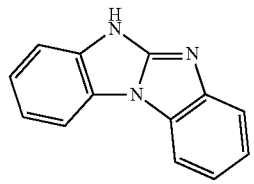 [SMILES: c1ccc2c(c1)nc1[nH]c3ccccc3n12]

to a halogenated compound of the formula

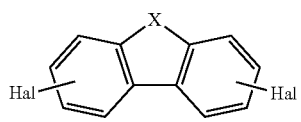

(Ullmann reaction).

The N-arylation was, for example, disclosed in H. Gilman and D. A. Shirley, J. Am. Chem. Soc. 66 (1944) 888; D. Li et al., Dyes and Pigments 49 (2001) 181-186 and Eur. J. Org. Chem. (2007) 2147-2151. The reaction can be performed in solvent or in a melt. Suitable solvents are, for example, (polar) aprotic solvents such as dimethyl sulfoxide, dimethylformamide, NMP, tridecane or alcohols.

The synthesis of 9-(8-bromodibenzofuran-2-yl)carbazole,

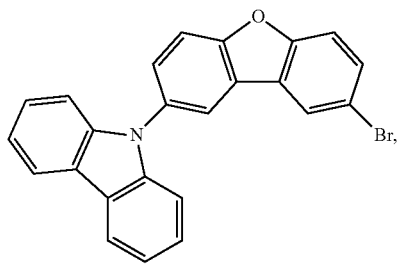 [SMILES: Brc1ccc2oc3ccc(-n4c5ccccc5c5ccccc54)cc3c2c1]

is described in WO2010079051. The synthesis of 2-bromo-8-iodo-dibenzofurane,

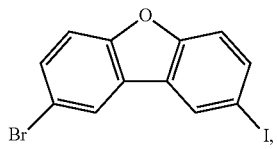

is described in EP1885818.

A possible synthesis route for the compound of formula

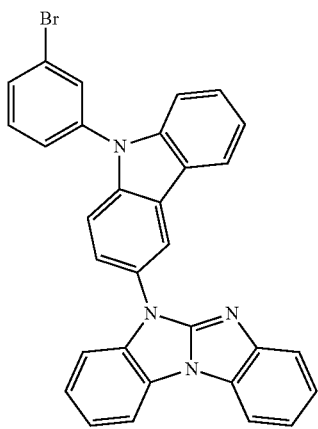 [SMILES: Brc1cccc(-n2c3ccccc3c3cc(-n4c5ccccc5n5c6ccccc6nc45)ccc32)c1]

is shown in the following scheme:

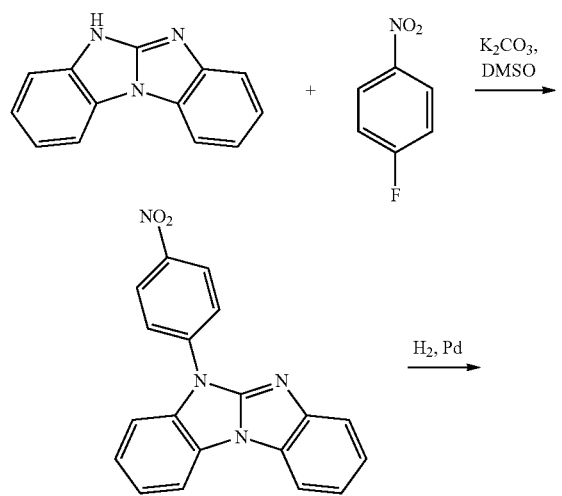

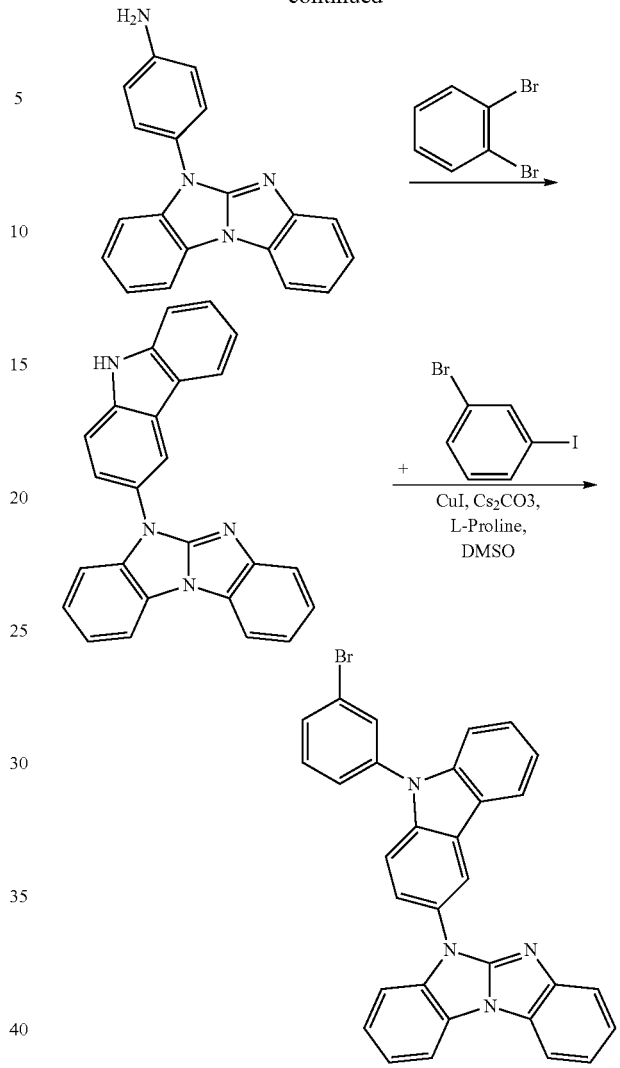

Reference is made to Angew. Chem. Int. Ed. 46 (2007) 1627-1629 and Synthesis 20 (2009) 3493.

Diboronic acid or diboronate group containing dibenzofurans, dibenzothiophenes and carbazoles can be readily prepared by an increasing number of routes. An overview of the synthetic routes is, for example, given in Angew. Chem. Int. Ed. 48 (2009) 9240-9261.

By one common route diboronic acid or diboronate group containing dibenzofurans, dibenzothiophenes, and carbazoles can be obtained by reacting halogenated dibenzofurans, dibenzothiophenes and carbazoles with $(Y^1O)_2B$—$B(OY^1)_2$,

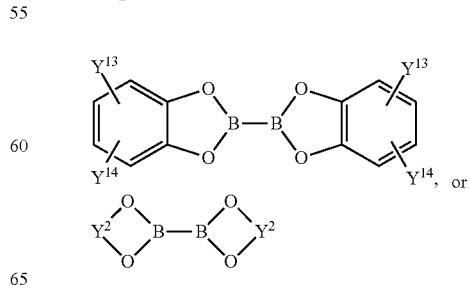

in the presence of a catalyst, such as, for example, [1,1'-bis(diphenylphosphino)ferrocene]dichloropalladium(II), complex (Pd(Cl)₂(dppf)), and a base, such as, for example, potassium acetate, in a solvent, such as, for example, dimethyl formamide, dimethyl sulfoxide, dioxane and/or toluene (cf. Prasad Appukkuttan et al., Synlett 8 (2003) 1204), wherein $Y^1$ is independently in each occurrence a $C_1$-$C_{18}$alkylgroup and $Y^2$ is independently in each occurrence a $C_2$-$C_{10}$alkylene group, such as —$CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{18}$alkylgroup, especially —C(CH₃)₂C(CH₃)₂—, —C(CH₃)₂CH₂C(CH₃)₂—, or —CH₂C(CH₃)₂CH₂—, and $Y^{13}$ and $Y^{14}$ are independently of each other hydrogen, or a $C_1$-$C_{18}$alkylgroup.

Diboronic acid or diboronate group containing dibenzofurans, dibenzothiophenes and carbazoles can also be prepared by reacting halogenated dibenzofurans, dibenzothiophenes and carbazoles with alkyl lithium reagents, such as, for example, n-butyl lithium, or t-butyl lithium, followed by reaction with boronic esters, such as, for example, B(isopropoxy)₃, B(methoxy)₃, or

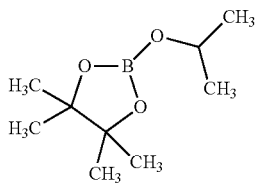

(cf. Synthesis (2000) 442-446).

Diboronic acid or diboronate group containing dibenzofurans, dibenzothiophenes and carbazoles can also be prepared by reacting dibenzofurans, dibenzothiophenes and carbazoles with lithium amides, such as, for example, lithium diisopropylamide (LDA) followed by reaction with boronic esters such as, for example, B(isopropoxy)₃, B(methoxy)₃, or

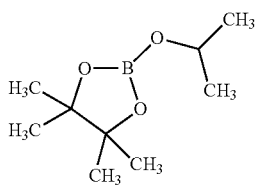

(J. Org. Chem. 73 (2008) 2176-2181).

Diboronic acid or diboronate group containing dibenzofurans, dibenzothiophenes and carbazoles, such as, for example,

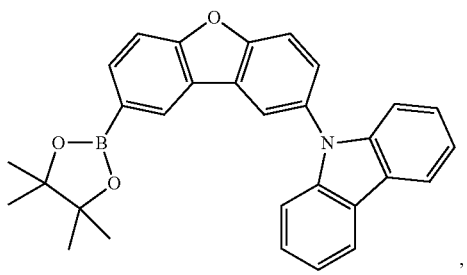 [SMILES: CC1(C)OB(c2ccc3oc4ccc(-n5c6ccccc6c6ccccc65)cc4c3c2)OC1(C)C]

can be reacted with equimolar amounts of halogenated dibenzofurans, dibenzothiophenes, carbazoles and 4H-imidazo[1,2-a]imidazoles, such as, for example,

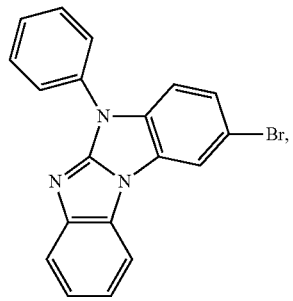 [SMILES: Brc1ccc2c(c1)n1c3ccccc3nc1n2-c1ccccc1]

in a solvent and in the presence of a catalyst. The catalyst may be one of the μ-halo(triisopropylphosphine)(η³-allyl)palladium(II) type (see for example WO99/47474).

Preferably, the Suzuki reaction is carried out in the presence of an organic solvent, such as an aromatic hydrocarbon or a usual polar organic solvent, such as benzene, toluene, xylene, tetrahydrofurane, or dioxane, or mixtures thereof, most preferred toluene. Usually, the amount of the solvent is chosen in the range of from 1 to 10 l per mol of boronic acid derivative. Also preferred, the reaction is carried out under an inert atmosphere such as nitrogen, or argon. Further, it is preferred to carry out the reaction in the presence of an aqueous base, such as an alkali metal hydroxide or carbonate such as NaOH, KOH, Na₂CO₃, K₂CO₃, Cs₂CO₃ and the like, preferably an aqueous K₂CO₃ solution is chosen. Usually, the molar ratio of the base to boronic acid or boronic ester derivative is chosen in the range of from 0.5:1 to 50:1, very especially 1:1. Generally, the reaction temperature is chosen in the range of from 40 to 180° C., preferably under reflux conditions. Preferred, the reaction time is chosen in the range of from 1 to 80 hours, more preferably from 20 to 72 hours. In a preferred embodiment a usual catalyst for coupling reactions or for polycondensation reactions is used, preferably Pd-based, which is described in WO2007/101820. The palladium compound is added in a ratio of from 1:10000 to 1:50, preferably from 1:5000 to 1:200, based on the number of bonds to be closed. Preference is given, for example, to the use of palladium(II) salts such as PdAc₂ or Pd₂dba₃ and to the addition of ligands selected from the group consisting of

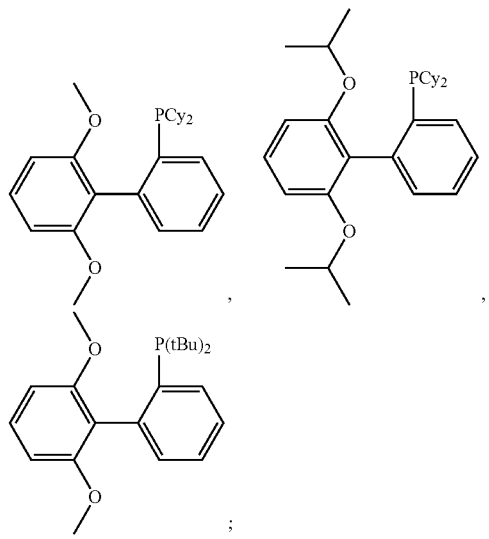

wherein

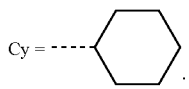

The ligand is added in a ratio of from 1:1 to 1:10, based on Pd. Also preferred, the catalyst is added as in solution or suspension. Preferably, an appropriate organic solvent such as the ones described above, preferably benzene, toluene, xylene, THF, dioxane, more preferably toluene, or mixtures thereof, is used. The amount of solvent usually is chosen in the range of from 1 to 10 I per mol of boronic acid derivative. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, G. Wegner in Macromol. Rapid Commun. 17 (1996) 239-252 and G. A. Molander and B. Canturk, Angew. Chem., 121 (2009) 9404-9425.

The synthesis of aza- and diaza-dibenzofuran starting materials is known in the literature, or can be done in analogy to known procedures.

JP2011084531 describes, for example, the synthesis of benzofuro[3,2-b]pyridine in two steps starting from 2-bromopyridin-3-ol using a base catalyzed cyclisation. The brominated compound is received by bromination with bromine in the presence of silver sulfate.

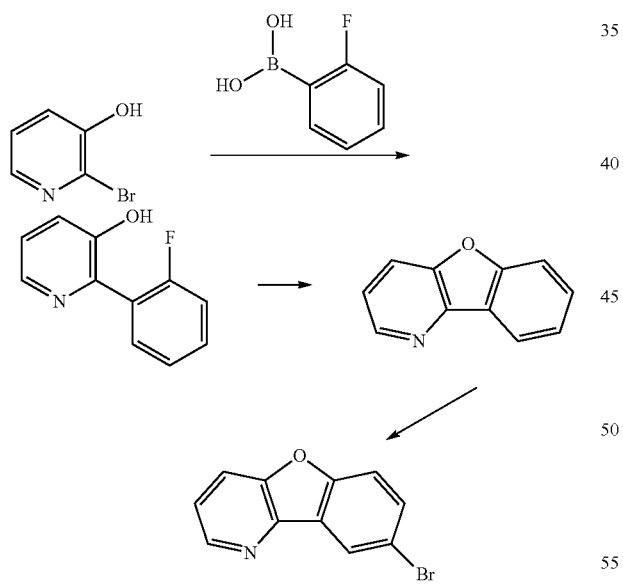

US2010/0187984 describes, for example, the synthesis of 3,6-dichloro-benzofuro[2,3-b]pyridine in three steps starting from 2-amino-5-chloropyridine using a cyclisation of a diazoniumion salt.

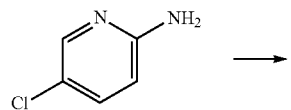

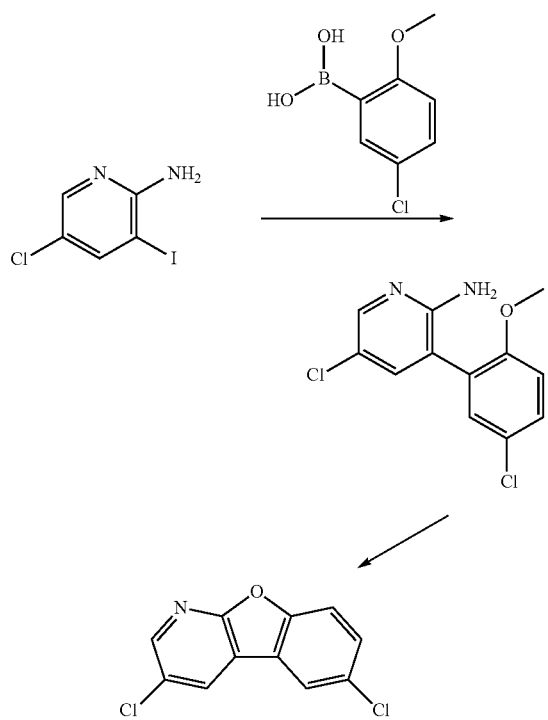

L. Kaczmarek, Polish Journal of Chemistry 59 (1985) 1141 describes the synthesis of furo[3,2-b:4,5-b]dipyridine starting from 2-(3-amino-2-pyridyl)pyridin-3-amine using an acid catalyzed cyclisation of a diazoniumion salt.

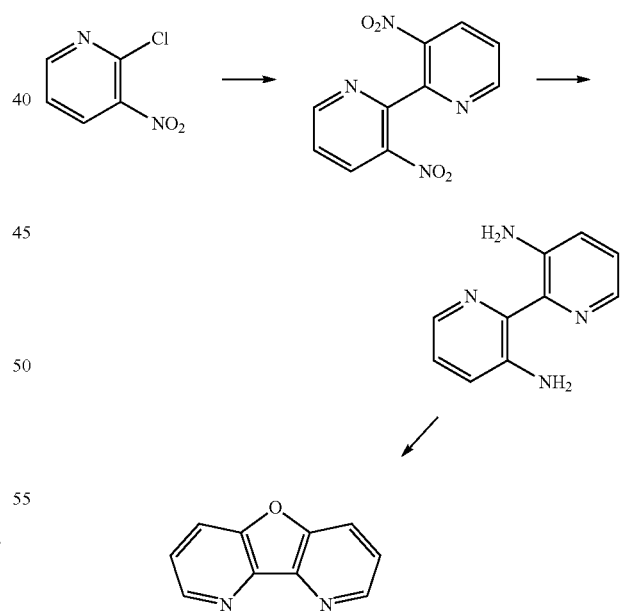

JP2002284862 describes the syntheses of 2,7-dibromo-furo[3,2-b:4,5-b]dipyridine starting from 2-(3-amino-5-bromo-2-pyridyl)-5-bromo-pyridin-3-amine using an acid catalyzed cyclisation of a diazoniumion salt. The synthesis of the starting material is described by Y. Fort, Tetrahedron 50 (41), 11893 (1994).

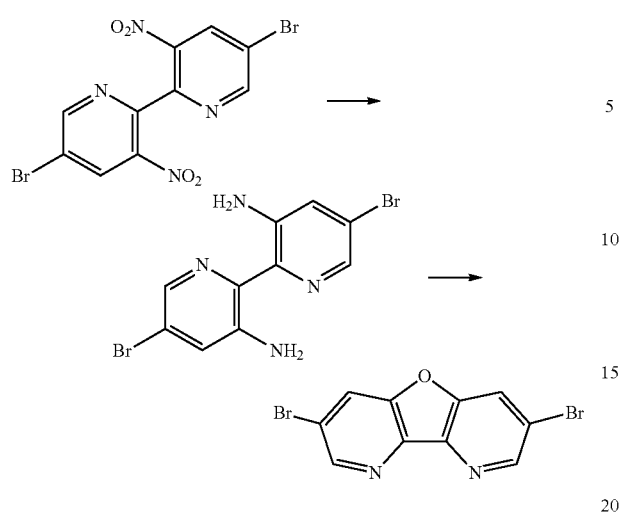

J. Liu, J. Org. Chem. 73, 2951 (2008) describes e.g. the synthesis of benzofuro[2,3-c]pyridine using a copper catalyzed cyclisation step.

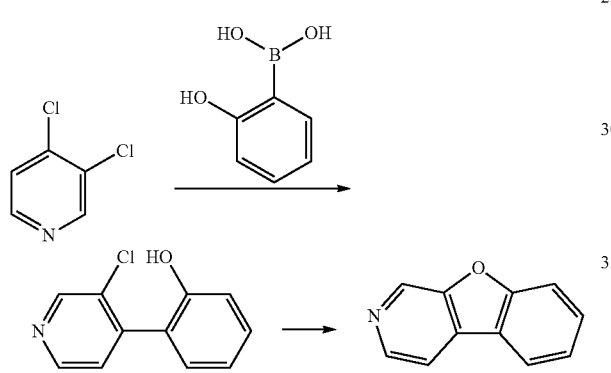

A possible synthetic route for compound E-57 is shown in the reaction scheme below:

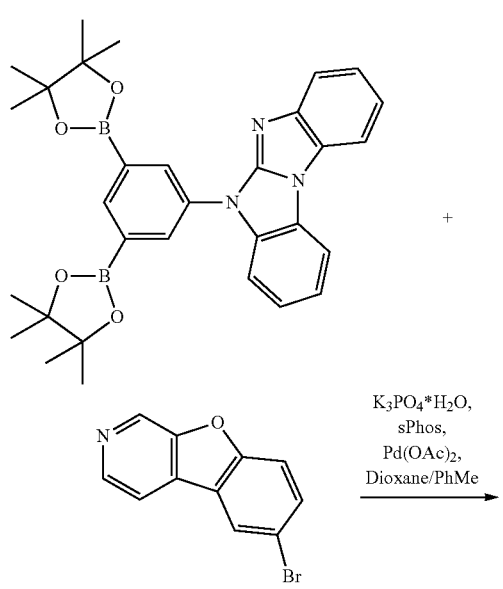

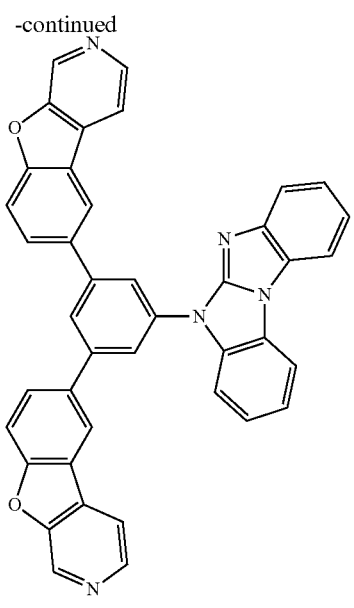

(E-57)

A possible synthetic route for compound E-12 is shown in the reaction scheme below:

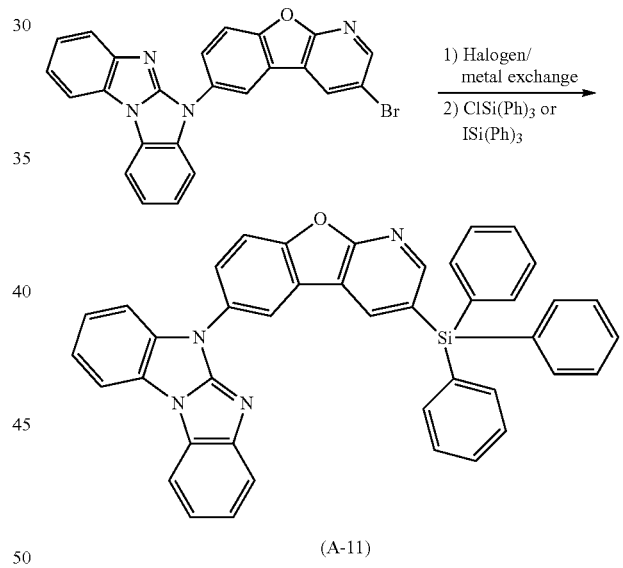

(A-11)

The halogen/metal exchange is done with nBuLi/THF at −78° C., or tBuLi/THF at −78° C. Reference is made to WO2010/079051, where the synthesis of such compounds is described.

Compounds of formula $$\underset{B^3=B^4}{\overset{B^1}{B^2}}\underset{}{\overset{O}{\diagdown}}\underset{B^8=B^7}{\overset{B^5}{B^6}} \qquad (II)$$

are new, intermediates in the production of compounds of formula (I) and form a further subject of the present invention.

B¹ is N, or CR⁸¹,
B² is N, or CR⁸²,
B³ is N, or CR⁸³,
B⁴ is N, or CR⁸⁴,
B⁵ is N, or CR⁸⁶,
B⁶ is N, or CR⁸⁶,
B⁷ is N, or CR⁸⁷,
B⁸ is N, or CR⁸⁸, wherein $R^{81}$, $R^{82}$, $R^{83}$, $R^{84}$, $R^{85}$, $R^{86}$, $R^{87}$ and $R^{88}$ are independently of each other H, a $C_1$-$C_{25}$alkyl group, which can optionally be substituted by E and or interrupted by D; a $C_6$-$C_{24}$aryl group, which can optionally be substituted by G, a $C_2$-$C_{30}$heteroaryl group, which can optionally be substituted by G; a group of formula -$(A^1)_o$-$(A^2)_p$-$(A^3)_q$-$(A^4)_r$-$R^{16}$, or -$(A^1)_o$-$(A^2)_p$-$(A^3)_q$-$(A^4)_r$-$X^1$,
o is 0, or 1, p is 0, or 1, q is 0, or 1, r is 0, or 1,
at least one of the substituents $R^{81}$, $R^{82}$, $R^{83}$, $R^{84}$, $R^{85}$, $R^{86}$, $R^{87}$ and $R^{88}$ represents a group of formula -$(A^1)_o$-$(A^2)_p$-$(A^3)_q$-$(A^4)_r$-$X^1$; wherein
$X^1$ is Cl, Br, or I, $ZnX^{12}$, $X^{12}$ is a halogen atom; —$SnR^{207}R^{208}R^{209}$, wherein $R^{207}$, $R^{208}$ and $R^{209}$ are identical or different and are H or $C_1$-$C_8$alkyl, wherein two radicals optionally form a common ring and these radicals are optionally branched or unbranched; —$B(OH)_2$, —$B(OY^1)_2$,

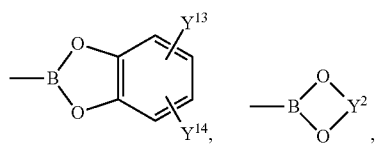

—$BF_4Na$, or —$BF_4K$, wherein $Y^1$ is independently in each occurrence a $C_1$-$C_{18}$alkyl group and $Y^2$ is independently in each occurrence a $C_2$-$C_{10}$alkylene group, and $Y^{13}$ and $Y^{14}$ are independently of each other hydrogen, or a $C_1$-$C_{18}$alkyl group, and o, p, q, r, G, $A^1$, $A^2$, $A^3$, $A^4$, $R^{81}$, $R^{82}$, $R^{83}$, $R^{84}$, $R^{85}$, $R^{86}$, $R^{87}$ and $R^{88}$ are as defined above. The following compounds are known from the prior art and are excluded:

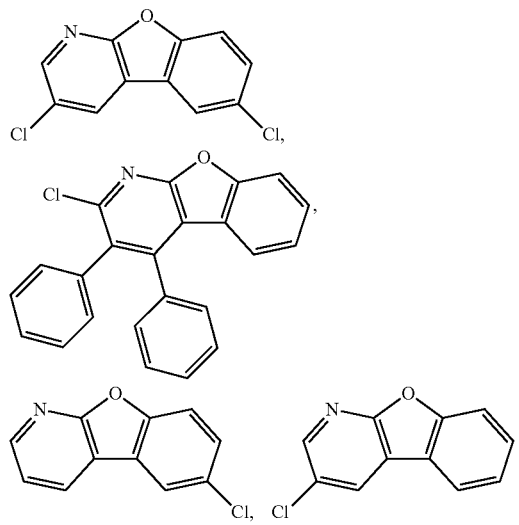

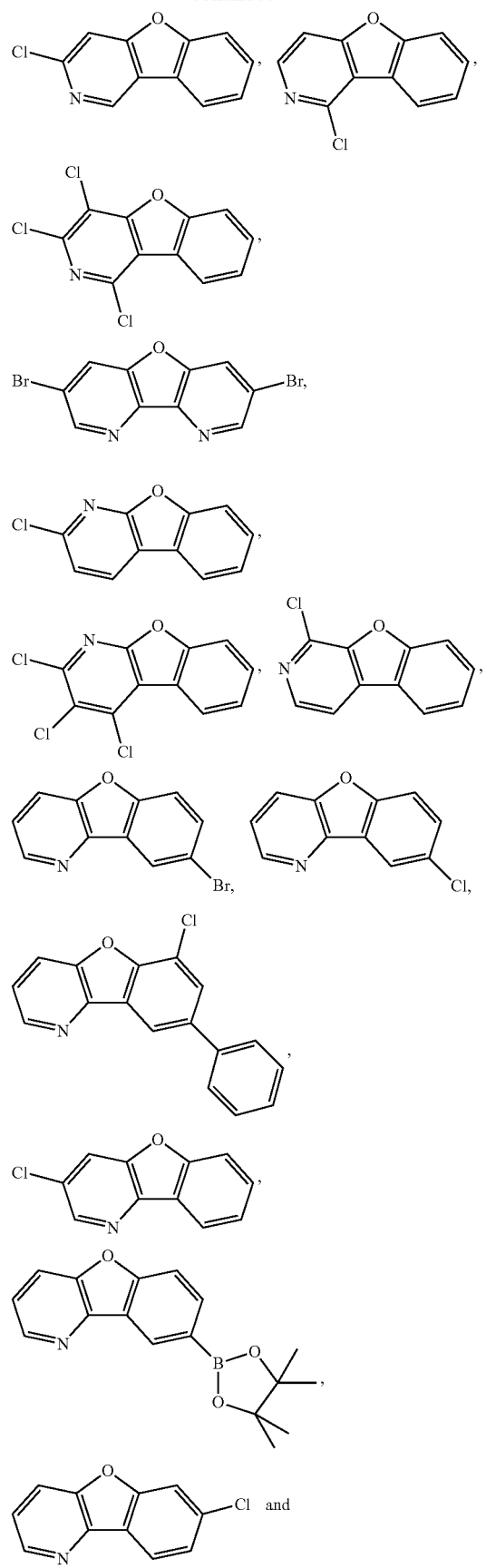

-continued

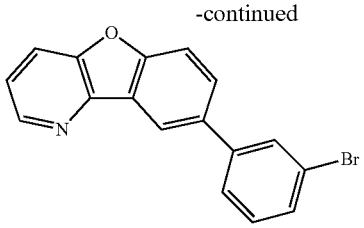

are excluded.

The preferences for $R^{81}$, $R^{82}$, $R^{83}$, $R^{84}$, $R^{85}$, $R^{86}$, $R^{87}$, $R^{88}$ $A^1$, $A^2$, $A^3$, $A^4$ and $R^{16}$ are in principal the same as in case of the compounds of formula (I).

If $X^1$ is Cl, Br, or I, p is 0, q is 0 and r is 0; o in the at least one group of formula -$(A^1)_o$-$(A^2)_p$-$(A^3)_q$-$(A^4)_r$-$X^1$ is preferably 1. Compounds of formula (II) are preferred, wherein $X^1$ is —B(OH)$_2$, —B(OY$^1$)$_2$,

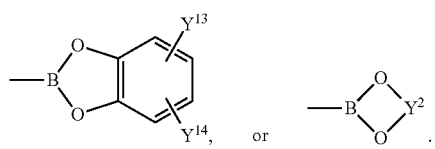

Among the compounds of formula (II) compounds of formula

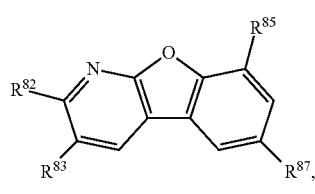
(II')

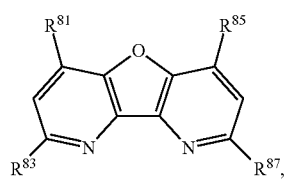
(II'')

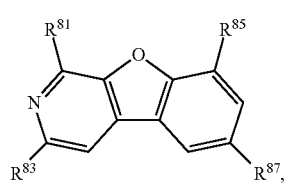
(II''')

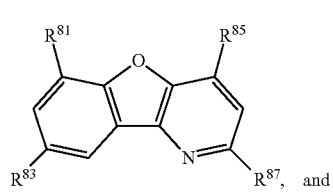
(II'''') and

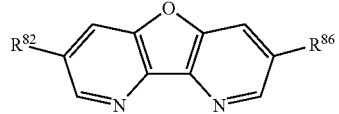
(II''''')

are preferred, where $R^{81}$, $R^{82}$, $R^{83}$, $R^{85}$, $R^{86}$ and $R^{87}$ have the meanings given above.

In a preferred embodiment of the present invention one of the substituents $R^{81}$, $R^{82}$, $R^{83}$, $R^{85}$, $R^{86}$ and $R^{87}$ in the compounds of formula (II'), (II''), (II'''), (II'''') and (II''''') is a group of formula -$(A^1)_o$-$(A^2)_p$-$(A^3)_q$-$(A^4)_r$-$X^1$.

In another preferred embodiment of the present invention two of the substituents $R^{81}$, $R^{82}$, $R^{83}$, $R^{85}$, $R^{86}$ and $R^{87}$ in the compounds of formula (II'), (II''), (II'''), (II'''') and (II''''') are a group of formula -$(A^1)_o$-$(A^2)_p$-$(A^3)_q$-$(A^4)_r$X$^1$.

In a preferred embodiment the present invention is directed to compounds of formula

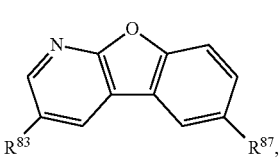
(IIa)

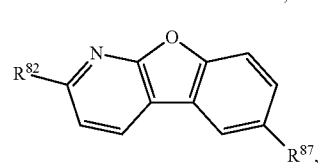
(IIb)

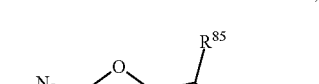
(IIc)

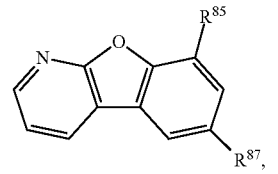
(IId)

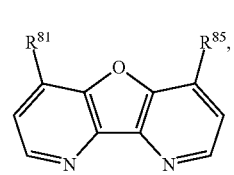
(IIe)

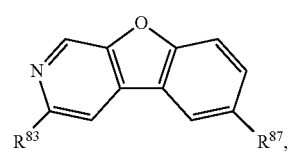
(IIf)

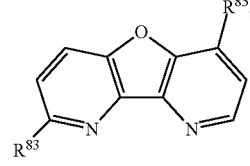
(IIg)

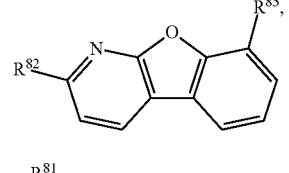
(IIh)

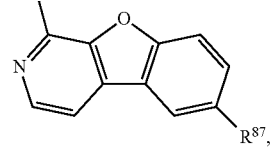

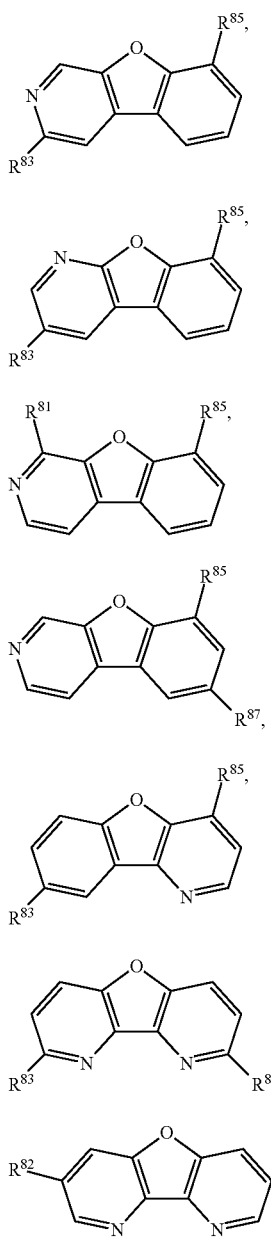

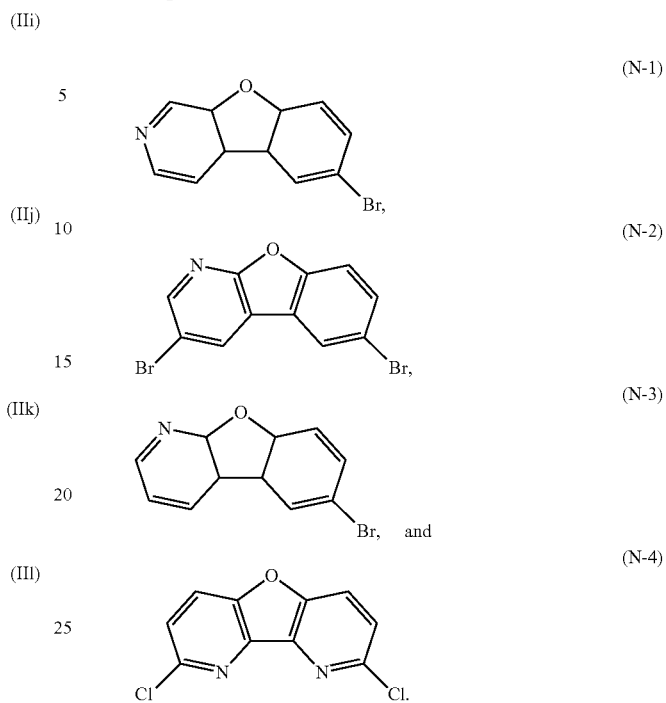

wherein $R^{81}$, $R^{82}$, $R^{83}$, $R^{85}$, $R^{86}$ and $R^{87}$ are as defined above.

In a preferred embodiment of the present invention one of the substituents $R^{81}$, $R^{82}$, $R^{83}$, $R^{85}$, $R^{86}$ and $R^{87}$ in the compounds of formula (IIa), (IIb), (IIc), (IId), (IIe), (IIf), (IIg), (IIh), (IIi), (IIj), (IIk), (III), (IIm), (IIn) and (IIo) is a group of formula $-(A^1)_o-(A^2)_p-(A^3)_q-(A^4)_r-X^1$.

In another preferred embodiment of the present invention two of the substituents $R^{81}$, $R^{82}$, $R^{83}$, $R^{85}$, $R^{86}$ and $R^{87}$ in the compounds of formula (IIa), (IIb), (IIc), (IId), (IIe), (IIf), (IIg), (IIh), (IIi), (IIj), (IIk), (III), (IIm), (IIn) and (IIo) are a group of formula $-(A^1)_o-(A^2)_p-(A^3)_q-(A^4)_r-X^1$.

Compounds of formula (IIa), (IIb), (IIc), (IId), (IIe), (IIf), (IIi), (IIj), (III) and (IIn) are preferred. Compounds of formula (IIa), (IIb), (IIc), (IId), (IIe), (IIf), (IIj) and (IIn) are especially preferred.

Examples of the intermediates are shown below:

The bromination of the azadibenzofurans can be carried out in analogy to the bromination of carbazole, which is, for example, described in J. Mater. Chem. 18 (2008) 1296-1301.

Other bromination methods are, for example, described in Helvetica Chimica Acta 89 (2006) 1123 and SYNLETT 17 (2006) 2841-2845. 10.206

Selective halogenation of (III) with a halogenation agent results in the compounds of formula (II). Halogenation agents are, for example, N-chlorosuccinimide (NCS) (Synlett 18 (2005) 2837-2842); $Br_2$ (Synthesis 10 (2005) 1619-1624), N-bromosuccinimide (NBS)(Organic Letters 12 (2010) 2194-2197; Synlett (2006) 2841-2845), 1,3-dibromo-5,5-dimethylhydantoin (DBH) (Organic Process Research & Development 10 (2006) 822-828, US2002/0151456), $CuBr_2$ (Synthetic Communications 37 (2007) 1381-1388); $R_4NBr_3$ (Can. J. Chem. 67 (1989) 2062), N-iodosuccinimide (NIS) (Synthesis 12 (2001) 1794-1799, J. Heterocyclic Chem. 39 (2002) 933), $KI/KIO_3$ (Org. Lett. 9 (2007) 797, Macromolecules 44 (2011) 1405-1413), $NaIO_4/I_2/H_2SO_4$ or $NaIO_4/KI/H_2SO_4$ (J. Heterocyclic Chem. 38 (2001) 77; J. Org. Chem. 75 (2010) 2578-2588); iodine monochloride (ICl; Synthesis (2008) 221-224). Additional methods are described in J. Org. Chem. 74 (2009) 3341-3349; J. Org. Chem. 71 (2006) 7422-7432, Eur. J. Org. Chem. (2008) 1065-1071, Chem. Asian J. 5 (2010) 2162-2167, Synthetic. Commun. 28 (1998) 3225.

Examples of solvents, which can be used in the halogenation, are dimethylformamide (DMF), $CH_2Cl_2$, $CHCl_3$, $CCl_4$, ethanol (EtOH), acetic acid (AcOH), $H_2SO_4$, $C_6H_5Cl$ and mixtures thereof. The halogenation can be done in the presence of acids and lewis acids, respectively, such as, for example, $H_2SO_4$, $ZrCl_4$, $TiCl_4$, $AlCl_3$, $HfCl_4$ and $AlCl_3$ (Synlett 18 (2005) 2837-2842).

The halogenated intermediates (II), wherein $X^3$ is Cl, Br, or I, can be transformed to the boronic ester intermediates (II) by reacting halogenated intermediates (II) with $(Y^1O)_2B—B(OY^1)_2$,

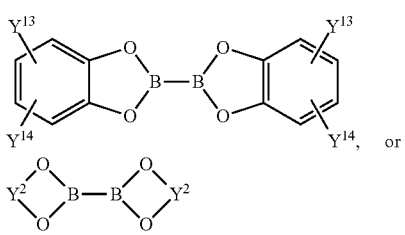

in the presence of a catalyst, such as, for example, [1,1'-bis(diphenylphosphino)ferrocene]dichloropalladium(II), complex (Pd(Cl)$_2$(dppf)), and a base, such as, for example, potassium acetate, in a solvent, such as, for example, dimethyl formamide, dimethyl sulfoxide, dioxane and/or toluene (cf. Prasad Appukkuttan et al., Synlett 8 (2003) 1204).

An overview of the preparation of boronic reagents is given in Angew. Chem. 121 (2009) 9404-9425, Chem. Rev. 95 (1995) 2457-2483, Angew. Chem. Int. Ed. 41 (2002) 4176-4211, Tetrahedron 66 (2010) 8121-8136.

Diboronic acid or diboronate intermediates (II) can also be prepared by reacting halogenated intermediates (II) with alkyl lithium reagents, such as, for example, n-butyl lithium, or t-butyl lithium, followed by reaction with boronic esters, such as, for example, B(isopropoxy)$_3$, B(methoxy)$_3$, or

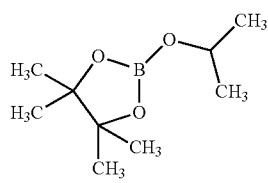

(cf. Synthesis (2000) 442-446).

The compounds of formula (I) can be obtained starting from the intermediates and suitable co-reactants, for example, by Suzuki-, Stille-, or Negishi-coupling reactions.

The halogenated intermediates, wherein $X^1$ is Cl, Br, or I, such as for example,

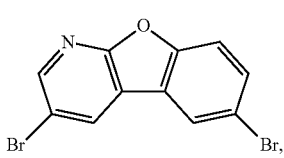
(N-2)

can, for example, be transformed to a compound of formula (I) by reacting intermediate (N-2) with $X^2$-$(A^1)_o$-$(A^2)_p$-$(A^3)_q$-$(A^4)_r$-$R^{16}$, wherein $X^2$ is $(Y^1O)_2B$—,

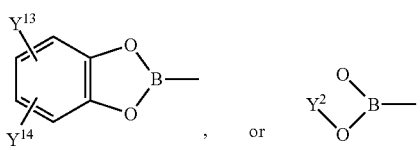

in the presence of a catalyst, such as, for example, [1,1'-bis(diphenylphosphino)ferrocene]dichloropalladium(II), complex (Pd(Cl)$_2$(dppf)), and a base, such as, for example, potassium acetate, in a solvent, such as, for example, dimethyl formamide, dimethyl sulfoxide, dioxane and/or toluene (cf. Prasad Appukkuttan et al., Synlett 8 (2003) 1204).

It has been found that the compounds of the formula I are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs), the compounds of the formula I being particularly suitable in OLEDs for use as matrix material in a light-emitting layer and/or as hole and/or exciton blocker material and/or as electron and/or exciton blocker material, especially in combination with a phosphorescence emitter. In the case of use of the inventive compounds of the formula I in OLEDs, OLEDs which have good efficiencies and a long lifetime and which can be operated especially at a low use and operating voltage are obtained. The inventive compounds of the formula I are suitable especially for use as matrix and/or hole/exciton blocker materials for blue and green emitters, for example light blue or deep blue emitters, these being especially phosphorescence emitters. Furthermore, the compounds of the formula I can be used as conductor/complementary materials in organic electronics applications selected from switching elements and organic solar cells.

The compounds of the formula I, especially of formula (Ia), (Ib), (Ic), (Id), (Ie), (If), (Ii), (Ij), (Il) and (In), can be used as matrix material and/or hole/exciton blocker material and/or electron/exciton blocker material and/or hole injection material and/or electron injection material and/or hole conductor material (hole transport material) and/or electron conductor material (electron transport material), preferably as matrix material and/or electron/exciton blocker and/or hole transporting material in organic electronics applications, especially in OLEDs. The inventive compounds of the formula I are more preferably used as matrix materials in organic electronics applications, especially in OLEDs.

In the emission layer or one of the emission layers of an OLED, it is also possible to combine an emitter material with a matrix material of the compound of the formula I and a further matrix material which has, for example, a good hole conductor (hole transport) property. This achieves a high quantum efficiency of this emission layer.

Certain compounds of formula I, such as, for example, G-1, have a ionisation potential of greater than 6 eV and, hence, suited as electron transport material.

When a compound of the formula I is used as matrix material in an emission layer and additionally as hole/exciton blocker material and/or electron/exciton blocker material, owing to the chemical identity or similarity of the materials, an improved interface between the emission layer and the adjacent hole/exciton blocker material and/or electron/exciton blocker material is obtained, which can lead to a decrease in the voltage with equal luminance and to an extension of the lifetime of the OLED. Moreover, the use of the same material for hole/exciton blocker material and/or electron/exciton blocker material and for the matrix of an emission layer allows the production process of an OLED to be simplified, since the same source can be used for the vapor deposition process of the material of one of the compounds of the formula I.

Suitable structures of organic electronic devices are known to those skilled in the art and are specified below.

The organic transistor generally includes a semiconductor layer formed from an organic layer with hole transport capacity and/or electron transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or electron transport capacity. In addition, it is possible for further layers known to those skilled in the art to be present in the organic solar cell. The layer with hole transport capacity may comprise the compounds of formula I.

It is likewise possible that the compounds of the formula I are present both in the light-emitting layer (preferably as matrix material) and in the blocking layer for electrons (as electron/exciton blockers).

The present invention further provides an organic light-emitting diode comprising an anode An and a cathode Ka and a light-emitting layer E arranged between the anode An and the cathode Ka, and if appropriate at least one further layer selected from the group consisting of at least one blocking layer for holes/excitons, at least one blocking layer for electrons/excitons, at least one hole injection layer, at least one hole conductor layer, at least one electron injection layer and at least one electron conductor layer, wherein the at least one compound of the formula I is present in the light-emitting layer E and/or in at least one of the further layers. The at least one compound of the formula I is preferably present in the light-emitting layer and/or the blocking layer for holes.

The present application further relates to a light-emitting layer comprising at least one compound of the formula I, especially a compound of formula (Ia), (Ib), (Ic), (Id), (Ie), (If), (Ii), (Ij), (Il), or (In), very especially a compound A-1 to A-65, B-1 to B-8, C-1 to C-65, D-1 to D-8, E-1 to E-65, or F-1 to F-65.

Structure of the Inventive OLED

The inventive organic light-emitting diode (OLED) thus generally has the following structure:
an anode (An) and a cathode (Ka) and a light-emitting layer E arranged between the anode (An) and the cathode (Ka).

The inventive OLED may, for example—in a preferred embodiment—be formed from the following layers:
1. Anode
2. Hole conductor layer
3. Light-emitting layer
4. Blocking layer for holes/excitons
5. Electron conductor layer
6. Cathode Layer sequences different than the aforementioned structure are also possible, and are known to those skilled in the art. For example, it is possible that the OLED does not have all of the layers mentioned; for example, an OLED with layers (1) (anode), (3) (light-emitting layer) and (6) (cathode) is likewise suitable, in which case the functions of the layers (2) (hole conductor layer) and (4) (blocking layer for holes/excitons) and (5) (electron conductor layer) are assumed by the adjacent layers. OLEDs which have layers (1), (2), (3) and (6), or layers (1), (3), (4), (5) and (6), are likewise suitable. In addition, the OLEDs may have a blocking layer for electrons/excitons between the hole conductor layer (2) and the Light-emitting layer (3).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole conductor layer, in one embodiment, may simultaneously block excitons and/or electrons.

Furthermore, the individual layers of the OLED among those specified above may in turn be formed from two or more layers. For example, the hole conductor layer may be formed from a layer into which holes are injected from the electrode, and a layer which transports the holes away from the hole-injecting layer into the light-emitting layer. The electron conduction layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used as emitter substances in accordance with the invention.

In order to obtain particularly efficient OLEDs, for example, the HOMO (highest occupied molecular orbital) of the hole conductor layer should be matched to the work function of the anode, and the LUMO (lowest unoccupied molecular orbital) of the electron conductor layer should be matched to the work function of the cathode, provided that the aforementioned layers are present in the inventive OLEDs.

The anode (1) is an electrode which provides positive charge carriers. It may be formed, for example, from materials which comprise a metal, a mixture of various metals, a metal alloy, a metal oxide or a mixture of various metal oxides. Alternatively, the anode may be a conductive polymer. Suitable metals comprise metals and alloys of the metals of the main groups, transition metals and of the lanthanoids, especially the metals of groups Ib, IVa, Va and VIa of the periodic table of the elements, and the transition metals of group VIIIa. When the anode is to be transparent, generally mixed metal oxides of groups IIb, IIIb and IVb of the periodic table of the elements (IUPAC version) are used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed. The material used for the anode (1) is preferably ITO.

Suitable hole conductor materials for layer (2) of the inventive OLEDs are disclosed, for example, in Kirk-Othmer Encyclopedia of Chemical Technology, 4th edition, Vol. 18, pages 837 to 860, 1996. Both hole-transporting molecules and polymers can be used as the hole transport material. Hole-transporting molecules typically used are selected from the group consisting of tris[N-(1-naphthyl)-N-(phenylamino)]triphenylamine (1-NaphDATA), 4,4'-bis[N-(1-naphthyl)-N-phenylamino]biphenyl (α-NPD), N,N'- diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)triphenylamine (TDTA), 4,4',4"-tris(N-carbazolyl)triphenylamine (TCTA), N,N'-bis(naphthalen-2-yl)-N,N'-bis(phenyl)benzidine (β-NPB), N,N'-bis(3-methylphenyl)-N,N'-bis(phenyl)-9,9-spirobifluorene (Spiro-TPD), N,N'-bis(naphthalen-1-yl)-N,N'-bis(phenyl)-9,9-spirobifluorene (Spiro-NPB), N,N'-bis(3-methylphenyl)-N,N'-bis(phenyl)-9,9-dimethylfluorene (DMFL-TPD), di[4-(N,N-ditolylamino)phenyl]cyclohexane, N,N'-bis(naphthalen-1-yl)-N,N'-bis(phenyl)-9,9-dimethylfluorene, N,N'-bis(naphthalen-1-yl)-N,N'-bis(phenyl)-2,2-dimethylbenzidine, N,N'-bis(naphthalen-1-yl)-N,N'-bis(phenyl)benzidine, N,N'-bis(3-methylphenyl)-N,N'-bis(phenyl)benzidine, 2,3,5,6-tetrafluoro-7,7,8,8-tetracyanoquinodimethane (F4-TCNQ), 4,4',4"-tris(N-3-methylphenyl-N-phenylamino)triphenylamine, 4,4',4"-tris(N-(2-naphthyl)-N-phenyl-amino)triphenylamine, pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di[4-(N,N-ditolylamino)phenyl]benzidine (NTNPB), N,N'-diphenyl-N,N'-di[4-(N,N-diphenylamino)phenyl]benzidine (NPNPB), N,N'-di(naphthalen-2-yl)-N,N'-diphenylbenzene-1,4-diamine (β-NPP), N,N'-bis(3-methylphenyl)-N,N'-bis(phenyl)-9,9-diphenylfluorene (DPFL-TPD), N,N'-bis(naphthalen-1-yl)-N,N'-bis(phenyl)-9,9-diphenylfluorene (DPFL-NPB), 2,2',7,7'-tetrakis(N,N-diphenylamino)-9,9'-spirobifluorene (Spiro-TAD), 9,9-bis[4-(N,N-bis(biphenyl-4-yl)amino)phenyl]-9H-fluorene (BPAPF), 9,9-bis[4-(N,N-bis(naphthalen-2-yl)amino)phenyl]-9H-fluorene (NPAPF), 9,9-bis[4-(N,N-bis(naphthalen-2-yl)-N,N'-bisphenylamino)phenyl]-9H-fluorene (NPBAPF), 2,2',7,7'-tetrakis[N-naphthalenyl(phenyl)amino]-9,9'-spirobifluorene (Spiro-2NPB), N,N'-bis(phenanthren-9-yl)-N,N'-bis(phenyl)benzidine (PAPB), 2,7-bis[N,N-bis(9,9-spirobifluoren-2-yl)amino]-9,9-spirobifluorene (Spiro-5), 2,2'-bis[N,N-bis(biphenyl-4-yl)amino]-9,9-spirobifluorene (2,2'-Spiro-DBP), 2,2'-bis(N,N-diphenylamino)-9,9-spirobifluorene (Spiro-BPA), 2,2',7,7'-tetra(N,N-ditolyl)aminospirobifluorene (Spiro-TTB), N,N,N',N'-tetranaphthalen-2-ylbenzidine (TNB), porphyrin compounds and phthalocyanines such as copper phthalocyanines and titanium oxide phthalocyanines. Hole-transporting polymers typically used are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above. In addition—in one embodiment—it is possible to use carbene complexes as hole conductor materials, the band gap of the at least one hole conductor material generally being greater than the band gap of the emitter material used. In the context of the present application, "band gap" is understood to mean the triplet energy. Suitable carbene complexes are, for example, carbene complexes as described in WO 2005/019373 A2, WO 2006/056418 A2, WO 2005/113704, WO 2007/115970, WO 2007/115981 and WO 2008/000727. One example of a suitable carbene complex is Ir(dpbic)$_3$ with the formula:

(HTM-1)

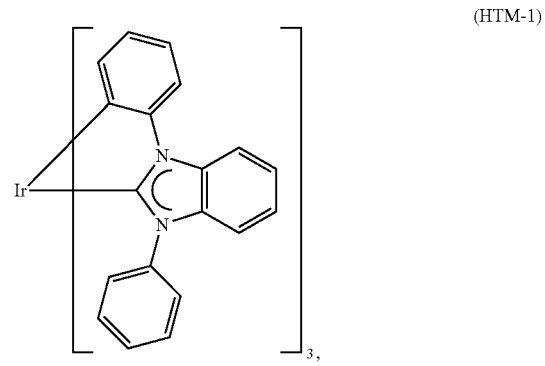

which is disclosed, for example, in WO2005/019373. In principle, it is possible that the hole conductor layer comprises at least one compound of the formula I as hole conductor material, especially a compound of formula (Ia), (Ib), (Ic), (Id), (Ie), (If), (Ii), (Ij), (Il), or (In), very especially a compound A-1 to A-65, B-1 to B-8, C-1 to C-65, D-1 to D-8, E-1 to E-65, or F-1 to F-65.

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, 2003, 359 (p-doped organic layers); A. G. Werner, F. Li, K. Harada, M. Pfeiffer, T. Fritz, K. Leo, Appl. Phys. Lett., Vol. 82, No. 25, 2003, 4495 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide, for example $MoO_2$, $MoO_3$, $WO_x$, $ReO_3$ and/or $V_2O_5$, preferably $MoO_3$ and/or $ReO_3$, more preferably $MoO_3$, or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane (F4-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho2,6-quinodimethane, 2-fluoro-7,7,8,8-tetracyanoquino-dimethane, 2,5-difluoro-7,7,8,8etracyanoquinodimethane, dicyanomethylene-1,3,4,5,7,8-hexafluoro-6H-naphthalen-2-ylidene)malononitrile (F$_6$-

TNAP), Mo(tfd)$_3$ (from Kahn et al., J. Am. Chem. Soc. 2009, 131 (35), 12530-12531), compounds as described in EP1988587, US2008265216, EP2180029, US20100102709, WO2010132236, EP2180029 and quinone compounds as mentioned in EP2401254. Preferred mixtures comprise the aforementioned carbene complexes, such as, for example, the carbene complex HTM-1, and MoO$_3$ and/or ReO$_3$, especially MoO$_3$. In a particularly preferred embodiment the hole transport layer comprises from 0.1 to 10 wt % of MoO$_3$ and 90 to 99.9 wt % carbene complex, especially of the carbene complex HTM-1, wherein the total amount of the MoO$_3$ and the carbene complex is 100 wt %.

The light-emitting layer (3) comprises at least one emitter material. In principle, it may be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance. The compounds of the formula I can be used as the matrix in the light-emitting layer.

Suitable metal complexes for use in the inventive OLEDs are described, for example, in documents WO02/60910A1, US2001/0015432A1, US2001/0019782A1, US2002/0055014A1, US2002/0024293A1, US2002/0048689A1, EP1191612A2, EP1191613A2, EP1211257A2, US2002/0094453A1, WO02/02714A2, WO00/70655A2, WO01/41512A1, WO02/15645A1, WO2005/019373A2, WO2005/113704A2, WO2006/115301 A1, WO2006/067074A1, WO2006/056418, WO2006121811A1, WO2007095118A2, WO2007/115970, WO2007/115981, WO2008/000727, WO2010129323, WO2010056669, WO10086089, US2011/0057559, WO2011/106344, US2011/0233528, WO2012/048266 and WO2012/172482.

Further suitable metal complexes are the commercially available metal complexes tris(2-phenylpyridine)iridium (III), iridium(III) tris(2-(4-tolyl)pyridinato-N,C$^{2'}$), bis(2-phenylpyridine)(acetylacetonato)iridium(III), iridium(III) tris(1-phenylisoquinoline), iridium(III) bis(2,2'-benzothienyOpyridinato-N,C$^{3'}$)(acetylacetonate), tris(2-phenylquinoline)iridium(III), iridium(III) bis(2-(4,6-difluorophenyl)pyridinato-N,C$^2$)picolinate, iridium(III) bis(1-phenylisoquinoline)(acetylacetonate), bis(2-phenylquinoline)(acetylacetonato)iridium(III), iridium(III) bis(di-benzo[f,h]quinoxaline)(acetylacetonate), iridium(III) bis(2-methyldibenzo[f, h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetylacetonato)iridium(III), bis(2-phenylbenzothiazolato)(acetylacetonato)iridium(III), bis(2-(9,9-dihexylfluorenyl)-1-pyridine)(acetylacetonato)iridium(III), bis(2-benzo[b]thiophen-2-ylpyridine)(acetylacetonato) iridium(III).

In addition, the following commercially available materials are suitable: tris(dibenzoylacetonato)mono(phenanthroline)europium(III), tris(dibenzoylmethane)mono (phenanthroline)europium(III), tris(dibenzoylmethane) mono(5-aminophenanthroline)europium(III), tris(di-2-naphthoylmethane)mono(phenanthroline)europium(III), tris (4-bromobenzoylmethane)mono(phenanthroline)europium (III), tris(di(biphenyl)methane)mono(phenanthroline) europium(III), tris(dibenzoylmethane)mono(4,7-diphenylphenanthroline)europium(III), tris (dibenzoylmethane)mono(4,7-di-methylphenanthroline) europium(III), tris(dibenzoylmethane)mono(4,7-dimethylphenanthrolinedisulfonic acid)europium(III) disodium salt, tris[di(4-(2-(2-ethoxyethoxy)ethoxy)benzoylmethane)]mono(phenanthroline)europium(III) and tris[di (4-(2-(2-ethoxyethoxy)ethoxy)benzoylmethane)]mono(5-aminophenanthroline)europium(III), osmium(II) bis(3-(trifluoromethyl)-5-(4-tert-butylpyridyl)-1,2,4-triazolato) diphenylmethylphosphine, osmium(II) bis(3-(trifluoromethyl)-5-(2-pyridyl)-1,2,4-triazole) dimethylphenylphosphine, osmium(II) bis(3-(trifluoromethyl)-5-(4-tert-butylpyridyl)-1,2,4-triazolato) dimethylphenylphosphine, osmium(II) bis(3-(trifluoromethyl)-5-(2-pyridyl)pyrazolato) dimethylphenylphosphine, tris[4,4'-di-tert-butyl(2,2')-bipyridine]ruthenium(III), osmium(II) bis(2-(9,9-dibutylfluorenyl)-1-isoquinoline(acetylacetonate).

Preferred phosphorescence emitters are carbene complexes. Suitable phosphorescent blue emitters are specified in the following publications: WO2006/056418A2, WO2005/113704, WO2007/115970, WO2007/115981, WO2008/000727, WO2009050281, WO2009050290, WO2011051404, US2011/057559 WO2011/073149, WO2012/121936A2, US2012/0305894A1, WO2012/170571, WO2012/170461, WO2012/170463, WO2006/121811, WO2007/095118, WO2008/156879, WO2008/156879, WO2010/068876, US2011/0057559, WO2011/106344, US2011/0233528, WO2012/048266 and WO2012/172482.

The light emitting layer comprises preferably a compound of the formula $[L]_{m1}[K]_{o1}M[carbene]_{n1}$ (IX), which are described in WO 2005/019373A2, wherein the symbols have the following meanings:

M is a metal atom selected from the group consisting of Co, Rh, Ir, Nb, Pd, Pt, Fe, Ru, Os, Cr, Mo, W, Mn, Tc, Re, Cu, Ag and Au in any oxidation state possible for the respective metal atom;

Carbene is a carbene ligand which may be uncharged or monoanionic and monodentate, bidentate or tridentate, with the carbene ligand also being able to be a biscarbene or triscarbene ligand;

L is a monoanionic or dianionic ligand, which may be monodentate or bidentate;

K is an uncharged monodentate or bidentate ligand selected from the group consisting of phosphines; phosphonates and derivatives thereof, arsenates and derivatives thereof; phosphites; CO; pyridines; nitriles and conjugated dienes which form a π complex with M$^1$;

n1 is the number of carbene ligands, where n1 is at least 1 and when n1>1 the carbene ligands in the complex of the formula (IX) can be identical or different;

m1 is the number of ligands L, where m1 can be 0 or ≥1 and when m1>1 the ligands L can be identical or different;

o1 is the number of ligands K, where o1 can be 0 or ≥1 and when o1>1 the ligands K can be identical or different;

where the sum n1+m1+o1 is dependent on the oxidation state and coordination number of the metal atom and on the denticity of the ligands carbene, L and K and also on the charge on the ligands, carbene and L, with the proviso that n1 is at least 1.

Carbene complexes which are suitable triplet emitters are described, for example, in WO 2006/056418 A2, WO 2005/113704, WO 2007/115970, WO 2007/115981 and WO 2008/000727, WO2009050281, WO2009050290, WO2011051404 and WO2011073149.

More preferred are metal-carbene complexes of the general formula

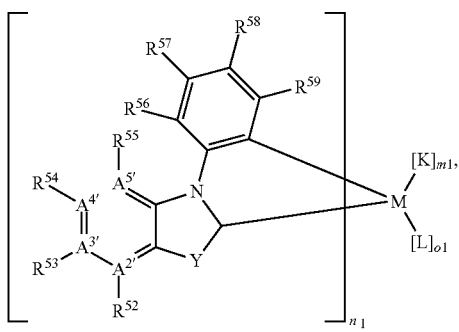

(IXa)

which are described in U.S. patent applications No. 61/286,046, 61/323,885 and European patent application 10187176.2 (PCT/EP2010/069541), where M, n1, Y, $A^{2'}$, $A^{3'}$, $A^{4'}$, $A^{5'}$, $R^{51}$, $R^{52}$, $R^{53}$, $R^{54}$, $R^{55}$, $R^{56}$, $R^{57}$, $R^{58}$, $R^{59}$, K, L, m1 and o1 are each defined as follows:

M is Ir, or Pt, n1 is an integer selected from 1, 2 and 3,

Y is $NR^{51}$, O, S or $C(R^{25})_2$, $A^{2'}$, $A^{3'}$, $A^{4'}$, and $A^{5'}$ are each independently N or C, where 2 A=nitrogen atoms and at least one carbon atom is present between two nitrogen atoms in the ring, $R^{51}$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, $R^{52}$, $R^{53}$, $R^{54}$ and $R^{55}$ are each, if $A^{2'}$, $A^{3'}$, $A^{4'}$ and/or $A^{5'}$ is N, a free electron pair, or, if $A^{2'}$, $A^{3'}$, $A^{4'}$ and/or $A^{5'}$ is C, each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{53}$ and $R^{54}$ together with $A^{3'}$ and $A^{4'}$ form an optionally substituted, unsaturated ring optionally interrupted by at least one further heteroatom and having a total of 5 to 18 carbon atoms and/or heteroatoms, $R^{56}$, $R^{57}$, $R^{58}$ and $R^{59}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{56}$ and $R^{57}$, $R^{57}$ and $R^{58}$ or $R^{58}$ and $R^{59}$, together with the carbon atoms to which they are bonded, form a saturated, unsaturated or aromatic, optionally substituted ring optionally interrupted by at least one heteroatom and having a total of 5 to 18 carbon atoms and/or heteroatoms, and/or if $A^{5'}$ is C, $R^{55}$ and $R^{56}$ together form a saturated or unsaturated, linear or branched bridge optionally comprising heteroatoms, an aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms, $R^{25}$ is independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, K is an uncharged mono- or bidentate ligand, L is a mono- or dianionic ligand, preferably monoanionic ligand, which may be mono- or bidentate, m1 is 0, 1 or 2, where, when m1 is 2, the K ligands may be the same or different, o1 is 0, 1 or 2, where, when o1 is 2, the L ligands may be the same or different.

The compound of formula IX is preferably a compound of the formula:

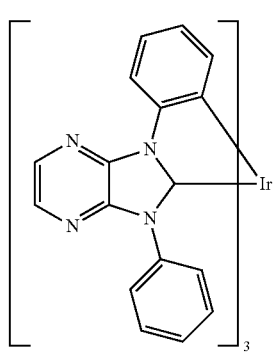

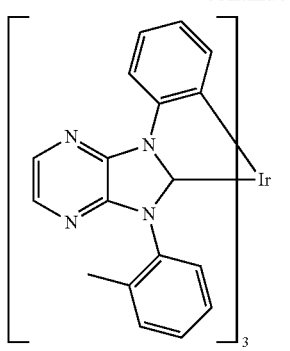
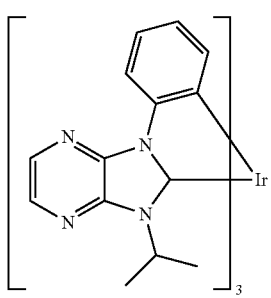
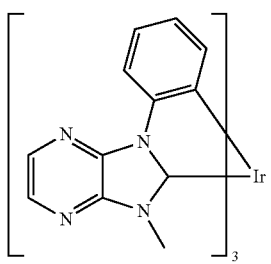
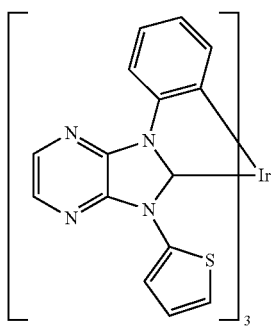
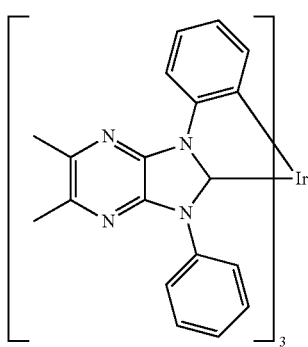
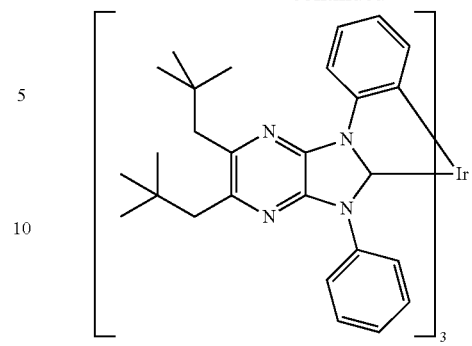
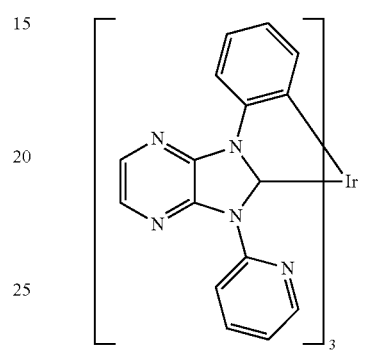
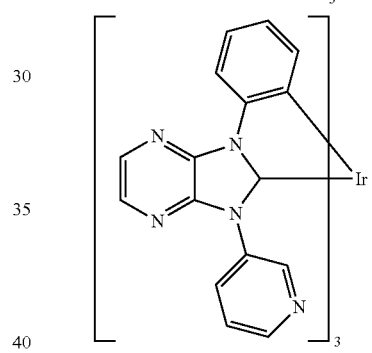
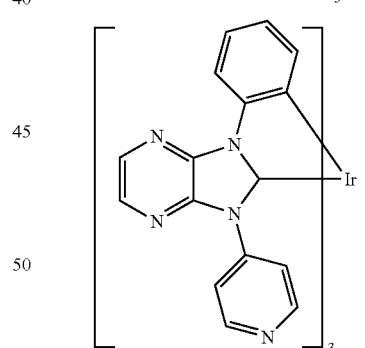
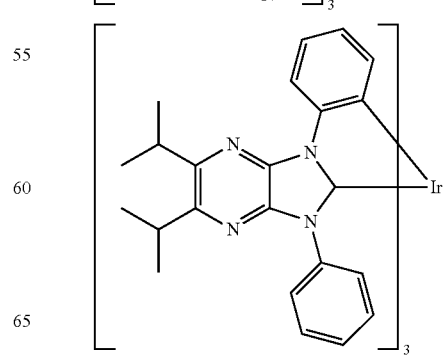

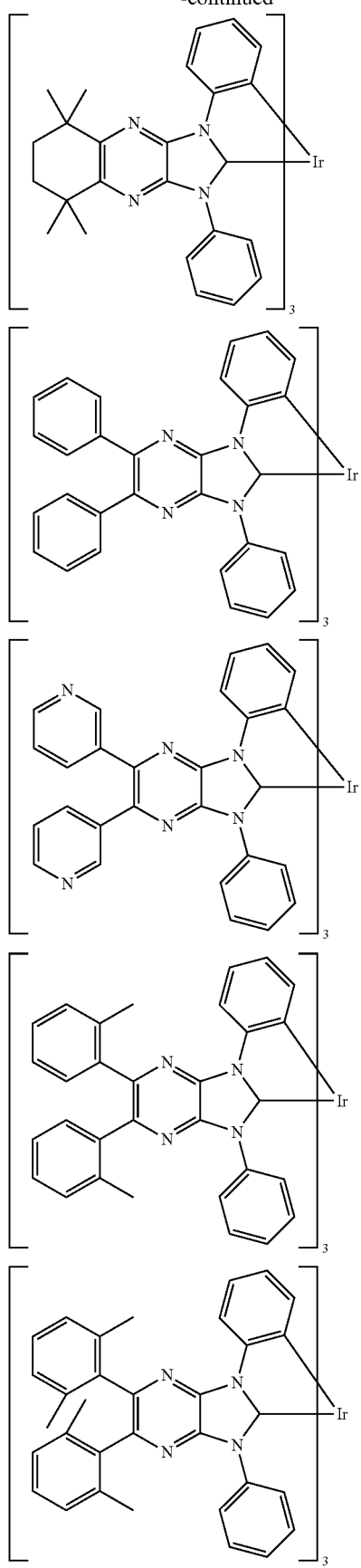
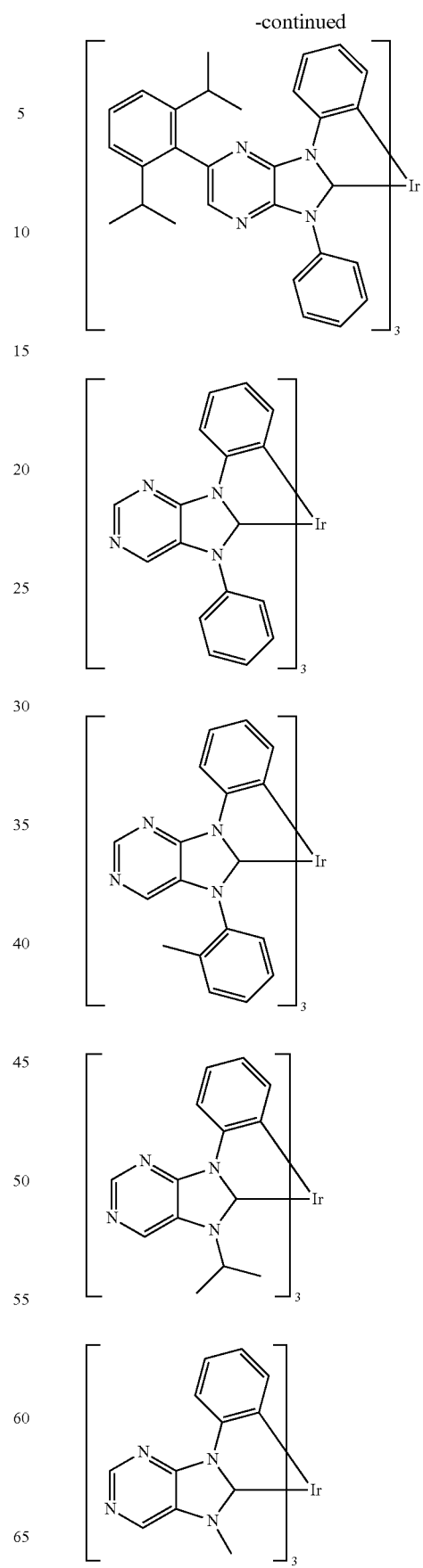

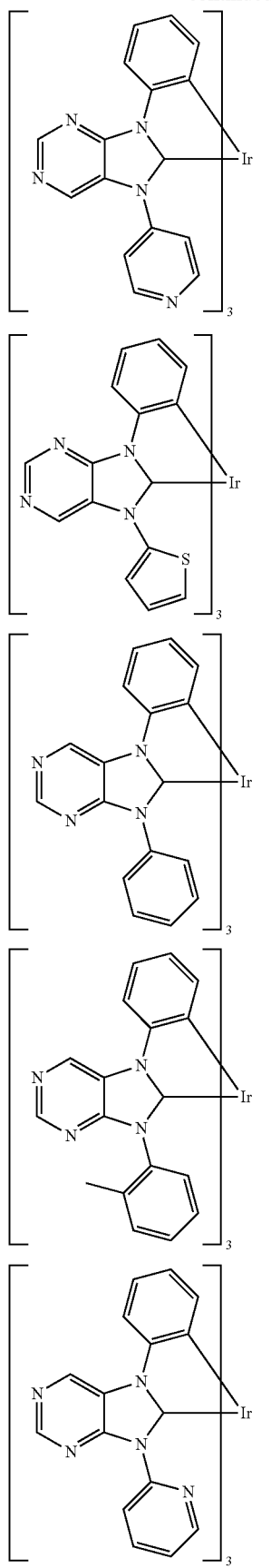
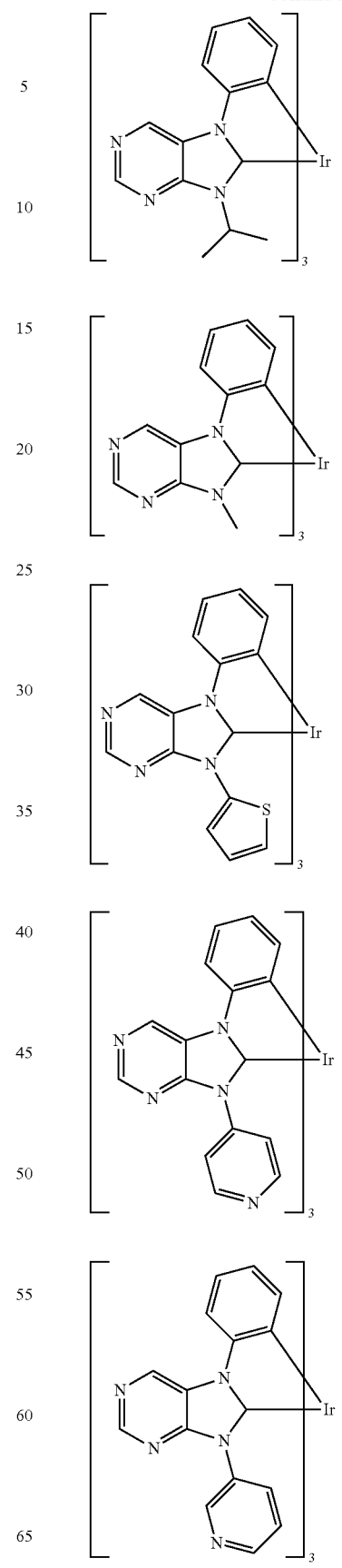

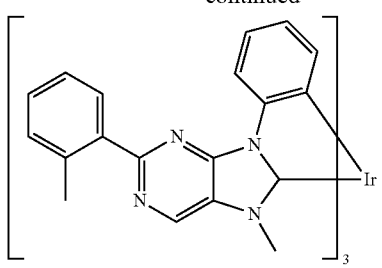
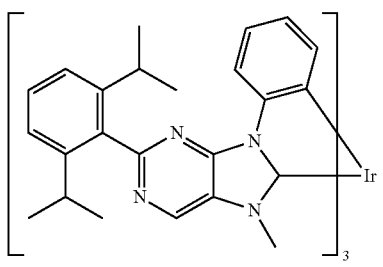
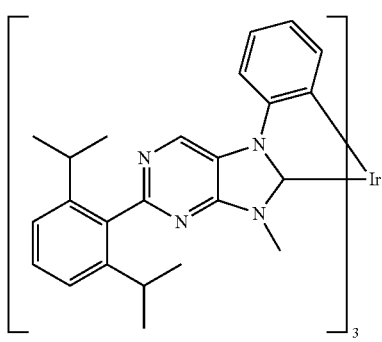
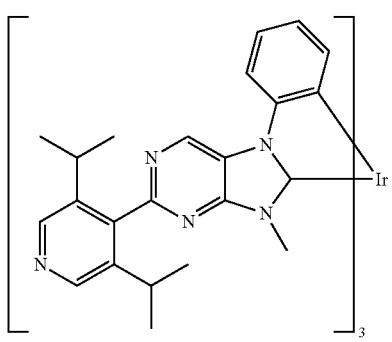
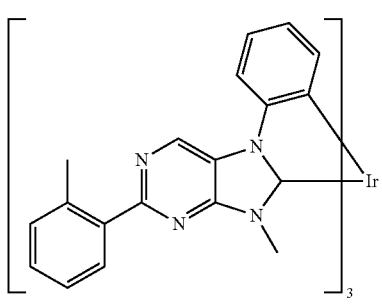
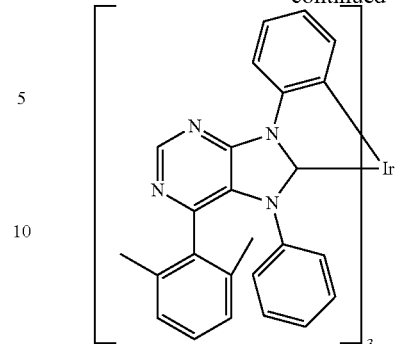
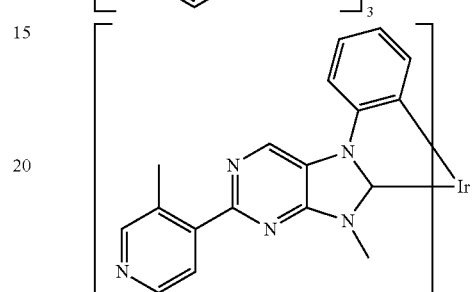
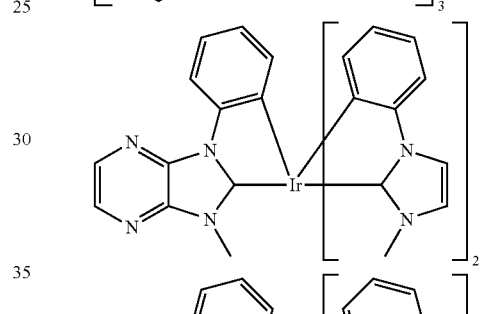
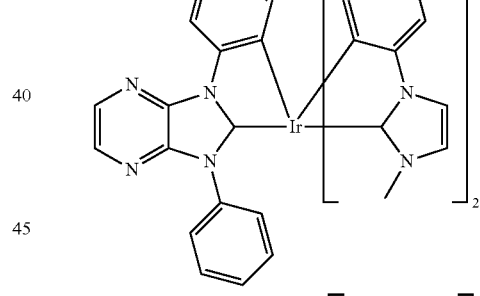
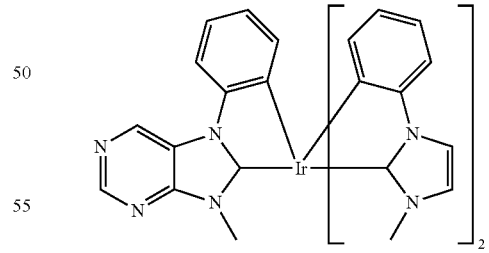
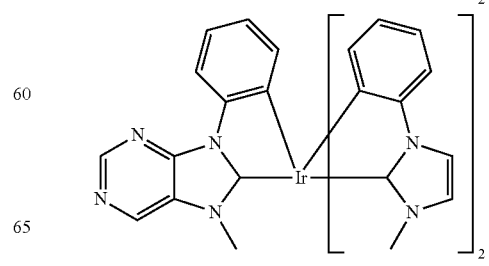

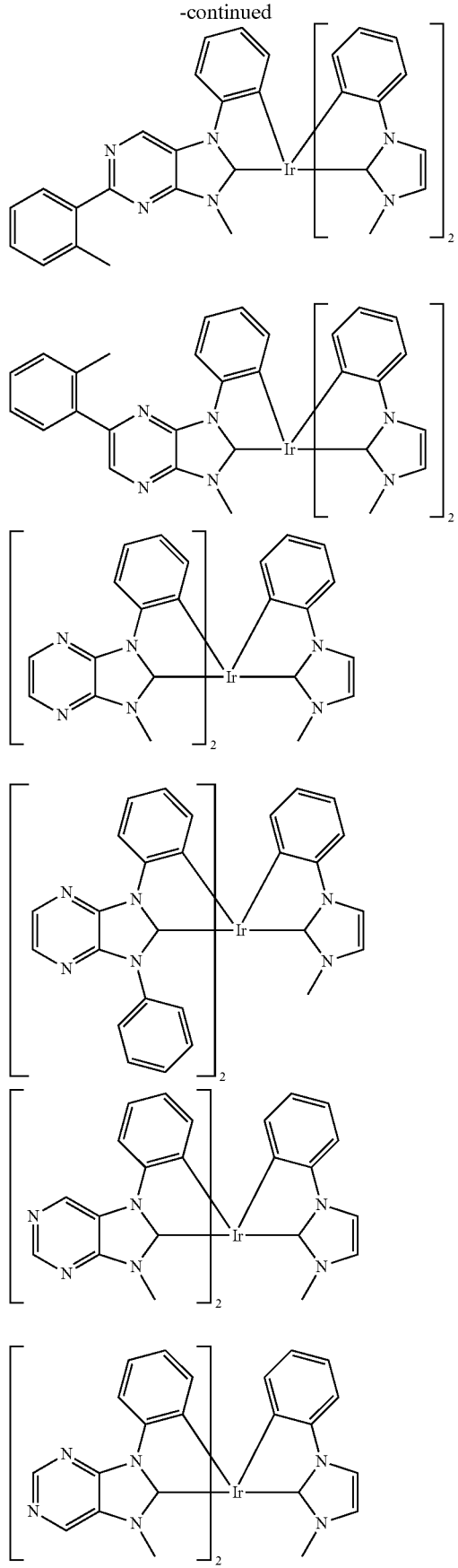
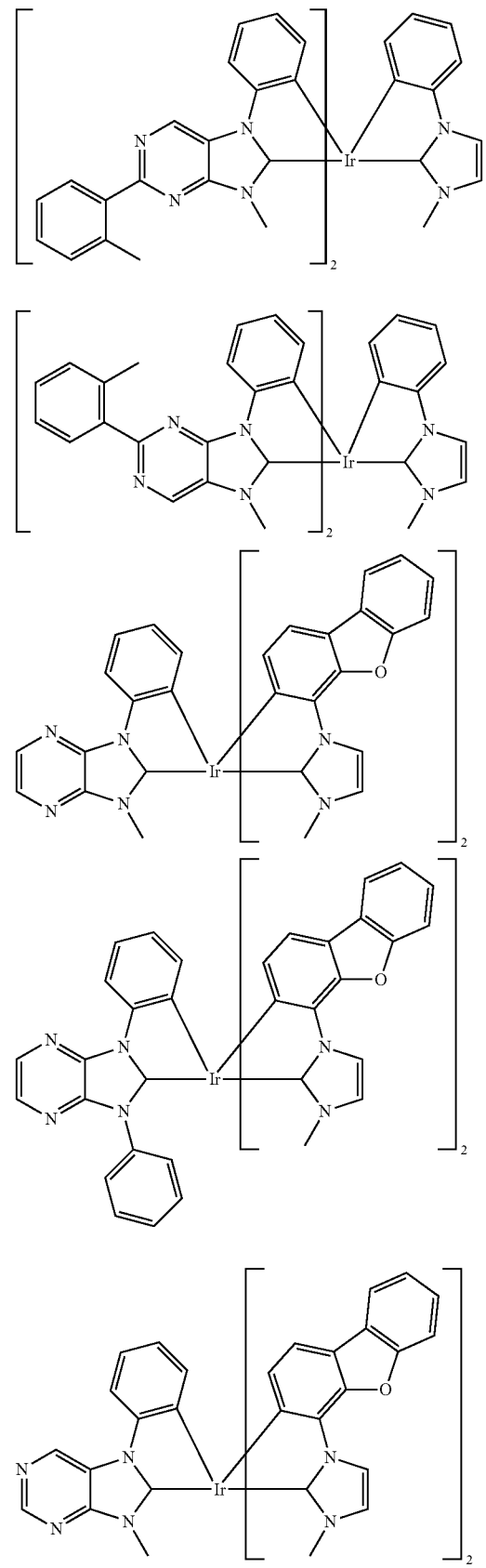

101
-continued
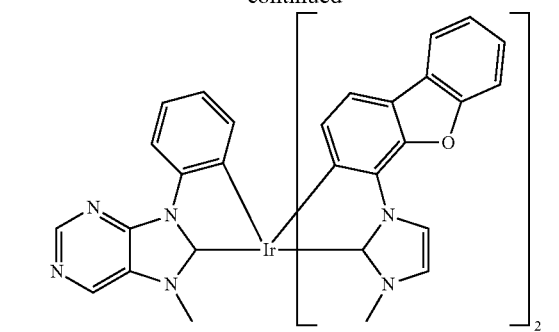
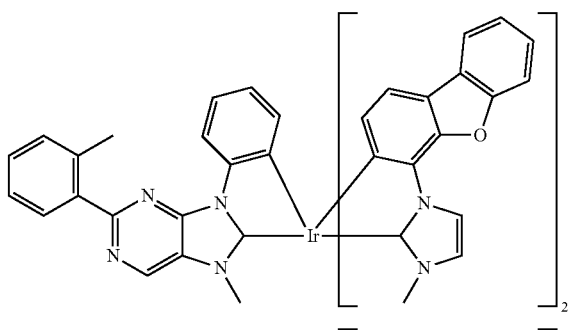
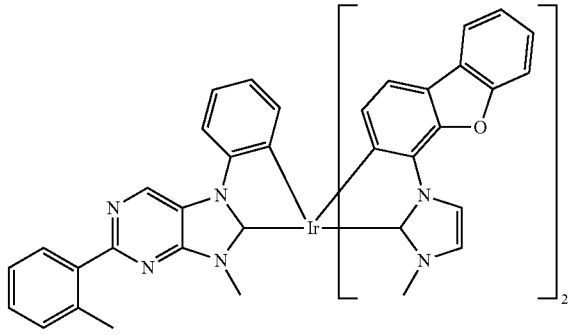
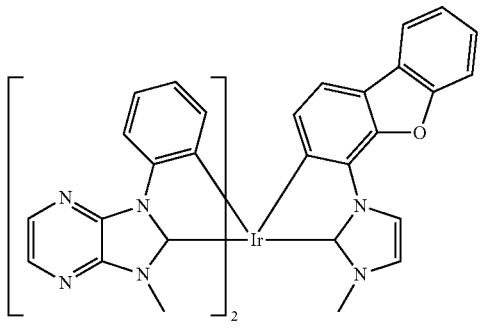
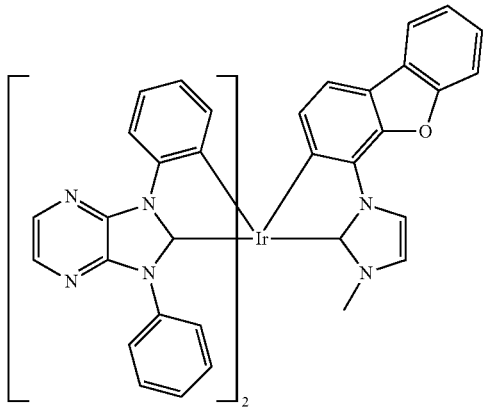
102
-continued
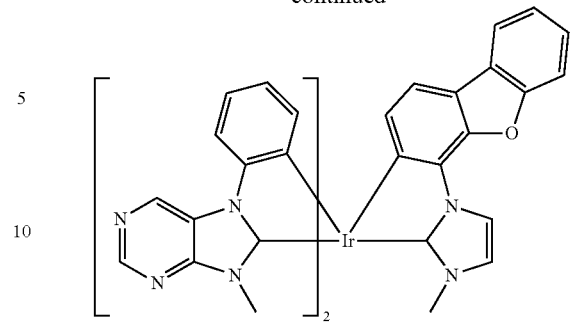
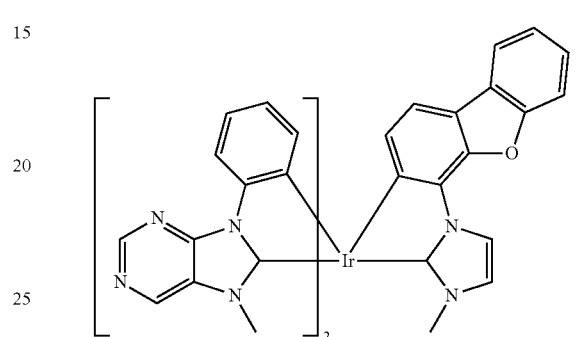
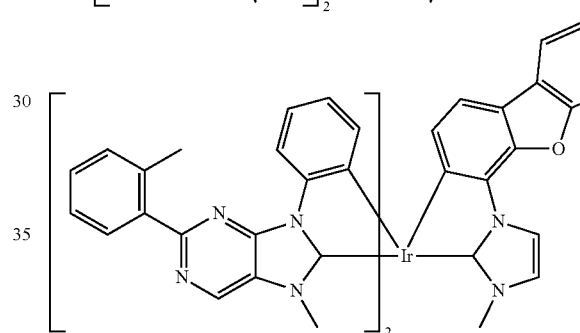
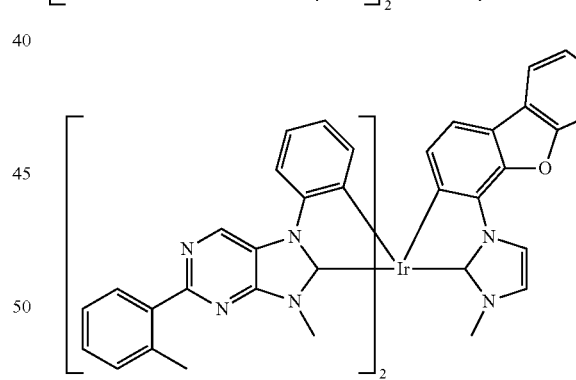
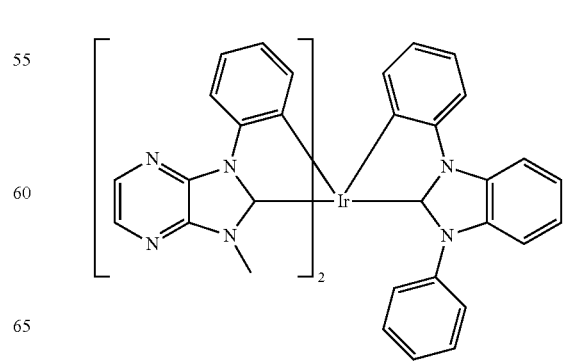

103
-continued
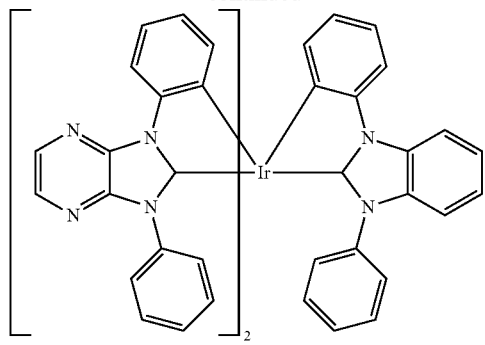
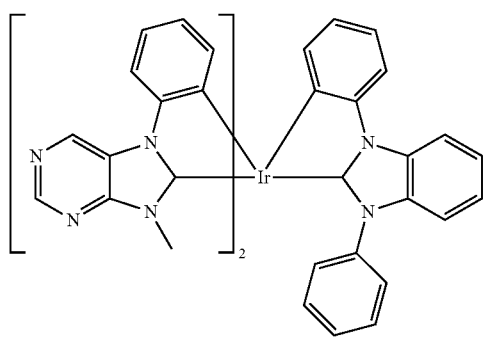
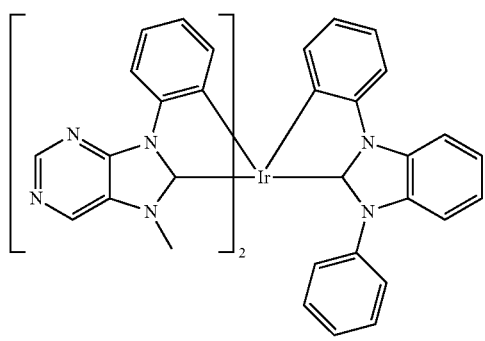
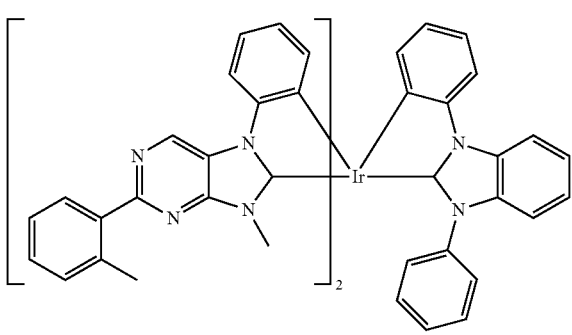
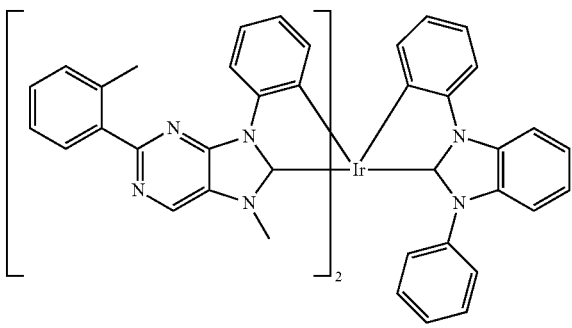
104
-continued
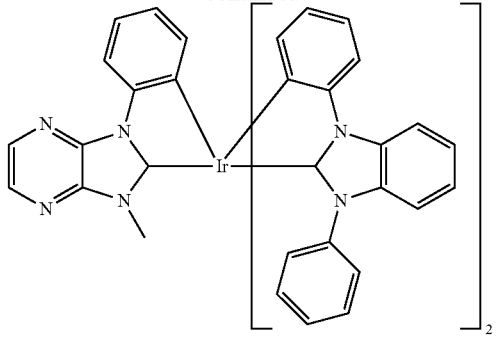
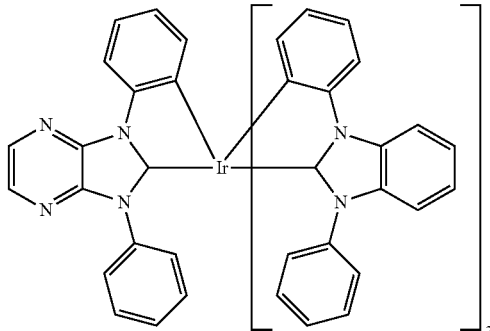

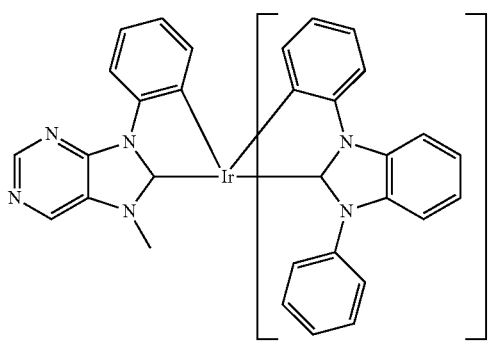
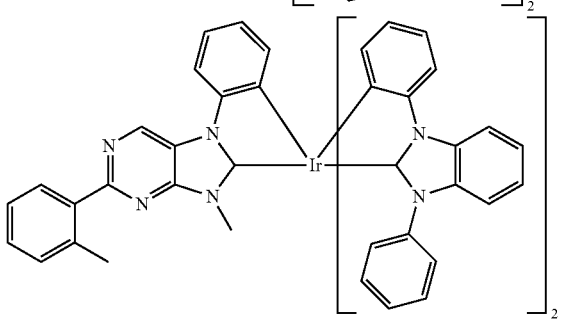

105
-continued
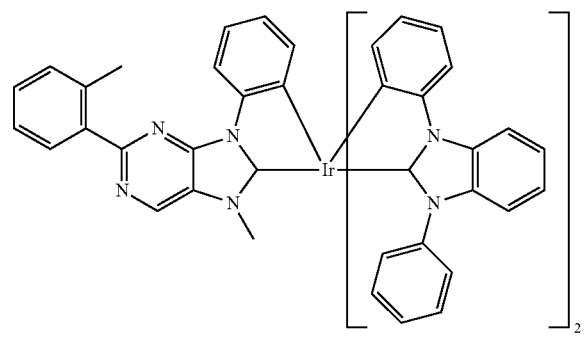
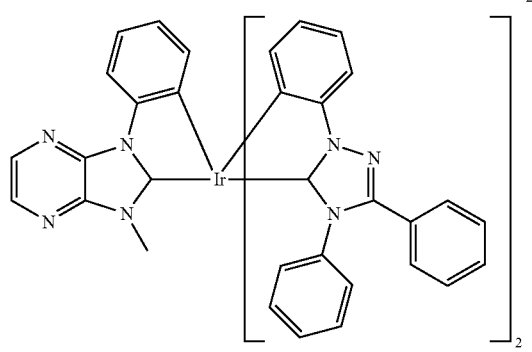
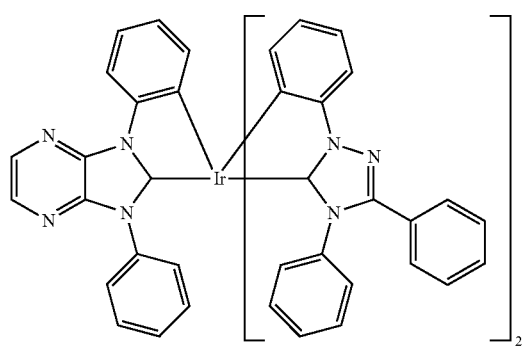
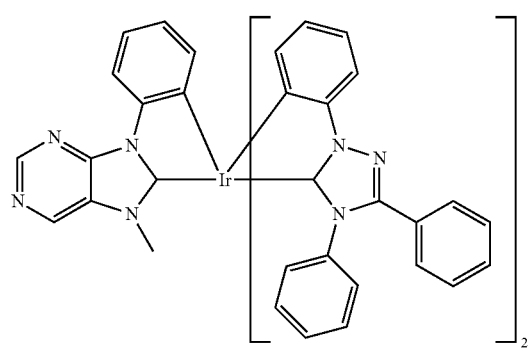
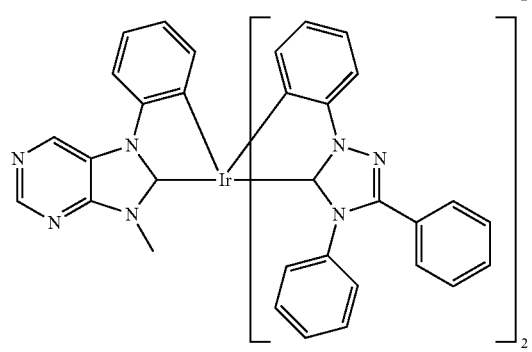
106
-continued
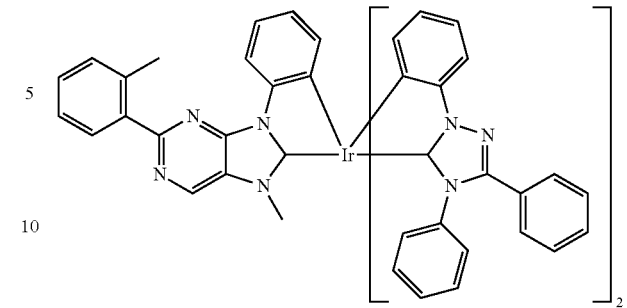
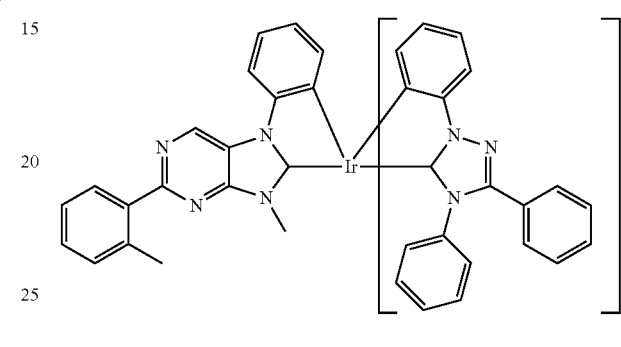
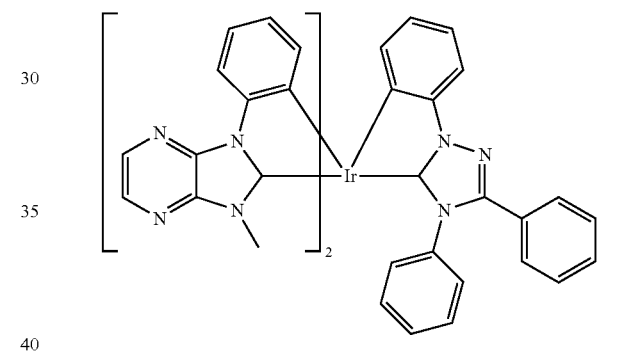
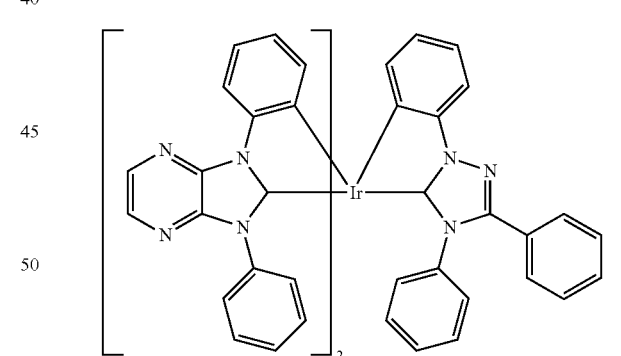
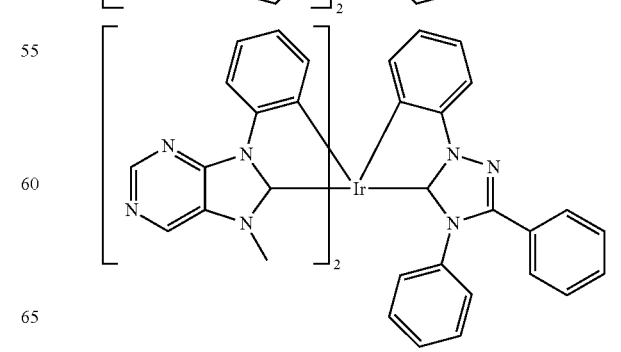

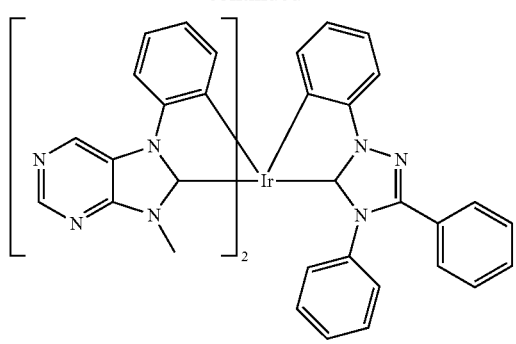
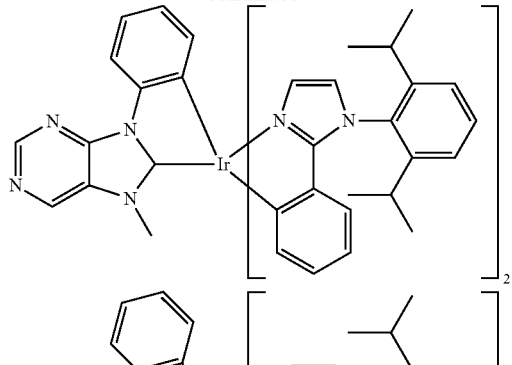
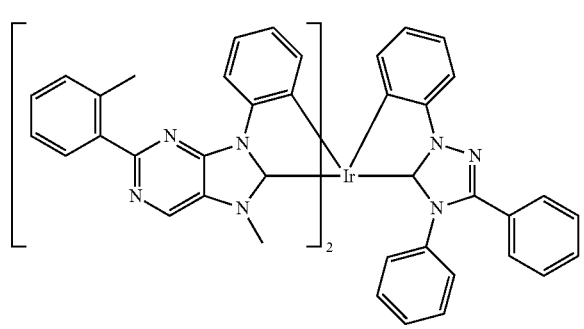
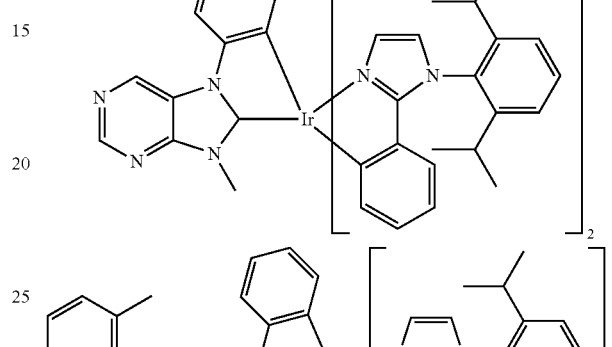
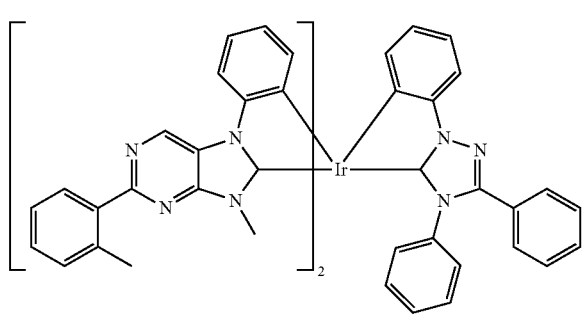
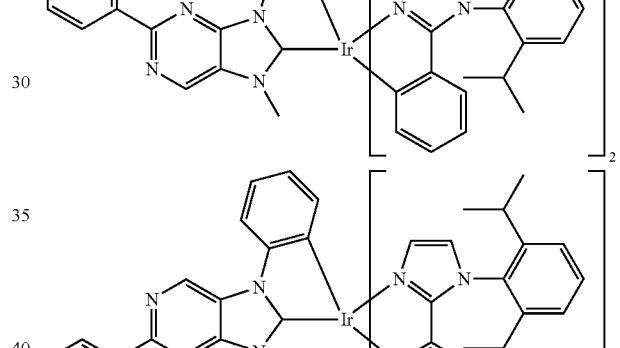
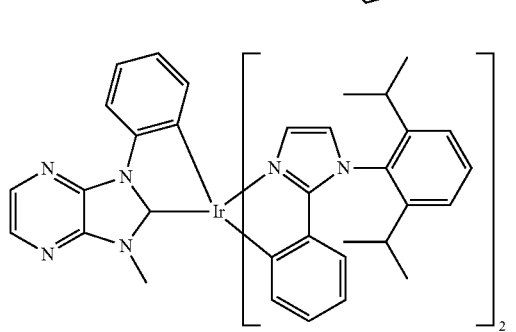
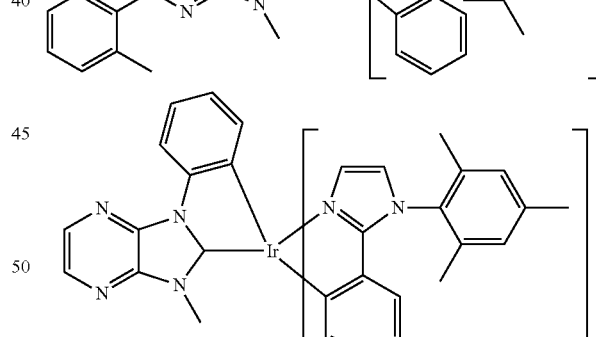
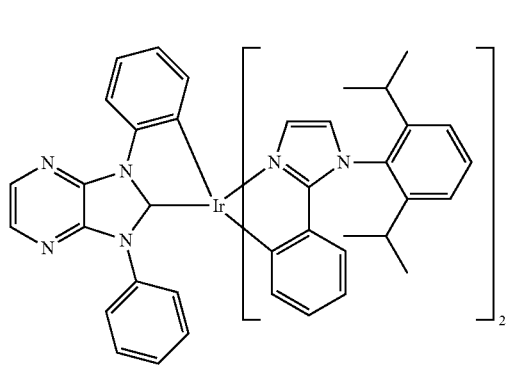
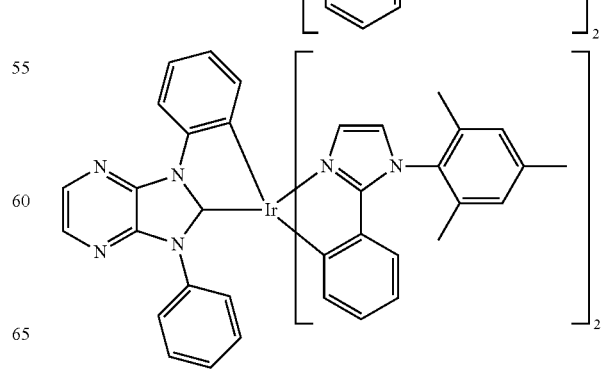

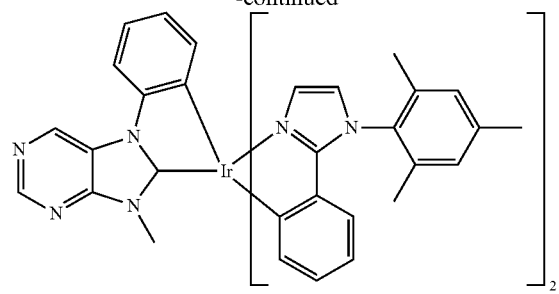
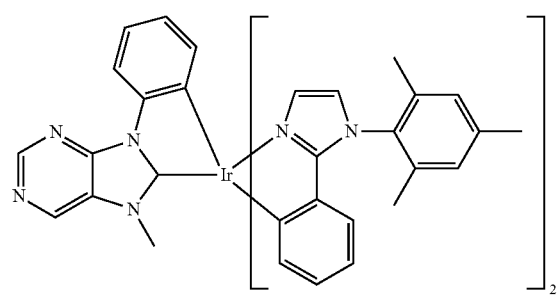
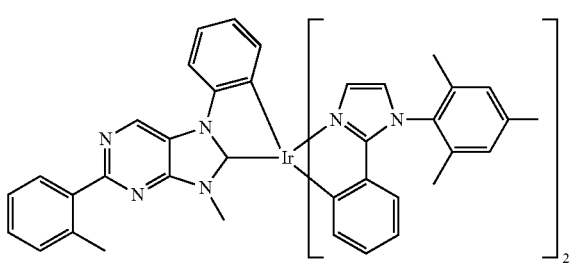
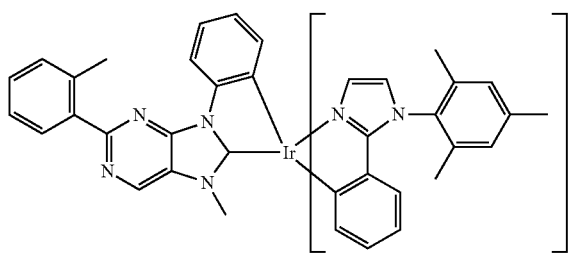
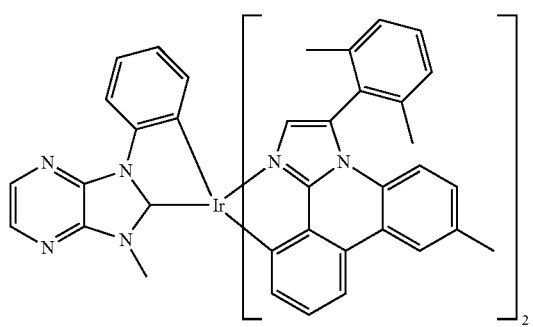
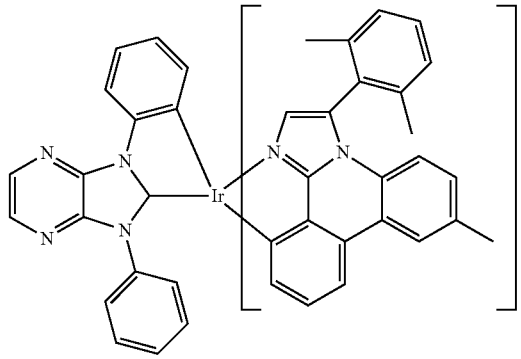
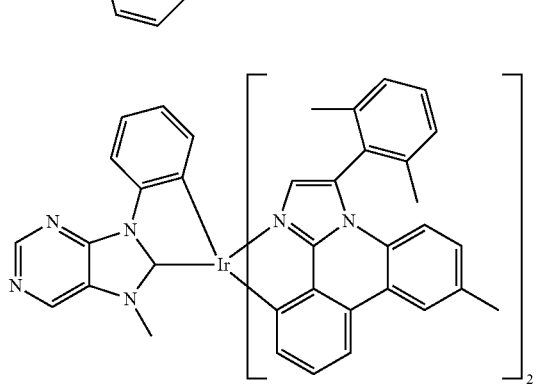
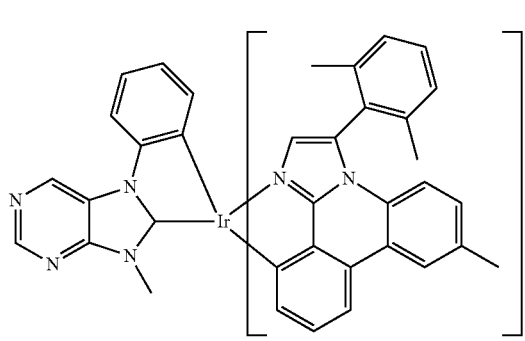
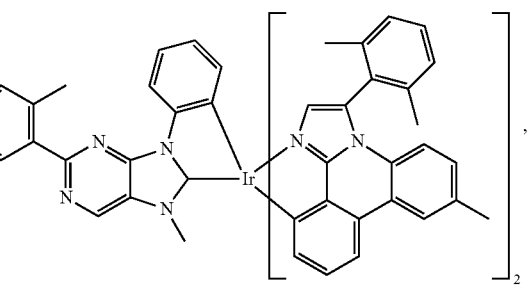
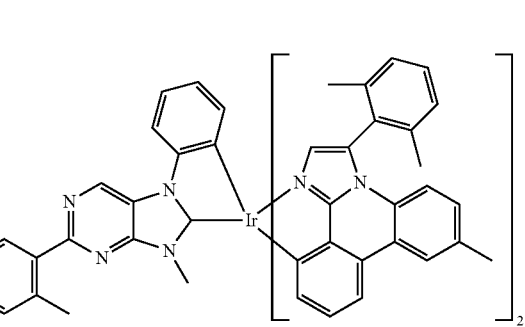

111
-continued
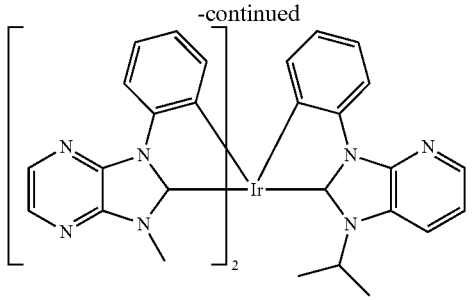
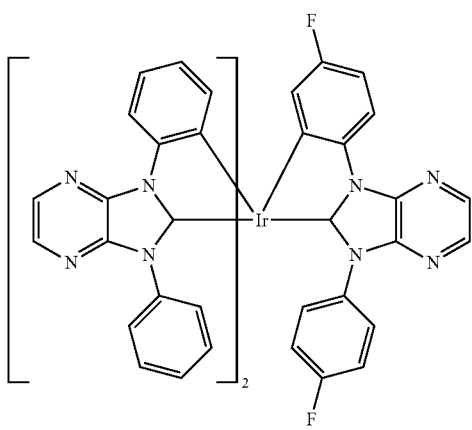
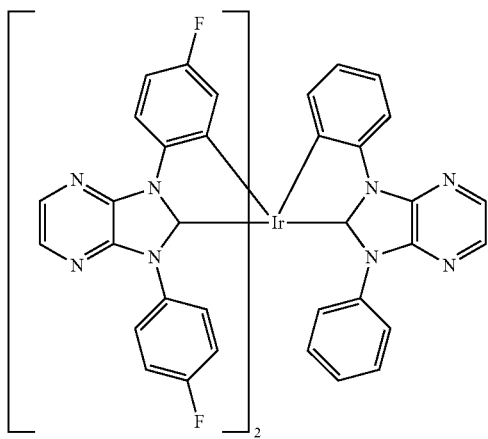
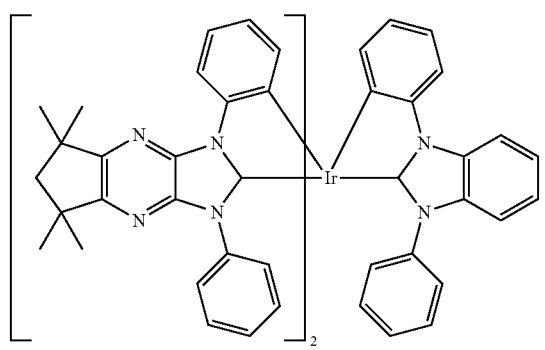
112
-continued
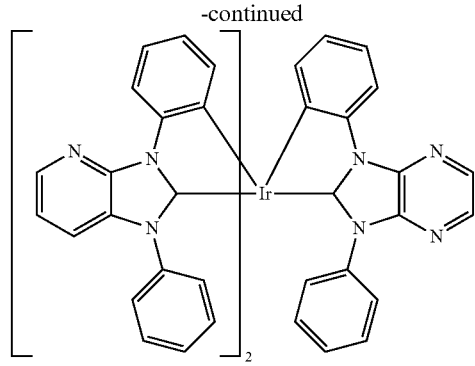
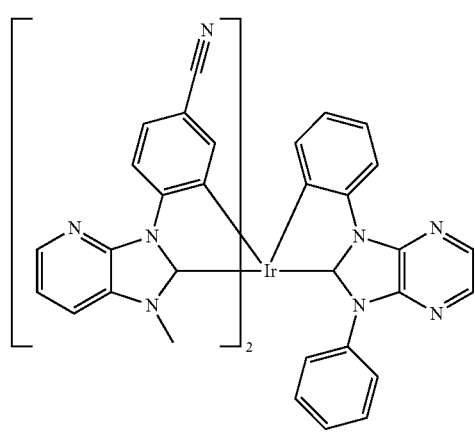
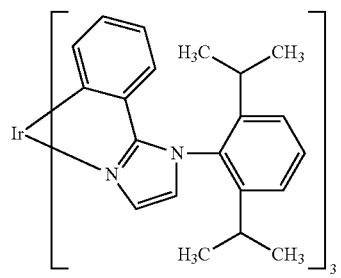
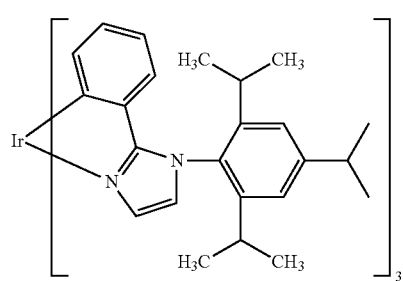
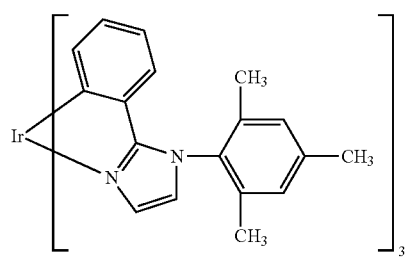

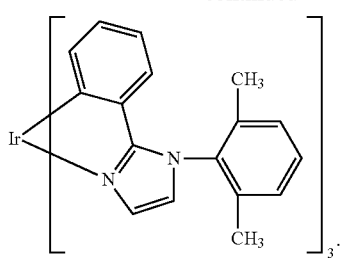
Further suitable non-carbene emitter materials are mentioned below:
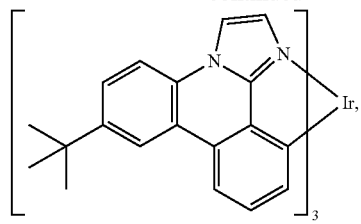
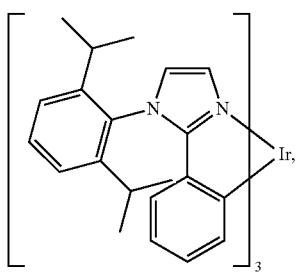
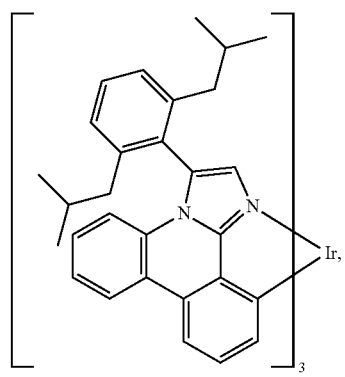
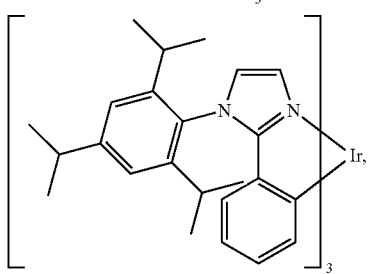
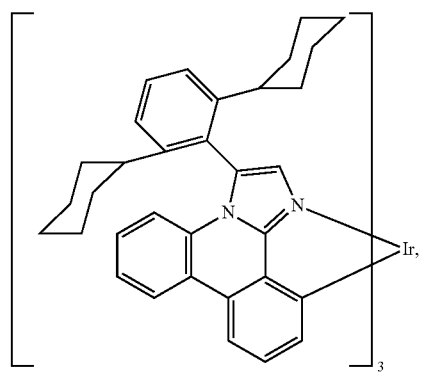
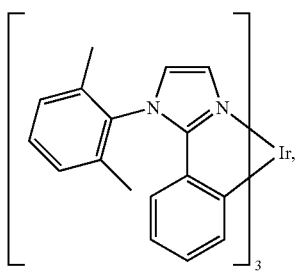
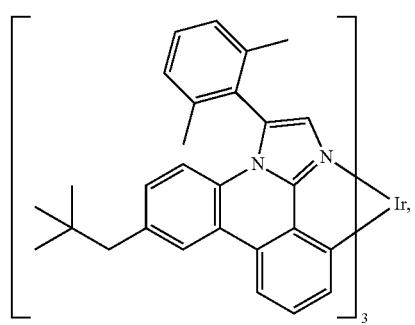
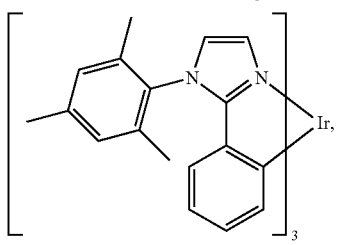
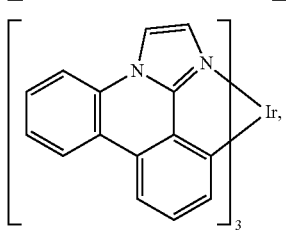

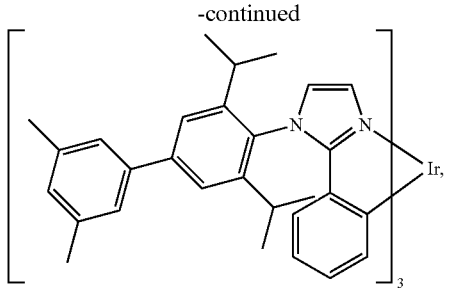
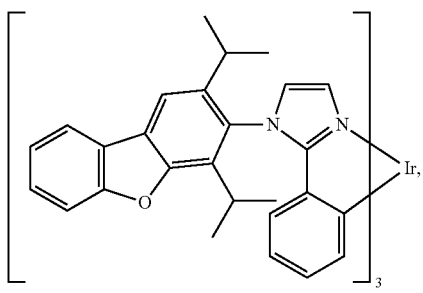
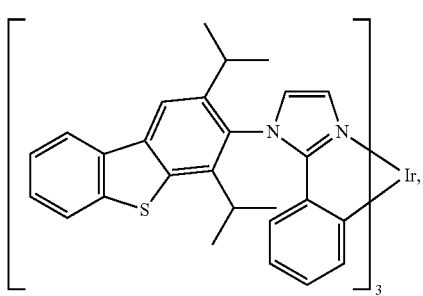
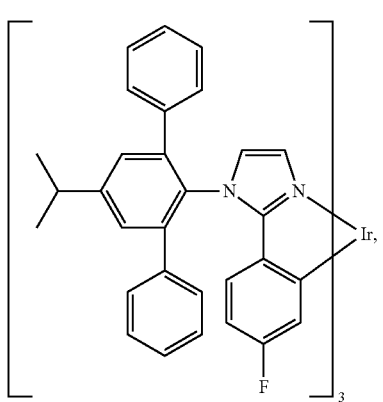
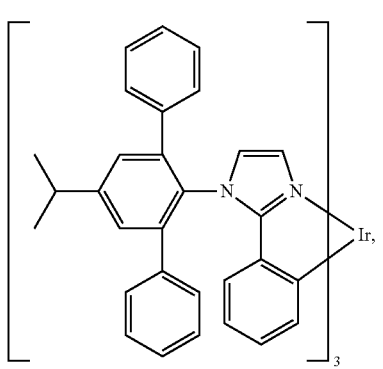
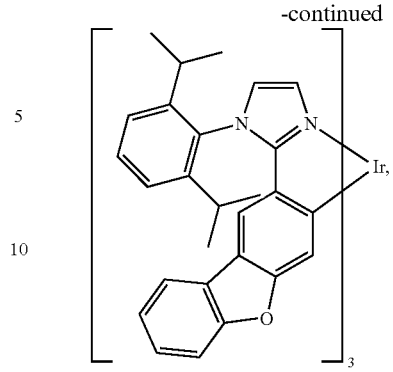
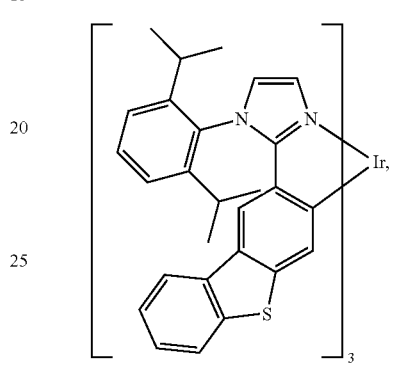
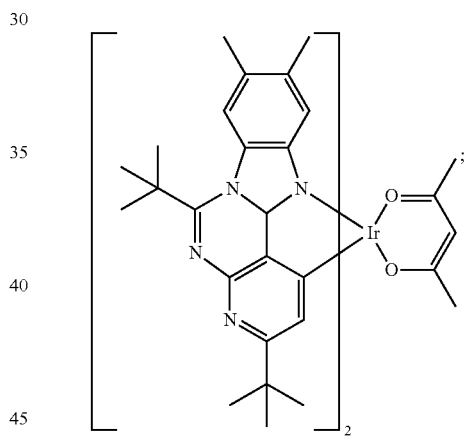
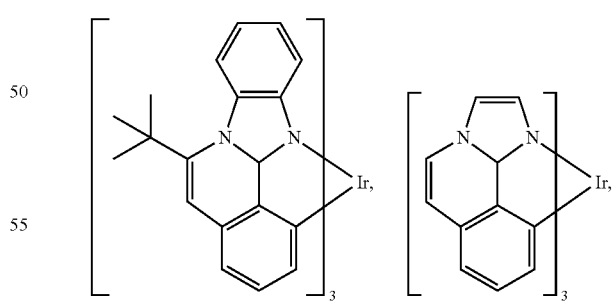
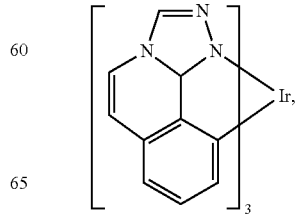

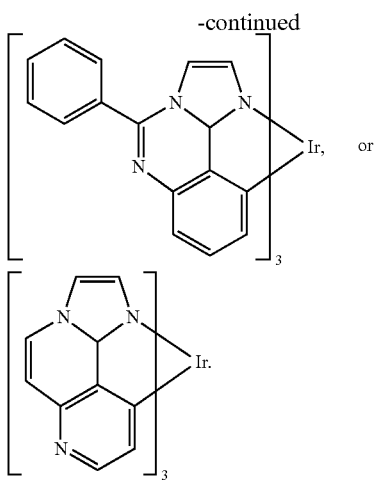

The most preferred phosphorescent blue emitters are compounds of formula

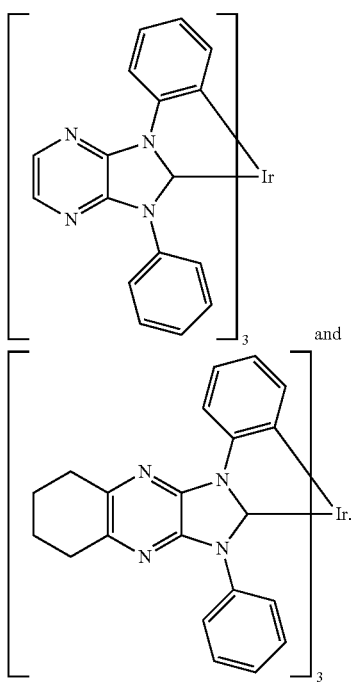

The homoleptic metal-carbene complexes may be present in the form of facial or meridional isomers, preference being given to the facial isomers.

In the case of the heteroleptic metal-carbene complexes, four different isomers may be present, preference being given to the pseudo-facial isomers.

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for example TCTA. In a preferred embodiment of the present invention, at least one compound of the formula I is used as matrix material.

In a preferred embodiment, the light-emitting layer is formed from 2 to 40% by weight, preferably 5 to 35% by weight, of at least one of the aforementioned emitter materials and 60 to 98% by weight, preferably 75 to 95% by weight, of at least one of the aforementioned matrix materials—in one embodiment at least one compound of the formula I—where the sum total of the emitter material and of the matrix material adds up to 100% by weight.

The compound of the formula I is especially a compound of formula (Ia), (Ib), (Ic), (Id), (Ie), (If), (Ii), (Ij), (Il), or (In), very especially a compound A-1 to A-65, B-1 to B-8, C-1 to C-65, D-1 to D-8, E-1 to E-65, or F-1 to F-65.

In particularly preferred embodiment, the light-emitting layer comprises a compound of formula I, such as, for example,

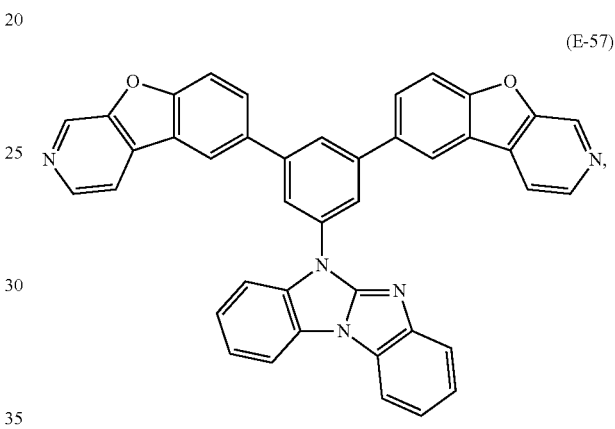

(E-57)

and two carbene complexes, preferably of formula

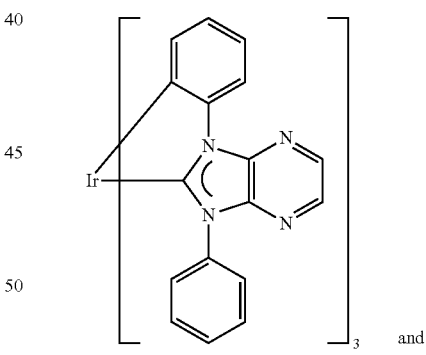

and

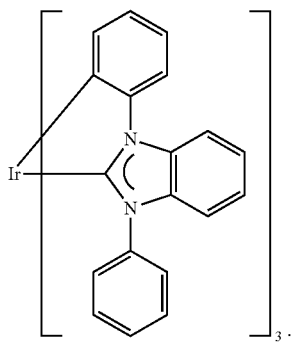

In said embodiment, the light-emitting layer is formed from 2 to 40% by weight, preferably 5 to 35% by weight, of

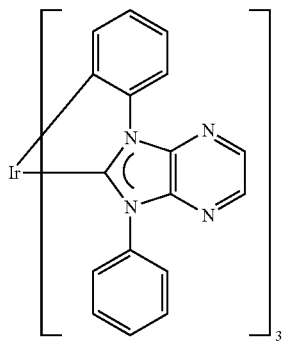

and 60 to 98% by weight, preferably 65 to 95% by weight, of a compound of the formula I and

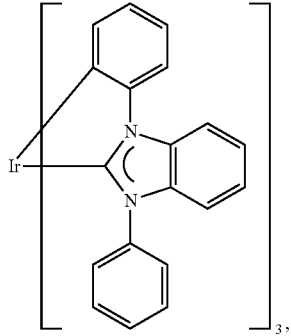

where the sum total of the carbon complexes and of the compound of formula I adds up to 100% by weight.

Suitable metal complexes for use together with the compounds of the formula I as matrix material and/or hole/exciton blocker material and/or electron/exciton blocker material and/or hole injection material and/or electron injection material and/or hole conductor material and/or electron conductor material, preferably as matrix material and/or hole/exciton blocker material, in OLEDs are thus, for example, also carbene complexes as described in WO 2005/019373 A2, WO 2006/056418 A2, WO 2005/113704, WO 2007/115970, WO 2007/115981 and WO 2008/000727. Explicit reference is made here to the disclosure of the WO applications cited, and these disclosures shall be considered to be incorporated into the content of the present application.

The compounds of the present invention can also be used as host for phosphorescent green emitters. Suitable phosphorescent green emitters are, for example, specified in the following publications: WO2006014599, WO20080220265, WO2009073245, WO2010027583, WO2010028151, US20110227049, WO2011090535, WO2012/08881, WO20100056669, WO20100118029, WO20100244004, WO2011109042, WO2012166608, US20120292600, EP2551933A1; U.S. Pat. No. 6,687,266, US20070190359, US20070190359, US20060008670; WO2006098460, US20110210316, WO 2012053627; U.S. Pat. No. 6,921,915, US20090039776; and JP2007123392.

Examples of suitable phosphorescent green emitters are shown below:

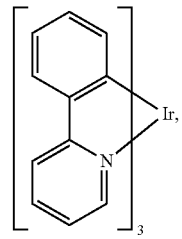 (GE-1)

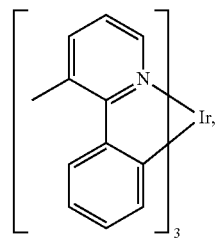 (GE-2)

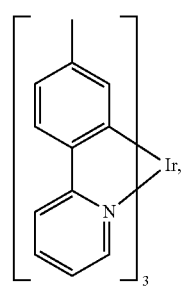 (GE-3)

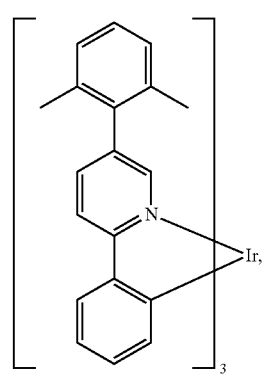 (GE-4)

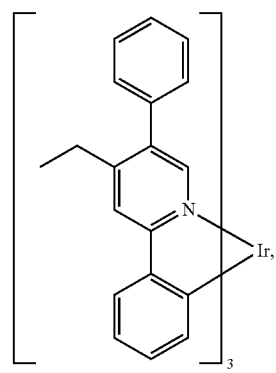 (GE-5)

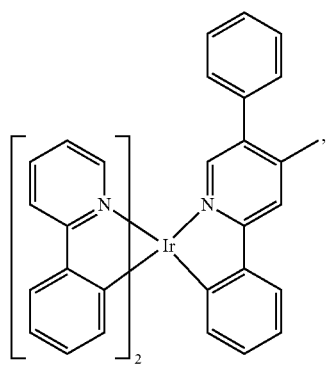
(GE-6)
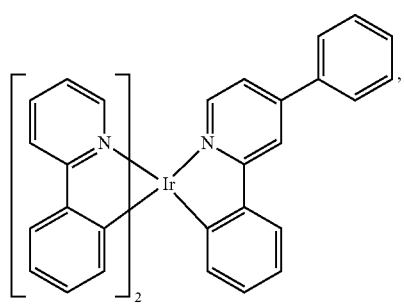
(GE-7)
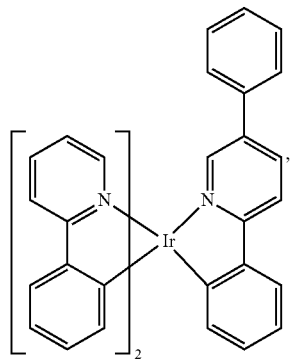
(GE-8)
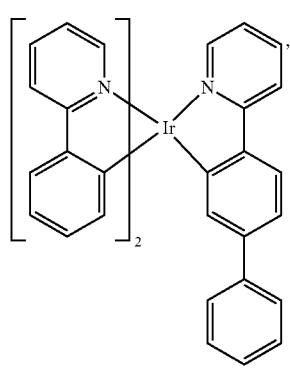
(GE-9)
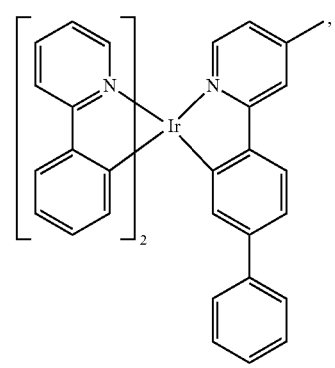
(GE-10)
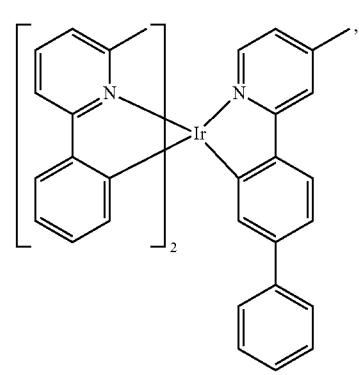
(GE-11)
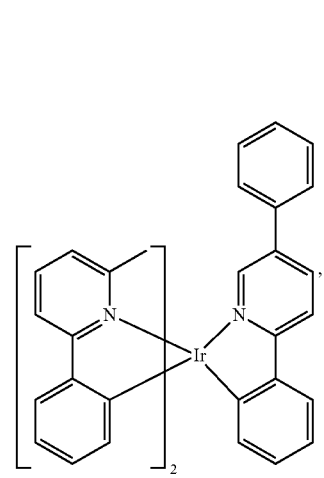
(GE-12)
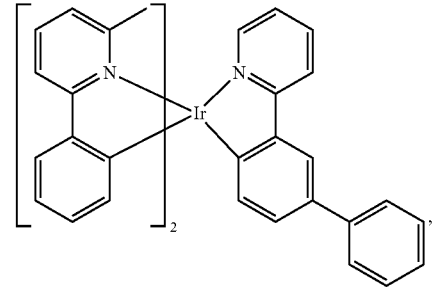
(GE-13)

(GE-14)
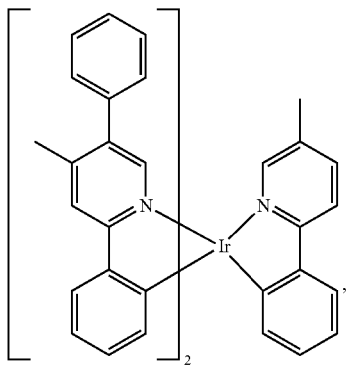
(GE-15)
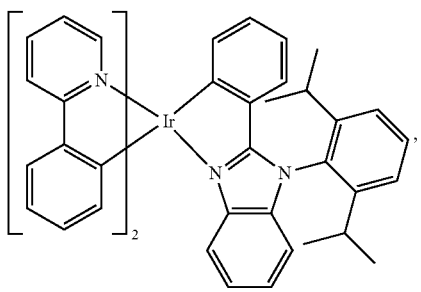
(GE-16)
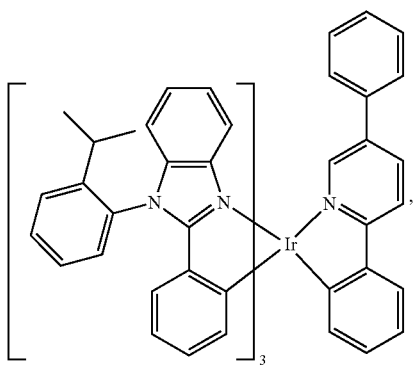
(GE-17)
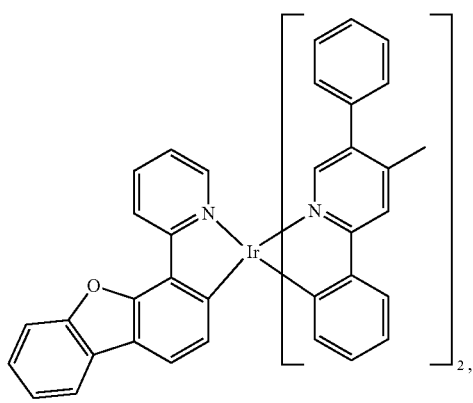
(GE-18)
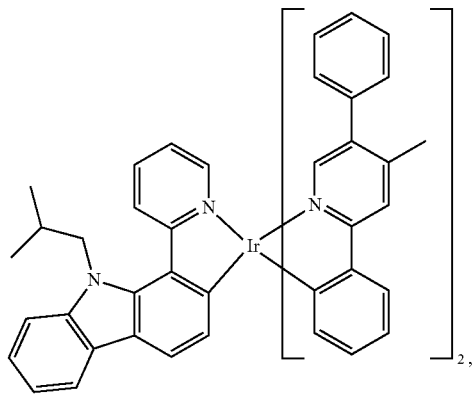
(GE-19)
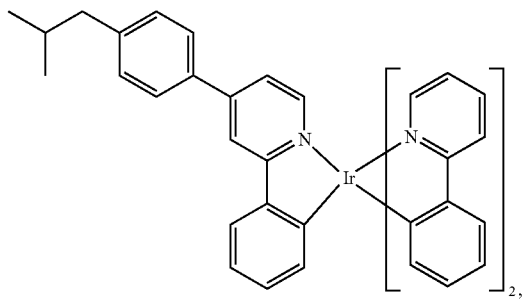
(GE-20)
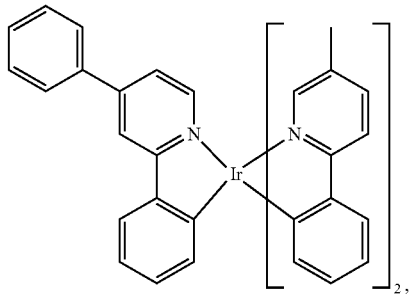
(GE-21)
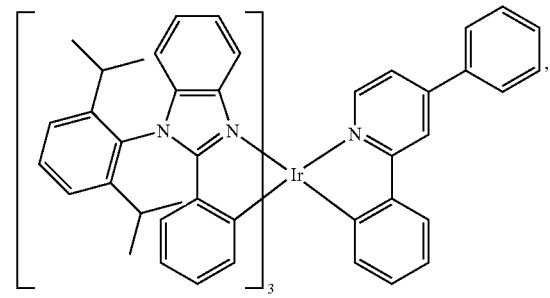

(GE-22)
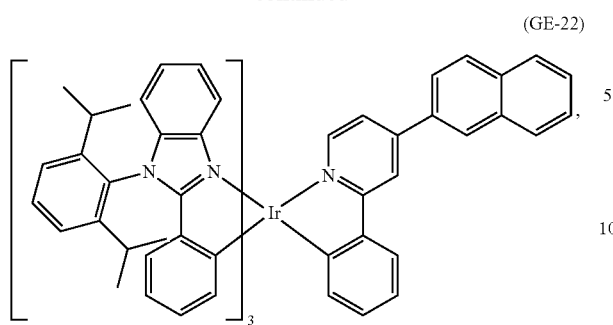
(GE-23)
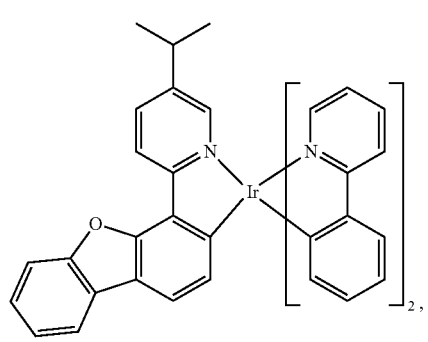
(GE-24)
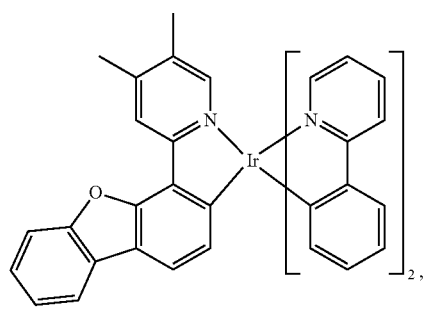
(GE-25)
(GE-26)
(GE-27)
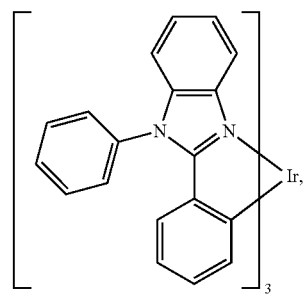
(GE-28)
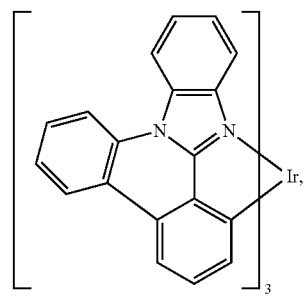
(GE-29)
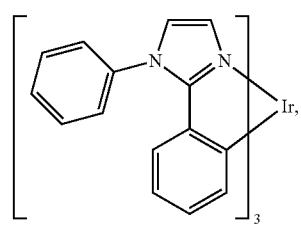
(GE-30)
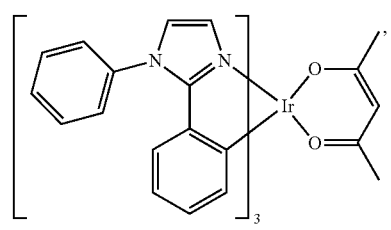
(GE-31)
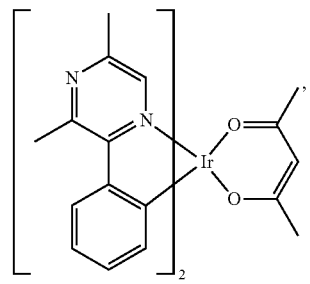
(GE-32)
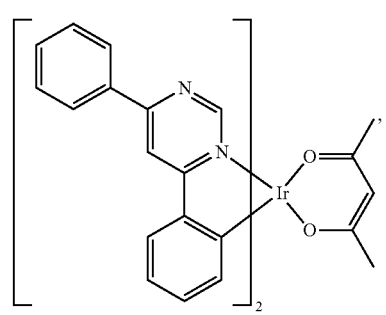

-continued (GE-33)

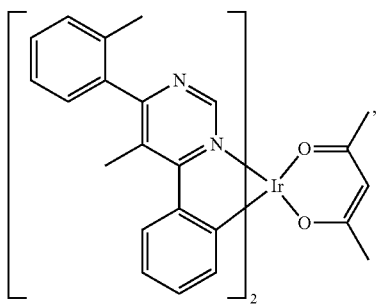

(GE-34)

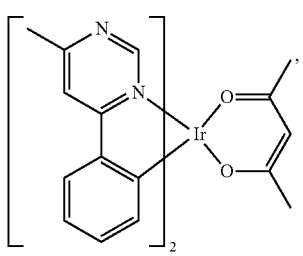

(GE-35)

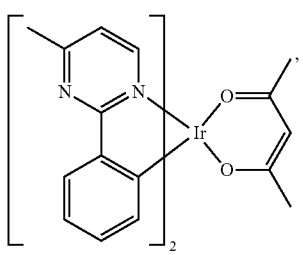

(GE-36)

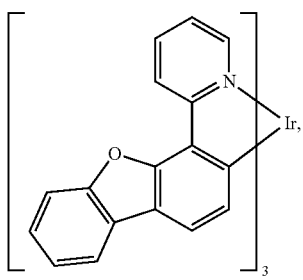

(GE-37)

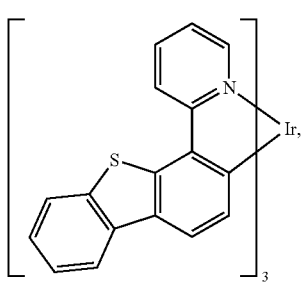

-continued (GE-38)

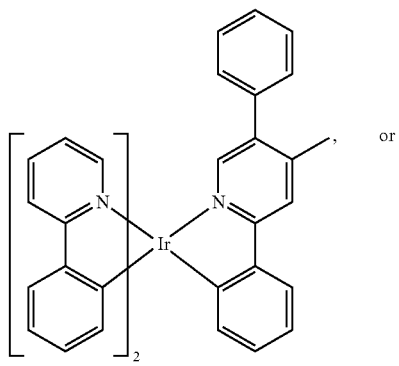

or (GE-39)


If a blocking layer for holes is present—hole blocker materials typically used in OLEDs, are, for example, as 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivates and 1,3,5-tris (N-phenyl-2-benzylimidazolyl)benzene) (TPBI), TPBI also being suitable as electron-conducting material. Further suitable hole blockers and/or electron conductor materials are 2,2',2''-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di (naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris (2,4,6-trimethyl-3-(pyridin-3-yl)phenyl)borane, 2,9-bis (naphthalene-2-yl)-4,7-diphenyl-1,10-phenanthroline, 1-methyl-2-(4-(naphthalene-2-yl)phenyl)-1H-imidazo[4,5-f][1,10]phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in WO2009/003919 and WO2009003898 and disilyl compounds as disclosed in WO2008/034758, as a blocking layer for holes/excitons (4) or as matrix materials in the light-emitting layer (3).

Suitable electron conductor materials for the layer (5) of the inventive OLEDs comprise metals chelated to oxinoid compounds, such as 2,2',2''-(1,3,5-phenylene)tris[1-phenyl-1H-benzimidazole] (TPBI), tris(8-quinolinolato)aluminum (Alq₃), compounds based on phenanthroline, such as 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), 8-hydroxyquinolinolatolithium (Liq), 4,7-diphenyl-1,10-phenanthroline (BPhen), bis(2-methyl-8-quinolinolato)-4-(phenylphenolato)aluminum (BAlq), 1,3-bis[2-(2,2'-bipyridin-6-yl)-1,3,4-oxadiazo-5-yl]benzene (Bpy-OXD), 6,6'-bis[5-(biphenyl-4-yl)-1,3,4-oxadiazo-2-yl]-2,2'-bipyridyl (BP-OXD-Bpy), 4-(naphthalen-1-yl)-3,5-diphenyl-4H-1,2,4-triazole (NTAZ), 2,9-bis(naphthalen-2-yl)-4,7-diphenyl-1,10-phenanthroline (NBphen), 2,7-bis[2-(2,2'-bipyridin-6-yl)-1,3,4-oxadiazo-5-yl]-9,9-dimethylfluorene (Bby-FOXD), 1,3-bis[2-(4-tert-butylphenyl)-1,3,4-oxadiazo-5-yl]benzene (OXD-7), tris(2,4,6-trimethyl-3-(pyridin-3-yl)phenyl)borane (3TPYMB), 1-methyl-2-(4-(naphthalen-2-yl)phenyl)-1H-imidazo[4,5-f][1,10]phenanthroline (2-NPIP), 2-phenyl-9,10-di(naphthalen-2-yl)anthracene (PADN), 2-(naphthalen-2-yl)-4,7-diphenyl-1,10-phenanthroline (HN-Bphen). The layer (5) may serve both to facilitate electron transport and as a buffer layer or barrier layer in order to prevent quenching of the exciton at the interfaces of the layers of the OLED. The layer (5) preferably improves the mobility of the electrons and reduces quenching of the exciton. In a preferred embodiment, TPBI is used as the electron conductor material. In another preferred embodiment, BCP is used as the electron conductor material. In principle, it is possible that the electron conductor layer comprises at least one compound of the formula I as electron conductor material.

The electron-transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233.

For example, it is possible to use mixtures which lead to electrical n-doping of the electron-transport layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, $Cs_2CO_3$, with alkali metal complexes, for example 8-hydroxyquinolatolithium (Liq), and with Y, Ce, Sm, Gd, Tb, Er, Tm, Yb, $Li_3N$, $Rb_2CO_3$, dipotassium phthalate, $W(hpp)_4$ from EP1786050, or with compounds described in EP1837926B1, EP1837927, EP2246862 and WO2010132236.

It is likewise possible to use mixtures of alkali metal hydroxyquinolate complexes, preferably Liq, and dibenzofuran compounds in the electron-transport layer. Reference is made to WO2011/157790. Dibenzofuran compounds A-1 to A-36 and B-1 to B-22 described in WO2011/157790 are preferred, wherein dibenzofuran compound

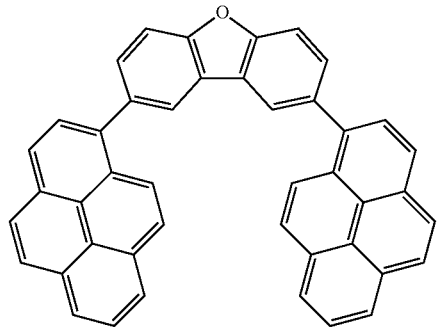

(A-10; = ETM-1)

is most preferred.

In a preferred embodiment, the electron-transport layer comprises Liq in an amount of 99 to 1% by weight, preferably 75 to 25% by weight, more preferably about 50% by weight, where the amount of Liq and the amount of the dibenzofuran compound(s), especially ETM-1, adds up to a total of 100% by weight.

It is likewise possible to use mixtures of alkali metal hydroxyquinolate complexes, preferably Liq, and pyridine compounds in the electron-transport layer. Reference is made to WO2011/157779. Particular preference is given to a pyridine compound of the formula

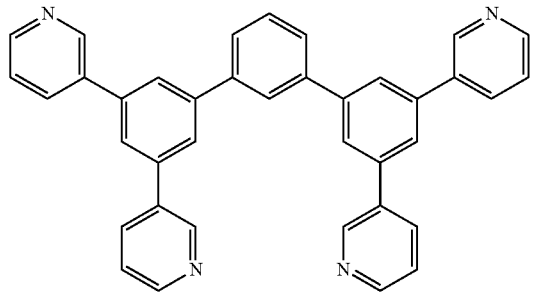

In a further preferred embodiment, the electron-transport layer comprises a compound described in WO2012/111462, WO2012/147397, WO2012014621, such as, for example, a compound of formula

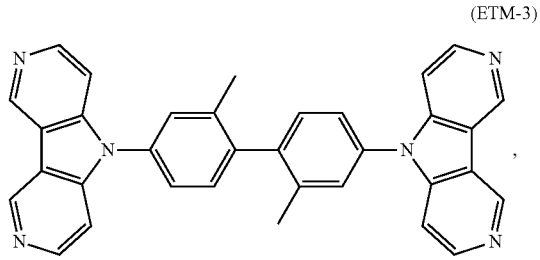 [SMILES: Cc1cc(-n2c3ccncc3c3cnccc32)ccc1-c1ccc(-n2c3ccncc3c3cnccc32)cc1C]

(ETM-3)

US2012/0261654, such as, for example, a compound of formula

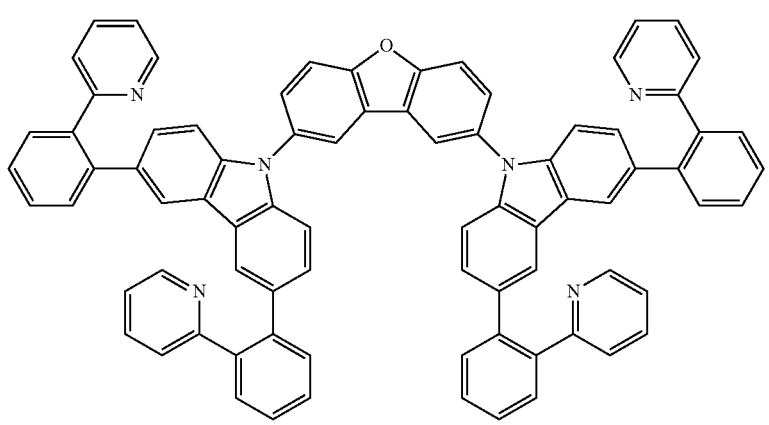

(ETM-4)

and WO2012/115034, such as for example, such as, for example, a compound of formula

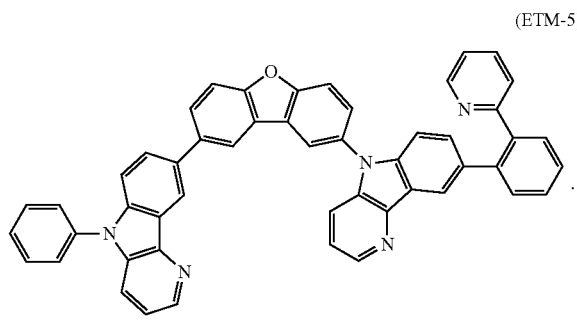

(ETM-5)

Among the materials mentioned above as hole conductor materials and electron conductor materials, some may fulfil several functions. For example, some of the electron-conducting materials are simultaneously hole-blocking materials when they have a low-lying HOMO. These can be used, for example, in the blocking layer for holes/excitons (4). However, it is likewise possible that the function as a hole/exciton blocker is also adopted by the layer (5), such that the layer (4) can be dispensed with.

The charge transport layers can also be electronically doped in order to improve the transport properties of the materials used, in order firstly to make the layer thicknesses more generous (avoidance of pinholes/short circuits) and in order secondly to minimize the operating voltage of the device. For example, the hole conductor materials can be doped with electron acceptors; for example, phthalocyanines or arylamines such as TPD or TDTA can be doped with tetrafluorotetracyanquinodimethane (F4-TCNQ) or with $MoO_3$ or $WO_3$. The electron conductor materials can be doped, for example, with alkali metals, for example $Alq_3$ with lithium. In addition, electron conductors can be doped with salts such as $Cs_2CO_3$, or 8-hydroxyquinolatolithium (Liq). Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo. Appl. Phys. Lett., Vol. 82, No. 25, 23 Jun. 2003 and Pfeiffer et al., Organic Electronics 2003, 4, 89-103. For example, the hole conductor layer may, in addition to a carbene complex, e.g. $Ir(dpbic)_3$, be doped with $MoO_3$ or $WO_3$. For example, the electron conductor layer may comprise BCP doped with $Cs_2CO_3$.

The cathode (6) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the periodic table of the elements (old IUPAC version), comprising the lanthanides and actinides, for example samarium. In addition, it is also possible to use metals such as aluminum or indium, and combinations of all metals mentioned. In addition, alkali metal, especially lithium-comprising organometallic compounds, or alkali metal fluorides, such as, for example, LiF, CsF, or KF can be applied between the organic layer and the cathode in order to reduce the operating voltage.

The OLED according to the present invention may additionally comprise further layers which are known to those skilled in the art. For example, a layer which facilitates the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to facilitate the transport of negative charge and/or to match the band gaps between the layers to one another. Alternatively, this layer may serve as a protective layer.

In a preferred embodiment, the inventive OLED, in addition to layers (1) to (6), comprises at least one of the following layers mentioned below:
 a hole injection layer between the anode (1) and the hole-transporting layer (2) having a thickness of 2 to 100 nm, preferably 5 to 50 nm;
 a blocking layer for electrons between the hole-transporting layer (2) and the light-emitting layer (3);
 an electron injection layer between the electron-transporting layer (5) and the cathode (6).

Materials for a hole injection layer may be selected from copper phthalocyanine, 4,4',4"-tris(N-3-methylphenyl-N-phenylamino)triphenylamine (m-MTDATA), 4,4',4"-tris(N-(2-naphthyl)-N-phenylamino)triphenylamine (2T-NATA), 4,4',4"-tris(N-(1-naphthyl)-N-phenylamino)triphenylamine (1T-NATA), 4,4',4"-tris(N,N-diphenylamino)triphenylamine (NATA), titanium oxide phthalocyanine, 2,3,5,6-tetrafluoro-7,7,8,8-tetracyanoquinodimethane (F4-TCNQ), pyrazino[2, 3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxy-phenyl)amino]-9,9-spirobifluorene (MeO-Spiro-TPD), 2,2'-bis[N,N-bis(4-methoxy-phenyl)amino]-9,9-spirobifluorene (2,2'-MeO-Spiro-TPD), N,N'-diphenyl-N,N'-di-[4-(N,N-ditolylamino)phenyl]benzidine (NTNPB), N,N'-diphenyl-N,N'-di-[4-(N,N-diphenylamino)phenyl]benzidine (NPNPB), N,N'-di(naphthalen-2-yl)-N,N'-diphenylbenzene-1,4-diamine ($\alpha$-NPP). In principle, it is possible that the hole injection layer comprises at least one compound of the formula I as hole injection material. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

The compound of formula I, especially the compound of formula (Ia), (Ib), (Ic), (Id), (Ie), (If), (Ii), (Ij), (Il), or (In), very especially a compound A-1 to A-65, B-1 to B-8, C-1 to C-65, D-1 to D-8, E-1 to E-65, or F-1 to F-65 can be used as electron/exciton blocker material. Suitable metal complexes for use as electron/exciton blocker material are, for example, carbene complexes as described in WO2005/019373A2, WO2006/056418A2, WO2005/113704, WO2007/115970, WO2007/115981 and WO2008/000727. One example of a suitable carbene complex is compound HTM-1.

As a material for the electron injection layer, LiF, for example, can be selected. In principle, it is possible that the electron injection layer comprises at least one compound of the formula I as electron injection material.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

In general, the different layers have the following thicknesses: anode (1) 50 to 500 nm, preferably 100 to 200 nm; hole-conducting layer (2) 5 to 100 nm, preferably 20 to 80 nm, light-emitting layer (3) 1 to 100 nm, preferably 10 to 80 nm, blocking layer for holes/excitons (4) 2 to 100 nm, preferably 5 to 50 nm, electron-conducting layer (5) 5 to 100 nm, preferably 20 to 80 nm, cathode (6) 20 to 1000 nm, preferably 30 to 500 nm. The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to those skilled in the art. It is possible that the electron-conducting layer and/or the hole-conducting layer have greater thicknesses than the layer thicknesses specified when they are electrically doped.

Use of the compounds of the formula I in at least one layer of the OLED, preferably in the light-emitting layer (preferably as a matrix material) and/or in the blocking layer for holes/excitons makes it possible to obtain OLEDs with high efficiency and with low use and operating voltage. Frequently, the OLEDs obtained by the use of the compounds of the formula I additionally have high lifetimes. The efficiency of the OLEDs can additionally be improved by optimizing the other layers of the OLEDs. For example, high-efficiency cathodes such as Ca or Ba, if appropriate in combination with an intermediate layer of LiF, can be used. Shaped substrates and novel hole-transporting materials which bring about a reduction in the operating voltage or an increase in the quantum efficiency are likewise usable in the inventive OLEDs. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

Example 1

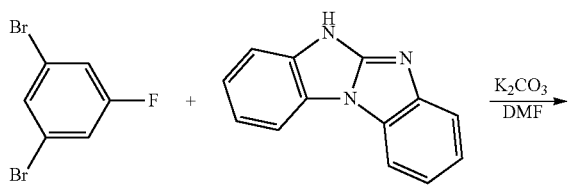

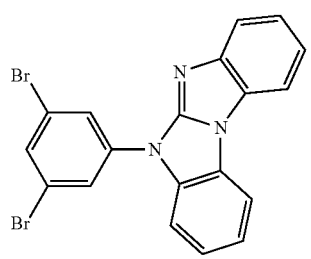

a) 20.0 g (78.8 mmol) of 1,3-dibromo-5-fluoro-benzene, 16.3 g (78.8 mmol) of 6H-benzimidazolo[1,2-a]benzimidazole and 43.5 g (0.315 mmol) of potassium carbonate in 200 ml of DMF are stirred for 17 h at 170° C. The reaction mixture is filtered hot and the precipitate from the mother liquor is filtered after cooling. The product is washed with water and ethanol and decocted with diethyl ether and ethanol. Yield 21.2 g (61%).

$^1$H NMR (400 MHz, CDCl$_3$): δ 8.00 (s, 2H); 7.90-7.80 (m, 3H); 7.77 (s, 1H); 7.60 (d, J=7.6 Hz, 1H); 7.45-7.30 (m, 4H).

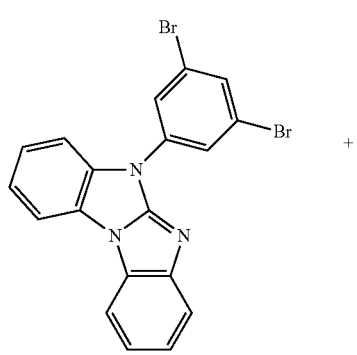

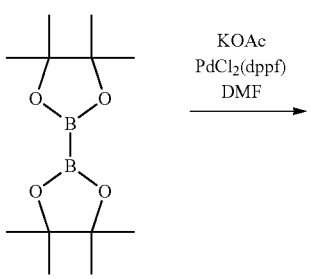

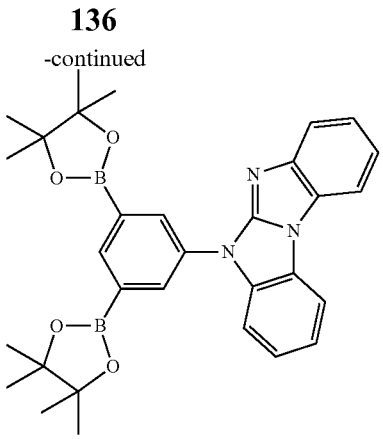

b) A mixture of 3.31 g (7.5 mmol) of the product of example 1a), 4.76 g (18.75 mmol) of 4,4,5,5-tetramethyl-2-(4,4,5,5-tetramethyl-1,3,2-dioxaborolan-2-yl)-1,3,2-dioxaborolane and 5.89 g (60 mmol) of potassium acetate is evacuated and flushed with argon 5 times. 40 ml of DMF are added and the mixture is evacuated and flushed. 428.7 mg (0.525 mmol) of 1,1'-bis(diphenylphosphino) ferrocene)dichloropalladium(II) are added under argon. The reaction mixture is heated to 65° C. and stirred for 3.5 hours, then cooled to room temperature and the solvent is removed at reduced pressure. The residue is solved in 120 ml of water and 120 ml of tert-butyl methyl ether (TBME), stirred for a few minutes and filtered. The phases are separated and the H$_2$O phase is extracted with TBME. The organic phases are dried and evaporated and then stirred with 50 ml of hot isopropanol for 15 minutes. The suspension is filtered, the residue washed with isopropanol and dried to yield 2.29 g. The filtrate is evaporated and crystallized in isopropanol to yield 319 mg. Total yield: 2.61 g (65%).

$^1$H NMR (400 MHz, CDCl$_3$): δ 8.38 (s, 1H); 8.26 (s, 2H); 7.89-7.77 (m, 3H); 7.43-7.28 (m, 5H); 1.37 (s, 12 H); 1.28 (s, 12 H).

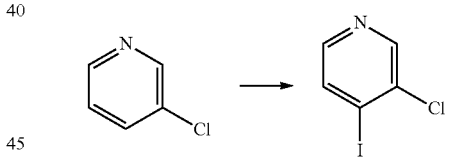

c) 3-chloro-4-iodo-pyridine is prepared starting from 3-chloro-pyridine in analogy to the procedure described by T. Jensen in Angew. Chem. Int. Ed. 47 (2008) 888 (yield: 52.9%).

$^1$H NMR (400 MHz, CDCl$_3$): δ 8.56 (s, 1H); 8.07 (d, J=4.8 Hz, 1H); 7.80 (d, J=4.8 Hz, 1H).

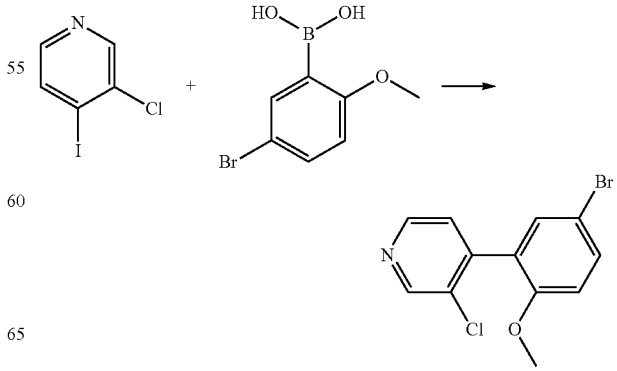

d) 11.1 g (46.35 mmol) of 3-chloro-4-iodo-pyridine, 10.17 g (44.03 mmol) of 5-bromo-2-methoxy-phenylboronic acid, 32.67 g (236.39 mmol) of potassium carbonate, 350 ml of toluene, 160 ml of ethanol and 88 ml of water are mixed and evacuated and flushed with argon four times. Then 2.68 g (2.31 mmol) of tetrakis triphenyl phosphine palladium are added and again evacuated and flushed with argon four times. The resulting clear mixture is heated to reflux for 3 h while stirring, then cooled to room temperature. The phases are separated and the aqueous phase extracted twice with toluene (200 ml each). The combined organic phases are washed three times with water (100 ml each), dried with magnesium sulfate, filtered and the solvent is evaporated on the rotavap. The crude product (16.07 g) is purified by flash chromatography using hexane/ethyl acetate as eluent yielding 10.94 g (83.2%) of 4-(4-bromo-2-methoxy-phenyl)-3-chloro-pyridine as a colorless oil that solidifies on standing.

$^1$H NMR (400 MHz, CDCl$_3$): δ 8.66 (s, 1H); 8.51 (d, J=4.8 Hz, 1H); 7.52 (dxd, J$_1$=8.8 Hz, J$_2$=2.4 Hz, 1H); 7.30 (d, J=2.4 Hz, 1H); 7.22 (d, J=4.8 Hz, 1H); 6.88 (d, J=8.8 Hz, 1H); 3.77 (s, 3H).

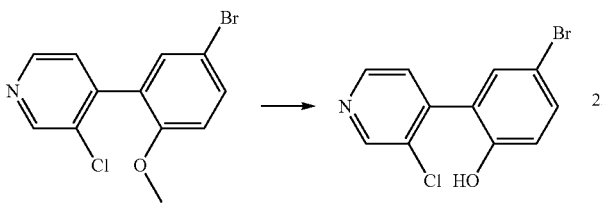

e) 10.94 g (36.64 mmol) of 4-(4-bromo-2-methoxy-phenyl)-3-chloro-pyridine are dissolved in 200 ml of dry dichloromethane. Within 20 min 145.9 ml (145.9 mmol) of a 1M boron tribromide solution in dichloromethane are added with a syringe while keeping the temperature at room temperature with a water bath. The cooling is removed and the solution stirred at room temperature for 18 h. Then 500 ml of water are added drop by drop. An exothermic reaction occurs and the mixture starts to reflux. The mixture is stirred for 30 minutes and then added to 200 ml of a buffer solution pH=7.2N NaOH solution is added until the pH reaches 7. Then 500 ml of ethyl acetate are added. The phases are separated and the aqueous phase extracted twice with ethyl acetate (250 ml each). The combined organic phases are washed three times with water (100 ml each), dried with magnesium sulfate, filtered and the solvent is evaporated on the rotavap to a volume of 100 ml. The suspension is cooled to 0° C. with an ice bath, filtered and the residue is washed three times with ice cold ethyl acetate (5 ml each). The product is dried at 50° C./125 mbar overnight, yielding 8.99 g (86.2%) of 5-bromo-2-(3-chloro-4-pyridyl)phenol.

$^1$H NMR (400 MHz, DMSO): δ 10.09 (s, 1H); 8.67 (s, 1H); 8.52 (d, J=4.8 Hz, 1H); 7.44 (d, J=2.8 Hz, 1H); 7.42 (d, J=2.8 Hz, 1H); 7.40 (d, J=4.8 Hz, 1H); 7.31 (d, J=2.8 Hz, 1H); 6.91 (d, J=8.8 Hz, 1H).

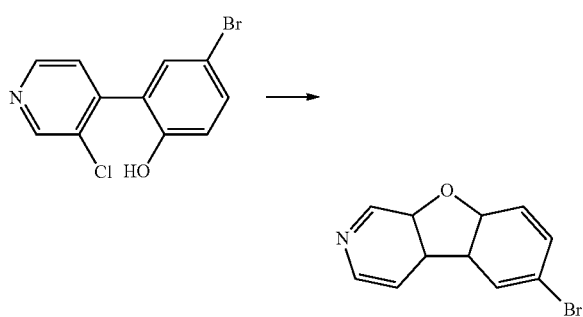

f) 7.85 g (27.59 mmol) of 5-bromo-2-(3-chloro-4-pyridyl)phenol are cyclized to 6-bromo-4a,4b,8a,9a-tetrahydrobenzofuro[2,3-c]pyridine using copper(I)-thiophene-2-carboxylate (CuTC) in analogy to the procedure described by J. Liu in J. Org. Chem. 73 (7), 2951 (2008) in 54.1% yield after flash chromatography using hexane/ethyl acetate 2:1 as eluent.

$^1$H NMR (400 MHz, CDCl$_3$): δ 9.00 (s, 1H); 8.61 (d, J=5.2 Hz, 1H); 8.16 (d, J=2.0 Hz, 1H); 7.85 (d, J=5.2 Hz, 1H); 7.71 (dxd, J$_1$=8.8 Hz, J$_2$=2.0 Hz, 1H); 7.54 (d, J=8.8 Hz, 1H).

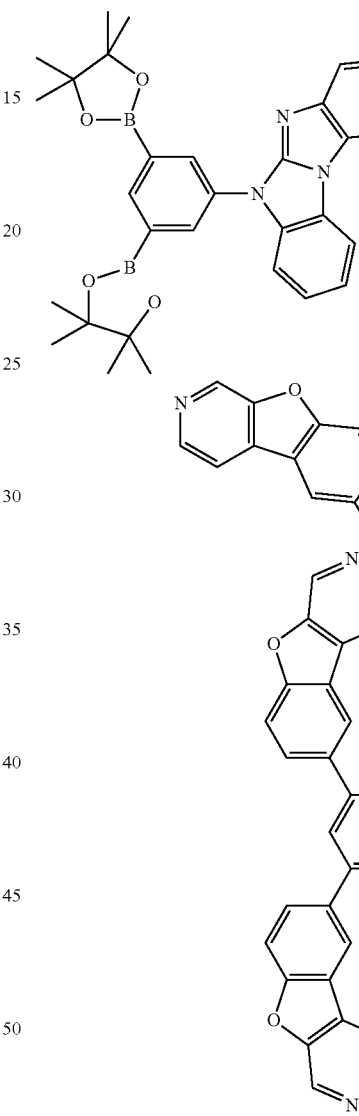

(E-57)

g) A mixture of 401.4 mg (0.75 mmol) of the product of example 1b) and 465.1 mg (1.875 mmol) of the product of example 1f) is evacuated and flushed with argon 3 times. 6 ml of tetrahydrofuran (THF) are added. 955.2 mg (4.5 mmol) of K$_3$PO$_4$ and 25 ml of water are bubbled with argon for 25 minutes in a separate flask. 13.1 mg (0.045 mmol) of tris t-butylphosphonium tetrafluoroborat and 20.6 mg (0.023 mmol) of Pd$_2$(dba)$_3$ are added to the mixture of the starting materials in THF, bubbled with argon for 3 minutes and then heated to 50° C. The K$_3$PO$_4$ solution is added in one portion with a syringe and the reaction mixture is heated at a bath temperature of 75° C. for 4 hours. The reaction mixture is cooled to room temperature and 20 ml of water are added. THF is evaporated, the reaction mixture is filtered, the residue washed with water and methanol and dried. The crude product is stirred in 100 ml of CHCl₃ for 30 minutes, filtered through Hyflo and washed with CHCl₃. The filtrate is evaporated and then stirred in 8 ml of hot CHCl₃, filtered, the residue washed with CHCl₃ and dried. Yield: 407.6 mg (88%)

$^1$H NMR (400 MHz, CDCl₃): δ 9.05 (s, 2H); 8.63 (d, J=5.2 Hz, 2H); 8.37 (s, 2H); 8.15 (s, 2H); 8.03-7.98 (m, 3H); 7.94 (d, J=5.2 Hz, 2H); 7.89 (d, J=7.6 Hz, 2H); 7.82-7.75 (m, 3H); 7.66 (d, J=8 Hz, 1H); 7.46-7.32 (m, 4H)

Example 2

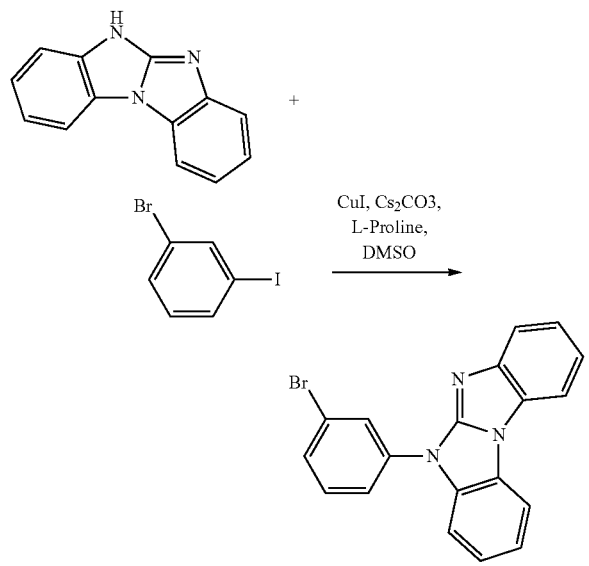

a) 7.78 g (25.0 mmol) of 1-bromo-3-iodo-benzene, 16.3 g (50.0 mmol) of caesium carbonate, 1.24 g (6.50 mmol) of copper(I) iodide and 1.50 g (13.0 mmol) of L-proline are added to 5.18 g (25.0 mmol) of 5H-benzimidazo[1,2-a]benzimidazole in 100 ml of dimethylsulfoxide (DMSO) under nitrogen. The reaction mixture is stirred for 18 h at 100° C. and then poured into water. The water phase is extracted with dichloromethane and dried with magnesium sulfate. The solvent is distilled off. Column chromatography on silica gel with toluene gives the product in a yield of 8.35 g (92%).

$^1$H NMR (400 MHz, CDCl₃): δ 8.25 (s, 1H); 8.05-7.90 (m, 3H); 7.71 (d, J=7.9 Hz, 1H); 7.65 (d, J=7.9 Hz, 1H); 7.65-7.50 (m, 2H); 7.45-7.26 (m, 4H).

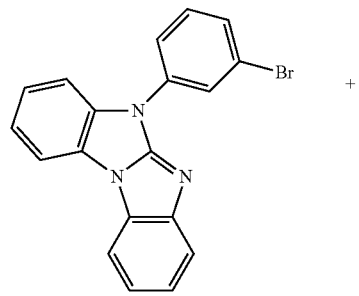

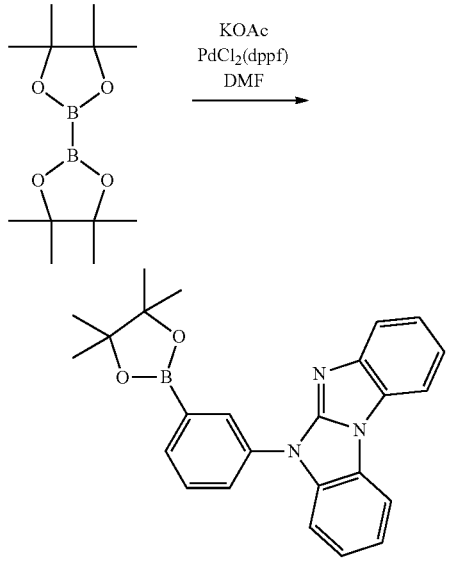

b) 1.0 g (2.73 mmol) of product of example 2a), 831.2 mg (3.27 mmol) of 4,4,5,5-tetramethyl-2-(4,4,5,5-tetramethyl-1,3,2-dioxaborolan-2-yl)-1,3,2-dioxaborolane, 1.61 g (16 mmol) of potassium acetate and 25 ml of DMF are evacuated and flushed with argon 5 times. 111.4 mg (0.136 mmol) of 1,1'-bis(diphenylphosphino) ferrocene)dichlorpalladium (II) are added, the reaction mixture is evacuated and flushed with argon 5 times. The reaction mixture is stirred for 20 h at 60° C., cooled to room temperature and then evaporated at reduced pressure. 50 ml of water, 50 ml of TBME and 3 ml of a solution of 1% NaCN in water are added, the mixture stirred for 30 minutes, filtered and washed with 100 ml of ethyl acetate. The phases are separated, the water phase extracted with ethyl acetate and the organic phases are dried and evaporated. Yield: 0.8 g (72%)

$^1$H NMR (400 MHz, THF-d8): δ 8.26 (s, 1H), 8.10-8.09 (m, 1H), 8.09-8.07 (m, 2H), 7.86 (d, J=7.6 Hz, 1H), 7.67-7.60 (m, 3H), 7.42-7.28 (m, 4H), 1.39 (s, 12H).

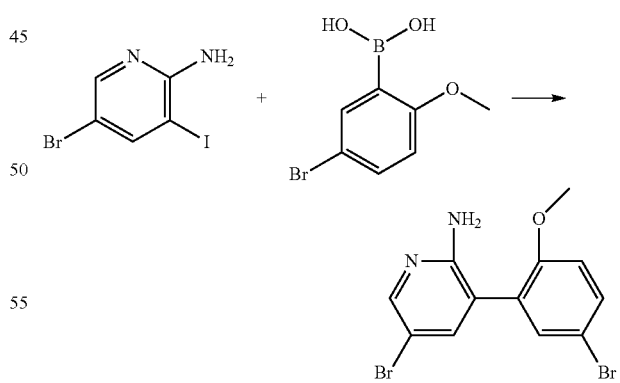

c) 13.92 g (46.56 mmol) of 2-amino-3-iodo-5-bromopyridine, 11.71 g (50.75 mmol) of 5-bromo-2-methoxy-phenylboronic acid, 32.82 g (237.44 mmol) of potassium carbonate, 700 ml of toluene, 280 ml of ethanol and 175 ml of water are mixed and evacuated and flushed with argon four times. Then 5.38 g (4.66 mmol) of tetrakis triphenyl phosphine palladium are added. The mixture is heated to reflux for 2.5 hours while stirring, then cooled to room temperature. The phases are separated and the aqueous phase extracted twice with toluene (250 ml each). The combined organic phases are washed three times with water (100 ml each), dried with magnesium sulfate, filtered and the solvent is evaporated on the rotavap. The crude product (16.8 g) is purified by flash chromatography using heptane/ethyl acetate as eluent yielding 12.4 g (74%) of 5-bromo-3-(5-bromo-2-methoxyphenyl)pyridine-2-amine.

$^1$H NMR (400 MHz, CDCl$_3$): δ 8.07 (s, 1H); 7.54-7.51 (m, 2H); 7.36 (s, 1H); 6.90 (d, J=8.8 Hz, 1H); 5.10 (s, 2H); 3.82 (s, 3H)

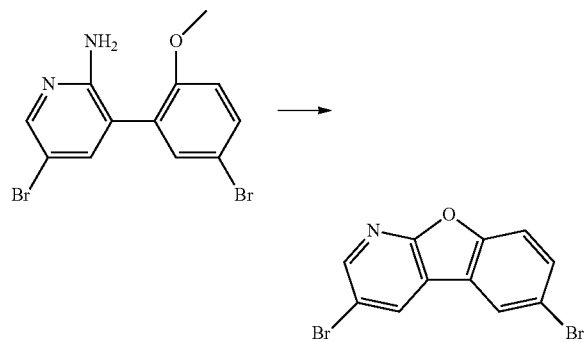

d) A solution of 12.4 g (35 mmol) of 5-bromo-3-(5-bromo-2-methoxyphenyl)pyridine-2-amine in 170 ml of THF and 430 ml of glacial acetic acid is cooled to 0° C. and 7.14 g (69 mmol) of tert-butyl nitrite is added tropwise. The reaction mixture is stirred over night at 0° C., warmed to room temperature, poured on 800 ml of ice water and stirred for one hour. The yellow suspension is filtered, washed with ice water and dried to yield 8.5 g (75%) of pure product.

$^1$H NMR (400 MHz, CDCl$_3$): δ 8.55 (s, 1H); 8.40 (s, 1H); 8.10 (s, 1H); 7.70 (d, J=8.7 Hz, 1H); 7.60 (d, J=8.7 Hz, 1H)

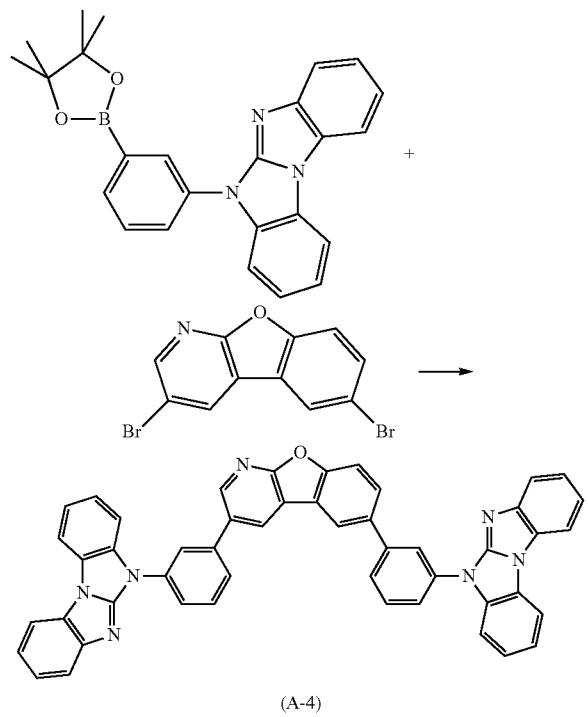

(A-4)

e) A mixture of 267.3 mg (0.818 mmol) of the product of example 2d), 702.7 mg (1.72 mmol) of the product of example 2b), 576.2 mg (4.17 mmol) of K$_2$CO$_3$, 50 ml of toluene, 25 ml of ethanol and 11 ml of water is evacuated and flushed with argon 5 times. 47.2 mg (0.041 mmol) of tetrakis triphenyl phosphine palladium are added and the reaction mixture is heated to reflux for 18 hours. 10 ml of a solution of 2% of NaCN in water are added and the reaction mixture is cooled to room temperature. 50 ml of water and 50 ml of toluene are added, the suspension stirred for 15 minutes, filtered, washed with toluene/water and dried. Yield: 330 mg (55%) of yellow crystals.

$^1$H NMR (400 MHz, DMSO): δ 9.15 (d, J=3.2 Hz, 1H); 8.93 (d, J=3.2 Hz, 1H); 8.73 (d, J=2.0 Hz, 1H); 8.40-8.14 (m, 6H); 8.10-7.56 (m, 12H); 7.53-7.13 (m, 8H).

Application Example 1

The ITO substrate used as the anode is first cleaned with an acetone/isopropanol mixture in an ultrasound bath. To eliminate any possible organic residues, the substrate is exposed to a continuous ozone flow in an ozone oven for further 25 minutes. This treatment also improves the hole injection properties of the ITO. Then Plexcore® OC AJ20-1000 (commercially available from Plextronics Inc.) is spin-coated and dried to form a hole injection layer (~40 nm).

Thereafter, the organic materials specified below are applied by vapor deposition to the clean substrate at a rate of approx. 0.5-5 nm/min at about 10$^{-7}$-10$^{-9}$ mbar. As a hole transport and exciton blocker,

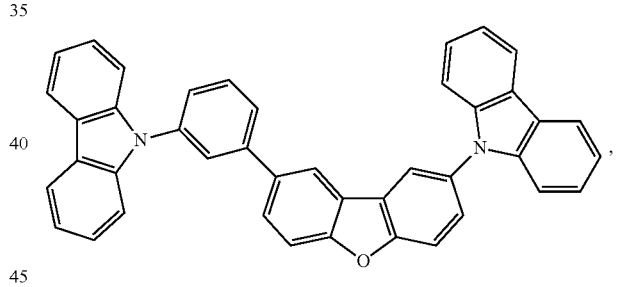

is applied to the substrate with a thickness of 20 nm, wherein the first 10 nm are doped with MoO$_x$ (~10%) to improve the conductivity.

Subsequently, a mixture of 10% by weight of emitter compound,

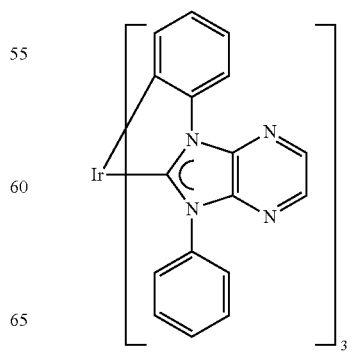

and 90% by weight compound

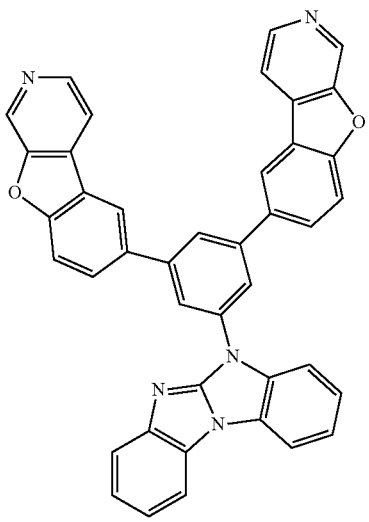

(E-57)

is applied by vapor deposition in a thickness of 40 nm. Compound (E-57) is deposited then with 5 nm thickness as the blocker. Thereafter, a 20 nm thick electron transport layer is deposited consisting of 50% by weight of

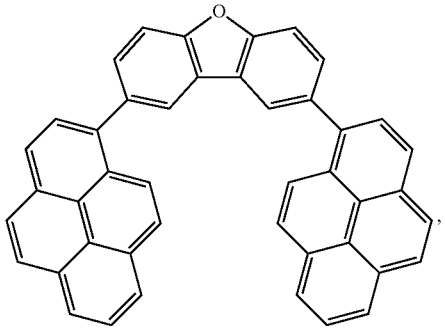 [SMILES: c1cc2ccc3ccc(-c4ccc5oc6ccc(-c7ccc8ccc9cccc%10ccc7c8c9%10)cc6c5c4)c4ccc(c1)c2c34]

and of 50% of

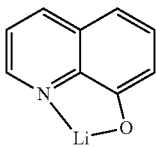

(Liq). Finally a 2 nm KF layer serves as an electron injection layer and a 100 nm-thick Al electrode completes the device.

All fabricated parts are sealed with a glass lid and a getter in an inert nitrogen atmosphere.

To characterize the OLED, electroluminescence spectra are recorded at various currents and voltages. In addition, the current-voltage characteristic is measured in combination with the light output emitted. The light output can be converted to photometric parameters by calibration with a photometer.

| | Voltage @ 300 nits [V] | EQE[1] @ 300 nits [%] | CIE |
|---|---|---|---|
| Appl. Ex. 1 | 3.66 V | 10.99% | 0.18/0.35 |

[1] External quantum efficiency (EQE) is # of generated photons escaped from a substance or a device/# of electrons flowing through it.

Application Example 2

92% by weight of compound

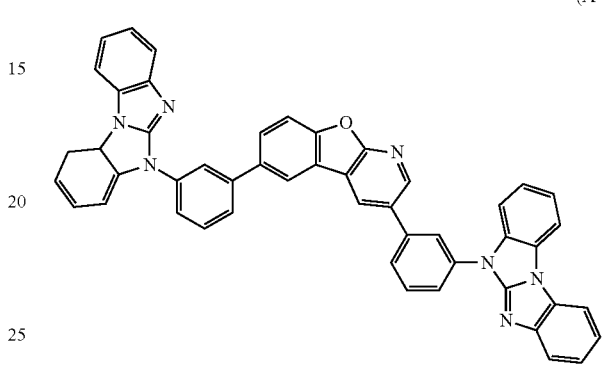

(A-4)

and 8% by weight of compound

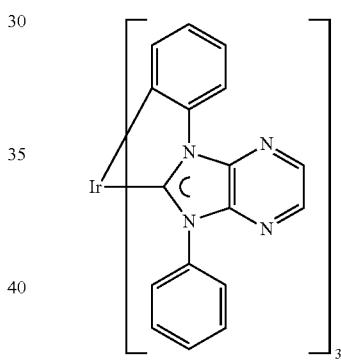

are applied by vapor deposition to a quartz substrate at a rate of approx. 0.5-5 nm/min at about $10^{-7}$-$10^{-9}$ mbar with a thickness of 80 nm.

The PL spectrum and the PL quantum efficiency are measured using an absolute quantum-yield measurement system "Quantaurus" (from Hamamatsu, Japan) at room temperature at an excitation wavelength of 370 nm.

| | PLQE [%] | CIE |
|---|---|---|
| Appl. Ex. 2 | 54.0% | 0.17/0.37 |

The invention claimed is:
1. A compound of the formula

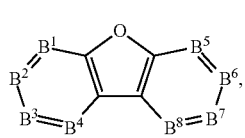

(I)

wherein
- $B^1$ is N, or $CR^{81}$,
- $B^2$ is N, or $CR^{82}$,
- $B^3$ is N, or $CR^{83}$,
- $B^4$ is N, or $CR^{84}$,
- $B^5$ is N, or $CR^{85}$,
- $B^6$ is N, or $CR^{86}$,
- $B^7$ is N, or $CR^{87}$,
- $B^8$ is N, or $CR^{88}$,
- $R^{81}$, $R^{82}$, $R^{83}$, $R^{84}$, $R^{85}$, $R^{86}$, $R^{87}$ and $R^{88}$ are independently of each other H, a $C_1$-$C_{25}$ alkyl group, which can optionally be substituted by E and or interrupted by D; a $C_6$-$C_{24}$ alkyl group, which can optionally be substituted by G, a $C_2$-$C_{30}$ heteroaryl group, which can optionally be substituted by G; or a group of formula -$(A^1)_o$-$(A^2)_p$-$(A^3)_q$-$(A^4)_r$-$R^{16}$,
- o is 0, or 1, p is 0, or 1, q is 0, or 1, r is 0, or 1,
- $A^1$, $A^2$, $A^3$ and $A^4$ are independently of each other a $C_6$-$C_{24}$ arylene group, which can optionally be substituted by G, or a $C_2$-$C_{30}$ heteroarylene group, which can optionally be substituted by G;
- $R^{16}$ is —$NR^{10}R^{11}$, or —$Si(R^{12})(R^{13})(R^{14})$, a $C_6$-$C_{24}$ aryl group, which can optionally be substituted by G; or a $C_2$-$C_{30}$ heteroarylene group, which can optionally be substituted by G;
- $R^{10}$ and $R^{11}$ are independently of each other a $C_6$-$C_{24}$ aryl group, which can optionally be substituted by G; or a $C_2$-$C_{30}$ heteroaryl group, which can optionally be substituted by G;
- $R^{12}$, $R^{13}$ and $R^{14}$ are independently of each other a $C_1$-$C_{25}$ alkyl group, which can optionally be substituted by E and or interrupted by D; $C_6$-$C_{24}$ aryl group, which can optionally be substituted by G; or a $C_2$-$C_{30}$ heteroaryl group, which can optionally be substituted by G;
- D is —CO—, —COO—, —S—, —SO—, —$SO_2$—, —O—, —$NR^{65}$—, —$SiR^{70}R^{71}$—, —$POR^{72}$—, —$CR^{63}$=$CR^{64}$—, or —C≡C—,
- E is —$OR^{69}$, —$SR^{69}$, —$NR^{65}R^{66}$, —$COR^{68}$, —$COOR^{67}$, —$CONR^{65}R^{66}$, —CN, or F,
- G is E, or a $C_1$-$C_{18}$ alkyl group, a $C_6$-$C_{24}$ aryl group, a $C_6$-$C_{24}$ aryl group, which is substituted by F, $C_1$-$C_{18}$ alkyl, or $C_1$-$C_{18}$ alkyl which is interrupted by O; a $C_2$-$C_{30}$ hereroaryl group, or a $C_2$-$C_{30}$ heteroaryl group, which is substituted by F, $C_1$-$C_{18}$ alkyl, or $C_1$-$C_{18}$ alkyl which is interrupted by —O—;
- $R^{63}$ and $R^{64}$ are independently of each other H, $C_6$-$C_{18}$ aryl; $C_6$-$C_{18}$ aryl which is substituted by $C_1$-$C_{18}$ alkyl, or $C_1$-$C_{18}$ alkoxy; $C_1$-$C_{18}$ alkyl; or $C_1$-$C_{18}$ alkyl which is interrupted by —O—;
- $R^{65}$ and $R^{66}$ are independently of each other a $C_6$-$C_{18}$ aryl group; a $C_6$-$C_{18}$ aryl which is substituted by $C_1$-$C_{18}$ alkyl, or $C_1$-$C_{18}$ alkoxy; a $C_1$-$C_{18}$ alkyl group; or a $C_1$-$C_{18}$ alkyl group, which is interrupted by —O—; or
- $R^{65}$ and $R^{66}$ together fonn a five or six membered ring,
- $R^{67}$ is a $C_6$-$C_{18}$ aryl group; a $C_6$-$C_{18}$ aryl group, which is substituted by $C_1$-$C_{18}$ alkyl, or $C_1$-$C_{18}$ alkoxy; a $C_1$-$C_{18}$ alkyl group; or a $C_1$-$C_{18}$ alkyl group, which is interrupted by —O—,
- $R^{68}$ is H; n a $C_6$-$C_{18}$ aryl group; a $C_6$-$C_{18}$ aryl group, which is substituted by $C_1$-$C_{18}$ alkyl, or $C_1$-$C_{18}$ alkoxy; a $C_1$-$C_{18}$ alkyl group; or a $C_1$-$C_{18}$ alkyl group, which is interrupted by —O—,
- $R^{69}$ is a $C_6$-$C_{18}$ aryl; a $C_6$-$C_{18}$ aryl, which is substituted by $C_1$-$C_{18}$ alkyl, or $C_1$-$C_{18}$ alkoxy, a $C_1$-$C_{18}$ alkyl group; or a $C_1$-$C_{18}$ alkyl group, which is interrupted by —O—,
- $R^{70}$ and $R^{71}$ are independently of each other a $C_1$-$C_{18}$ alkyl group, a $C_6$-$C_{18}$ aryl group, or a $C_6$-$C_{18}$ aryl group, which is substituted by $C_1$-$C_{18}$ alkyl, and
- $R^{72}$ is a $C_1$-$C_{18}$ alkyl group, a $C_6$-$C_{18}$ aryl group, or a $C_6$-$C_{18}$ aryl group, which is substituted by $C_1$-$C_{18}$ alkyl, with the proviso that
- at least one of the substituents $B^1$, $B^2$, $B^3$, $B^4$, $B^5$, $B^6$, $B^7$ and $B^8$ represents N;
- not more than two of the groups $B^1$, $B^2$, $B^3$ and $B^4$ represent N; and
- not more than two of the groups $B^5$, $B^6$, $B^7$ and $B^8$ represent N; and
- with the further proviso that at least one of the substituents $R^{81}$, $R^{82}$, $R^{83}$, $R^{84}$, $R^{85}$, $R^{86}$, $R^{87}$ and $R^{88}$ represent a group of formula -$(A^1)_o$-$(A^2)_p$-$(A^3)_q$-$(A^4)_r$-$R^{16}$, wherein $R^{16}$ represents a benzimidazo[1,2-a]benzimidazo-5-yl group, which can optionally be substituted by G; and/or at least one of the groups $A^1$, $A^2$, $A^3$ and $A^4$ represents a benzimidazo[1,2-a]benzimidazo-2,5-ylene group, which can optionally be substituted by G.

2. The compound according to claim 1, which is a compound of formula

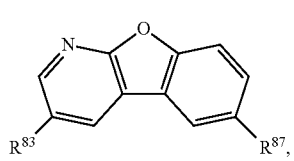
(Ia)

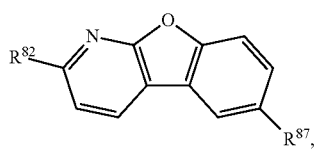
(Ib)

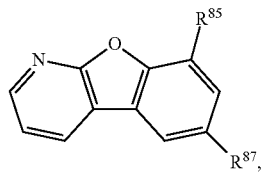
(Ic)

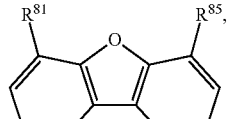
(Id)

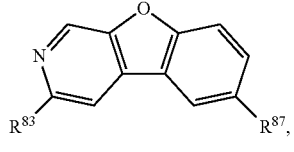
(Ie)

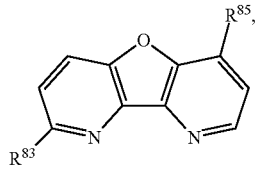
(If)

-continued

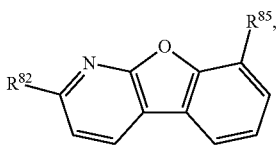 (Ig)

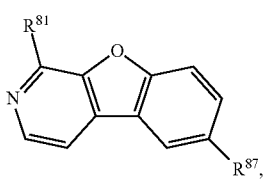 (Ih)

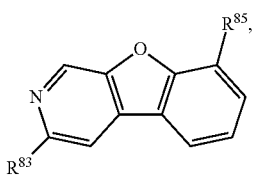 (Ii)

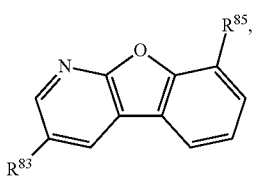 (Ij)

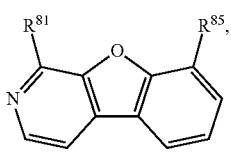 (Ik)

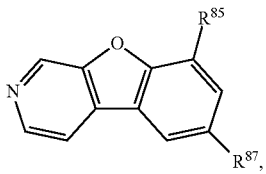 (Il)

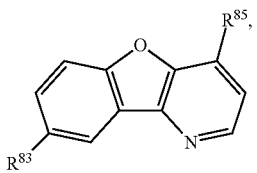 (Im)

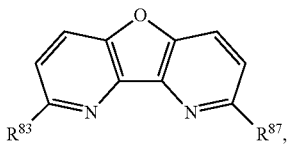 (In)

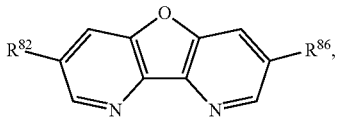 (Io)

wherein $R^{81}$, $R^{82}$, $R^{83}$, $R^{85}$, $R^{86}$ and $R^{87}$ are as defined in claim 1.

3. The compound according to claim 2, wherein
in the compounds of formula (Ia)
$R^{83}$ is a group of the formula -$(A^1)_o$-$(A^2)_p$-$(A^3)_q$-$(A^4)_r$-$R^{16}$; and
$R^{87}$ is H, or a group of the formula -$(A^1)_o$-$(A^2)_p$-$(A^3)_q$-$(A^4)_r$-$R^{16'}$; or
$R^{83}$ is H, or a group of the formula -$(A^1)_o$-$(A^2)_p$-$(A^3)_q$-$(A^4)_r$-$R^{16'}$; and
$R^{87}$ is a group of the formula -$(A^1)_o$-$(A^2)_p$-$(A^3)_q$-$(A^4)_r$-$R^{16}$;
in the compounds of formula (Ib)
$R^{82}$ is a group of the formula -$(A^1)_o$-$(A^2)_p$-$(A^3)_q$-$(A^4)_r$-$R^{16}$; and
$R^{87}$ is H, or a group of the formula -$(A^1)_o$-$(A^2)_p$-$(A^3)_q$-$(A^4)_r$-$R^{16'}$; or
$R^{82}$ is H, or a group of the formula -$(A^1)_o$-$(A^2)_p$-$(A^3)_q$-$(A^4)_r$-$R^{16'}$; and
$R^{87}$ is a group of the formula -$(A^1)_o$-$(A^2)_p$-$(A^3)_q$-$(A^4)_r$-$R^{16}$;
in the compounds of formula (Ic)
$R^{85}$ is a group of the formula -$(A^1)_o$-$(A^2)_p$-$(A^3)_q$-$(A^4)_r$-$R^{16}$; and
$R^{87}$ is H, or a group of the formula -$(A^1)_o$-$(A^2)_p$-$(A^3)_q$-$(A^4)_r$-$R^{16'}$; or
$R^{85}$ is H, or a group of the formula -$(A^1)_o$-$(A^2)_p$-$(A^3)_q$-$(A^4)_r$-$R^{16'}$; and
$R^{87}$ is a group of the formula -$(A^1)_o$-$(A^2)_p$-$(A^3)_q$-$(A^4)_r$-$R^{16}$;
in the compounds of formula (Id)
$R^{81}$ is a group of the formula -$(A^1)_o$-$(A^2)_p$-$(A^3)_q$-$(A^4)_r$-$R^{16}$; and
$R^{85}$ is H, or a group of the formula -$(A^1)_o$-$(A^2)_p$-$(A^3)_q$-$(A^4)_r$-$R^{16'}$; or
$R^{81}$ is H, or a group of the formula -$(A^1)_o$-$(A^2)_p$-$(A^3)_q$-$(A^4)_r$-$R^{16'}$; and
$R^{85}$ is a group of the formula -$(A^1)_o$-$(A^2)_p$-$(A^3)_q$-$(A^4)_r$-$R^{16}$;
the compounds of formula (Ie)
$R^{83}$ is a group of the formula -$(A^1)_o$-$(A^2)_p$-$(A^3)_q$-$(A^4)_r$-$R^{16}$; and
$R^{87}$ is H, or a group of the formula -$(A^1)_o$-$(A^2)_p$-$(A^3)_q$-$(A^4)_r$-$R^{16'}$; or
$R^{83}$ is H, or a group of the formula -$(A^1)_o$-$(A^2)_p$-$(A^3)_q$-$(A^4)_r$-$R^{16'}$; and
$R^{87}$ is a group of the formula -$(A^1)_o$-$(A^2)_p$-$(A^3)_q$-$(A^4)_r$-$R^{16}$;
in the compounds of formula (If)
$R^{83}$ is a group of the formula -$(A^1)_o$-$(A^2)_p$-$(A^3)_q$-$(A^4)_r$-$R^{16}$; and
$R^{85}$ is H, or a group of the formula -$(A^1)_o$-$(A^2)_p$-$(A^3)_q$-$(A^4)_r$-$R^{16'}$; or
$R^{83}$ is H, or a group of the formula -$(A^1)_o$-$(A^2)_p$-$(A^3)_q$-$(A^4)_r$-$R^{16'}$; and
$R^{85}$ is a group of the formula -$(A^1)_o$-$(A^2)_p$-$(A^3)_q$-$(A^4)_r$-$R^{16}$;
in the compounds of formula (Ig)
$R^{82}$ is a group of the formula -$(A^1)_o$-$(A^2)_p$-$(A^3)_q$-$(A^4)_r$-$R^{16}$; and
$R^{85}$ is H, or a group of the formula -$(A^1)_o$-$(A^2)_p$-$(A^3)_q$-$(A^4)_r$-$R^{16'}$; or
$R^{82}$ is H, or a group of the formula -$(A^1)_o$-$(A^2)_p$-$(A^3)_q$-$(A^4)_r$-$R^{16'}$; and
$R^{85}$ is a group of the formula -$(A^1)_o$-$(A^2)_p$-$(A^3)_q$-$(A^4)_r$-$R^{16}$;
in the compounds of formula (Ih)
$R^{81}$ is a group of the formula -$(A^1)_o$-$(A^2)_p$-$(A^3)_q$-$(A^4)_r$-$R^{16}$; and $R^{87}$ is H, or a group of the formula -$(A^1)_o$-$(A^2)_p$-$(A^3)_q$-$(A^4)_r$-$R^{16'}$; or $R^{81}$ is H, or a group of the formula -$(A^1)_o$-$(A^2)_p$-$(A^3)_q$-$(A^4)_r$-$R^{16'}$; and $R^{87}$ is a group of the formula -$(A^1)_o$-$(A^2)_p$-$(A^3)_q$-$(A^4)_r$-$R^{16}$;

the compounds of formula (Ii)

$R^{83}$ is a group of the formula -$(A^1)_o$-$(A^2)_p$-$(A^3)_q$-$(A^4)_r$-$R^{16}$; and $R^{85}$ is H, or a group of the formula -$(A^1)_o$-$(A^2)_p$-$(A^3)_q$-$(A^4)_r$-$R^{16'}$; or $R^{83}$ is H, or a group of the formula -$(A^1)_o$-$(A^2)_p$-$(A^3)_q$-$(A^4)_r$-$R^{16'}$; and $R^{85}$ is a group of the formula -$(A^1)_o$-$(A^2)_p$-$(A^3)_q$-$(A^4)_r$-$R^{16}$;

in the compounds of formula (Ij)

$R^{83}$ is a group of the formula -$(A^1)_o$-$(A^2)_p$-$(A^3)_q$-$(A^4)_r$-$R^{16}$; and $R^{85}$ is H, or a group of the formula -$(A^1)_o$-$(A^2)_p$-$(A^3)_q$-$(A^4)_r$-$R^{16'}$; or $R^{83}$ is H, or a group of the formula -$(A^1)_o$-$(A^2)_p$-$(A^3)_q$-$(A^4)_r$-$R^{16'}$; and $R^{85}$ is a group of the formula -$(A^1)_o$-$(A^2)_p$-$(A^3)_q$-$(A^4)_r$-$R^{16}$;

in the compounds of formula (Ik)

$R^{81}$ is a group of the formula -$(A^1)_o$-$(A^2)_p$-$(A^3)_q$-$(A^4)_r$-$R^{16}$; and $R^{85}$ is H, or a group of the formula -$(A^1)_o$-$(A^2)_p$-$(A^3)_q$-$(A^4)_r$-$R^{16'}$; or $R^{81}$ is H, or a group of the formula -$(A^1)_o$-$(A^2)_p$-$(A^3)_q$-$(A^4)_r$-$R^{16'}$; and $R^{85}$ is a group of the formula -$(A^1)_o$-$(A^2)_p$-$(A^3)_q$-$(A^4)_r$-$R^{16}$;

in the compounds of formula (Il)

$R^{85}$ is a group of the formula -$(A^1)_o$-$(A^2)_p$-$(A^3)_q$-$(A^4)_r$-$R^{16}$; and $R^{87}$ is H, or a group of the formula -$(A^1)_o$-$(A^2)_p$-$(A^3)_q$-$(A^4)_r$-$R^{16'}$; or $R^{85}$ is H, or a group of the formula -$(A^1)_o$-$(A^2)_p$-$(A^3)_q$-$(A^4)_r$-$R^{16'}$; and $R^{87}$ is a group of the formula -$(A^1)_o$-$(A^2)_p$-$(A^3)_q$-$(A^4)_r$-$R^{16}$;

in the compounds of formula (Im)

$R^{83}$ is a group of the formula -$(A^1)_o$-$(A^2)_p$-$(A^3)_q$-$(A^4)_r$-$R^{16}$; and $R^{85}$ is H, or a group of the formula -$(A^1)_o$-$(A^2)_p$-$(A^3)_q$-$(A^4)_r$-$R^{16'}$; or $R^{83}$ is H, or a group of the formula -$(A^1)_o$-$(A^2)_p$-$(A^3)_q$-$(A^4)_r$-$R^{16'}$; and $R^{85}$ is a group of the formula -$(A^1)_o$-$(A^2)_p$-$(A^3)_q$-$(A^4)_r$-$R^{16}$;

the compounds of formula (In)

$R^{83}$ is a group of the formula -$(A^1)_o$-$(A^2)_p$-$(A^3)_q$-$(A^4)_r$-$R^{16}$; and $R^{87}$ is H, or a group of the formula -$(A^1)_o$-$(A^2)_p$-$(A^3)_q$-$(A^4)_r$-$R^{16'}$; or $R^{83}$ is H, or a group of the formula -$(A^1)_o$-$(A^2)_p$-$(A^3)_q$-$(A^4)_r$-$R^{16'}$; and $R^{87}$ is a group of the formula -$(A^1)_o$-$(A^2)_p$-$(A^3)_q$-$(A^4)_r$-$R^{16}$; wherein in the compounds of formula (Io)

$R^{82}$ is a group of the formula -$(A^1)_o$-$(A^2)_p$-$(A^3)_q$-$(A^4)_r$-$R^{16}$; and $R^{86}$ is H, or a group of the formula -$(A^1)_o$-$(A^2)_p$-$(A^3)_q$-$(A^4)_r$-$R^{16'}$; or $R^{82}$ is H, or a group of the formula -$(A^1)_o$-$(A^2)_p$-$(A^3)_q$-$(A^4)_r$-$R^{16'}$; and $R^{86}$ is a group of the formula -$(A^1)_o$-$(A^2)_p$-$(A^3)_q$-$(A^4)_r$-$R^{16}$;

o is 0, or 1, p is 0, or 1, q is 0, or 1, r is 0, or 1;

$A^1$, $A^2$, $A^3$ and $A^4$ are independently of each other a group of the formula

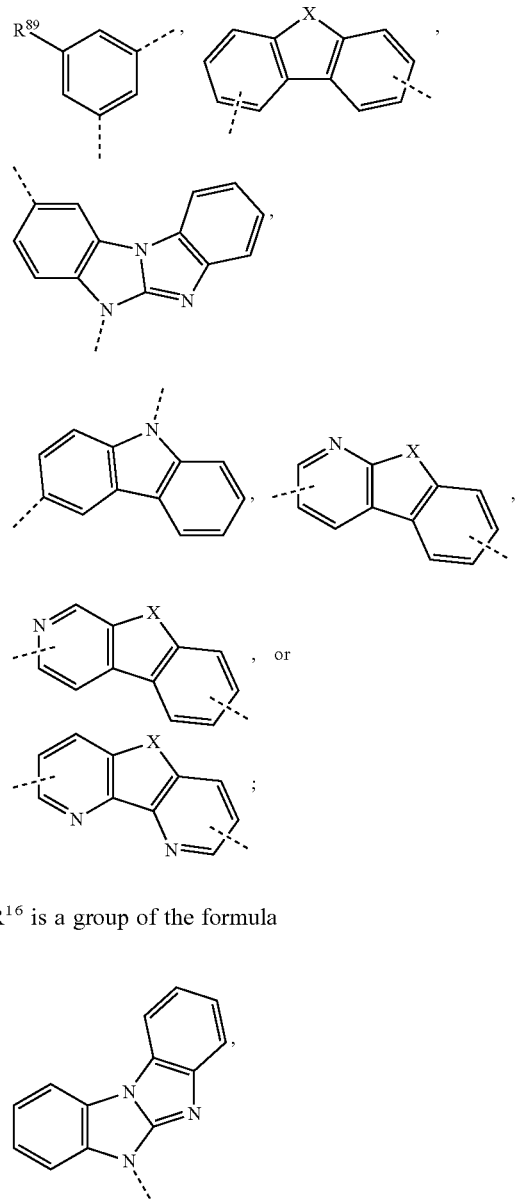

$R^{16}$ is a group of the formula

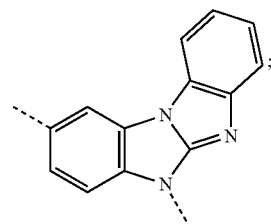

or $R^{16}$ has the meaning of $R^{16'}$, if at least one of the groups $A^1$, $A^2$, $A^3$ and $A^4$ represent a group of formula $R^{16'}$ is H, or a group of the formula —Si($R^{12}$)($R^{13}$)($R^{14}$),

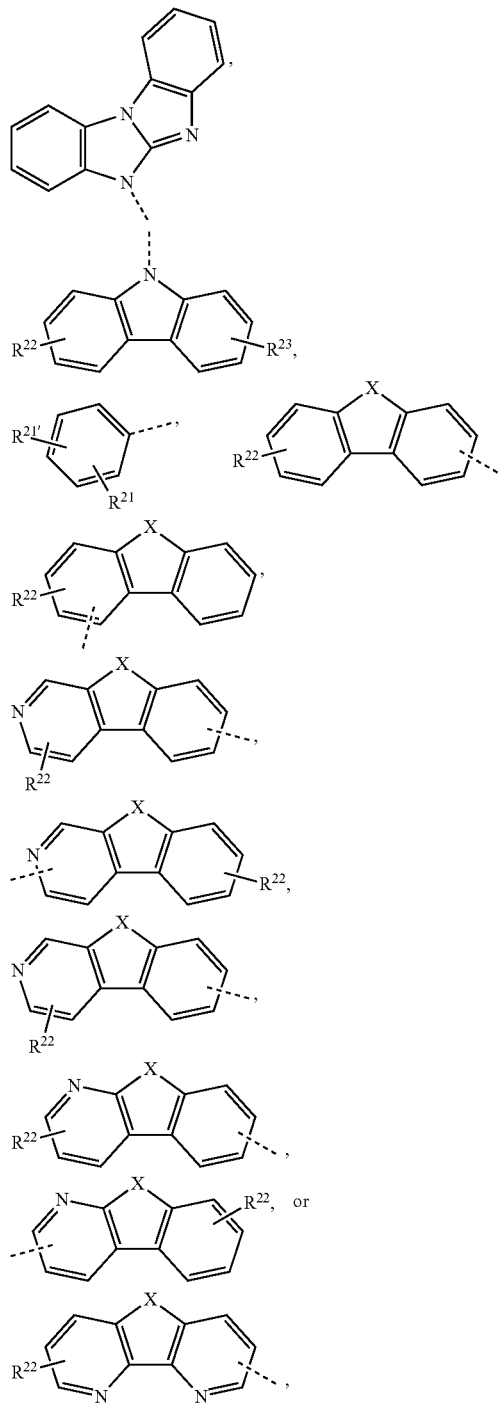

wherein $R^{12}$, $R^{13}$ and $R^{14}$ are independently of each other a phenyl group, which can optionally be substituted by one, or more alkyl groups;

$R^{21}$ and $R^{21'}$ are independently of each other H, a phenyl group, or a $C_1$-$C_{18}$ alkyl group;

$R^{22}$ and $R^{23}$ are independently of each other H, or a group of the formula

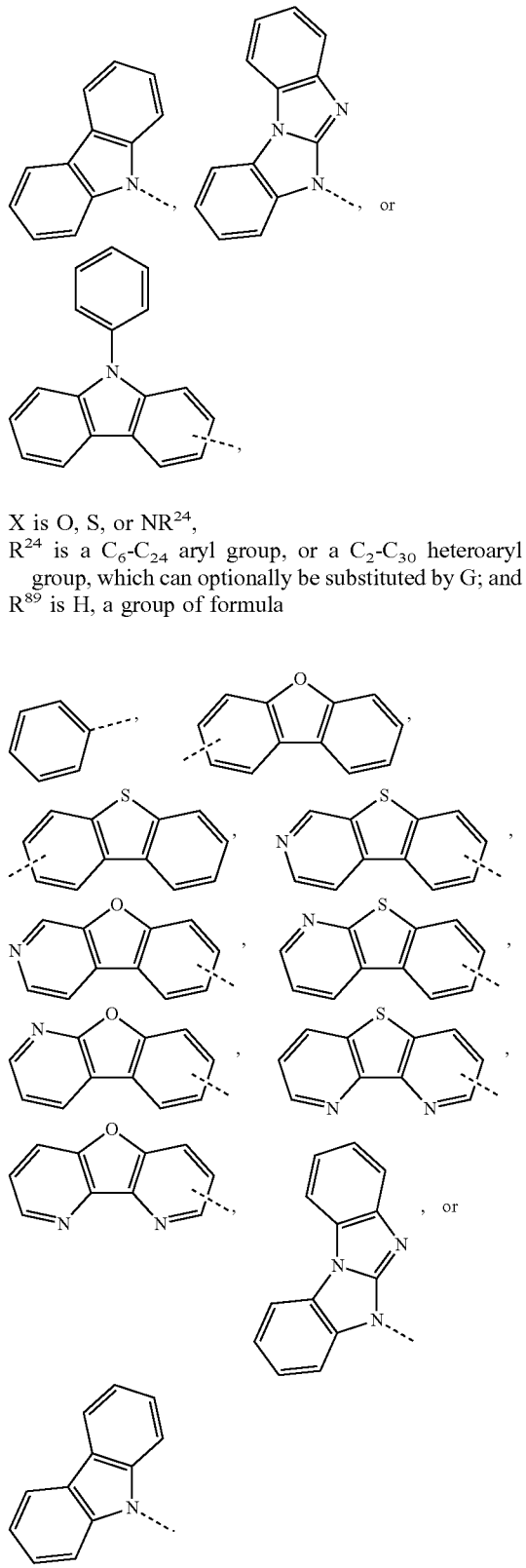

X is O, S, or $NR^{24}$, $R^{24}$ is a $C_6$-$C_{24}$ aryl group, or a $C_2$-$C_{30}$ heteroaryl group, which can optionally be substituted by G; and $R^{89}$ is H, a group of formula

4. The compound according to claim 2, wherein
o is 0, or 1, p is 0, or 1, q is 0, or 1, r is 0, or 1,
$A^1$, $A^2$, $A^3$ and $A^4$ are independently of each other a group of the formula

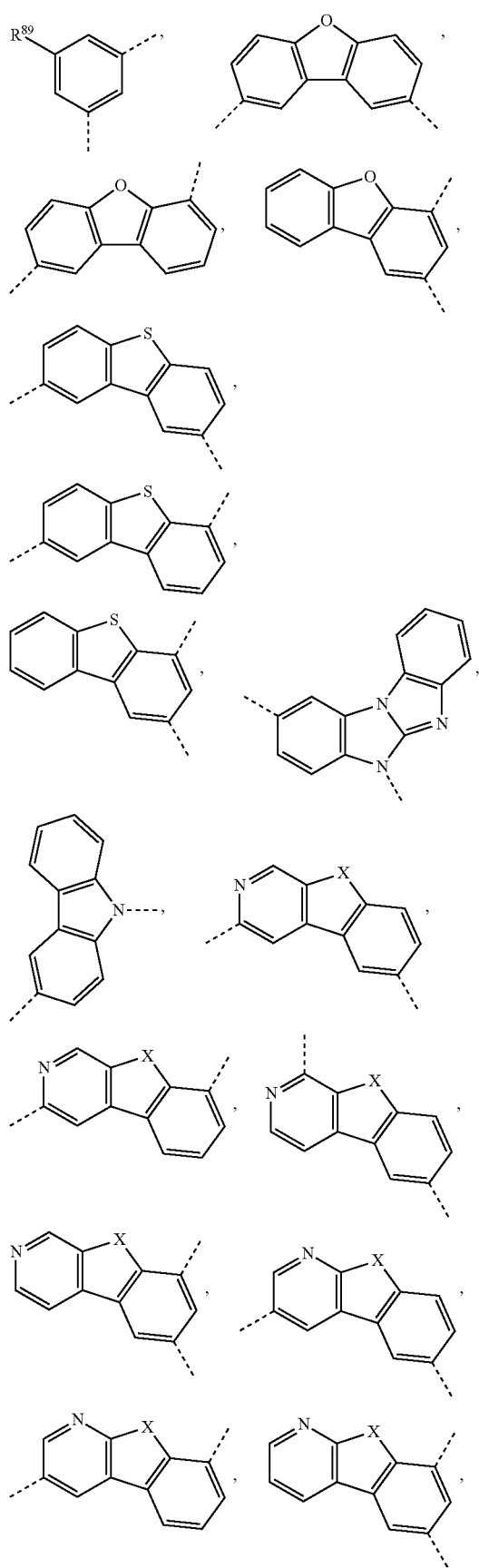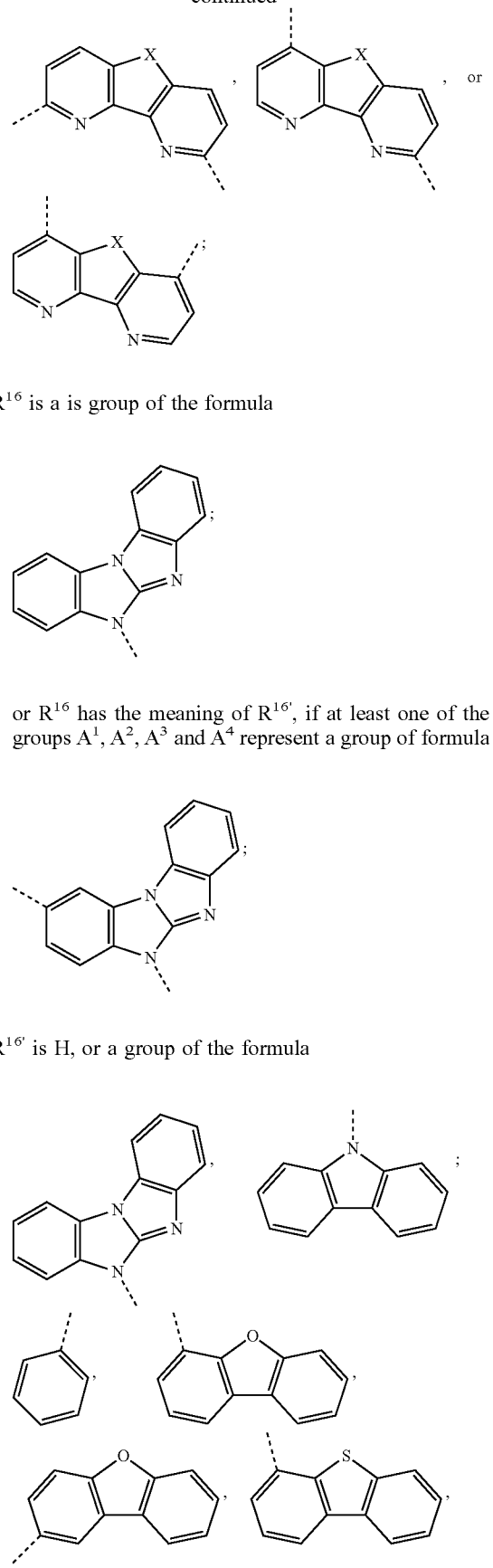
$R^{16}$ is a is group of the formula
or $R^{16}$ has the meaning of $R^{16'}$, if at least one of the groups $A^1$, $A^2$, $A^3$ and $A^4$ represent a group of formula
$R^{16'}$ is H, or a group of the formula -continued
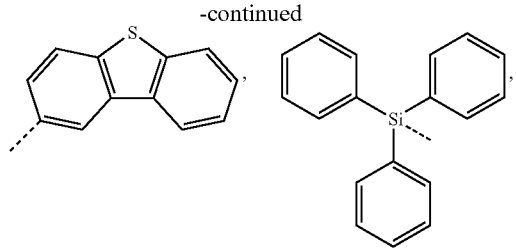
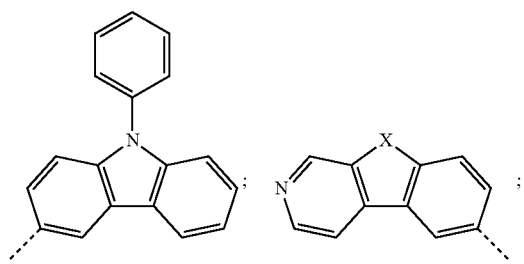
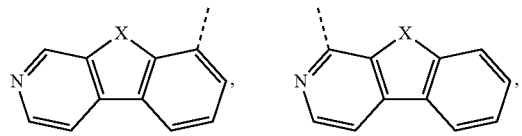
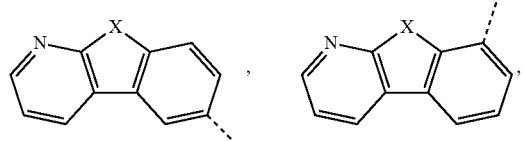
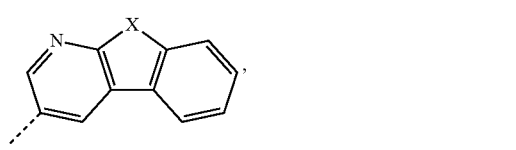
and R$^{89}$ is H, a group of formula
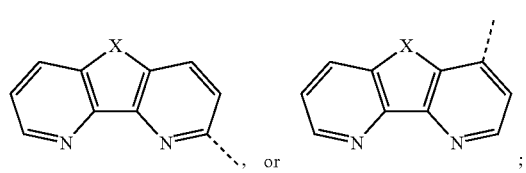
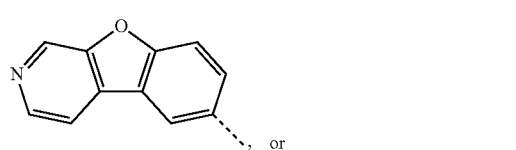
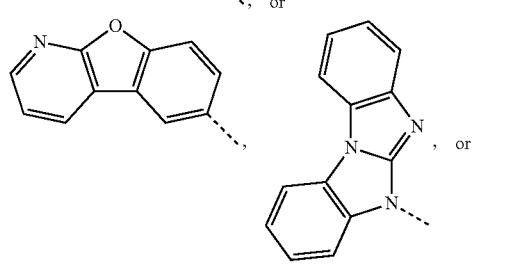
-continued
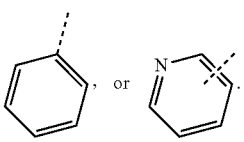
wherein X is O, S, or NR$^{24}$, wherein R$^{24}$ is
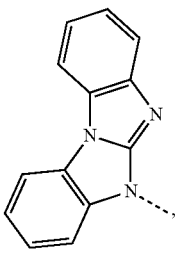
5. The compound according to claim 2, wherein the group of the formula -(A$^1$)$_o$-(A$^2$)$_p$-(A$^3$)$_q$-(A$^4$)$_r$-R$^{16}$ is a group of formula
(XIIa)
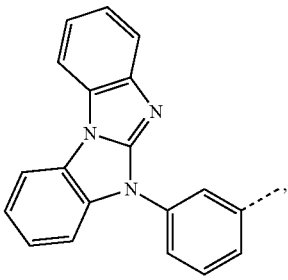
(XIIb)
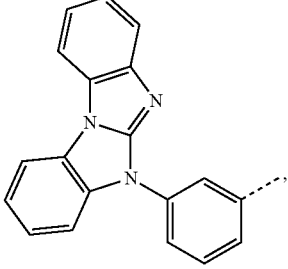
(XIIc)
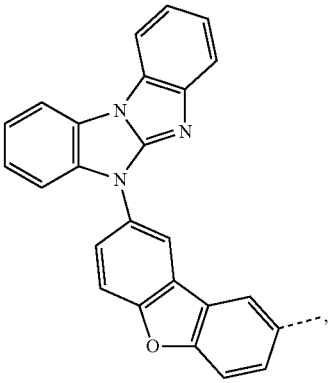

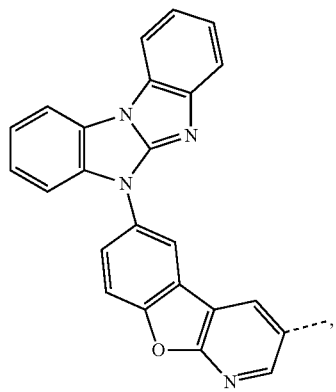
(XIId)
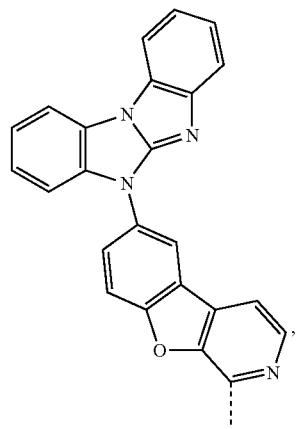
(XIIh)
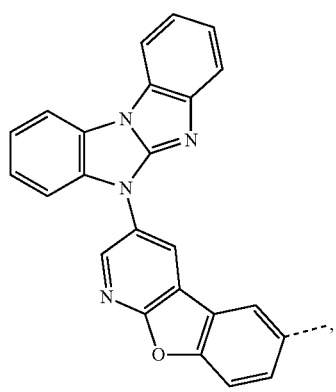
(XIIe)
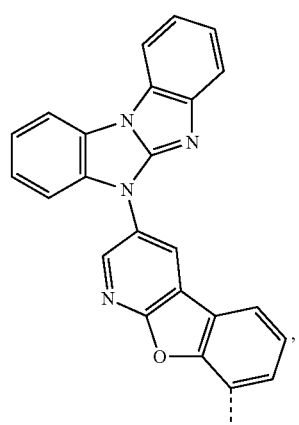
(XIIi)
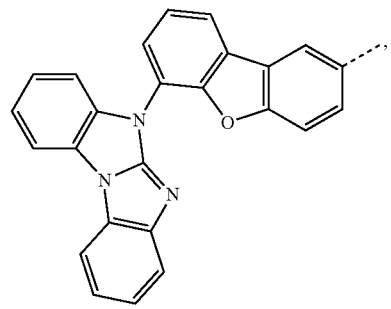
(XIIj)
(XIIf)
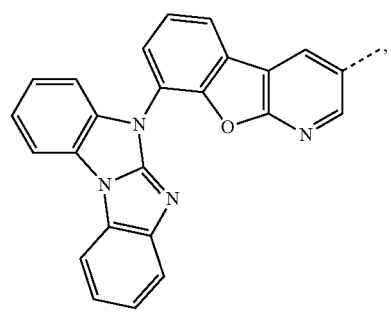
(XIIk)
(XIIg)

-continued
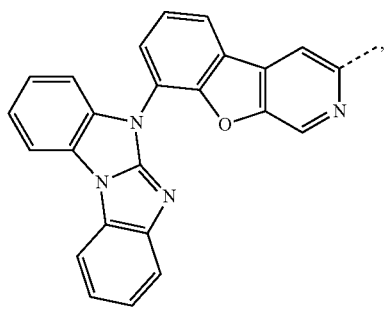
((XIII))
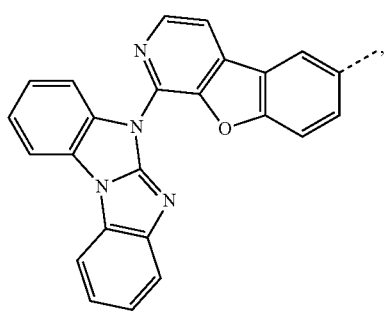
(XIIm)
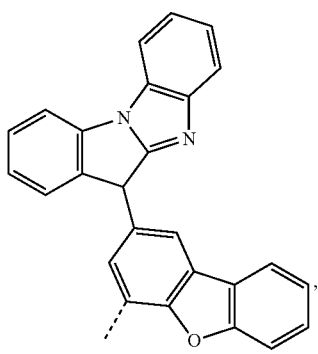
(XIIn)
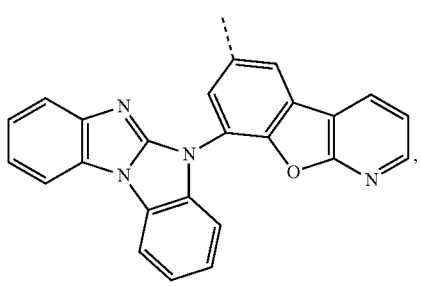
(XIIo)
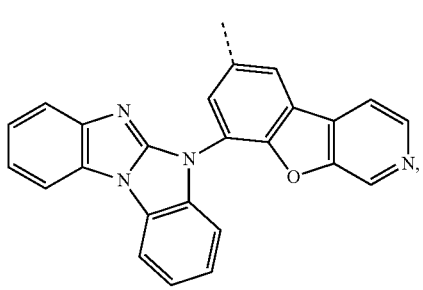
(XIIp)
-continued
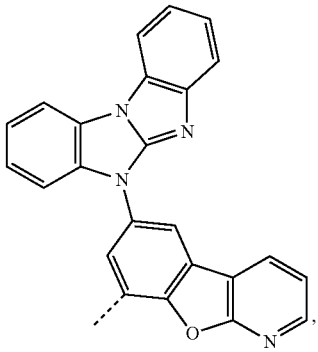
(XIIq)
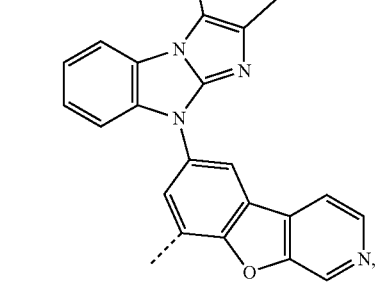
(XIIr)
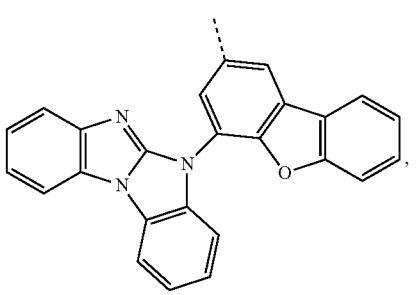
(XIIs)
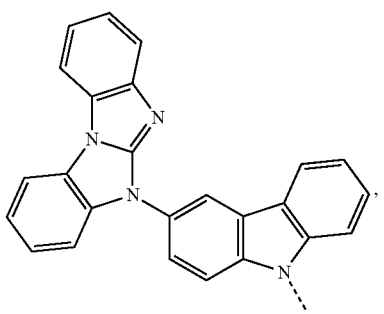
(XIIt)

-continued
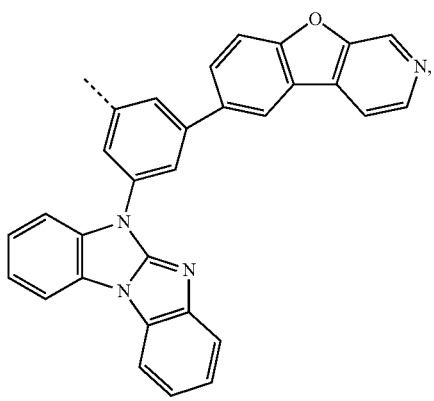
(XIIu)
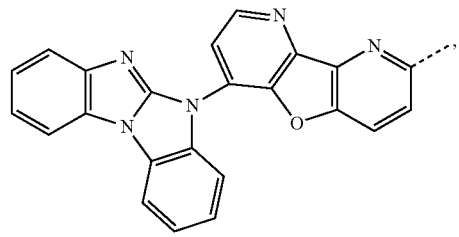
(XIIy)
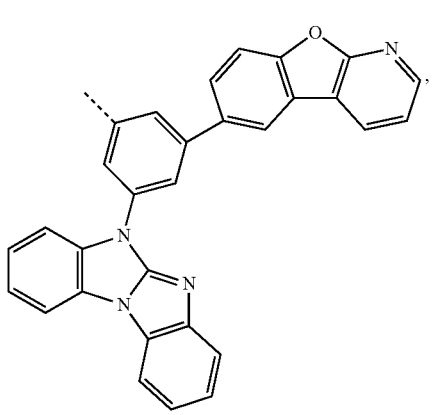
(XIIv)
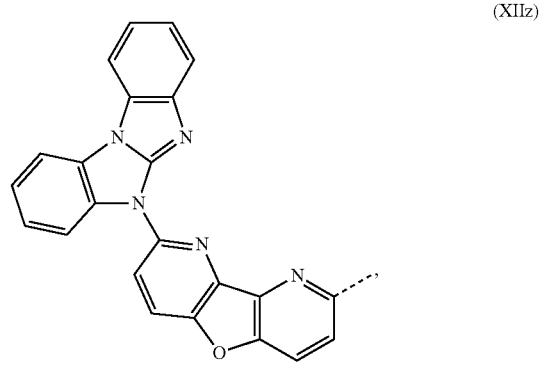
(XIIz)
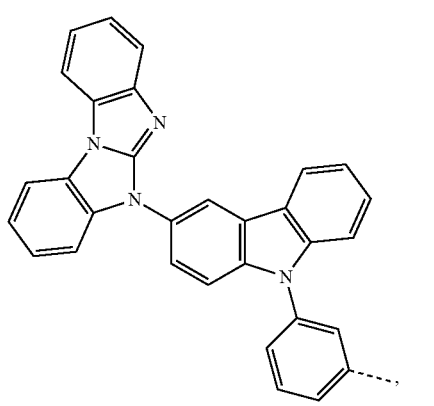
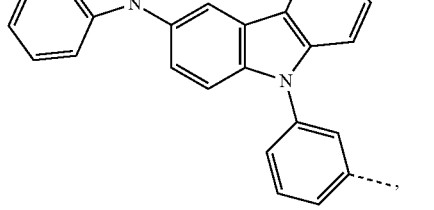
(XIIw)
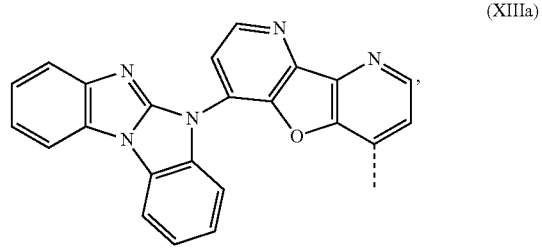
(XIIIa)
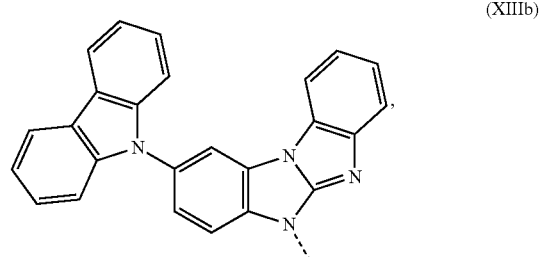
(XIIIb)
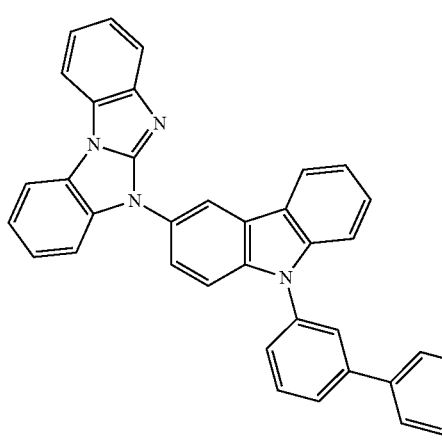
(XIIx)
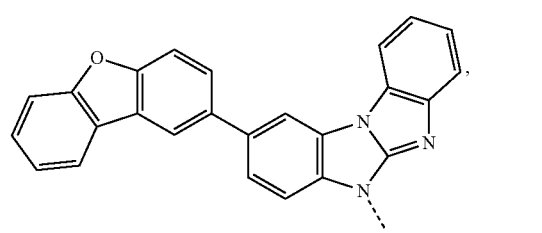
(XIIIc)

-continued (XIIId)
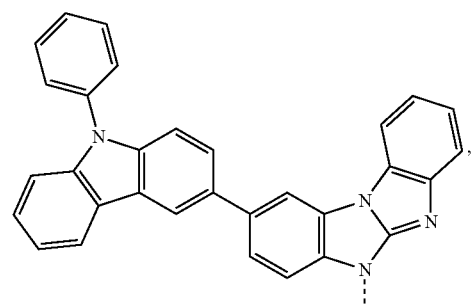

(XIIIe)
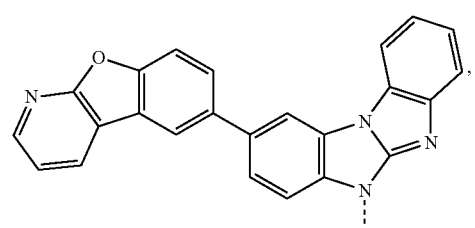

, or (XIIIf)
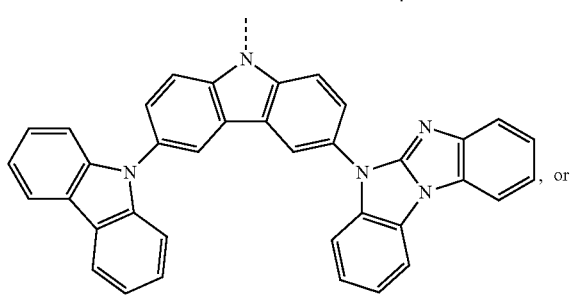

(XIIIg)
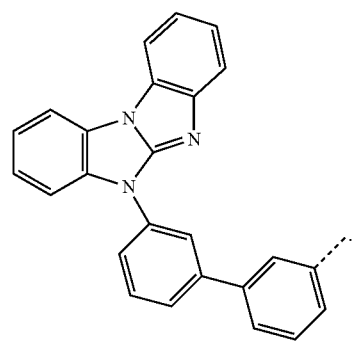

6. The compound according to claim 5, wherein the group of the formula -(A$^1$)$_o$-(A$^2$)$_p$-(A$^3$)$_q$-(A$^4$)$_r$-R$^{16'}$ is H, or a group of formula (XIIa), (XIIb), (XIIc), (XIId), (XIIe), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf), or (XIIIg); or a group of formula (XIVa)
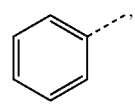

-continued (XIVb)
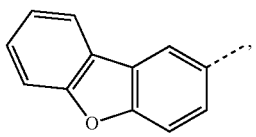

(XIVc)
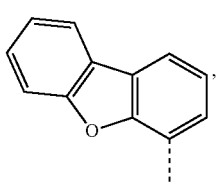

(XIVd)
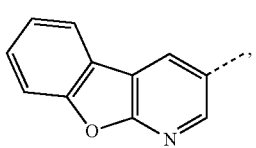

(XIVe)
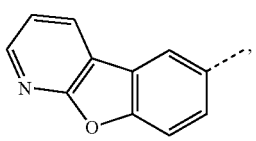

(XIVf)
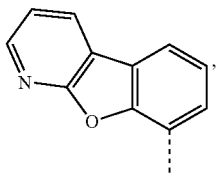

(XIVg)
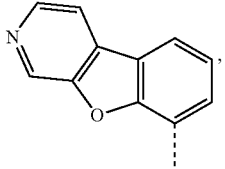

(XIVh)

(XIVi)
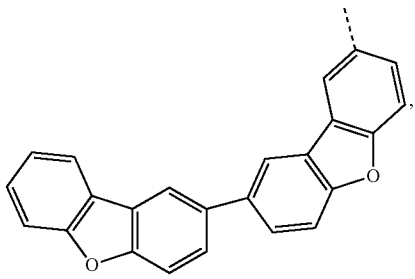

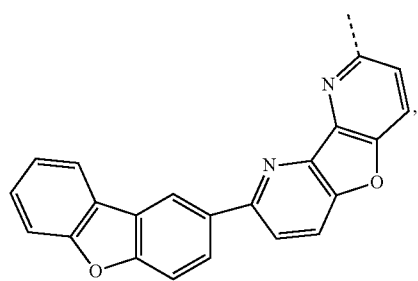
(XIVj)
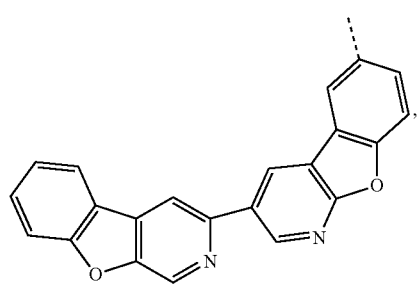
(XIVk)
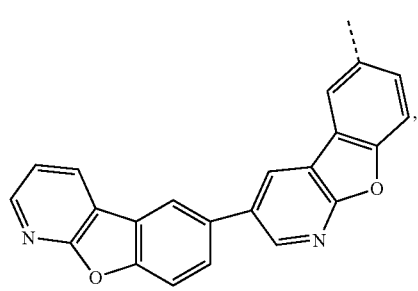
(XIVl)
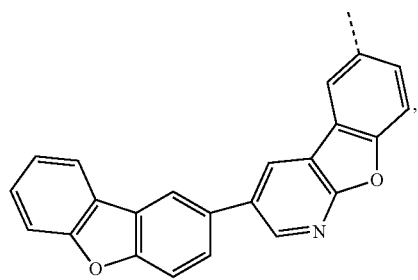
(XIVm)
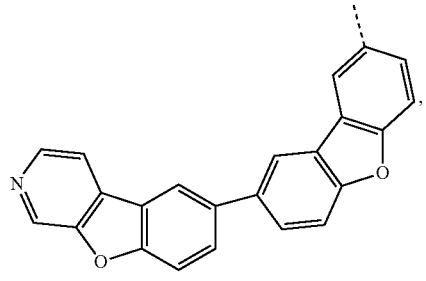
(XIVn)
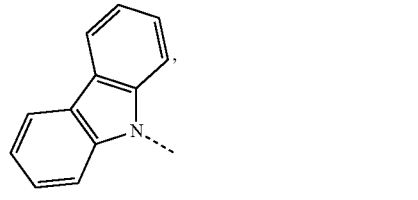
(XIVo)
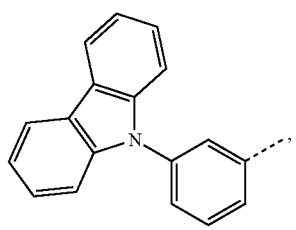
(XIVp)
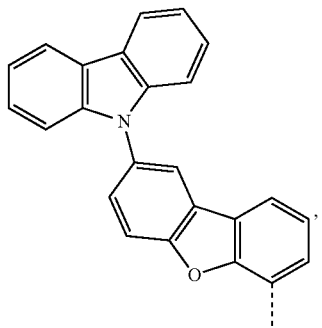
(XIVq)
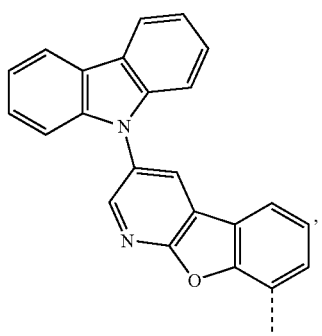
(XIVr)
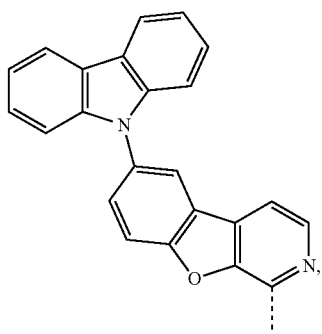
(XIVs)
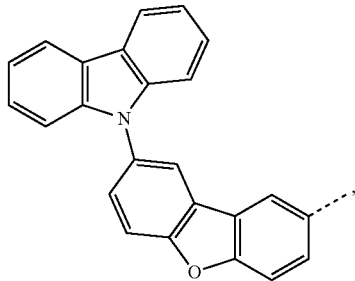
(XIVt)

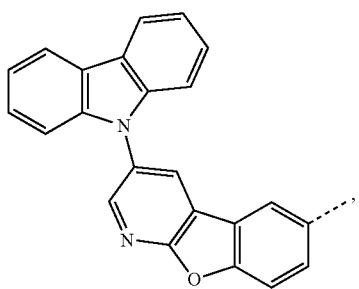 (XIVu)
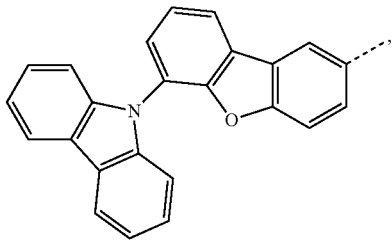 (XIVz)
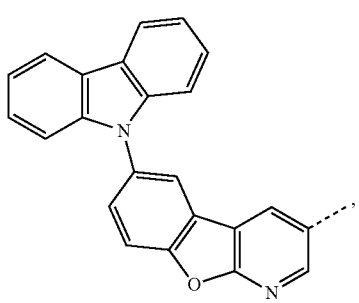 (XIVv)
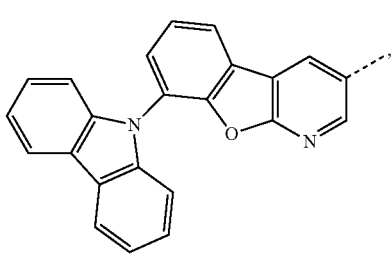 (XVa)
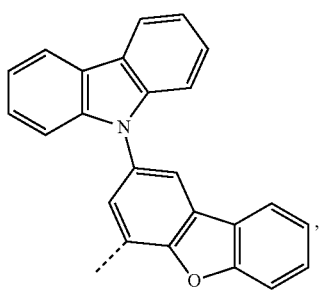 (XIVw)
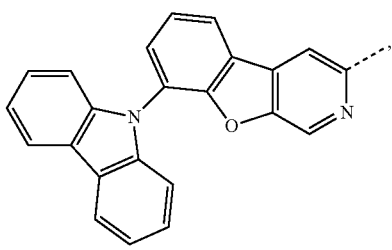 (XVb)
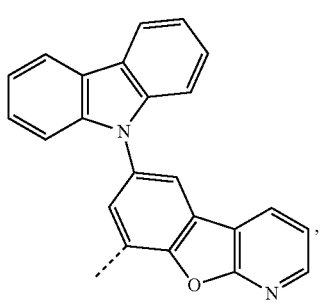 (XIVx)
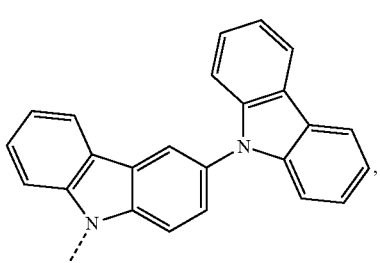 (XVc)
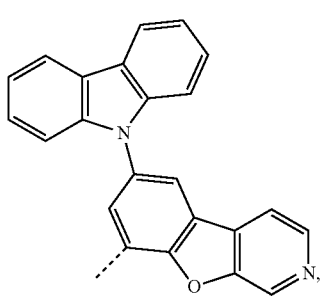 (XIVy)
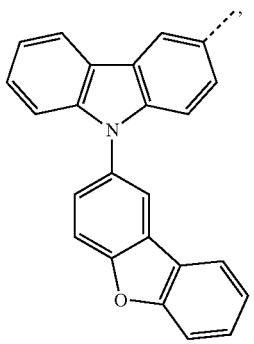 (XVd)

(XVe) 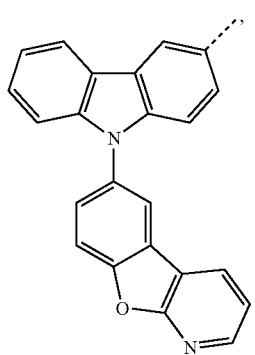
(XVf) 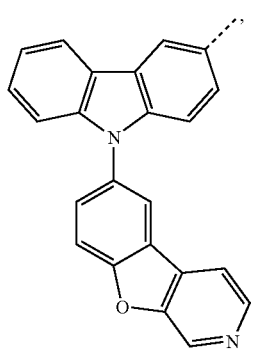
(XVg) 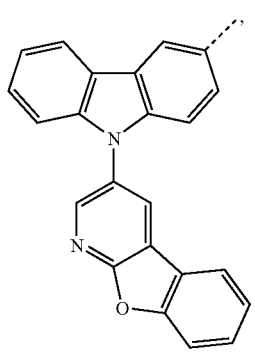
(XVh) 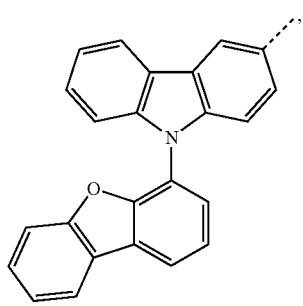
(XVi) 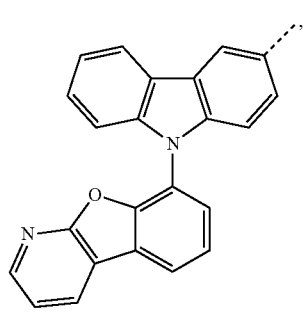
(XVj) 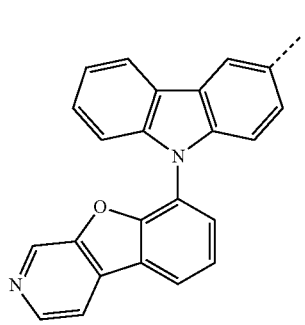
(XVk) 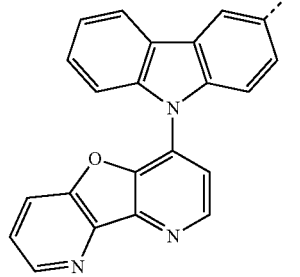
(XVl) 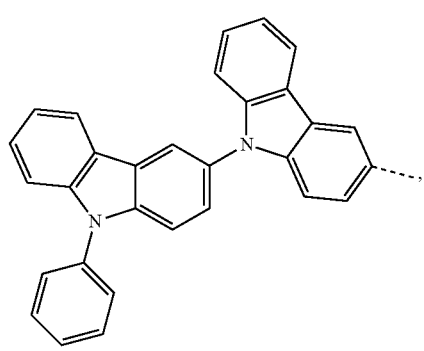

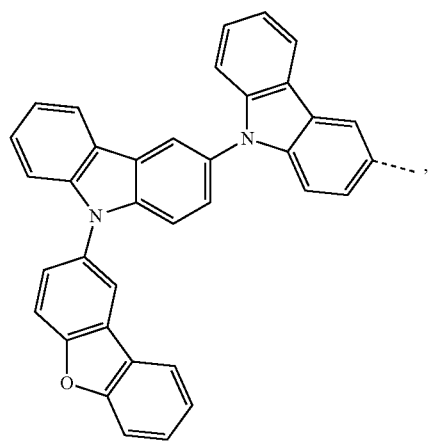
(XVm)
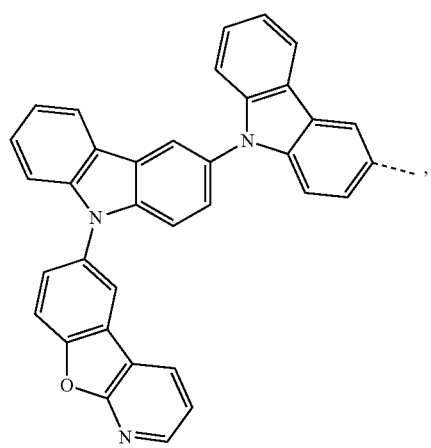
(XVn)
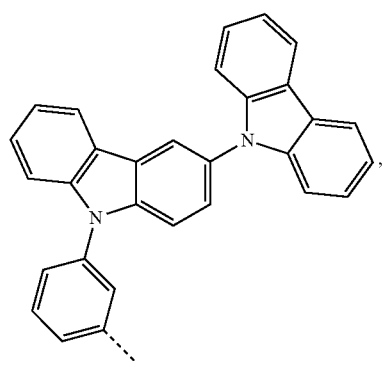
(XVo)
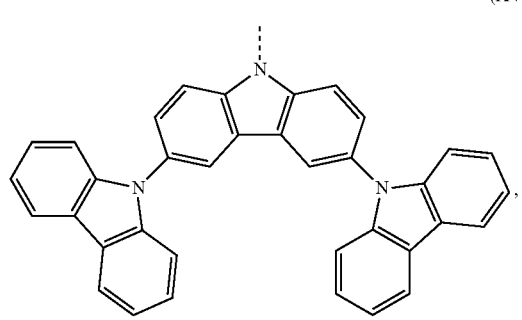
(XVp)
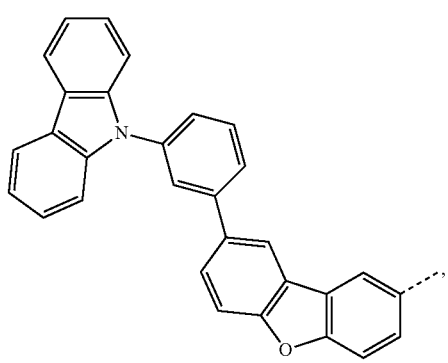
(XVq)
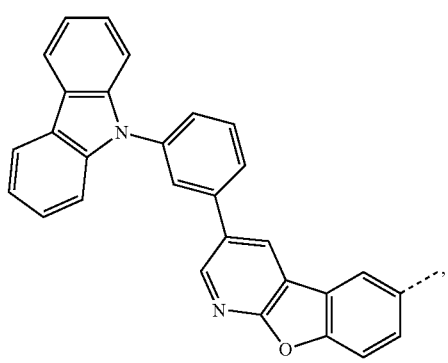
(XVr)
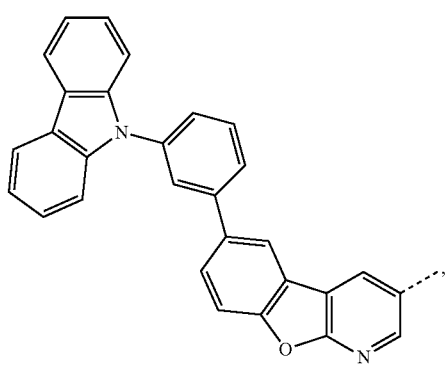
(XVs)
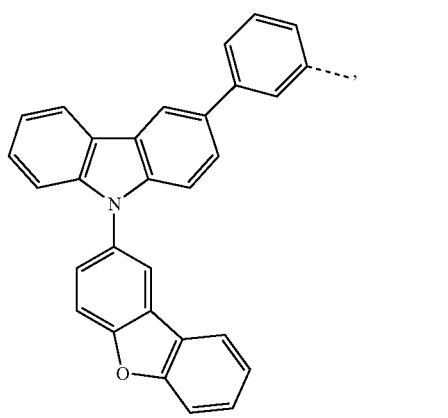
(XVt)

(XVu) 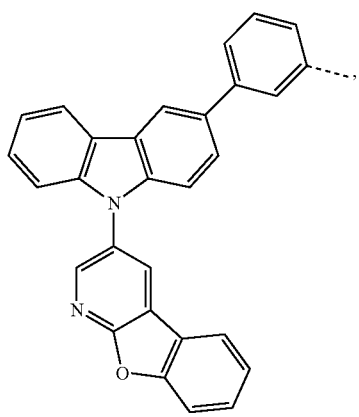

(XVv) 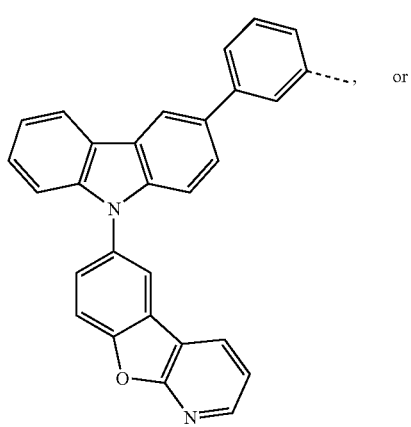 or (XVw) 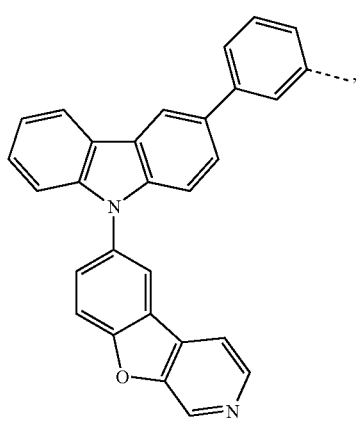, (XVx) 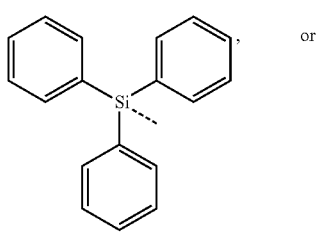 or (XVy) 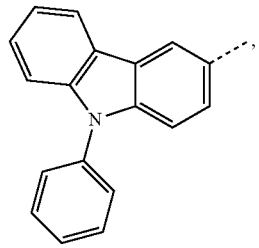, (XVz) 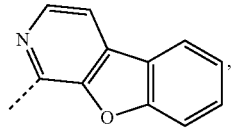, (XVIa) 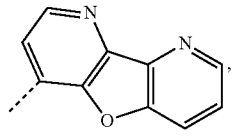, (XVIb) 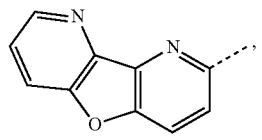, (XVIc) 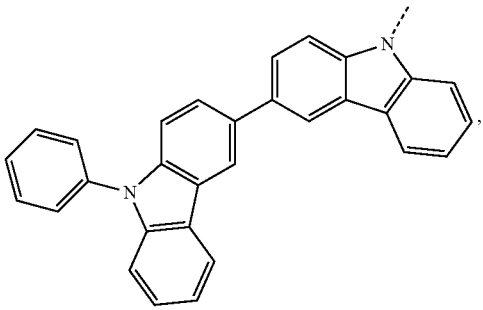 or (XVId) 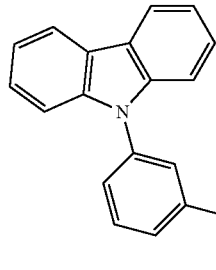

7. The compound according to claim 6, which is a compound of formula (Ia), wherein $R^{83}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{87}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Ia), wherein $R^{87}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and
$R^{83}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Ib), wherein $R^{82}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and
$R^{87}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo),(XVp), (XVq), (XVr), (XVs), (XVt), (XVu), (XVv), (XVw), (XVx), (XVy), (XVz), (XVIa), (XVIb), (XVIc) or (XVId); or a compound of formula (Ib), wherein $R^{87}$ is a group of formula (XIIa), (XIIb), (XIIc), (XIId), (XIIe), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIII), (XIIw), (XIIx), (XIIy), (XIIz), (XIIIa), (XIIIb), (XIIIc), (XIIId), (XIIIe), (XIIIf) or (XIIIg), and
$R^{82}$ is H, a group of formula (XIIa), (XIIb), (XIIc), (XIId), (XIIe), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Ic), wherein $R^{85}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and
$R^{87}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Ic), wherein $R^{87}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg); and
$R^{85}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIII), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Id), wherein $R^{81}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIII), (XIIu), (XIIv), (XIIw), (XIIx), (XIIy), (XIIz), (XIIIa), (XIIIb), (XIIIc), (XIIId), (XIIIe), (XIIIf) or (XIIIg), and
$R^{85}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIII), (XIIu), (XIIv) (XIIw), (XIIx), (XIIy), (XIIz), (XIIIa), (XIIIb), (XIIIc), (XIIId), (XIIIe), (XIIIf) or (XIIIg); or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Id), wherein $R^{85}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg); and R$^{81}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIII), (XIIu), (XIII) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Ie), wherein R$^{83}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIII), (XIIw), (XIIx), (XIIy), (XIIz), (XIIIa), (XIIIb), (XIIIc), (XIIId), (XIIIe), (XIIIf) or (XIIIg), and R$^{87}$ is H, a group of formula (XIIa), (XIIb), (XIIc), (XIId), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIII) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Ie), wherein R$^{87}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and R$^{83}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (If), wherein R$^{83}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and R$^{85}$ is H, a group of formula (XIIa), (XIIb), (XIIc), (XIId), (XIIe), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (If), wherein R$^{85}$ is a group of formula (XIIa), (XIII)), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and R$^{83}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Ii), wherein R$^{83}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and R$^{85}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIII) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Ii), wherein R$^{85}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIII), (XIIw), (XIIx), (XIIy), (XIIz), (XIIIa), (XIIIb), (XIIIc), (XIIId), (XIIIe), (XIIIf) or (XIIIg), and R$^{83}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIII) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Ij), wherein $R^{83}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIII), (XIIu), (XIII), (XIIw), (XIIx), (XIIy), (XIIz), (XIIIa), (XIIIb), (XIIIc), (XIIId), (XIIIe), (XIIIf) or (XIIIg), and $R^{85}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIII) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Ij), wherein $R^{85}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIII), (XIIw), (XIIx), (XIIy), (XIIz), (XIIIa), (XIIIb), (XIIIc), (XIIId), (XIIIe), (XIIIf) or (XIIIg), and $R^{83}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIII) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId);

a compound of formula (Il), wherein $R^{85}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{87}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (Il), wherein $R^{87}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{85}$ is H, a group of formula (XIIa), (XIIb), (XIIc), (XIId), (XIIe), (XIIf), (XIIg), (XIIh), XIIi), (XIIj), (XIIk), ((XIII)), (XIIm), (XIIn), (XIIo), (XIIp), (XIIq), (XIIr), (XIIs), (XIIt), (XIIu), (XIII) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (In), wherein $R^{83}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIII), (XIIw), (XIIx), (XIIy), (XIIz), (XIIIa), (XIIIb), (XIIIc), (XIIId), (XIIIe), (XIIIf) or (XIIIg), and $R^{87}$ is H, a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIII) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId); or a compound of formula (In), wherein $R^{87}$ is a group of formula (XIIa), (XIIb), (XIIc), (XIId), (XIIe), (XIIf), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIII), (XIIw), (XIIx), (XIIy), (XIIz), (XIIIa), (XIIIb), (XIIIc), (XIIId), (XIIIe), (XIIIf) or (XIIIg), and $R^{83}$ is H, a group of formula (XIIa), (XIIb), (XIIc), (XIId), (XIIe), (XIIg), (XIIh), (XIIi), (XIIj), (XIIk), ((XIII)), (XIIm), (XIIn), (XIIo), (XIIp), (XIIq), (XIIr), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVh), (XIVo), (XIVp), (XIVq), (XIVr), (XIVs), (XIVt), (XIVu), (XIVv), (XIVw), (XIVx), (XIVy), (XIVz), (XVa), (XVb), (XVc), (XVd), (XVe), (XVf), (XVg), (XVh), (XVi), (XVj), (XVk), (XVl), (XVm), (XVn), (XVo), (XVp), (XVq), (XVr), (XVs), (XVt), (XVu), (XVv), (XVw), (XVx), (XVy), (XVz), (XVIa), (XVIb), (XVIc) or (XVId).

8. The compound according to claim 6, which is a compound of formula (Ia), wherein $R^{83}$ is a group of formula (XIIa), (XIIb), (XIIc), (XIId), (XIIe), (XIIg), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{87}$ is H, a group of formula (XIIa), (XIIb), (XIIc), (XIId), (XIIe), (XIIg), (XIIh), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId); or a compound of formula (Ia), wherein $R^{87}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{83}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId);

a compound of formula (Ib), wherein $R^{82}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{87}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId); or a compound of formula (Ib), wherein $R^{87}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{82}$ is H, a group of formula (XIIa), (XIIb), (XIIc), (XIId), (XIIe), (XIIf), (XIIg), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId);

a compound of formula (Ic), wherein $R^{85}$ is a group of formula (XIIa), (XIIb), (XIIc), (XIId), (XIIe), (XIIg), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{87}$ is H, a group of formula (XIIa), (XIIb), (XIIc), (XIId), (XIIe), (XIIg), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId); or a compound of formula (Ic), wherein $R^{87}$ is a group of formula (XIIa), (XIIb), (XIIc), (XIId), (XIIe), (XIIg), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), or (XIIIg), and $R^{85}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId); or a compound of formula (Id), wherein $R^{81}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{85}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId); or a compound of formula (Id), wherein $R^{85}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{81}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId);

a compound of formula (Ie), wherein $R^{83}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{87}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId); or a compound of formula (Ie), wherein $R^{87}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{83}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId);

a compound of formula (If), wherein $R^{83}$ is a group of formula (XIIa), (XIIb), (XIIc), (XIId), (XIIe), (XIIf), (XIIg), (XIIk), (XIIn), (XIIo), (XIIq), (XIIs), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{85}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId); or a compound of formula (If), wherein $R^{85}$ is a group of formula (XIIa), (XIIb), (XIIc), (XIId), (XIIe), (XIIf), (XIIg), (XIIk), (XIIn), (XIIo), (XIIq), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{83}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId); or a compound of formula (Ij), wherein $R^{83}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{85}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId); or a compound of formula (Ij), wherein $R^{85}$ is a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{83}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId); or a compound of formula (In), wherein $R^{83}$ is a group of formula (XIIa), (XIIb), (XIIc), (XIId), (XIIe), (XIIg), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{87}$ is H, a group of formula (XIIa), (XIIb), (XIIc), (XIId), (XIIe), (XIIf), (XIIg), (XIIj), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId); or a compound of formula (In), wherein $R^{87}$ is a group of formula (XIIa), (XIIb), (XIIc), (XIId), (XIIe), (XIIf), (XIIg), (XIIk), (XIIn), (XIIo), (XIIq), (XIIs), (XIIt), (XIIu), (XIIv), (XIIw), (XIIx), (XIIy), (XIIz), (XIIIa), (XIIIb), (XIIIc), (XIIId), (XIIIe), (XIIIf) or (XIIIg), and $R^{83}$ is H, a group of formula (XIIa), (XIIb), (XIIc), (XIId), (XIIe), (XIIf), (XIIg), (XIIk), (XIIn), (XIIo), (XIIq), (XIIs), (XIIt), (XIIu), (XIIv) (XIIw), (XIIx), (XIIy), (XIIz), (XIIIa), (XIIIb), (XIIIc), (XIIId), (XIIIe), (XIIIf) or (XIIIg), or a group of formula (XIVb), (XIVc), (XIVd), (XIVe), (XIVf), (XIVg), (XIVo), (XIVp), (XIVq), (XIVr), (XIVt), (XIVu), (XIVv), (XIVw), (XIVx), (XIVz), (XVa), (XVb), (XVc), (XVk), (XVl), (XVo), (XVp), (XVs), (XVw), (XVx), (XVy), (XVIa), (XVIb), (XVIc) or (XVId).

9. The compound according to claim 1:
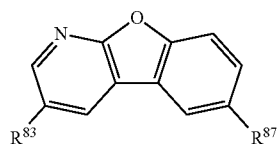
| Compound | R⁸³ | R⁸⁷ |
|---|---|---|
| A-1 | benzimidazo-fused benzimidazole | benzimidazo-fused benzimidazole |
| A-2 | N-(carbazol-9-yl)phenyl | benzimidazo-fused benzimidazole |
| A-3 | benzimidazo-fused benzimidazole | N-(carbazol-9-yl)phenyl |
| A-4 | N-phenyl-benzimidazo-fused benzimidazole | N-phenyl-benzimidazo-fused benzimidazole |
| A-5 | H | benzimidazo-fused benzimidazole |

-continued
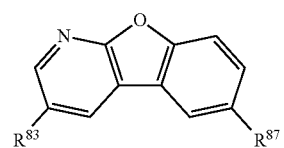
| Compound | R⁸³ | R⁸⁷ |
|---|---|---|
| A-6 | 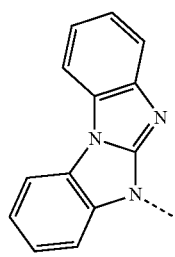 | H |
| A-7 | H | 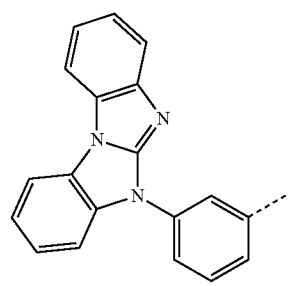 |
| A-8 | 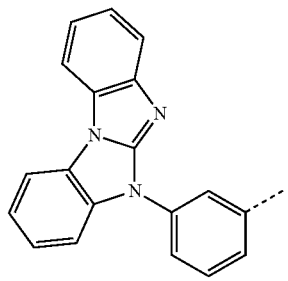 | H |
| A-9 | H | 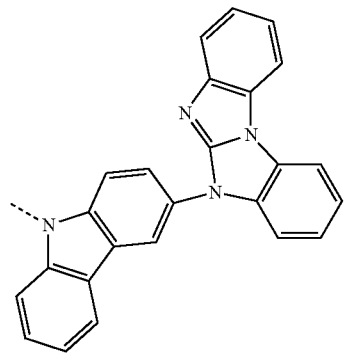 |

-continued

| Compound | R⁸³ | R⁸⁷ |
|---|---|---|
| A-10 | (benzimidazole-carbazole-benzimidazole fused substituent with N-methyl carbazole and N-phenyl benzimidazole) | H |
| A-11 | triphenylsilyl | benzimidazo[1,2-a]benzimidazole (N-linked) |
| A-12 | benzimidazo[1,2-a]benzimidazole (N-linked) | triphenylsilyl |
| A-13 | triphenylsilyl | benzimidazo[1,2-a]benzimidazole N-(3-phenyl) linked |
| A-14 | benzimidazo[1,2-a]benzimidazole N-(3-phenyl) linked | triphenylsilyl |

-continued
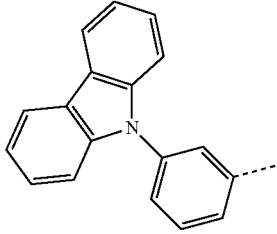
| Compound | R83 | R87 |
|---|---|---|
| A-15 | 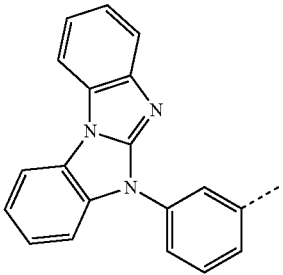 | 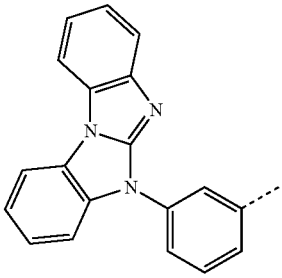 |
| A-16 | 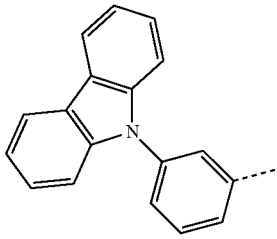 | 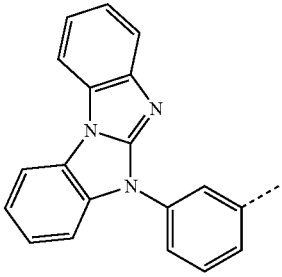 |
| A-17 | 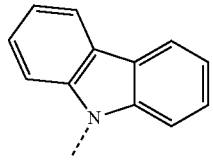 | 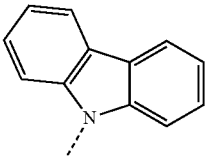 |
| A-18 | 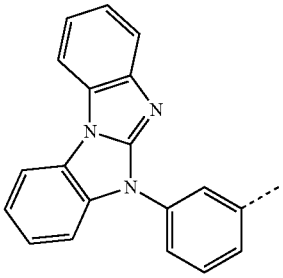 | 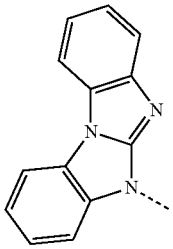 |
| A-19 | 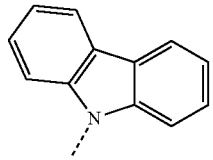 | |

-continued
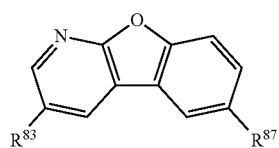
| Compound | R<sup>83</sup> | R<sup>87</sup> |
|---|---|---|
| A-20 | 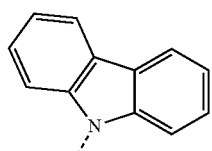 | 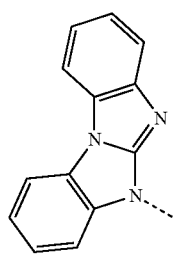 |
| A-21 | 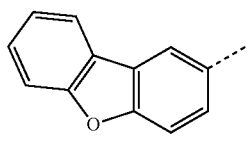 | 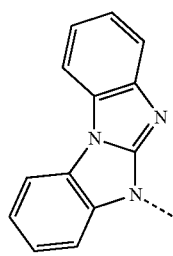 |
| A-22 | 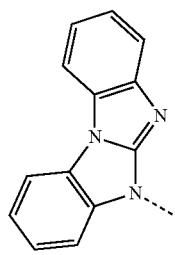 | 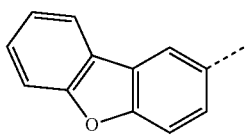 |
| A-23 | 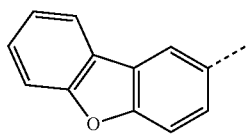 | 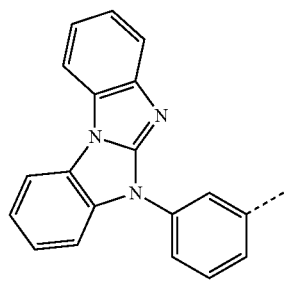 |
| A-24 | 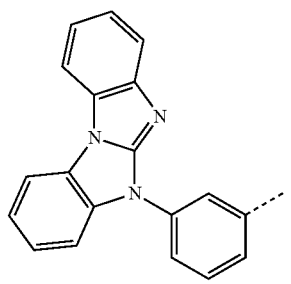 | 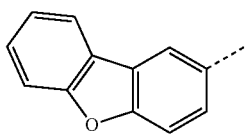 |

-continued

| Compound | R⁸³ | R⁸⁷ |
|---|---|---|
| A-25 | pyrido-benzofuran | benzimidazo-benzimidazole |
| A-26 | benzimidazo-benzimidazole | pyrido-benzofuran |
| A-27 | pyrido-benzofuran | N-phenyl benzimidazo-benzimidazole |
| A-28 | N-phenyl benzimidazo-benzimidazole | pyrido-benzofuran |
| A-29 | pyrido-benzofuran | benzimidazo-benzimidazole |

-continued
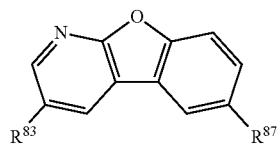
| Compound | R<sup>83</sup> | R<sup>87</sup> |
|---|---|---|
| A-30 | 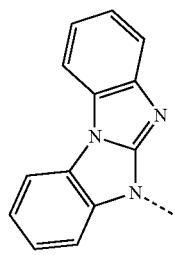 | 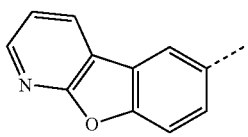 |
| A-31 | 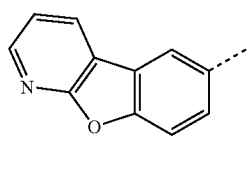 | 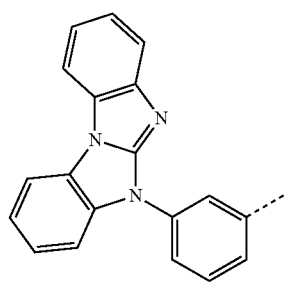 |
| A-32 | 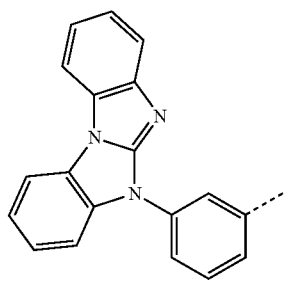 | 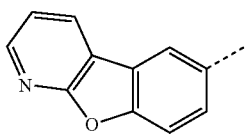 |
| A-33 | 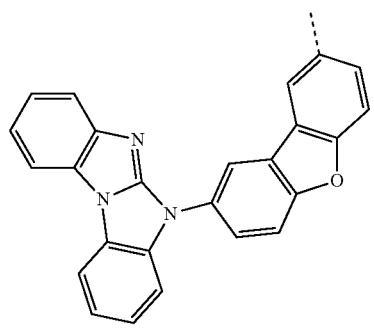 | 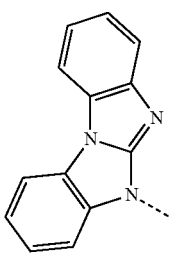 |

-continued
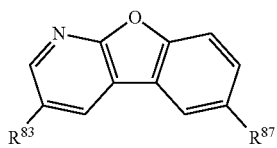
| Compound | R⁸³ | R⁸⁷ |
|---|---|---|
| A-34 | 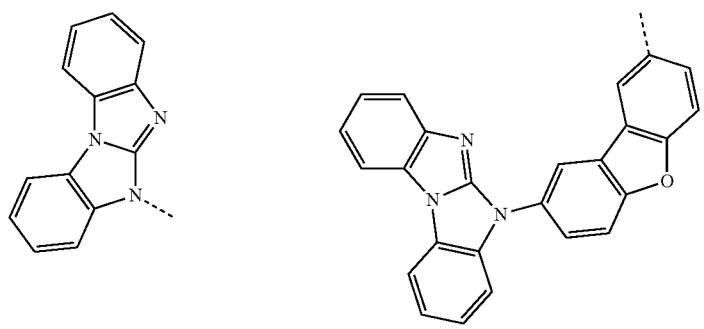 | |
| A-35 | 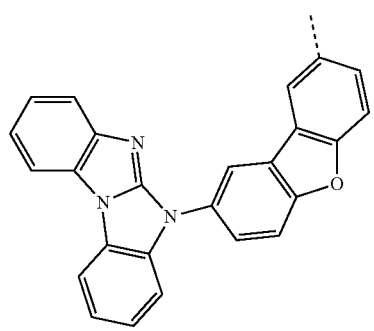 | H |
| A-36 | H | 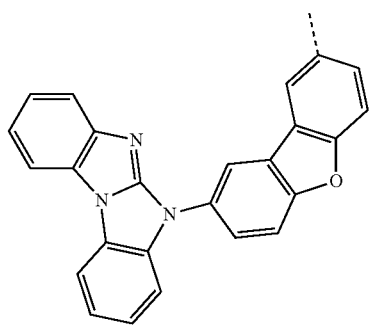 |
| A-37 | 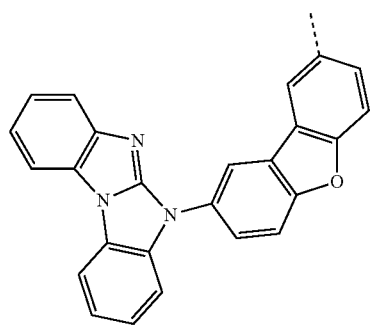 | 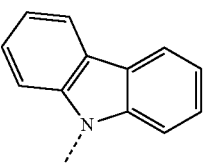 |

-continued

| Compound | R⁸³ | R⁸⁷ |
|---|---|---|
| A-38 | (N-carbazolyl) | (benzimidazole-dibenzofuran substituent) |
| A-39 | (N-carbazolyl) | (benzimidazole-pyrido-benzofuran substituent) |
| A-40 | (benzimidazole-pyrido-benzofuran substituent) | (N-carbazolyl) |
| A-41 | (benzimidazole-pyrido-benzofuran substituent) | H |

-continued
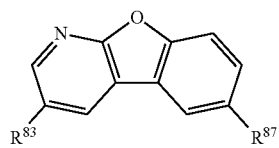
| Compound | R$^{83}$ | R$^{87}$ |
|---|---|---|
| A-42 | H | 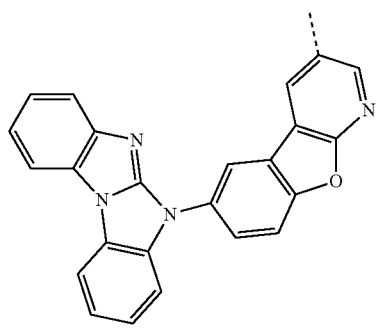 |
| A-43 | 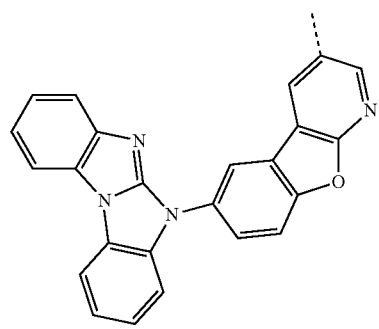 | 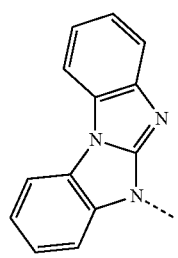 |
| A-44 | 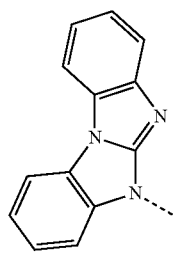 | 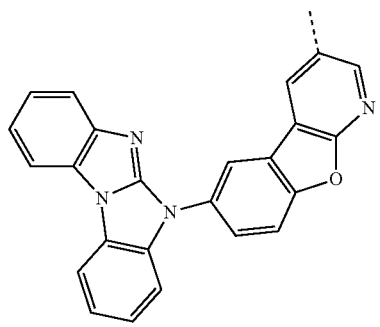 |
| A-45 | 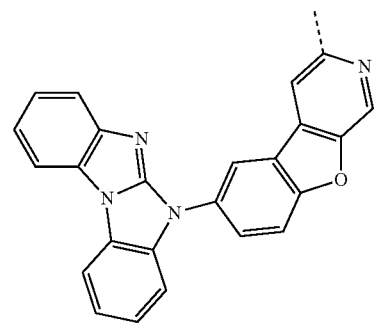 | 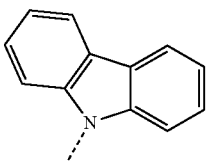 |

-continued
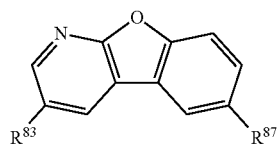
| Compound | R<sup>83</sup> | R<sup>87</sup> |
|---|---|---|
| A-46 | 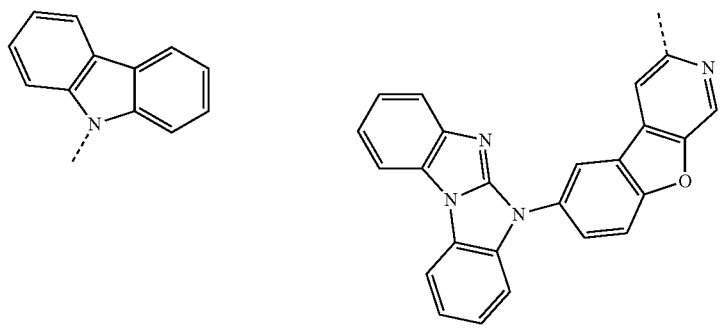 | |
| A-47 | 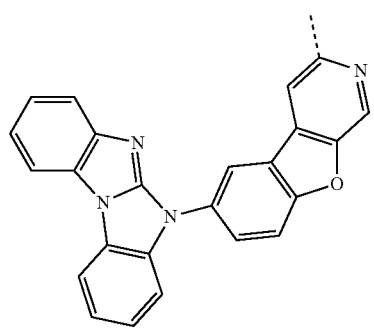 | H |
| A-48 | H | 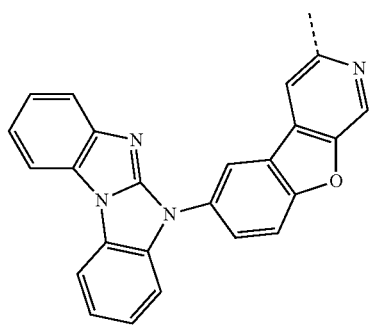 |
| A-49 | 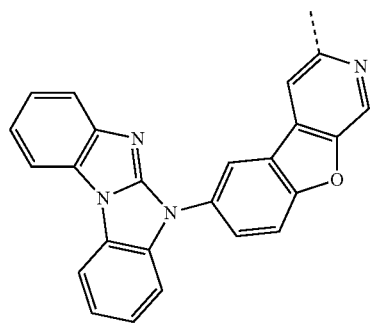 | 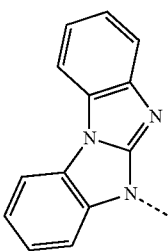 |

-continued
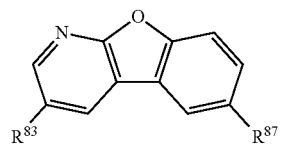
| Compound | R⁸³ | R⁸⁷ |
|---|---|---|
| A-50 | 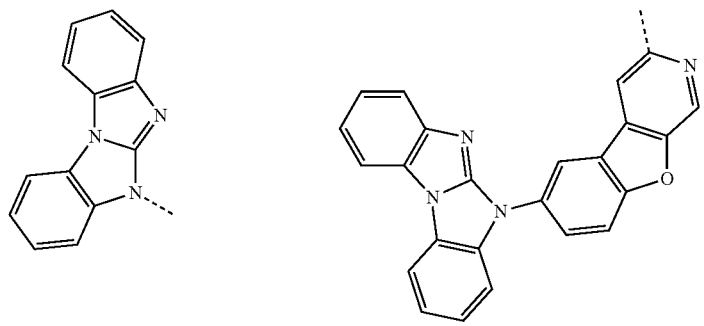 | |
| A-51 | 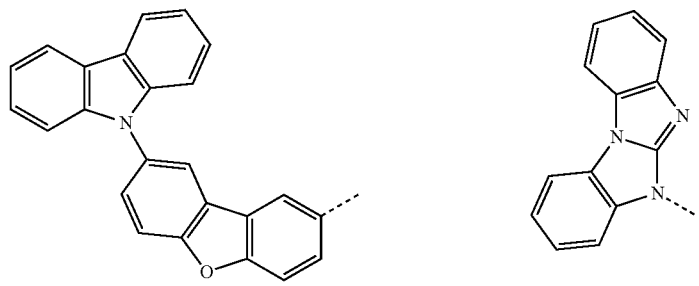 | |
| A-52 | 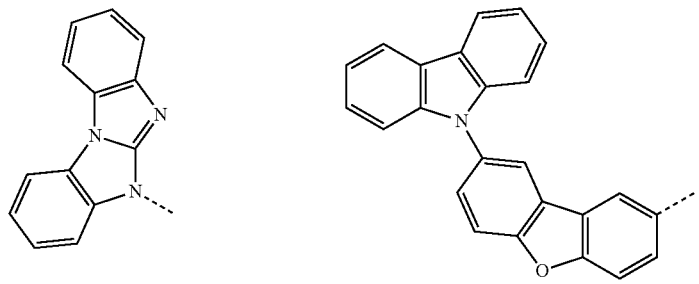 | |
| A-53 | 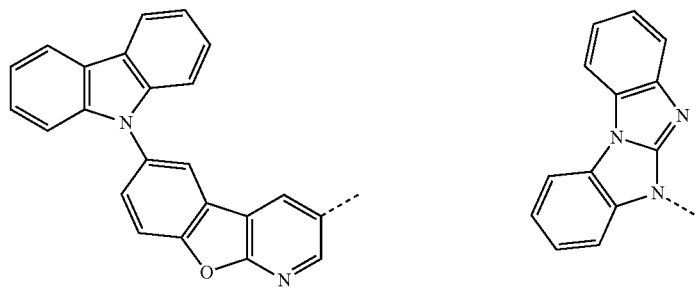 | |

-continued
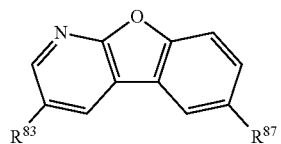
| Compound | R<sup>83</sup> | R<sup>87</sup> |
|---|---|---|
| A-54 | | |
| A-55 | | |
| A-56 | | |
| A-57 | H | |
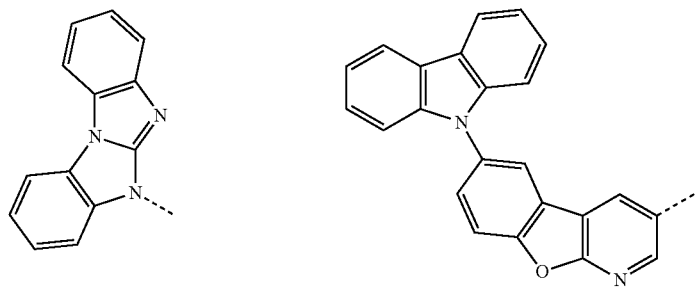
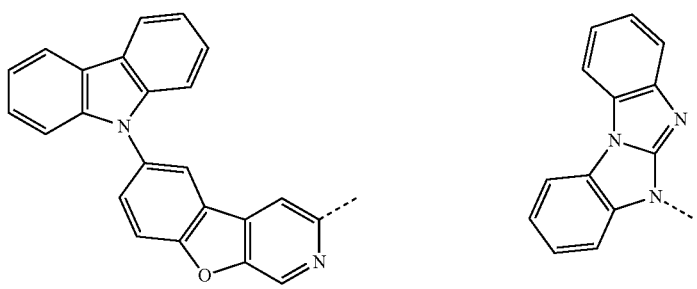
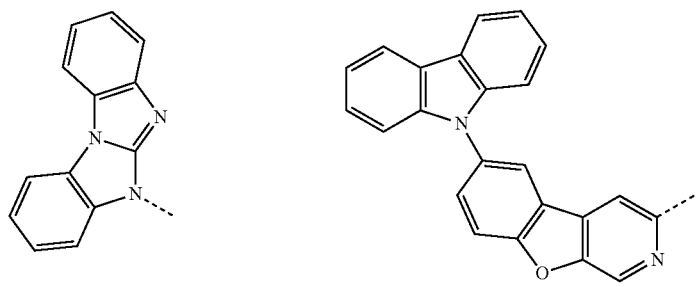
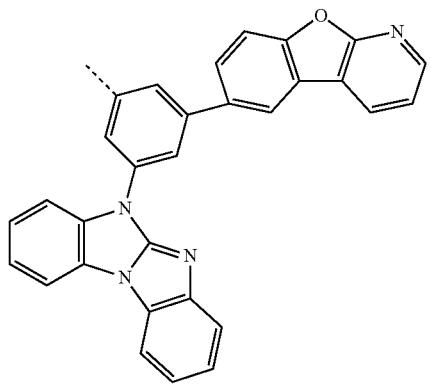

-continued
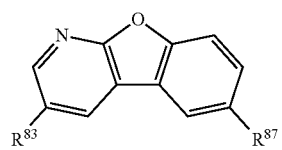
| Compound | R⁸³ | R⁸⁷ |
|---|---|---|
| A-58 | | |
| A-59 | | |
| A-60 | | H |
| A-61 | H | |

-continued
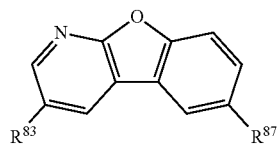
| Compound | R[83] | R[87] |
|---|---|---|
| A-62 | H | 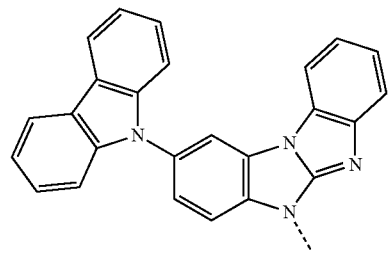 |
| A-63 | H | 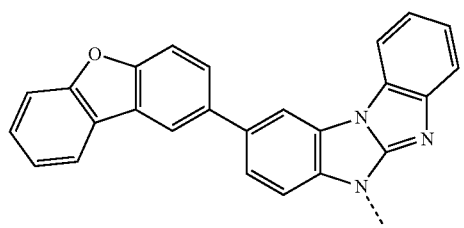 |
| A-64 | H | 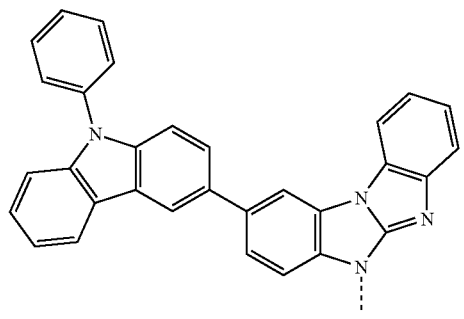 |
| A-65 | H | 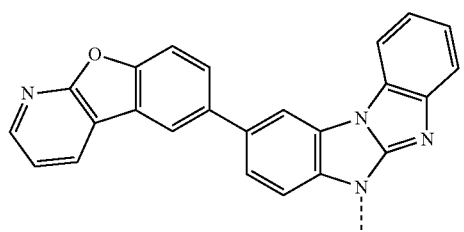 |

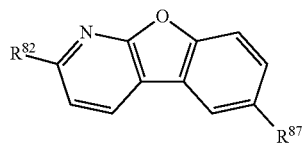
| Compound | R⁸² | R⁸⁷ |
|---|---|---|
| B-1 | | |
| B-2 | | |
| B-3 | | |
| B-4 | | |
| B-5 | | |

-continued
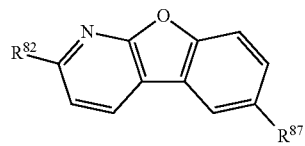
| Compound | R<sup>82</sup> | R<sup>87</sup> |
|---|---|---|
| B-6 | 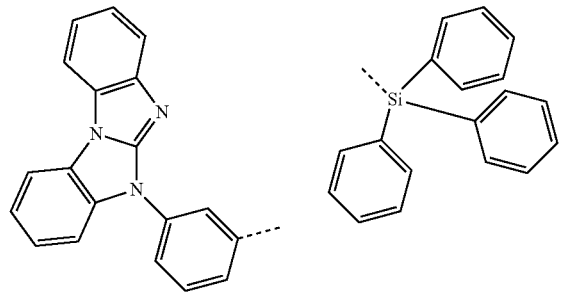 | |
| B-7 | 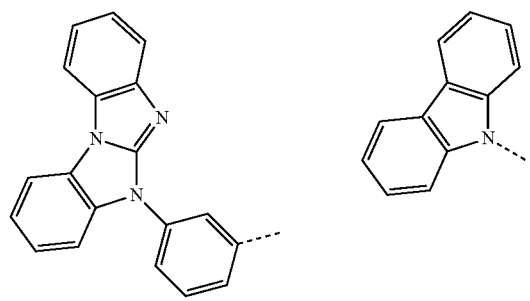 | |
| B-8 | 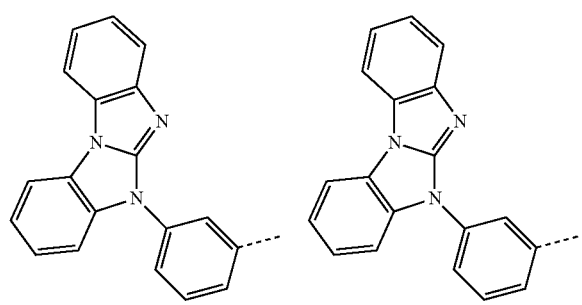 | |
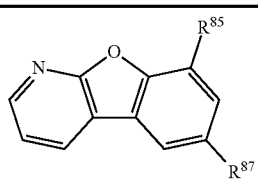
| Compound | R<sup>85</sup> | R<sup>87</sup> |
|---|---|---|
| C-1 | 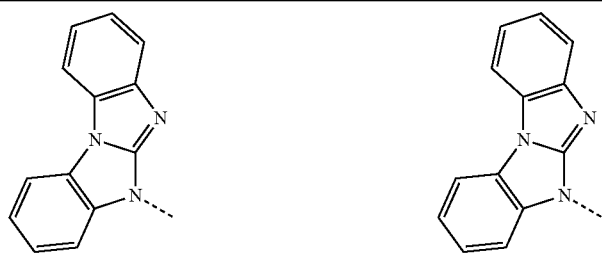 | |

-continued
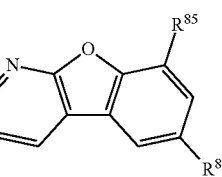
| Compound | R⁸⁵ | R⁸⁷ |
| --- | --- | --- |
| C-2 | 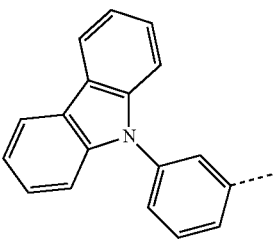 | 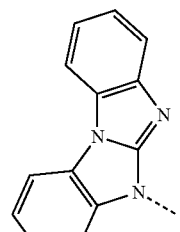 |
| C-3 | 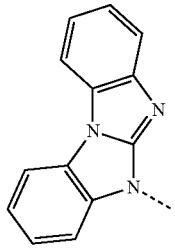 | 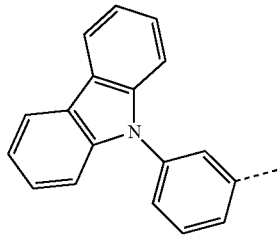 |
| C-4 | 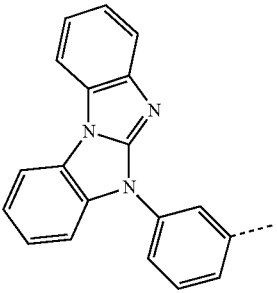 | 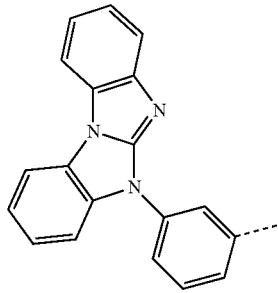 |
| C-5 | H | 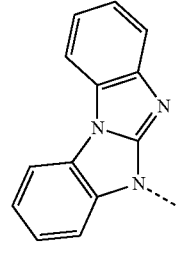 |
| C-6 | 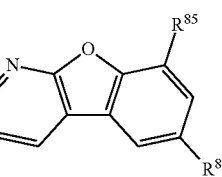 | H |

-continued
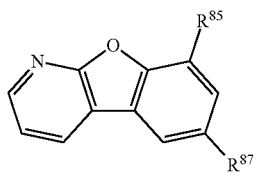
| Compound | R⁸⁵ | R⁸⁷ |
|---|---|---|
| C-7 | H | 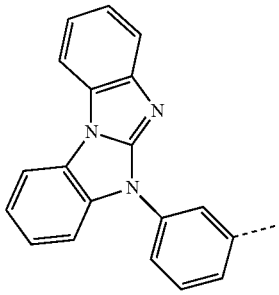 |
| C-8 | 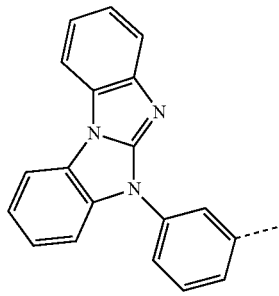 | H |
| C-9 | H | 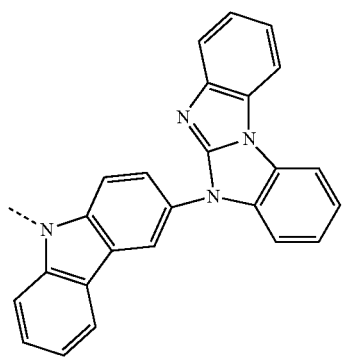 |
| C-10 | 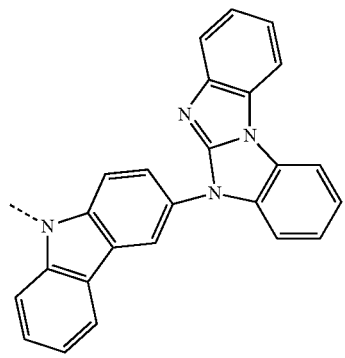 | H |

-continued
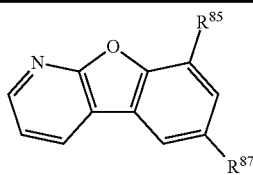
| Compound | R<sup>85</sup> | R<sup>87</sup> |
|---|---|---|
| C-11 | 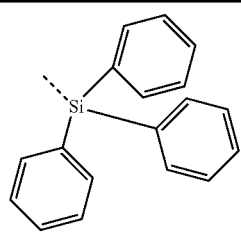 | 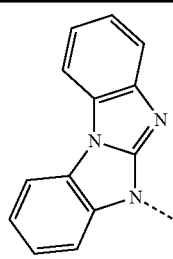 |
| C-12 | 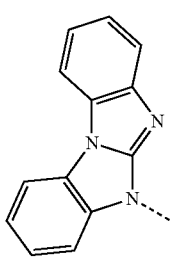 | 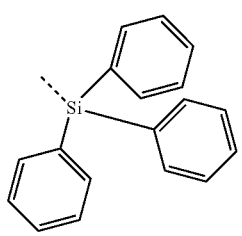 |
| C-13 | 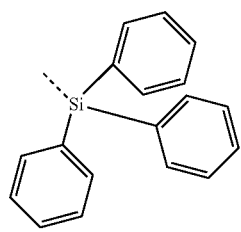 | 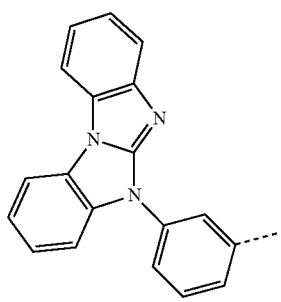 |
| C-14 | 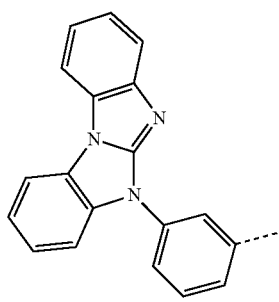 | 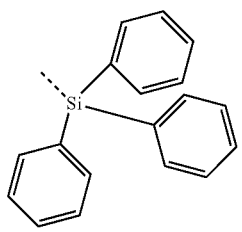 |
| C-15 | 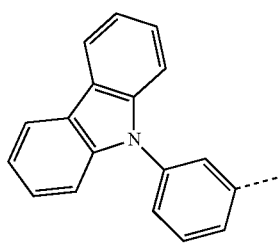 | 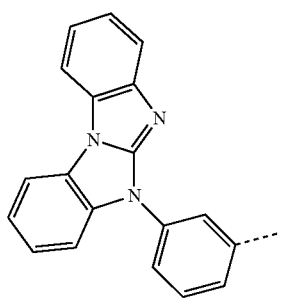 |

-continued
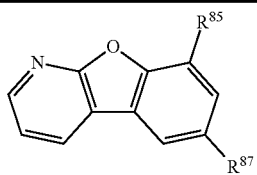
| Compound | R⁸⁵ | R⁸⁷ |
|---|---|---|
| C-16 | 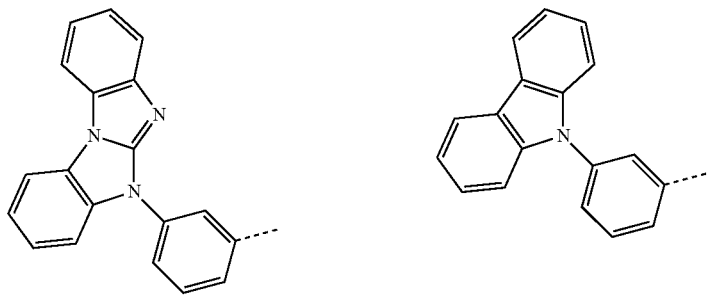 | |
| C-17 | 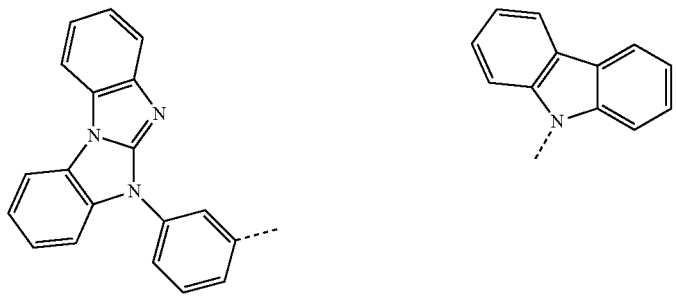 | |
| C-18 | 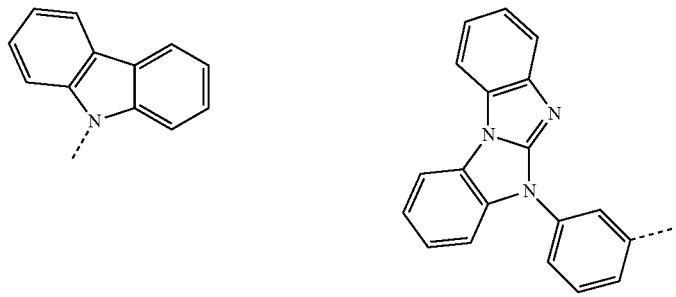 | |
| C-19 |  | |
| C-20 | 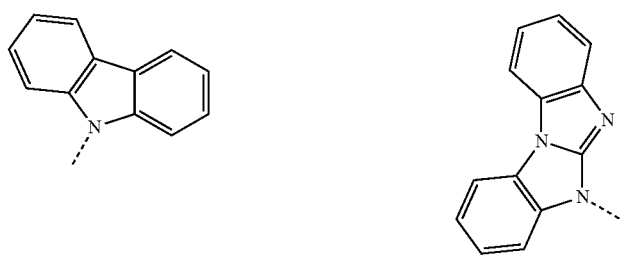 | |

-continued
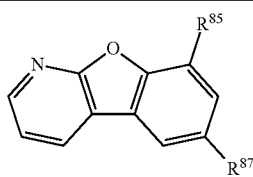
| Compound | R⁸⁵ | R⁸⁷ |
|---|---|---|
| C-21 | 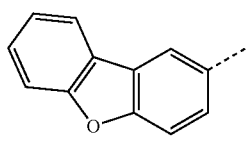 | 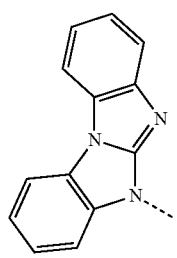 |
| C-22 | 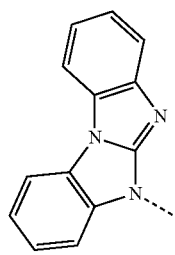 | 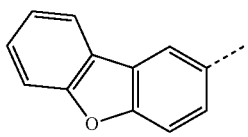 |
| C-23 | 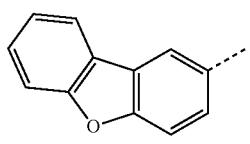 | 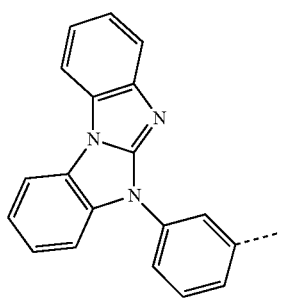 |
| C-24 | 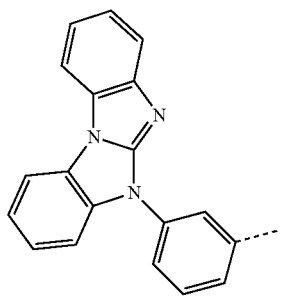 | 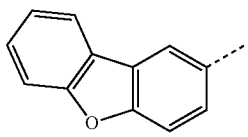 |
| C-25 | 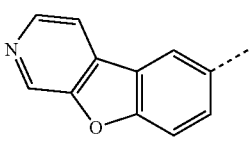 | 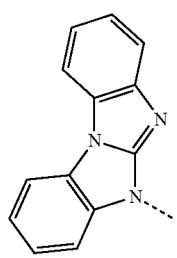 |

-continued
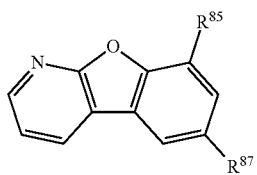
| Compound | R85 | R87 |
|---|---|---|
| C-26 | 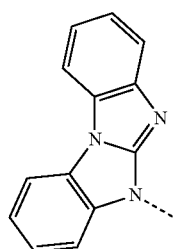 | 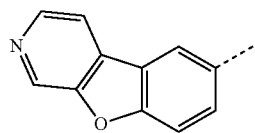 |
| C-27 | 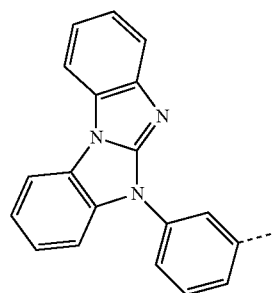 wait | |
| Compound | R85 | R87 |
|---|---|---|
| C-26 | 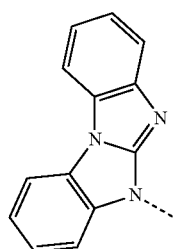 | 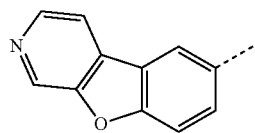 |
| C-27 | 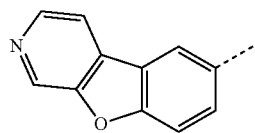 | 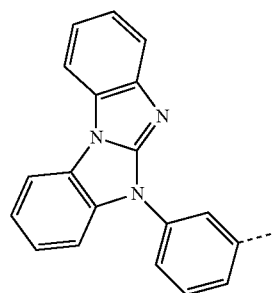 |
| C-28 | 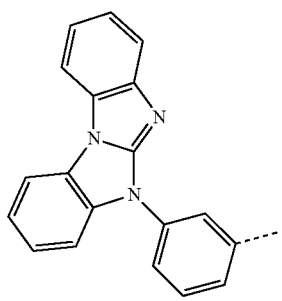 | 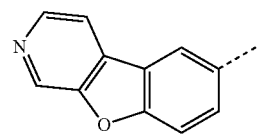 |
| C-29 | 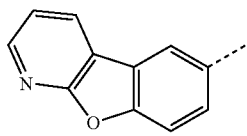 | 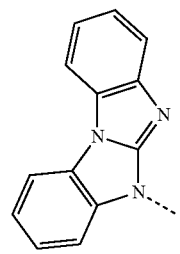 |
| C-30 | 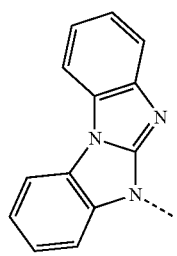 | 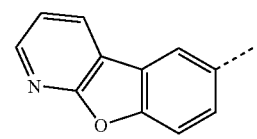 |

-continued
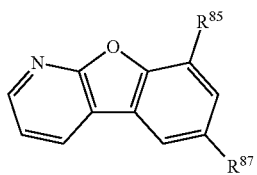
| Compound | $R^{85}$ | $R^{87}$ |
|---|---|---|
| C-31 | 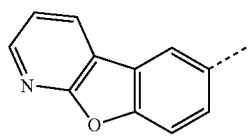 | 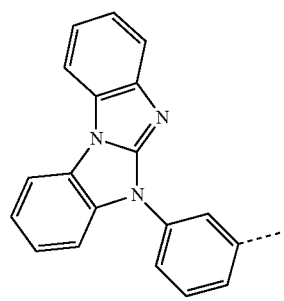 |
| C-32 | 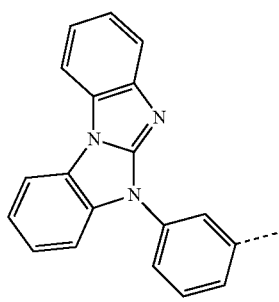 | 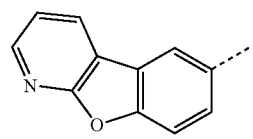 |
| C-33 | 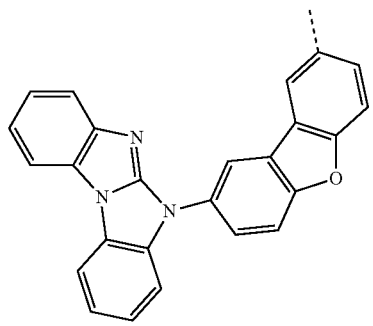 | 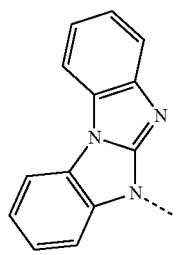 |
| C-34 | 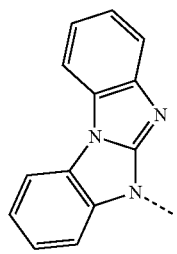 | 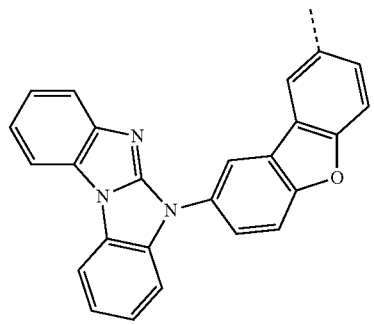 |

-continued
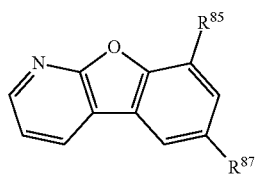
| Compound | R85 | R87 |
|---|---|---|
| C-35 | 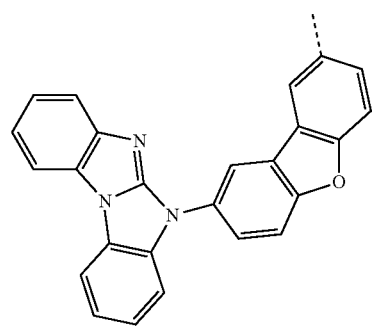 | H |
| C-36 | H | 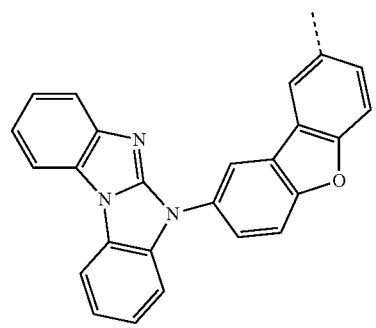 |
| C-37 | 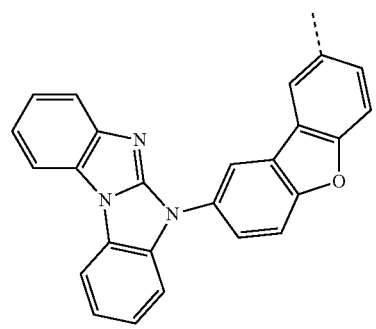 | 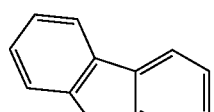 |
| C-38 | 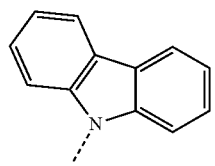 | 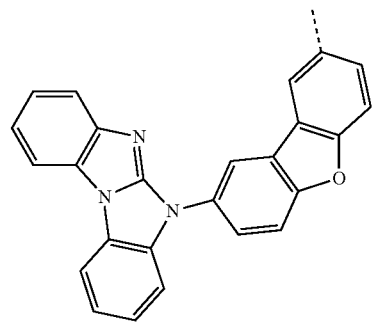 |

-continued
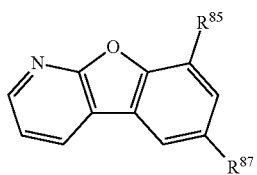
| Compound | R85 | R87 |
|---|---|---|
| C-39 | 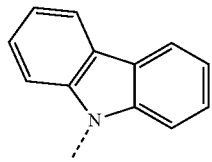 | 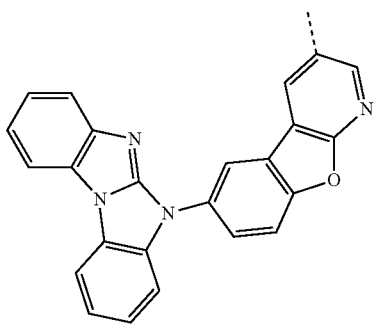 |
| C-40 | 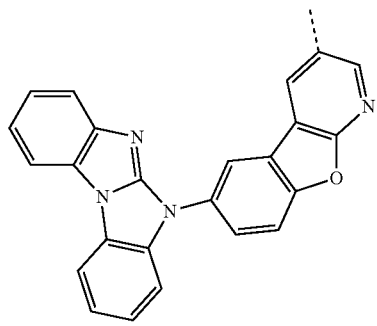 | 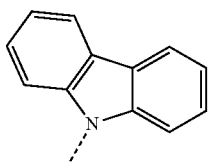 |
| C-41 | 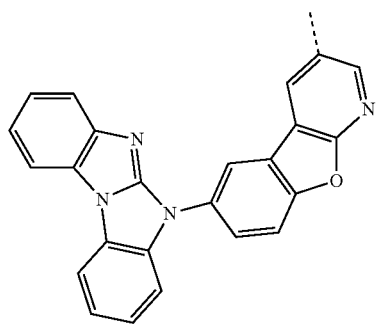 | H |
| C-42 | H | 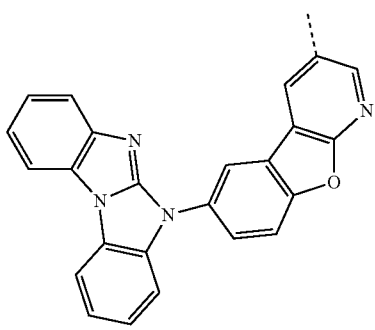 |

-continued
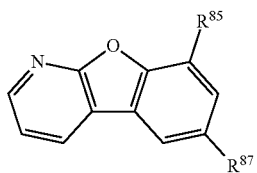
| Compound | R85 | R87 |
|---|---|---|
| C-43 | 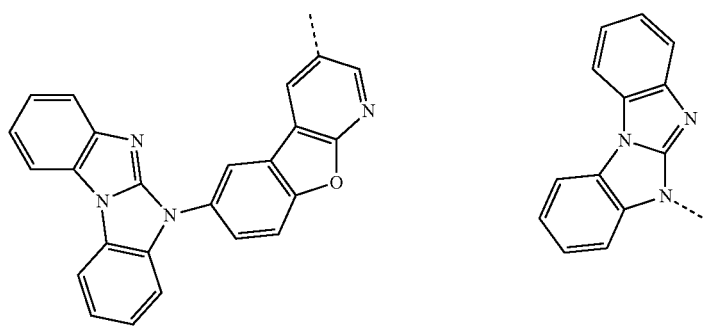 | |
| C-44 | | 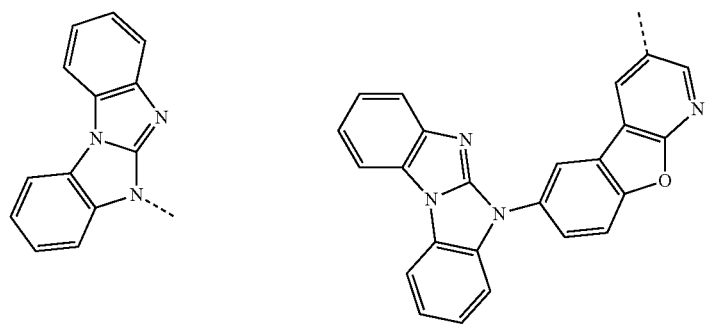 |
| C-45 | 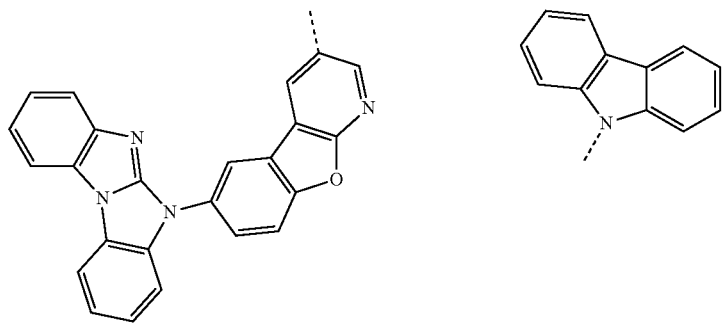 | |
| C-46 | | 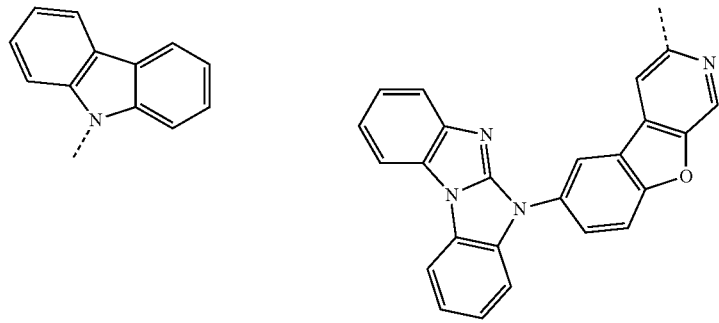 |

-continued
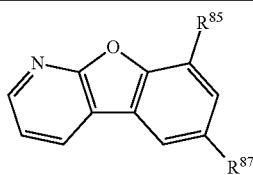
| Compound | R85 | R87 |
|---|---|---|
| C-47 | (structure) | H |
| C-48 | H | (structure) |
| C-49 | (structure) | (structure) |
| C-50 | (structure) | (structure) |

-continued
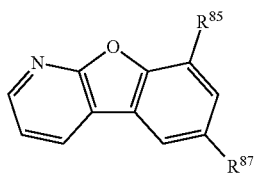
| Compound | R85 | R87 |
|---|---|---|
| C-51 | 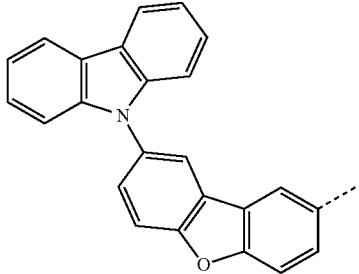 | 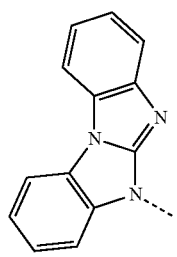 |
| C-52 | | 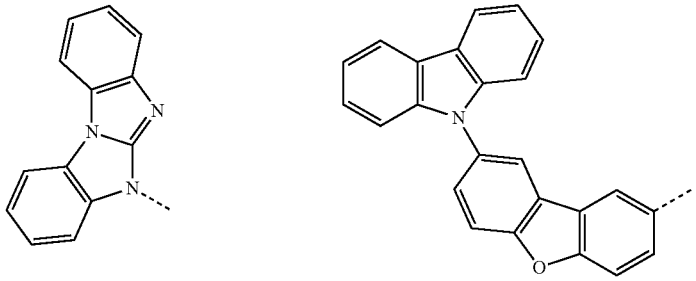 |
| C-53 | 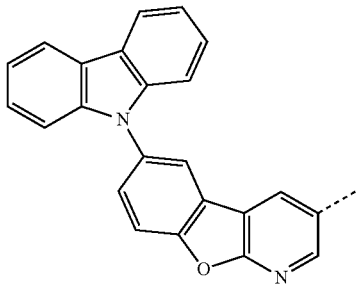 | 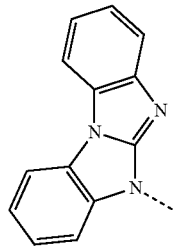 |
| C-54 | | 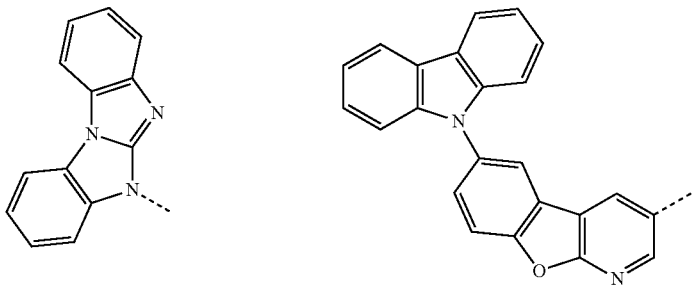 |

-continued
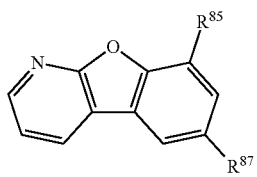
| Compound | R85 | R87 |
|---|---|---|
| C-55 | 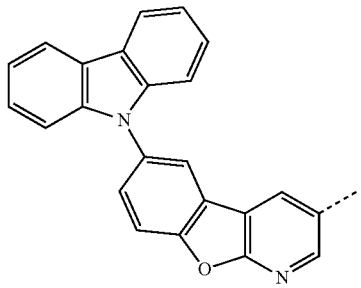 | 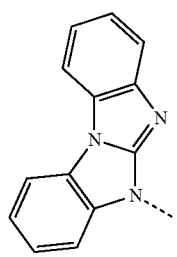 |
| C-56 | 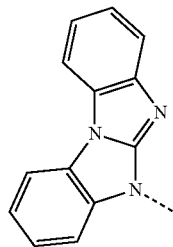 | 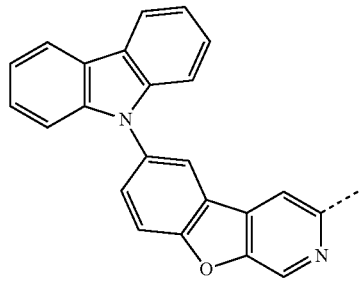 |
| C-57 | H | 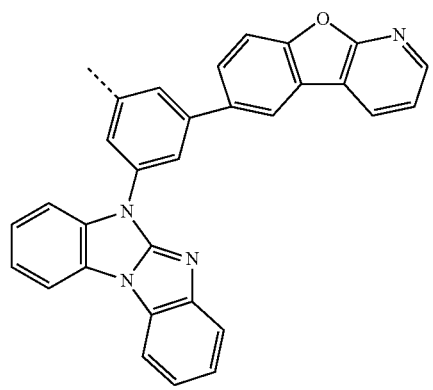 |
| C-58 | 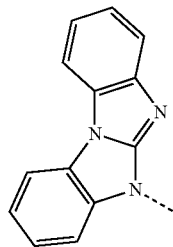 | 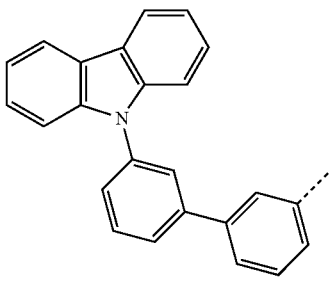 |

-continued
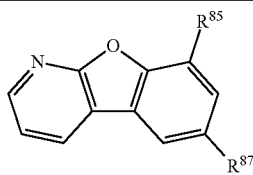
| Compound | R⁸⁵ | R⁸⁷ |
| --- | --- | --- |
| C-59 | 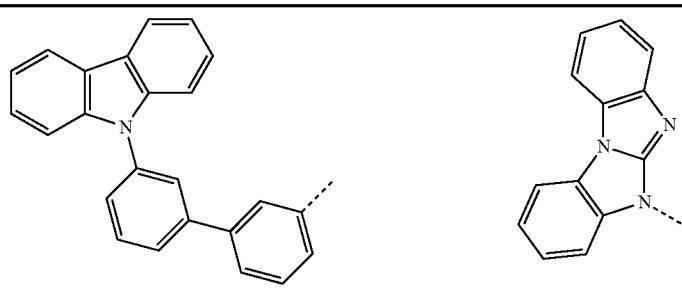 | |
| C-60 | 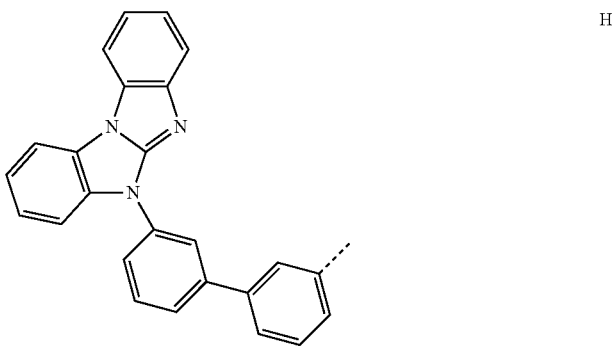 | H |
| C-61 | H | 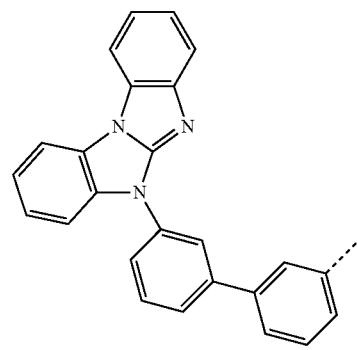 |
| C-62 | H | 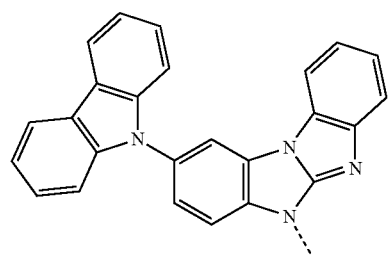 |

-continued
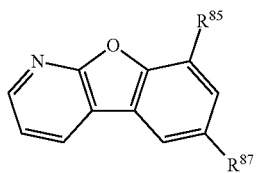
| Compound | R⁸⁵ | R⁸⁷ |
|---|---|---|
| C-63 | H | 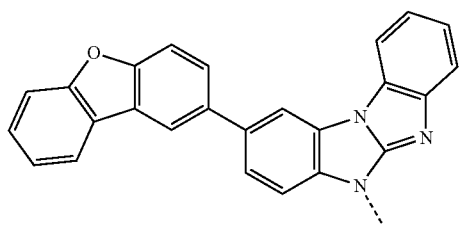 |
| C-64 | H | 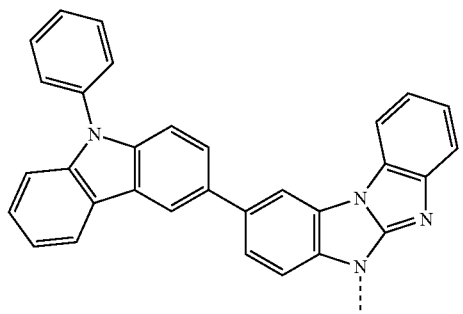 |
| C-65 | H | 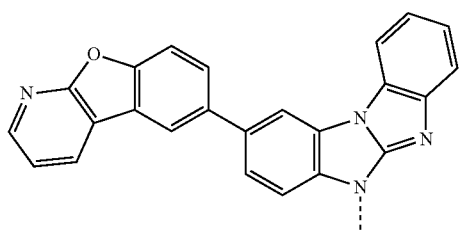 |
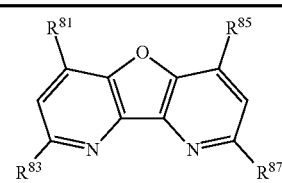
| Cmp. | R⁸¹ | R⁸³ | R⁸⁵ | R⁸⁷ |
|---|---|---|---|---|
| D-1 | 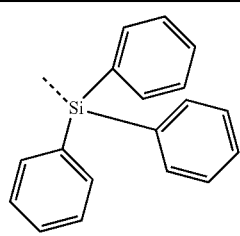 | 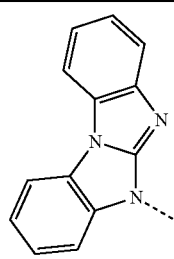 | 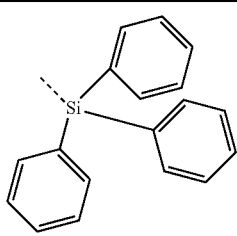 | 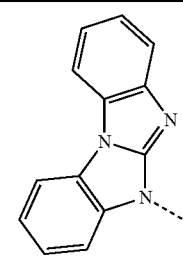 |

-continued
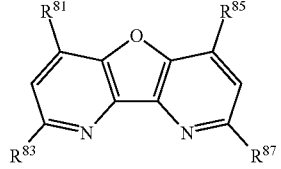
| Cmp. | R⁸¹ | R⁸³ | R⁸⁵ | R⁸⁷ |
|---|---|---|---|---|
| D-2 | H | 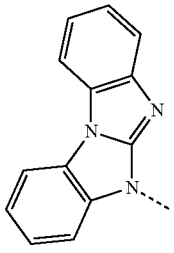 | H | 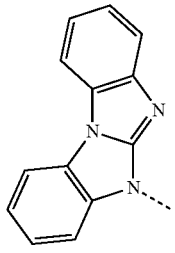 |
| D-3 | H | 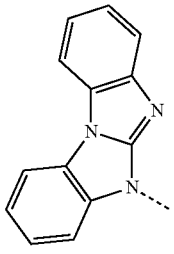 | H | H |
| D-4 | H | 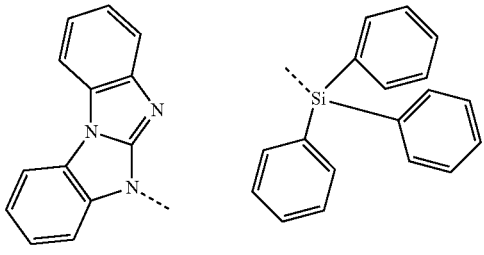 | 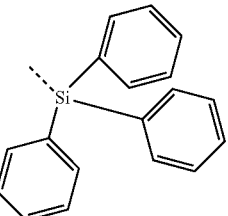 | 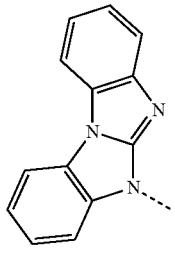 |
| D-5 | 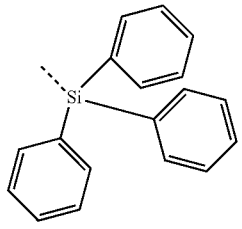 | 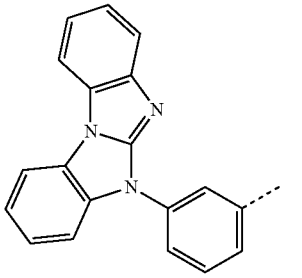 | 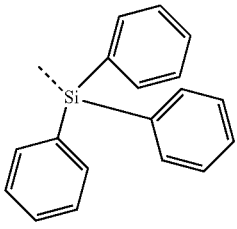 | 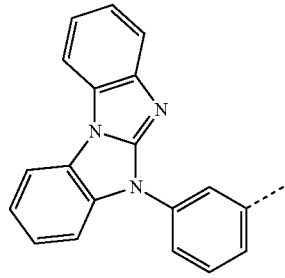 |
| D-6 | H | 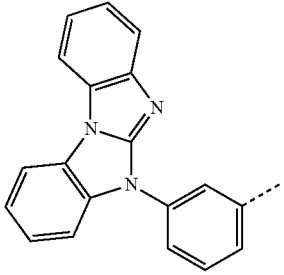 | H | 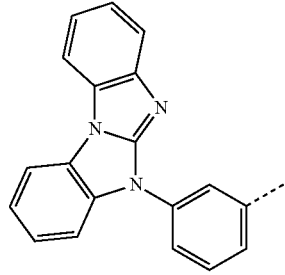 |

-continued
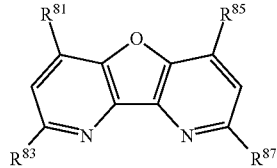
| Cmp. | R⁸¹ | R⁸³ | R⁸⁵ | R⁸⁷ |
|---|---|---|---|---|
| D-7 | H | 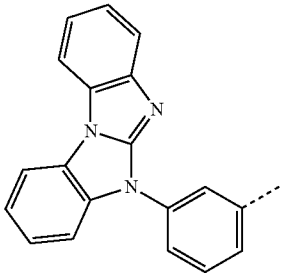 | H | |
| D-8 | H | 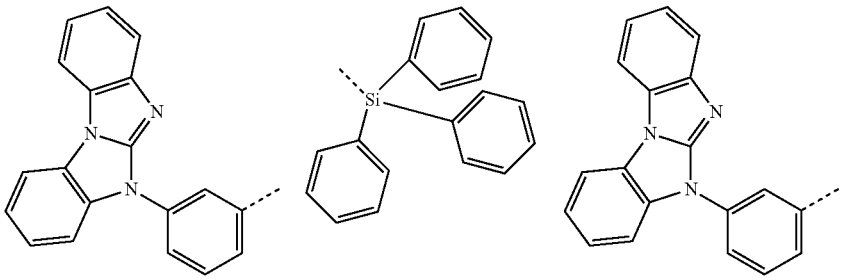 | 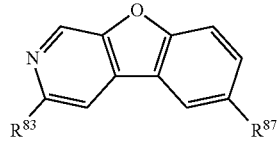 | 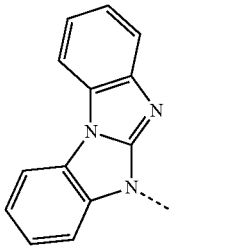 |
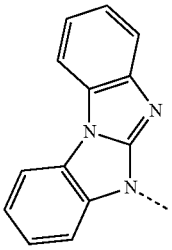
| Compound | R⁸³ | R⁸⁷ |
|---|---|---|
| E-1 | 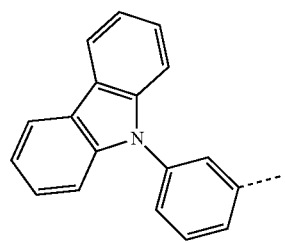 | |
| E-2 | 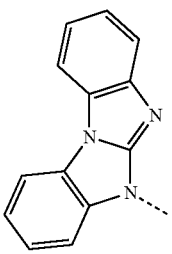 | |

-continued
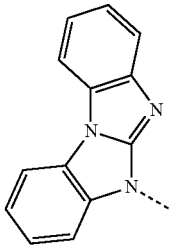
| Compound | R<sup>83</sup> | R<sup>87</sup> |
|---|---|---|
| E-3 | 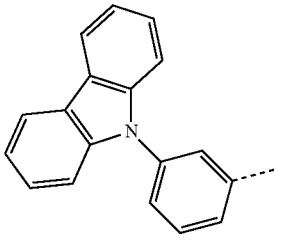 | 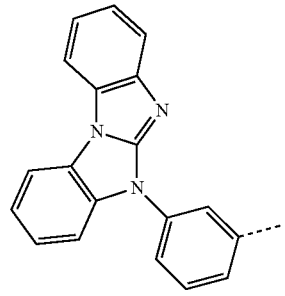 |
| E-4 | 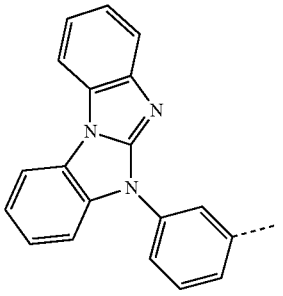 | 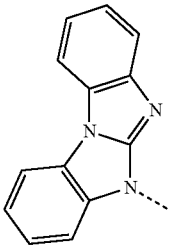 |
| E-5 | H | 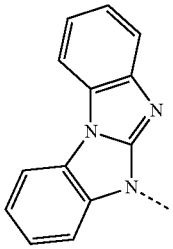 |
| E-6 | 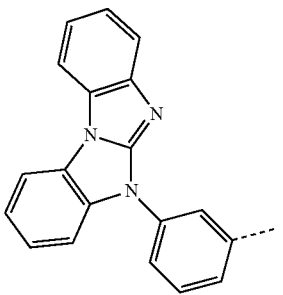 | H |
| E-7 | H |  |

-continued
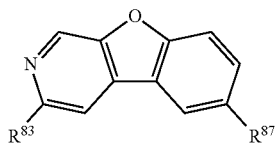
| Compound | R⁸³ | R⁸⁷ |
|---|---|---|
| E-8 | 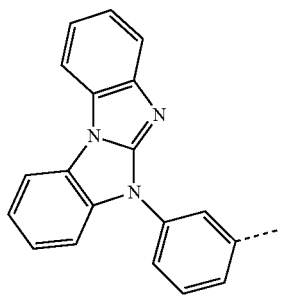 | H |
| E-9 | H | 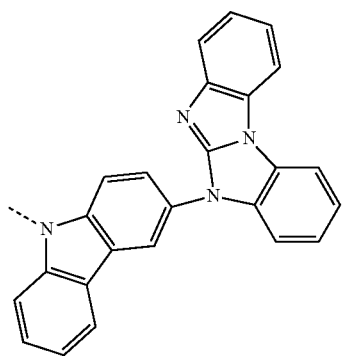 |
| E-10 | 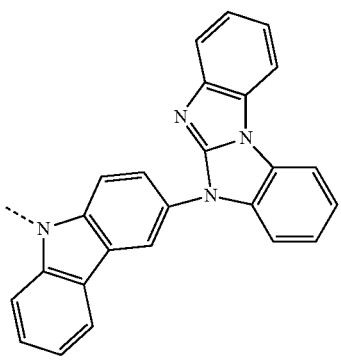 | H |
| E-11 | 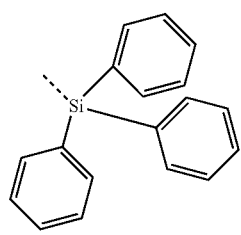 | 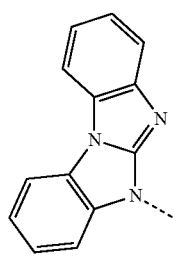 |

-continued
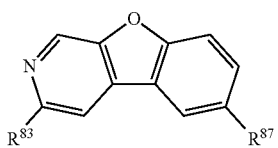
| Compound | R⁸³ | R⁸⁷ |
|---|---|---|
| E-12 | 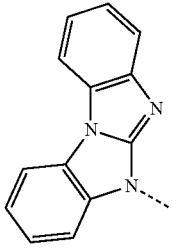 | 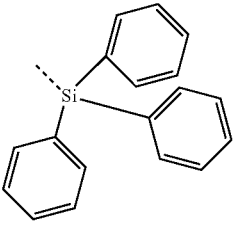 |
| E-13 | 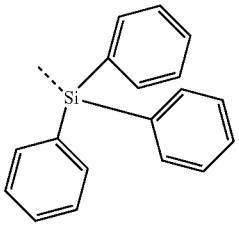 | 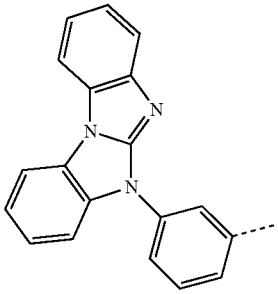 |
| E-14 | 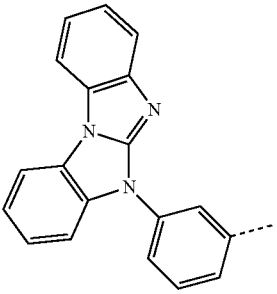 | 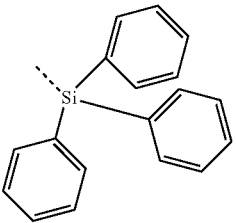 |
| E-15 | 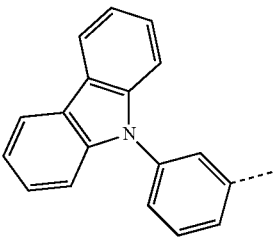 | 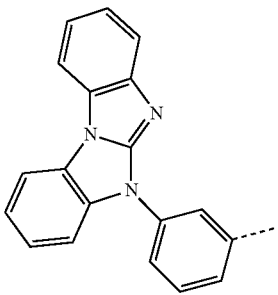 |

-continued

| Compound | R⁸³ | R⁸⁷ |
|---|---|---|
| E-16 | | |
| E-17 | | |
| E-18 | | |
| E-19 | | |
| E-20 | | |

-continued

| Compound | R⁸³ | R⁸⁷ |
|---|---|---|
| E-21 | dibenzofuran-yl | benzimidazo-benzimidazole-N-yl |
| E-22 | benzimidazo-benzimidazole-N-yl | dibenzofuran-yl |
| E-23 | dibenzofuran-yl | benzimidazo-benzimidazole-N-(phenyl)-yl |
| E-24 | benzimidazo-benzimidazole-N-(phenyl)-yl | dibenzofuran-yl |
| E-25 | pyrido-benzofuran-yl | benzimidazo-benzimidazole-N-yl |

-continued
| Compound | R⁸³ | R⁸⁷ |
|---|---|---|
| E-26 | 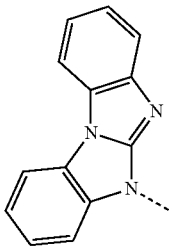 | 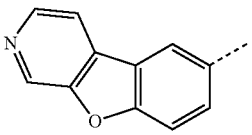 |
| E-27 | 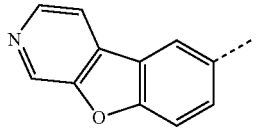 | 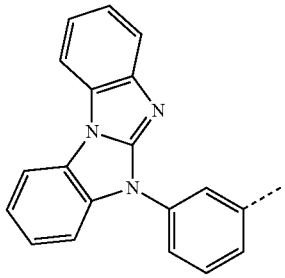 |
| E-28 | 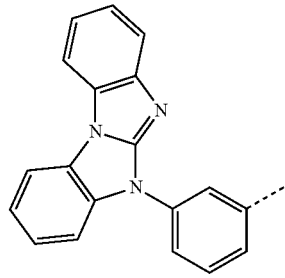 | 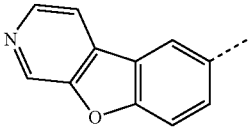 |
| E-29 | 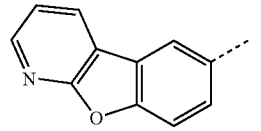 | 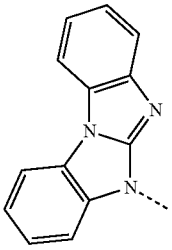 |
| E-30 | 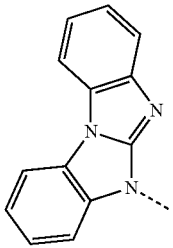 | 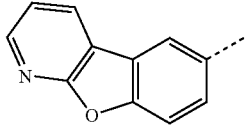 |

-continued

| Compound | R⁸³ | R⁸⁷ |
|---|---|---|
| E-31 | [pyrido-benzofuran] | [benzimidazole-N-phenyl] |
| E-32 | [benzimidazole-N-phenyl] | [pyrido-benzofuran] |
| E-33 | [benzimidazole-N-(dibenzofuranyl)] | [benzimidazole] |
| E-34 | [benzimidazole] | [benzimidazole-N-(dibenzofuranyl)] |

-continued
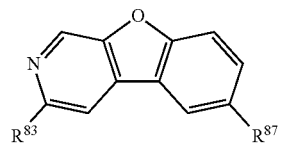
| Compound | R83 | R87 |
|---|---|---|
| E-35 | (benzimidazole-fused dibenzofuranyl group) | H |
| E-36 | H | (benzimidazole-fused dibenzofuranyl group) |
| E-37 | (benzimidazole-fused dibenzofuranyl group) | (carbazolyl group) |
| E-38 | (carbazolyl group) | (benzimidazole-fused dibenzofuranyl group) |

-continued
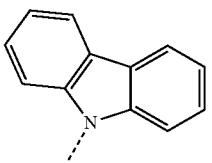
| Compound | R83 | R87 |
|---|---|---|
| E-39 | 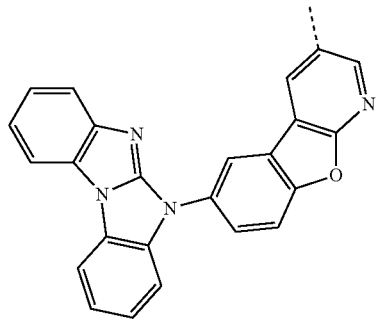 | 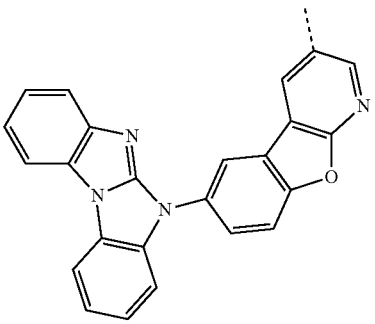 |
| E-40 | 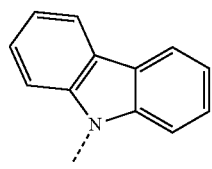 | 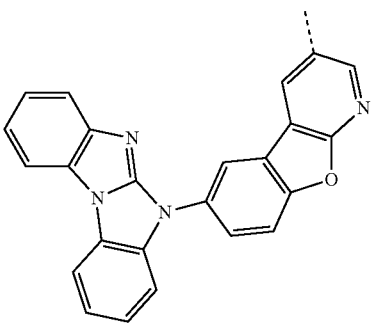 |
| E-41 | 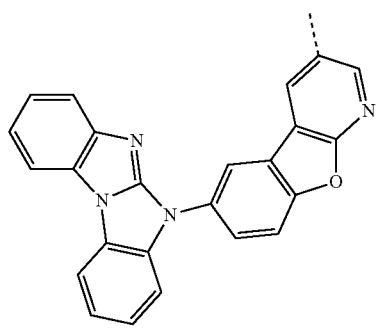 | H |
| E-42 | H |  |

-continued
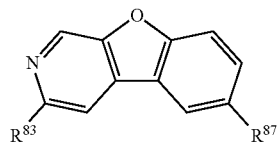
| Compound | R<sup>83</sup> | R<sup>87</sup> |
|---|---|---|
| E-43 | | |
| E-44 | | |
| E-45 | | |
| E-46 | | |
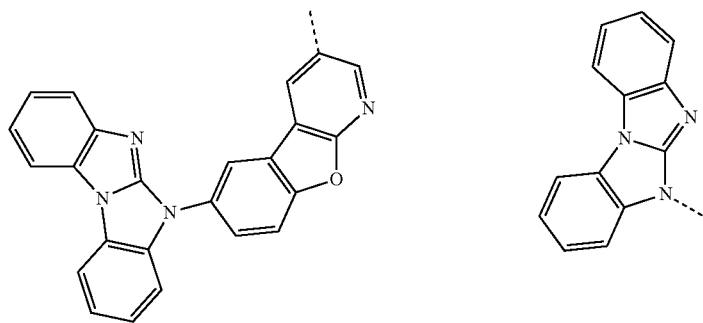
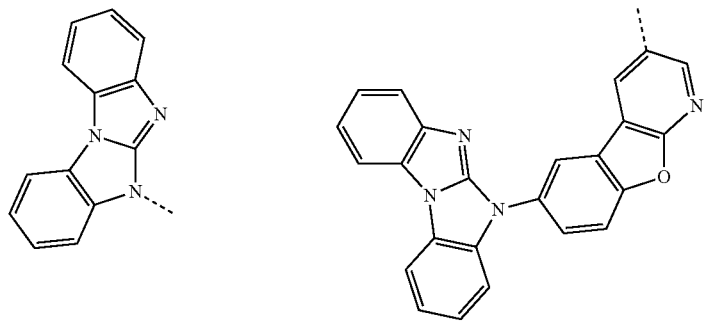
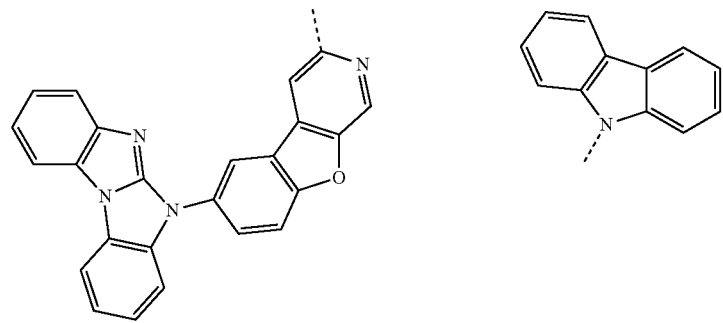
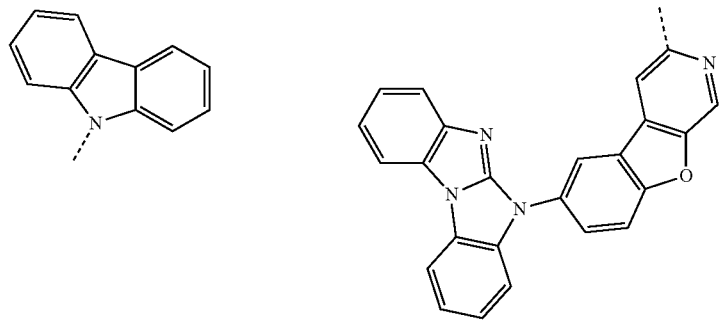

-continued
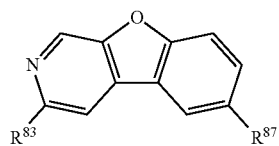
| Compound | R<sup>83</sup> | R<sup>87</sup> |
| --- | --- | --- |
| E-47 | 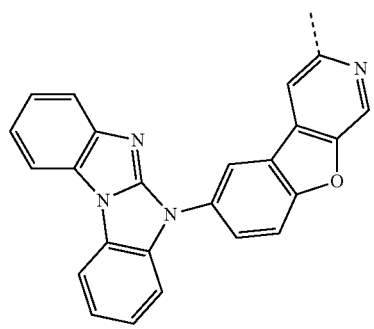 | H |
| E-48 | H | 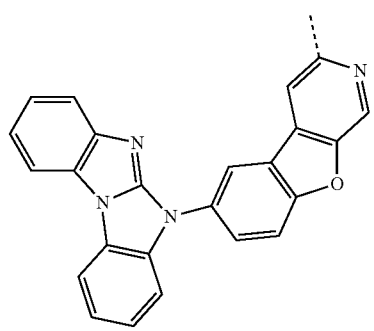 |
| E-49 | 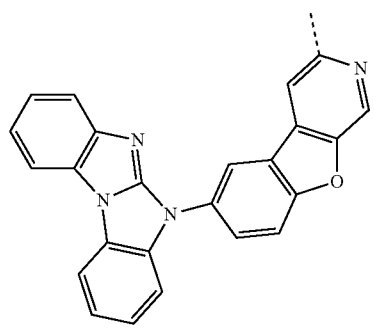 | 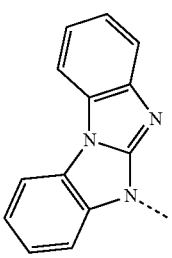 |
| E-50 | 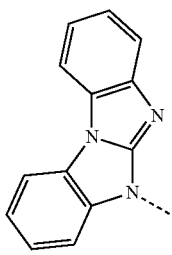 | 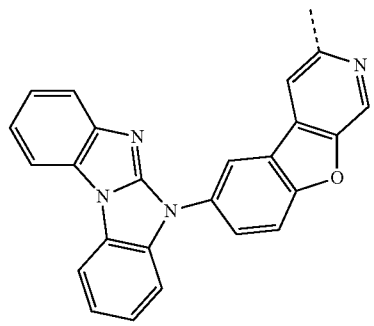 |

-continued

| Compound | R⁸³ | R⁸⁷ |
|---|---|---|
| E-51 | | |
| E-52 | | |
| E-53 | | |
| E-54 | | |
| E-55 | | |

-continued
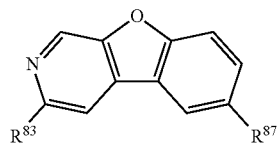
| Compound | R83 | R87 |
|---|---|---|
| E-56 | 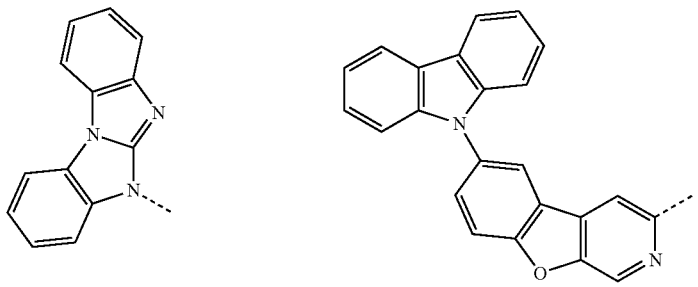 | |
| E-57 | H | 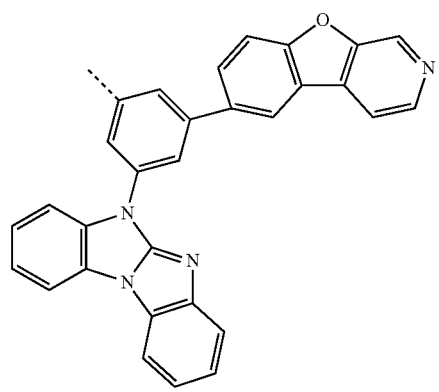 |
| E-58 | 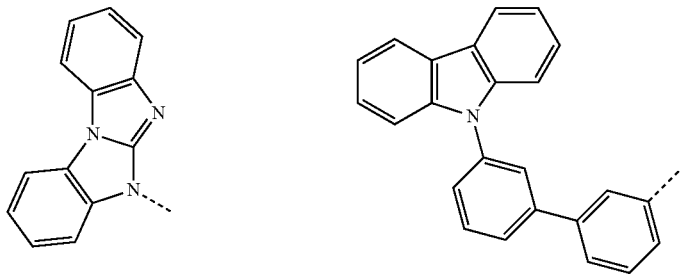 | |
| E-59 | 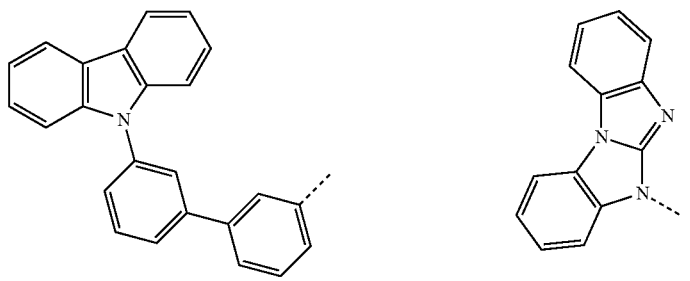 | |

-continued
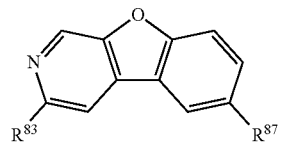
| Compound | R83 | R87 |
|---|---|---|
| E-60 | 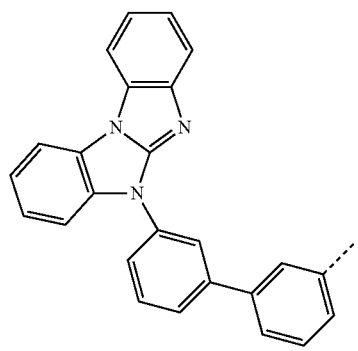 | H |
| E-61 | H | 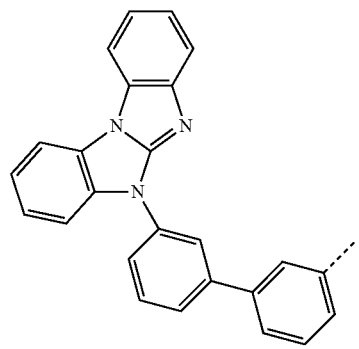 |
| E-62 | H | 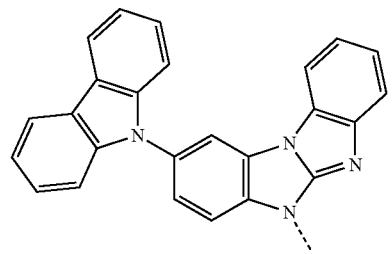 |
| E-63 | H | 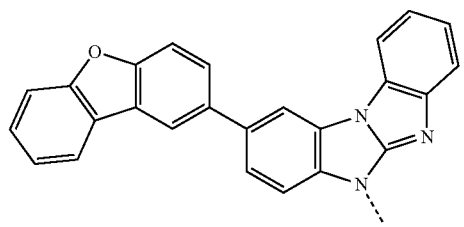 |

-continued
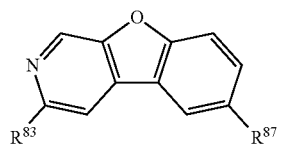
| Compound | R83 | R87 |
|---|---|---|
| E-64 | H | |
| E-65 | H | |
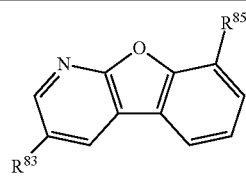
| Compound | R83 | R85 |
|---|---|---|
| F-1 | | |
| F-2 | | |

-continued
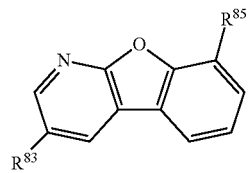
| Compound | R<sup>83</sup> | R<sup>85</sup> |
|---|---|---|
| F-3 | 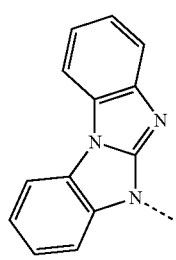 | 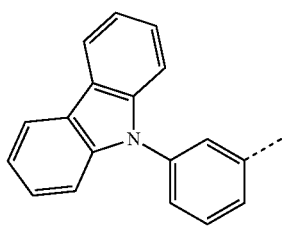 |
| F-4 | 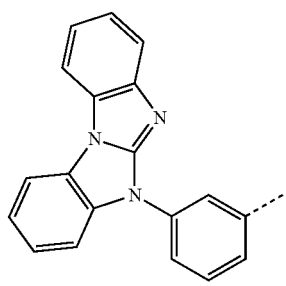 | 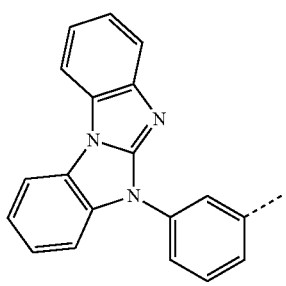 |
| F-5 | H | 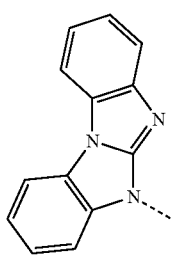 |
| F-6 | 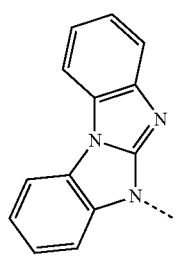 | H |
| F-7 | H | 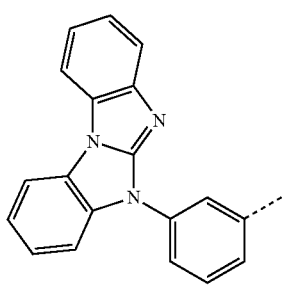 |

-continued
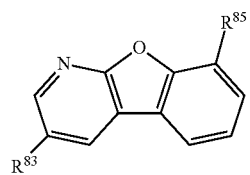
| Compound | R$^{83}$ | R$^{85}$ |
|---|---|---|
| F-8 | 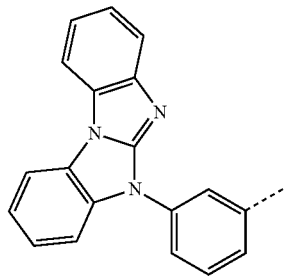 | H |
| F-9 | H | 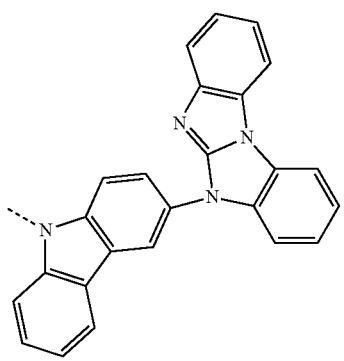 |
| F-10 | 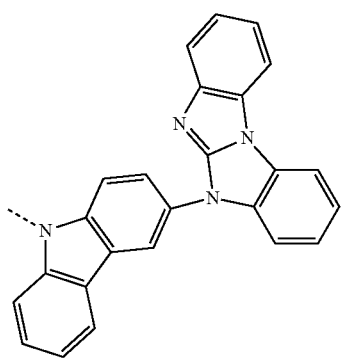 | H |
| F-11 | 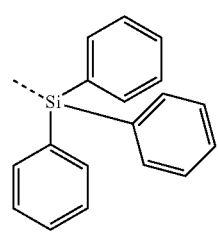 | 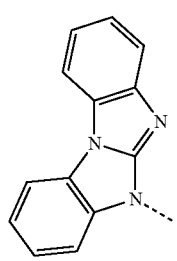 |

-continued

| Compound | R⁸³ | R⁸⁵ |
|---|---|---|
| F-12 | | |
| F-13 | | |
| F-14 | | |
| F-15 | | |
| F-16 | | |

-continued

| Compound | R⁸³ | R⁸⁵ |
|---|---|---|
| F-17 | | |
| F-18 | | |
| F-19 | | |
| F-20 | | |
| F-21 | | |

-continued

[Structure: pyrido-benzofuran core with R⁸⁵ and R⁸³ substituents]

| Compound | R⁸³ | R⁸⁵ |
| --- | --- | --- |
| F-22 | benzimidazo-benzimidazole | dibenzofuran |
| F-23 | dibenzofuran | N-phenyl-benzimidazo-benzimidazole |
| F-24 | N-phenyl-benzimidazo-benzimidazole | dibenzofuran |
| F-25 | pyrido-benzofuran | benzimidazo-benzimidazole |
| F-26 | benzimidazo-benzimidazole | pyrido-benzofuran |

-continued

| Compound | R<sup>83</sup> | R<sup>85</sup> |
|---|---|---|
| F-27 | | |
| F-28 | | |
| F-29 | | |
| F-30 | | |
| F-31 | | |

-continued

| Compound | R<sup>83</sup> | R<sup>85</sup> |
|---|---|---|
| F-32 | | |
| F-33 | | |
| F-34 | | |
| F-35 | | H |

-continued
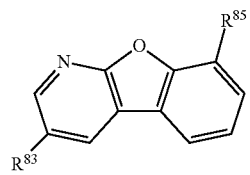
| Compound | R83 | R85 |
|---|---|---|
| F-36 | H | (structure) |
| F-37 | (structure) | (structure) |
| F-38 | (structure) | (structure) |
| F-39 | (structure) | (structure) |

-continued

| Compound | R⁸³ | R⁸⁵ |
|---|---|---|
| F-40 | (benzimidazo-fused carbazole-pyridobenzofuran substituent) | (carbazol-9-yl) |
| F-41 | (benzimidazo-fused carbazole-pyridobenzofuran substituent) | H |
| F-42 | H | (benzimidazo-fused carbazole-pyridobenzofuran substituent) |
| F-43 | (benzimidazo-fused carbazole-pyridobenzofuran substituent) | (benzimidazo[1,2-a]benzimidazol-yl) |

-continued
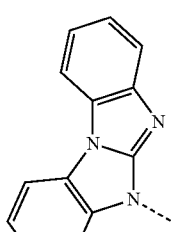
| Compound | R83 | R85 |
|---|---|---|
| F-44 | 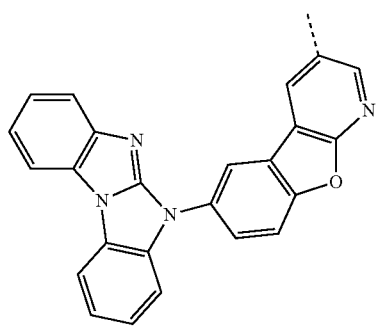 | 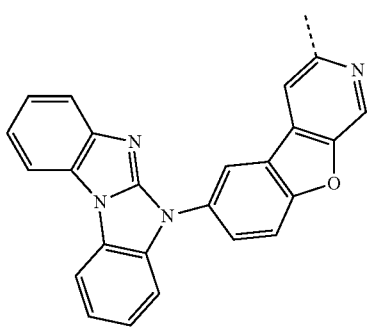 |
| F-45 | 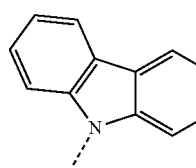 | 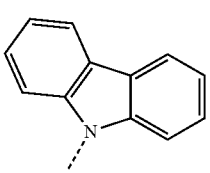 |
| F-46 | 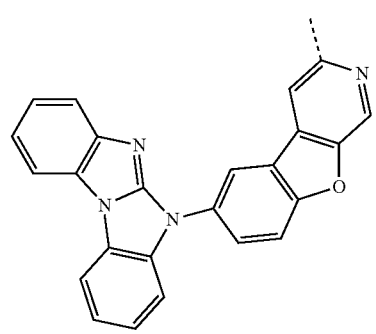 | 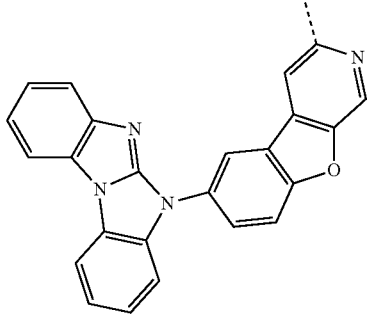 |
| F-47 |  | H |

-continued
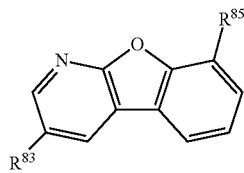
| Compound | R83 | R85 |
|---|---|---|
| F-48 | H | 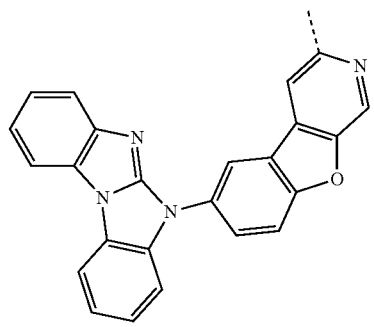 |
| F-49 | 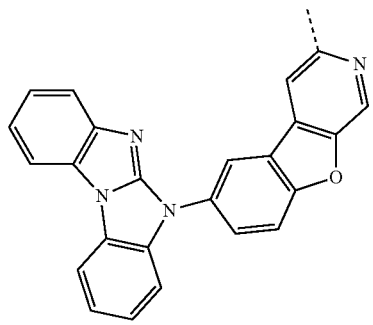 | 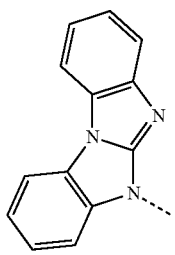 |
| F-50 | 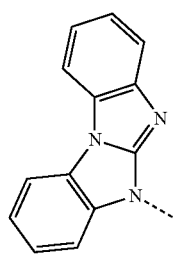 | 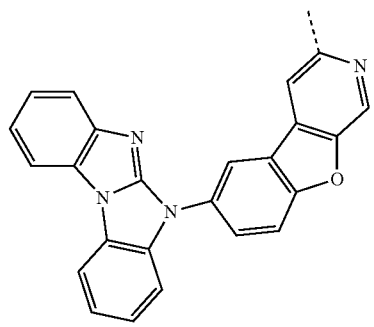 |
| F-51 | 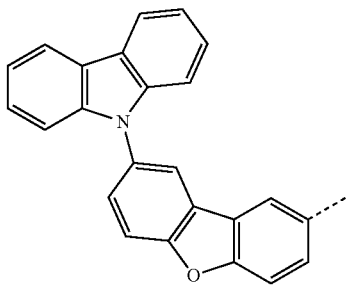 | 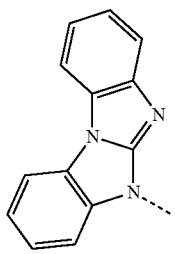 |

-continued
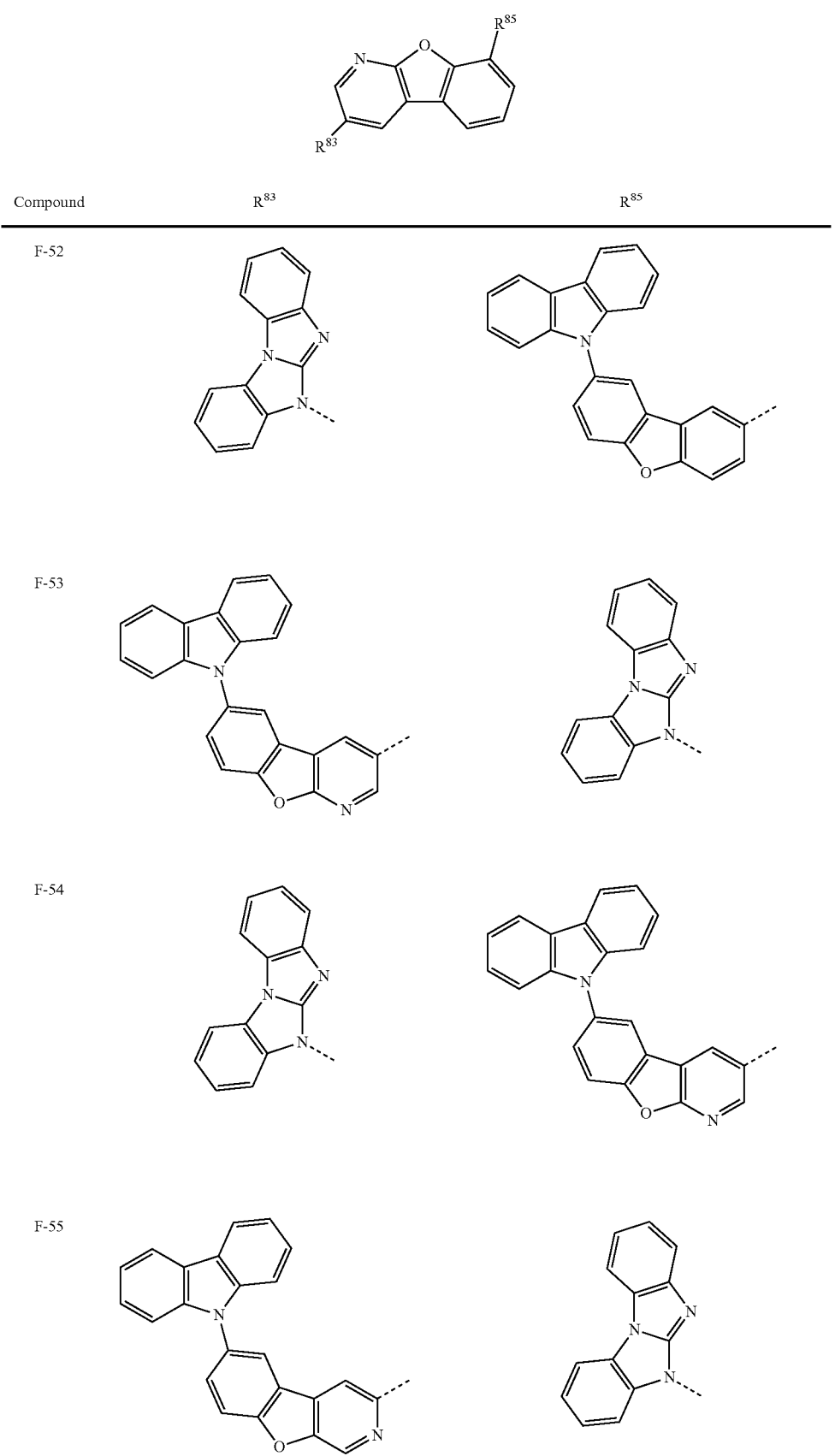

-continued
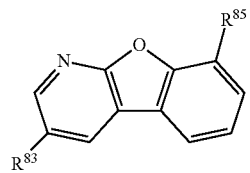
| Compound | R⁸³ | R⁸⁵ |
|---|---|---|
| F-56 | 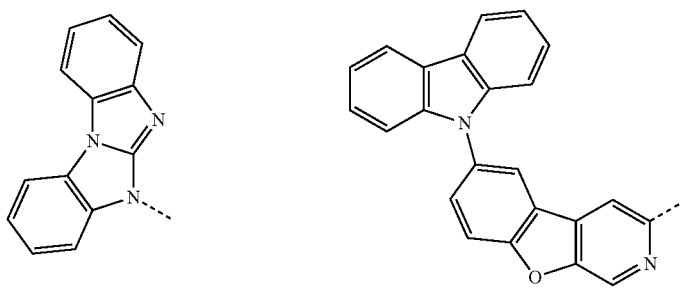 | |
| F-57 | H | 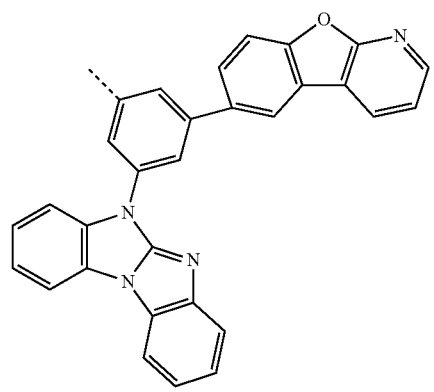 |
| F-58 | 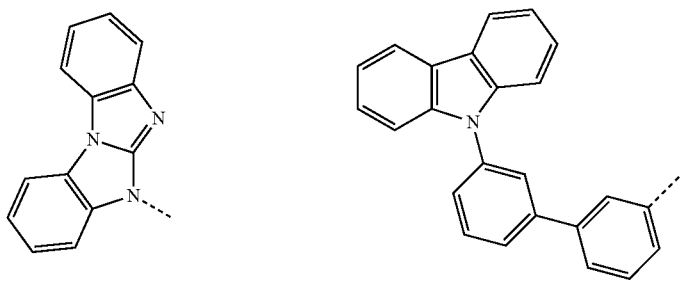 | |
| F-59 | 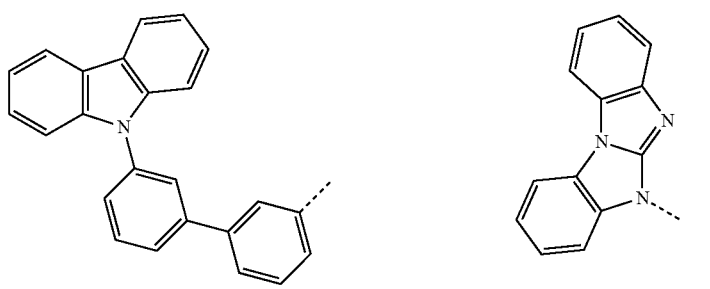 | |

-continued
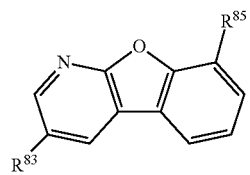
| Compound | R<sup>83</sup> | R<sup>85</sup> |
|---|---|---|
| F-60 | | H |
| F-61 | H | |
| F-62 | H | |
| F-63 | H | |

-continued

| Compound | R<sup>83</sup> | R<sup>85</sup> |
|---|---|---|
| F-64 | H | 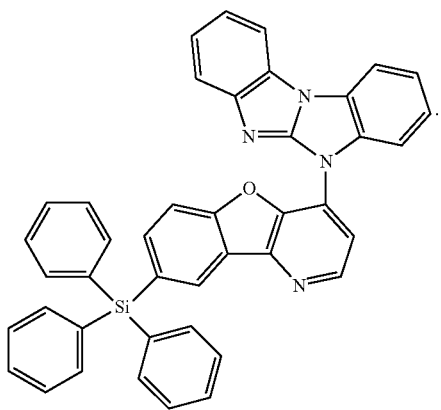 |
| F-65 | H | 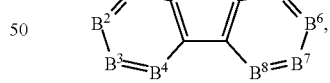 | or (G-1)

10. An electronic device, comprising a compound according to claim 1.

11. The electronic device according to claim 10, which is an electroluminescent device.

12. A hole transport layer, or an emitting layer comprising a compound according to claim 1.

13. The emitting layer according to claim 12, comprising the compound as host material in combination with a phosphorescent emitter.

14. An apparatus selected from the group consisting of stationary visual display units; mobile visual display units; illumination units; keyboards; items of clothing; furniture; wallpaper, comprising the organic electronic device according to claim 10.

15. A device selected from the group consisting of electrophotographic photoreceptors, photoelectric converters, organic solar cells, switching elements, organic light emitting field effect transistors, image sensors, dye lasers and electroluminescent devices comprising the compound according to claim 1.

16. A compound of the formula (II)

wherein
$B^1$ is N, or $CR^{81}$,
$B^2$ is N, or $CR^{82}$,
$B^3$ is N, or $CR^{83}$,
$B^4$ is N, or $CR^{84}$,
$B^5$ is N, or $CR^{85}$,
$B^6$ is N, or $CR^{86}$,
$B^7$ is N, or $CR^{87}$,
$B^8$ is N, or $CR^{88}$, wherein $R^{81}$, $R^{82}$, $R^{83}$, $R^{84}$, $R^{85}$, $R^{86}$, $R^{87}$ and $R^{88}$ are independently of each other H, a $C_1$-$C_{25}$ alkyl group, which can optionally be substituted by E and or interrupted by D; a $C_6$-$C_{24}$ aryl group, which can optionally be substituted by G, a $C_2$-$C_{30}$ heteroaryl group, which can optionally be substituted by G; a group of formula -(A$^1$)$_o$-(A$^2$)$_p$-(A$^3$)$_q$-(A$^4$)$_r$-R$^{16}$, or -(A$^1$)$_o$-(A$^2$)$_p$-(A$^3$)$_q$-(A$^4$)$_r$-X$^1$,
wherein R$^{84}$ does not include a Cl atom;
o is 0, or 1, p is 0, or 1, q is 0, or 1, r is 0, or 1,
at least one of the substituents R$^{81}$, R$^{82}$, R$^{83}$, R$^{84}$, R$^{85}$, R$^{86}$, R$^{87}$ and R$^{88}$ represents a group of formula -(A$^1$)$_o$-(A$^2$)$_p$-(A$^3$)$_q$-(A$^4$)$_r$-X$^1$; wherein
X$^1$ is Cl, Br, or I, ZnX$^{12}$, X$^{12}$ is a halogen atom; —SnR$^{207}$R$^{208}$R$^{209}$, wherein R$^{207}$, R$^{208}$ and R$^{209}$ are identical or different and are H or C$_1$-C$_8$ alkyl, wherein two radicals optionally form a common ring and these radicals are optionally branched or unbranched; —B(OH)$_2$, —B(OY$^1$)$_2$,

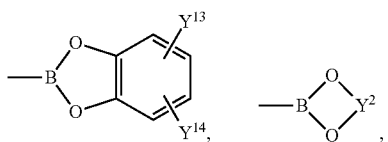

—BF$_4$Na, or —BF$_4$K, wherein Y$^1$ is independently in each occurrence a C$_1$-C$_{18}$ alkyl group and Y$^2$ is independently in each occurrence a C$_2$-C$_{10}$ alkylene group, and Y$^{13}$ and Y$^{14}$ are independently of each other hydrogen, or a C$_1$-C$_{18}$ alkyl group, and o, p, q, r, G, A$^1$, A$^2$, A$^3$, A$^4$, R$^{81}$, R$^{82}$, R$^{83}$, R$^{84}$, R$^{85}$, R$^{86}$, R$^{87}$ and R$^{88}$ are as defined in claim 1, with the proviso that the following compounds are excluded:

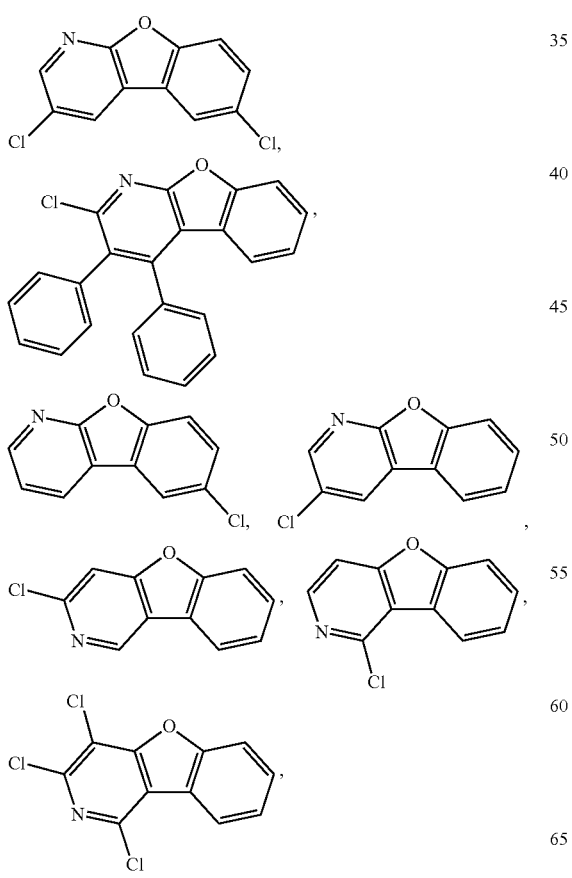

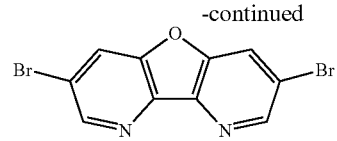

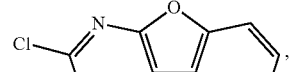

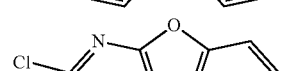

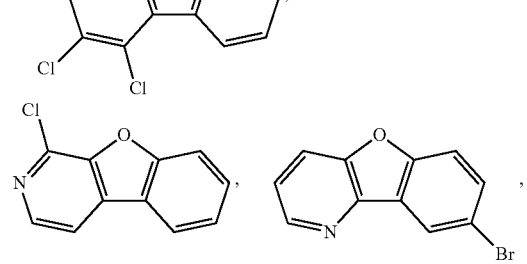

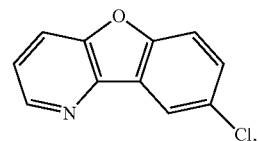

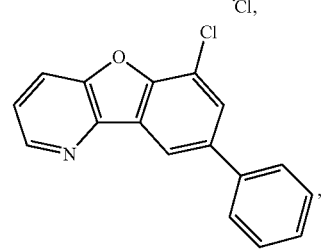

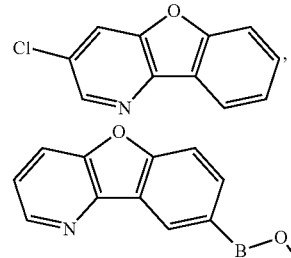

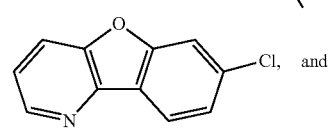

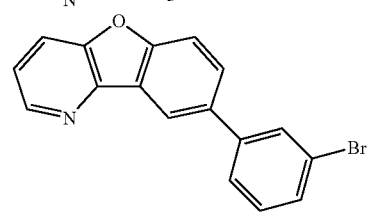

are excluded.

17. The electronic device according to claim 10, comprising a compound of formula

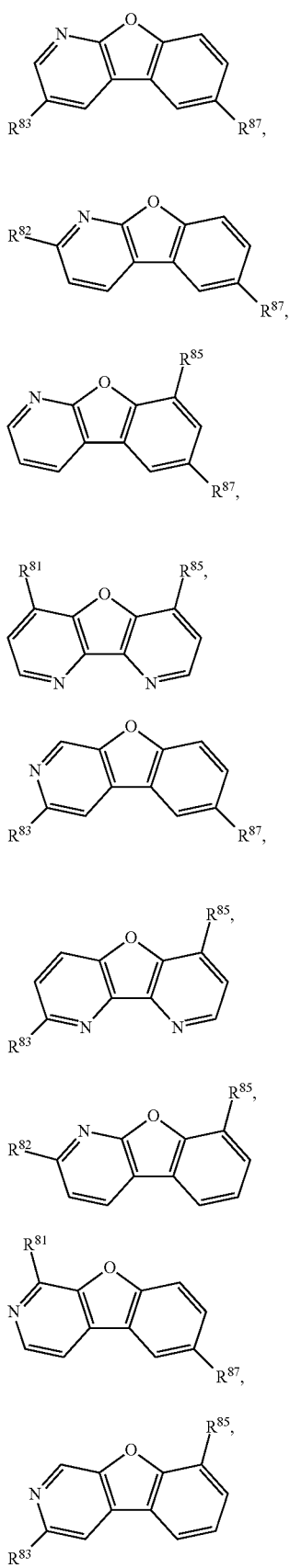
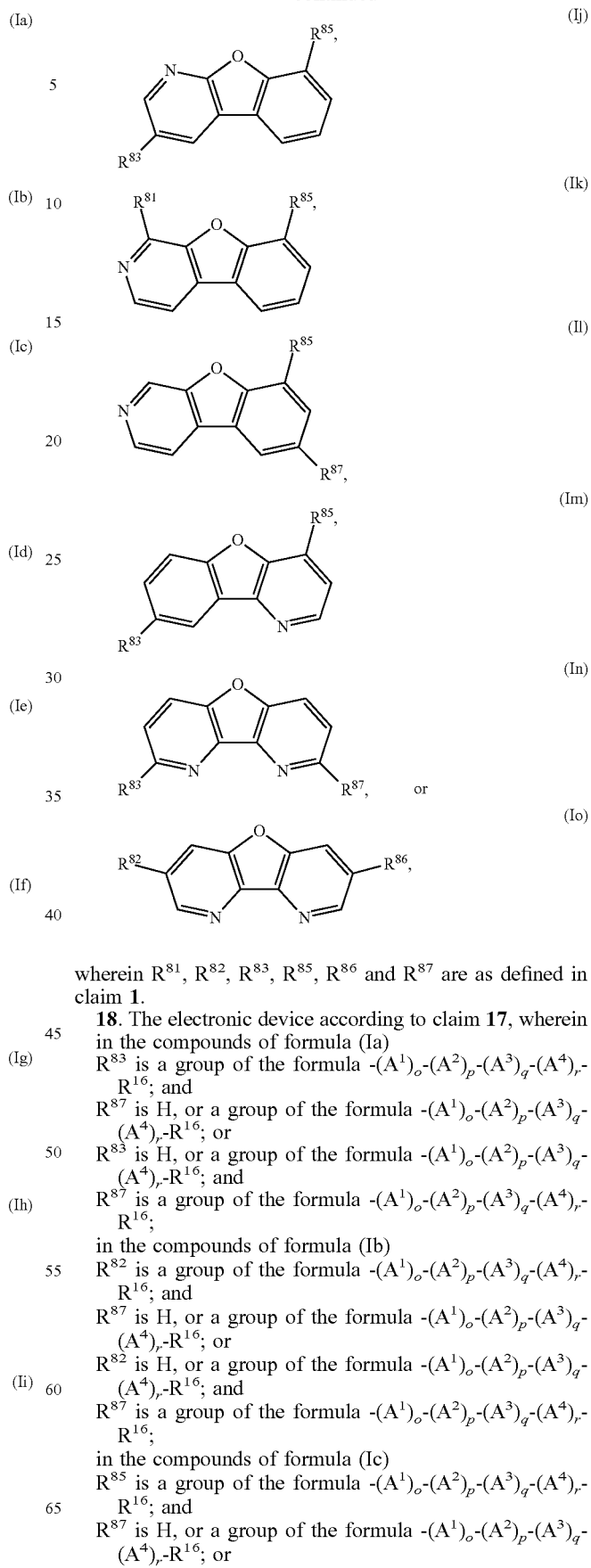

wherein $R^{81}$, $R^{82}$, $R^{83}$, $R^{85}$, $R^{86}$ and $R^{87}$ are as defined in claim 1.

18. The electronic device according to claim 17, wherein in the compounds of formula (Ia)
$R^{83}$ is a group of the formula -$(A^1)_o$-$(A^2)_p$-$(A^3)_q$-$(A^4)_r$-$R^{16}$; and
$R^{87}$ is H, or a group of the formula -$(A^1)_o$-$(A^2)_p$-$(A^3)_q$-$(A^4)_r$-$R^{16}$; or
$R^{83}$ is H, or a group of the formula -$(A^1)_o$-$(A^2)_p$-$(A^3)_q$-$(A^4)_r$-$R^{16}$; and
$R^{87}$ is a group of the formula -$(A^1)_o$-$(A^2)_p$-$(A^3)_q$-$(A^4)_r$-$R^{16}$;
in the compounds of formula (Ib)
$R^{82}$ is a group of the formula -$(A^1)_o$-$(A^2)_p$-$(A^3)_q$-$(A^4)_r$-$R^{16}$; and
$R^{87}$ is H, or a group of the formula -$(A^1)_o$-$(A^2)_p$-$(A^3)_q$-$(A^4)_r$-$R^{16}$; or
$R^{82}$ is H, or a group of the formula -$(A^1)_o$-$(A^2)_p$-$(A^3)_q$-$(A^4)_r$-$R^{16}$; and
$R^{87}$ is a group of the formula -$(A^1)_o$-$(A^2)_p$-$(A^3)_q$-$(A^4)_r$-$R^{16}$;
in the compounds of formula (Ic)
$R^{85}$ is a group of the formula -$(A^1)_o$-$(A^2)_p$-$(A^3)_q$-$(A^4)_r$-$R^{16}$; and
$R^{87}$ is H, or a group of the formula -$(A^1)_o$-$(A^2)_p$-$(A^3)_q$-$(A^4)_r$-$R^{16}$; or $R^{85}$ is H, or a group of the formula -(A$^1$)$_o$-(A$^2$)$_p$-(A$^3$)$_q$-(A$^4$)$_r$-R$^{16}$; and $R^{87}$ is a group of the formula -(A$^1$)$_o$-(A$^2$)$_p$-(A$^3$)$_q$-(A$^4$)$_r$-R$^{16}$;

in the compounds of formula (Id)

$R^{81}$ is a group of the formula -(A$^1$)$_o$-(A$^2$)$_p$-(A$^3$)$_q$-(A$^4$)$_r$-R$^{16}$; and $R^{85}$ is H, or a group of the formula -(A$^1$)$_o$-(A$^2$)$_p$-(A$^3$)$_q$-(A$^4$)$_r$-R$^{16}$; or $R^{81}$ is H, or a group of the formula -(A$^1$)$_o$-(A$^2$)$_p$-(A$^3$)$_q$-(A$^4$)$_r$-R$^{16}$; and $R^{85}$ is a group of the formula -(A$^1$)$_o$-(A$^2$)$_p$-(A$^3$)$_q$-(A$^4$)$_r$-R$^{16}$;

the compounds of formula (Ie)

$R^{83}$ is a group of the formula -(A$^1$)$_o$-(A$^2$)$_p$-(A$^3$)$_q$-(A$^4$)$_r$-R$^{16}$; and $R^{87}$ is H, or a group of the formula -(A$^1$)$_o$-(A$^2$)$_p$-(A$^3$)$_q$-(A$^4$)$_r$-R$^{16}$; or $R^{83}$ is H, or a group of the formula -(A$^1$)$_o$-(A$^2$)$_p$-(A$^3$)$_q$-(A$^4$)$_r$-R$^{16}$; and $R^{87}$ is a group of the formula -(A$^1$)$_o$-(A$^2$)$_p$-(A$^3$)$_q$-(A$^4$)$_r$-R$^{16}$;

in the compounds of formula (If)

$R^{83}$ is a group of the formula -(A$^1$)$_o$-(A$^2$)$_p$-(A$^3$)$_q$-(A$^4$)$_r$-R$^{16}$; and $R^{85}$ is H, or a group of the formula -(A$^1$)$_o$-(A$^2$)$_p$-(A$^3$)$_q$-(A$^4$)$_r$-R$^{16}$; or $R^{83}$ is H, or a group of the formula -(A$^1$)$_o$-(A$^2$)$_p$-(A$^3$)$_q$-(A$^4$)$_r$-R$^{16}$; and $R^{85}$ is a group of the formula -(A$^1$)$_o$-(A$^2$)$_p$-(A$^3$)$_q$-(A$^4$)$_r$-R$^{16}$;

in the compounds of formula (Ig)

$R^{82}$ is a group of the formula -(A$^1$)$_o$-(A$^2$)$_p$-(A$^3$)$_q$-(A$^4$)$_r$-R$^{16}$; and $R^{85}$ is H, or a group of the formula -(A$^1$)$_o$-(A$^2$)$_p$-(A$^3$)$_q$-(A$^4$)$_r$-R$^{16}$; or $R^{82}$ is H, or a group of the formula -(A$^1$)$_o$-(A$^2$)$_p$-(A$^3$)$_q$-(A$^4$)$_r$-R$^{16}$; and $R^{85}$ is a group of the formula -(A$^1$)$_o$-(A$^2$)$_p$-(A$^3$)$_q$-(A$^4$)$_r$-R$^{16}$;

in the compounds of formula (Ih)

$R^{81}$ is a group of the formula -(A$^1$)$_o$-(A$^2$)$_p$-(A$^3$)$_q$-(A$^4$)$_r$-R$^{16}$; and $R^{87}$ is H, or a group of the formula -(A$^1$)$_o$-(A$^2$)$_p$-(A$^3$)$_q$-(A$^4$)$_r$-R$^{16}$; or $R^{81}$ is H, or a group of the formula -(A$^1$)$_o$-(A$^2$)$_p$-(A$^3$)$_q$-(A$^4$)$_r$-R$^{16}$; and $R^{87}$ is a group of the formula -(A$^1$)$_o$-(A$^2$)$_p$-(A$^3$)$_q$-(A$^4$)$_r$-R$^{16}$;

the compounds of formula (Ii)

$R^{83}$ is a group of the formula -(A$^1$)$_o$-(A$^2$)$_p$-(A$^3$)$_q$-(A$^4$)$_r$-R$^{16}$; and $R^{85}$ is H, or a group of the formula -(A$^1$)$_o$-(A$^2$)$_p$-(A$^3$)$_q$-(A$^4$)$_r$-R$^{16}$; or $R^{83}$ is H, or a group of the formula -(A$^1$)$_o$-(A$^2$)$_p$-(A$^3$)$_q$-(A$^4$)$_r$-R$^{16}$; and $R^{85}$ is a group of the formula -(A$^1$)$_o$-(A$^2$)$_p$-(A$^3$)$_q$-(A$^4$)$_r$-R$^{16}$;

in the compounds of formula (Ij)

$R^{83}$ is a group of the formula -(A$^1$)$_o$-(A$^2$)$_p$-(A$^3$)$_q$-(A$^4$)$_r$-R$^{16}$; and $R^{85}$ is H, or a group of the formula -(A$^1$)$_o$-(A$^2$)$_p$-(A$^3$)$_q$-(A$^4$)$_r$-R$^{16}$; or $R^{83}$ is H, or a group of the formula -(A$^1$)$_o$-(A$^2$)$_p$-(A$^3$)$_q$-(A$^4$)$_r$-R$^{16}$; and $R^{85}$ is a group of the formula -(A$^1$)$_o$-(A$^2$)$_p$-(A$^3$)$_q$-(A$^4$)$_r$-R$^{16}$;

in the compounds of formula (Ik)

$R^{81}$ is a group of the formula -(A$^1$)$_o$-(A$^2$)$_p$-(A$^3$)$_q$-(A$^4$)$_r$-R$^{16}$; and $R^{85}$ is H, or a group of the formula -(A$^1$)$_o$-(A$^2$)$_p$-(A$^3$)$_q$-(A$^4$)$_r$-R$^{16}$; or $R^{81}$ is H, or a group of the formula -(A$^1$)$_o$-(A$^2$)$_p$-(A$^3$)$_q$-(A$^4$)$_r$-R$^{16}$; and $R^{85}$ is a group of the formula -(A$^1$)$_o$-(A$^2$)$_p$-(A$^3$)$_q$-(A$^4$)$_r$-R$^{16}$;

in the compounds of formula (Il)

$R^{85}$ is a group of the formula -(A$^1$)$_o$-(A$^2$)$_p$-(A$^3$)$_q$-(A$^4$)$_r$-R$^{16}$; and $R^{87}$ is H, or a group of the formula -(A$^1$)$_o$-(A$^2$)$_p$-(A$^3$)$_q$-(A$^4$)$_r$-R$^{16}$; or $R^{85}$ is H, or a group of the formula -(A$^1$)$_o$-(A$^2$)$_p$-(A$^3$)$_q$-(A$^4$)$_r$-R$^{16}$; and $R^{87}$ is a group of the formula -(A$^1$)$_o$-(A$^2$)$_p$-(A$^3$)$_q$-(A$^4$)$_r$-R$^{16}$;

in the compounds of formula (Im)

$R^{83}$ is a group of the formula -(A$^1$)$_o$-(A$^2$)$_p$-(A$^3$)$_q$-(A$^4$)$_r$-R$^{16}$; and $R^{85}$ is H, or a group of the formula -(A$^1$)$_o$-(A$^2$)$_p$-(A$^3$)$_q$-(A$^4$)$_r$-R$^{16}$; or $R^{83}$ is H, or a group of the formula -(A$^1$)$_o$-(A$^2$)$_p$-(A$^3$)$_q$-(A$^4$)$_r$-R$^{16}$; and $R^{85}$ is a group of the formula -(A$^1$)$_o$-(A$^2$)$_p$-(A$^3$)$_q$-(A$^4$)$_r$-R$^{16}$;

the compounds of formula (In)

$R^{83}$ is a group of the formula -(A$^1$)$_o$-(A$^2$)$_p$-(A$^3$)$_q$-(A$^4$)$_r$-R$^{16}$; and $R^{87}$ is H, or a group of the formula -(A$^1$)$_o$-(A$^2$)$_p$-(A$^3$)$_q$-(A$^4$)$_r$-R$^{16}$; or $R^{83}$ is H, or a group of the formula -(A$^1$)$_o$-(A$^2$)$_p$-(A$^3$)$_q$-(A$^4$)$_r$-R$^{16}$; and $R^{87}$ is a group of the formula -(A$^1$)$_o$-(A$^2$)$_p$-(A$^3$)$_q$-(A$^4$)$_r$-R$^{16}$; wherein in the compounds of formula (Io)

$R^{82}$ is a group of the formula -(A$^1$)$_o$-(A$^2$)$_p$-(A$^3$)$_q$-(A$^4$)$_r$-R$^{16}$; and $R^{86}$ is H, or a group of the formula -(A$^1$)$_o$-(A$^2$)$_p$-(A$^3$)$_q$-(A$^4$)$_r$-R$^{16}$; or $R^{82}$ is H, or a group of the formula -(A$^1$)$_o$-(A$^2$)$_p$-(A$^3$)$_q$-(A$^4$)$_r$-R$^{16}$; and $R^{86}$ is a group of the formula -(A$^1$)$_o$-(A$^2$)$_p$-(A$^3$)$_q$-(A$^4$)$_r$-R$^{16}$;

o is 0, or 1, p is 0, or 1, q is 0, or 1, r is 0, or 1;

$A^1, A^2, A^3$ and $A^4$ are independently of each other a group of the formula

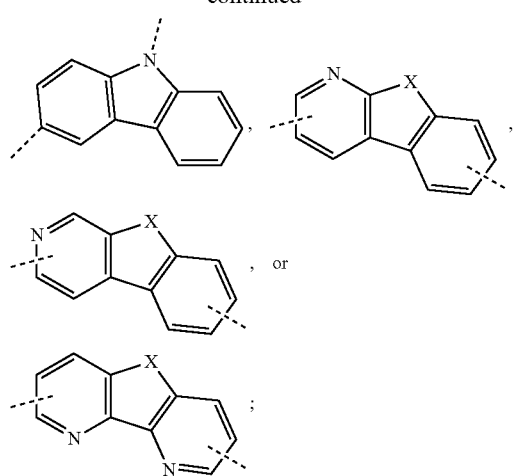

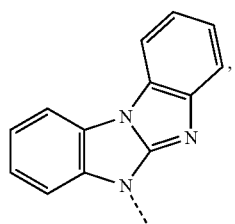

$R^{16}$ is a group of the formula

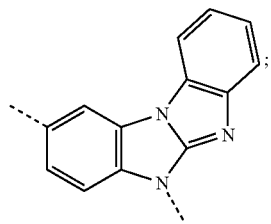

or $R^{16}$ has the meaning of $R^{16'}$, if at least one of the groups $A^1$, $A^2$, $A^3$ and $A^4$ represent a group of formula

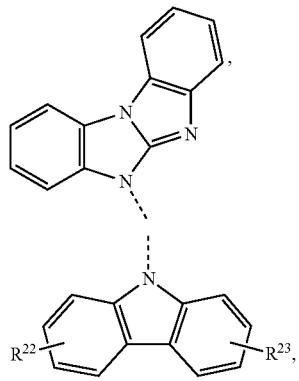

$R^{16''}$ is H, or a group of the formula —Si($R^{12}$)($R^{13}$)($R^{14}$),

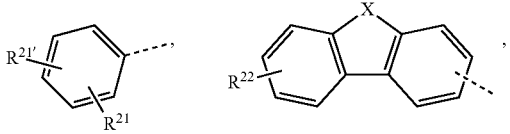

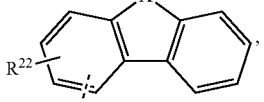

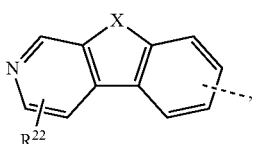

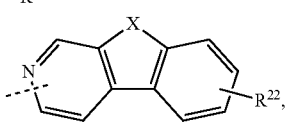

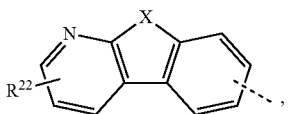

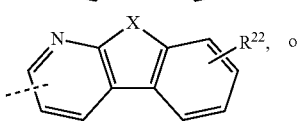

wherein
  $R^{12}$, $R^{13}$, $R^{14}$ are independently of each other a phenyl group, which can optionally be substituted by one, or more alkyl groups;
  $R^{21}$ and $R^{21'}$ are independently of each other H, a phenyl group, or a $C_1$-$C_{18}$ alkyl group;
  $R^{22}$ and $R^{23}$ are independently of each other H, or a group of the formula

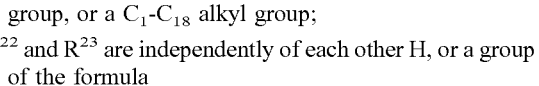

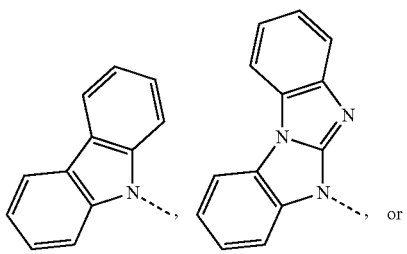

-continued
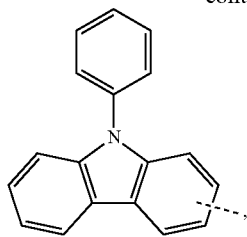
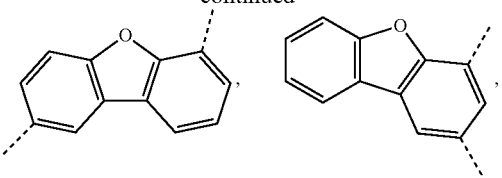
X is O, S, or NR$^{24}$,
R$^{24}$ is a C$_6$-C$_{24}$ aryl group, or a C$_2$-C$_{30}$ heteroaryl group, which can optionally be substituted by G; and
R$^{89}$ is H, a group of formula
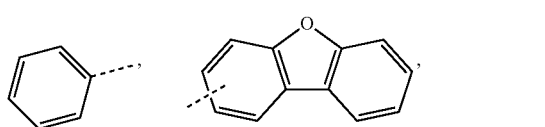
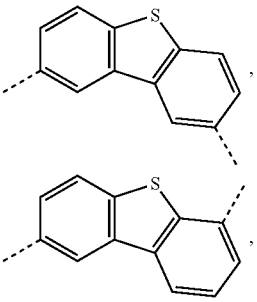
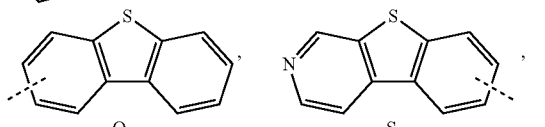
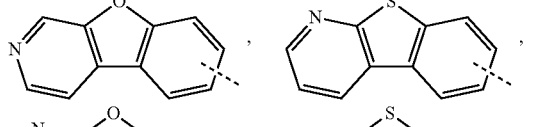
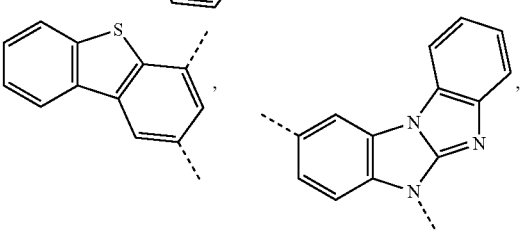
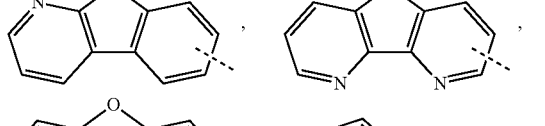
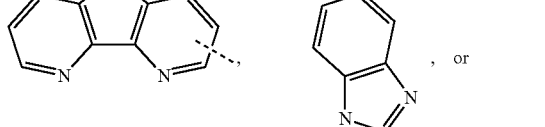
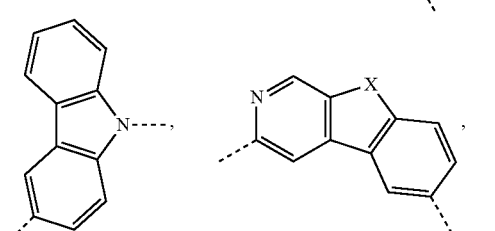
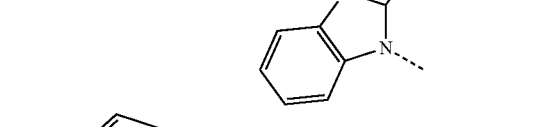
, or
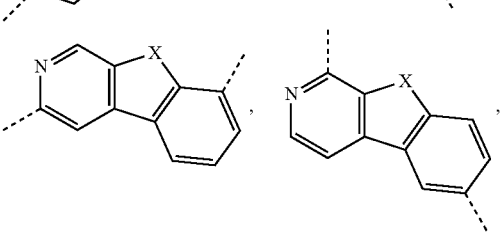
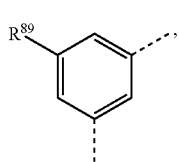
19. The electronic device according to claim 17, wherein o is 0, or 1, p is 0, or 1, q is 0, or 1, r is 0, or 1, A$^1$, A$^2$, A$^3$ and A$^4$ are independently of each other a group of the formula
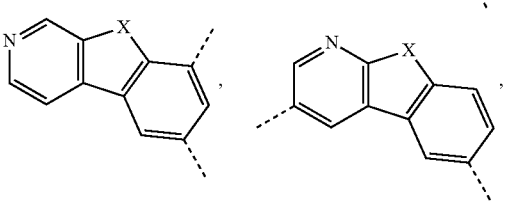
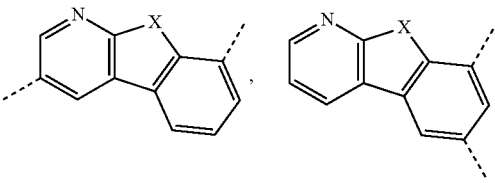
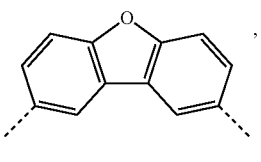
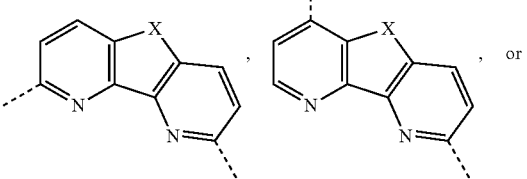, or -continued
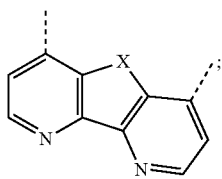
$R^{16}$ is a group of the formula
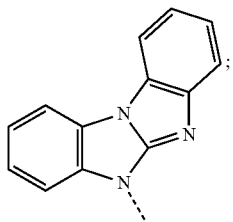
or $R^{16}$ has the meaning of $R^{16'}$, if at least one of the groups $A^1$, $A^2$, $A^3$ and $A^4$ represent a group of formula
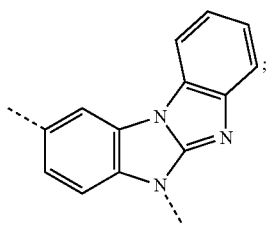
$R^{16'}$ is H, or a group of the formula
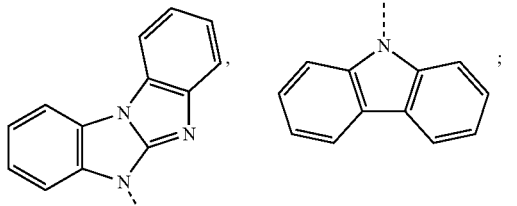
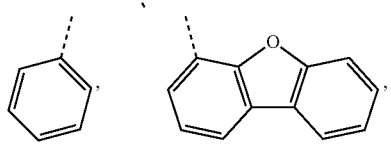
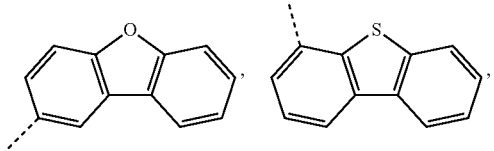
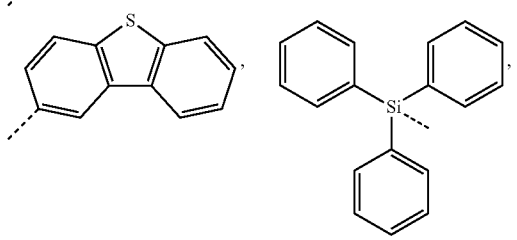
-continued
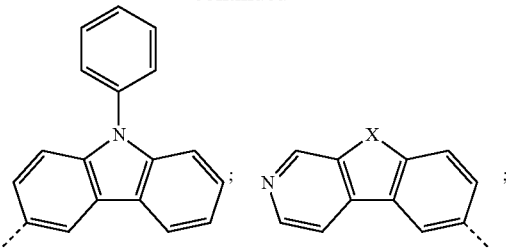
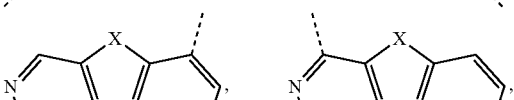
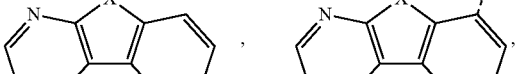
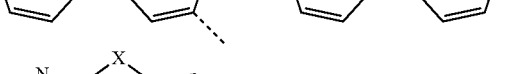
and $R^{89}$ is H, a group of formula
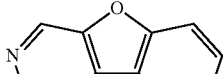
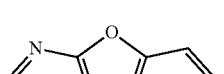
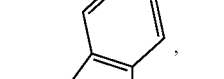
wherein X is O, S, or $NR^{24}$, wherein $R^{24}$ is

20. The electronic device according to claim 17, comprising a compound selected from the group consisting of:
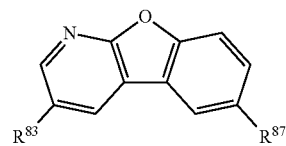
| Compound | $R^{83}$ | $R^{87}$ |
|---|---|---|
| A-1 | 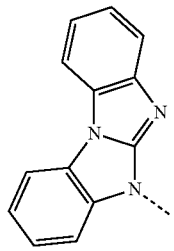 | 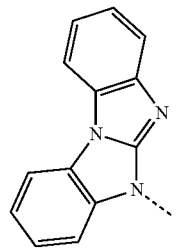 |
| A-2 | 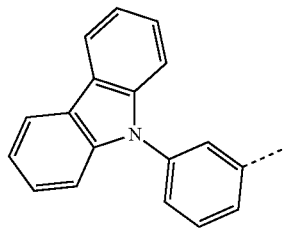 | 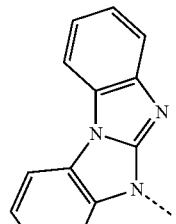 |
| A-3 | 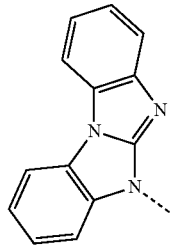 | 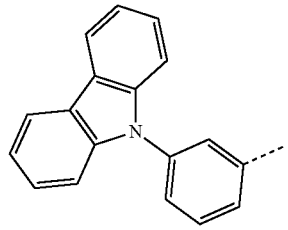 |
| A-4 | 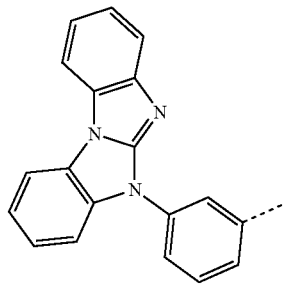 | 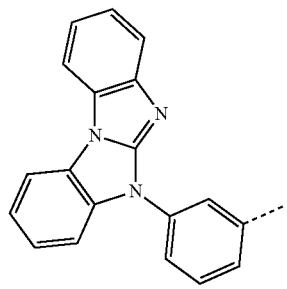 |
| A-5 | H | 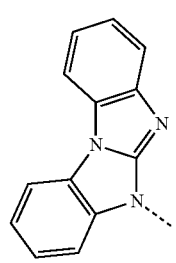 |

-continued
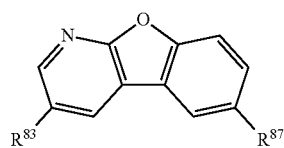
| Compound | R[83] | R[87] |
|---|---|---|
| A-6 | 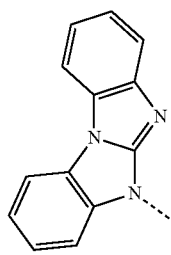 | H |
| A-7 | H | 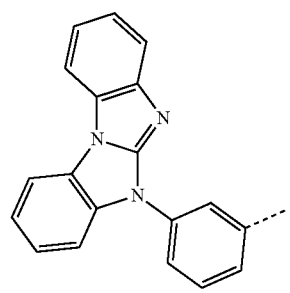 |
| A-8 | 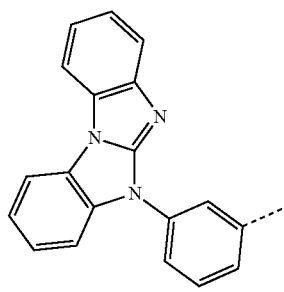 | H |
| A-9 | H | 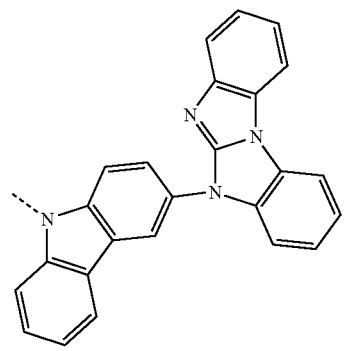 |

-continued
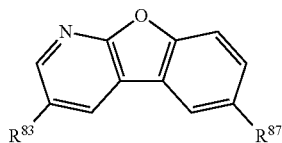
| Compound | R⁸³ | R⁸⁷ |
|---|---|---|
| A-10 | 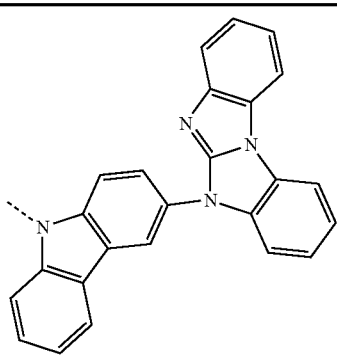 | H |
| A-11 | 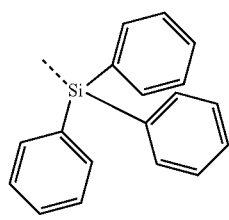 | 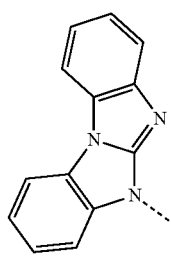 |
| A-12 | 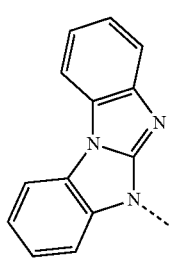 | 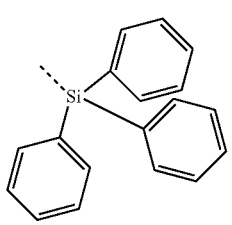 |
| A-13 | 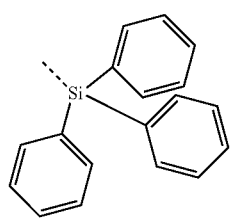 | 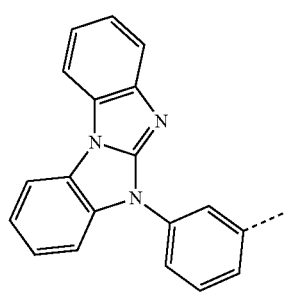 |
| A-14 | 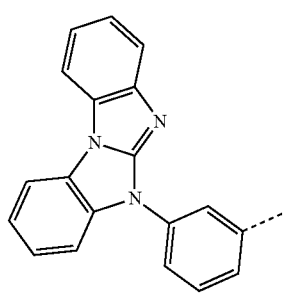 | 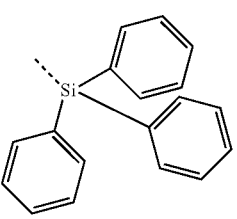 |

-continued
| Compound | R<sup>83</sup> | R<sup>87</sup> |
|---|---|---|
| A-15 | 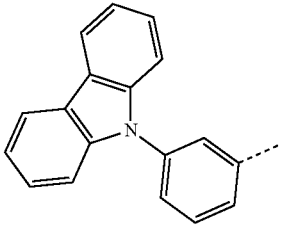 | 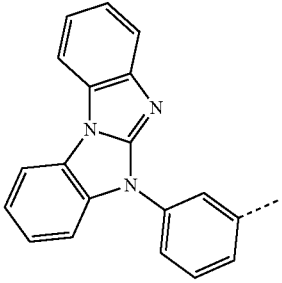 |
| A-16 | 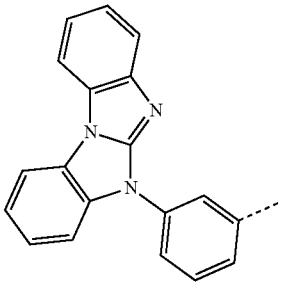 | 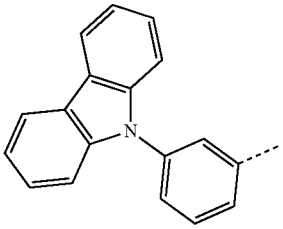 |
| A-17 | 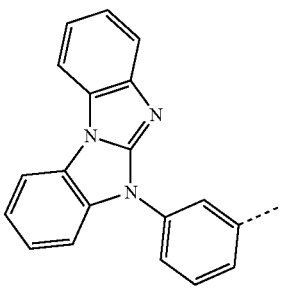 | 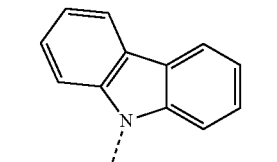 |
| A-18 | 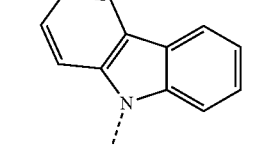 | 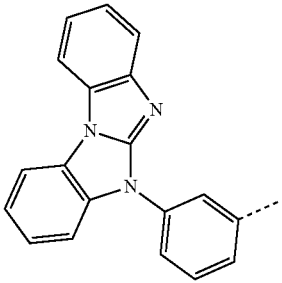 |
| A-19 | 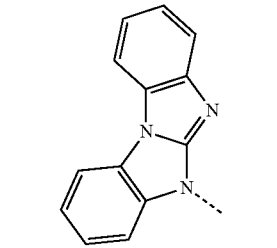 | 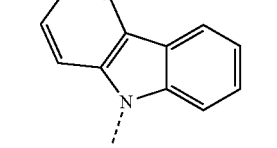 |

-continued
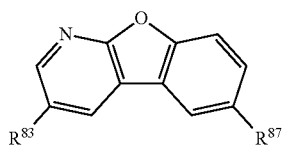
| Compound | R<sup>83</sup> | R<sup>87</sup> |
|---|---|---|
| A-20 | 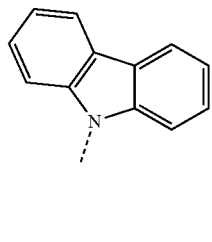 | 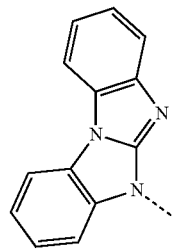 |
| A-21 | 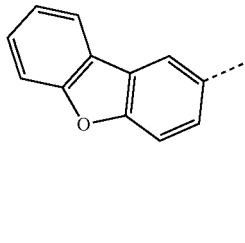 | 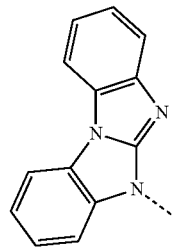 |
| A-22 | 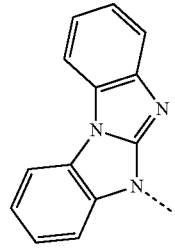 | 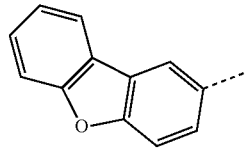 |
| A-23 | 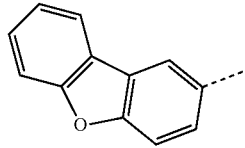 | 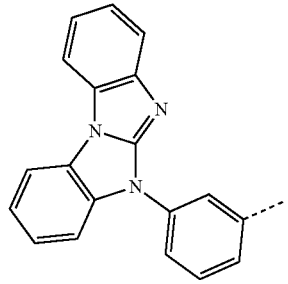 |
| A-24 | 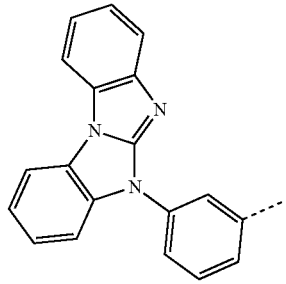 | 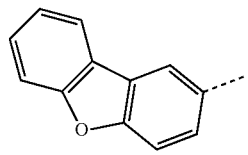 |

-continued

| Compound | R⁸³ | R⁸⁷ |
|---|---|---|
| A-25 | [pyrido-benzofuran] | [benzimidazo-benzimidazole] |
| A-26 | [benzimidazo-benzimidazole] | [pyrido-benzofuran] |
| A-27 | [pyrido-benzofuran] | [N-phenyl benzimidazo-benzimidazole] |
| A-28 | [N-phenyl benzimidazo-benzimidazole] | [pyrido-benzofuran] |
| A-29 | [pyrido-benzofuran] | [pyrido-benzimidazo-benzimidazole] |

-continued
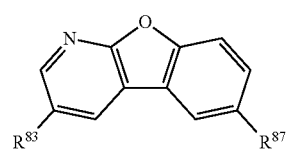
| Compound | R83 | R87 |
|---|---|---|
| A-30 | 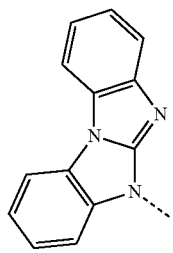 | 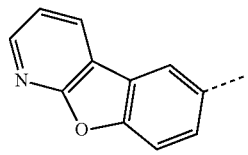 |
| A-31 | 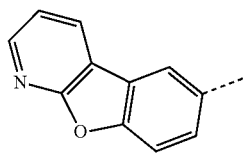 | 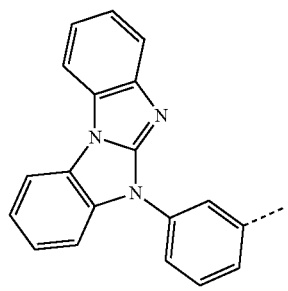 |
| A-32 | 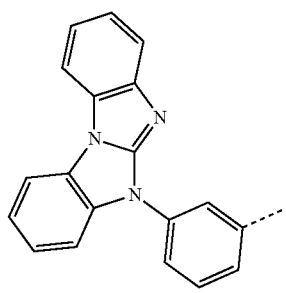 | 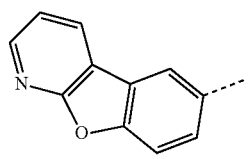 |
| A-33 | 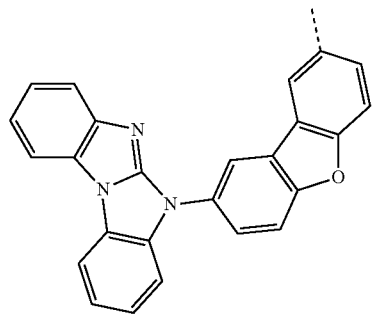 | 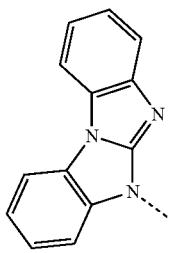 |

-continued
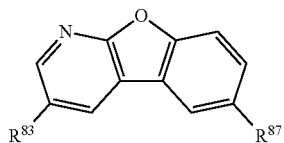
| Compound | R⁸³ | R⁸⁷ |
|---|---|---|
| A-34 | 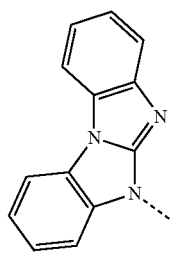 | 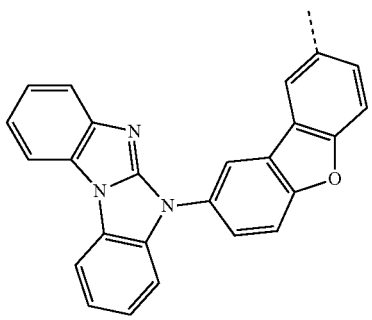 |
| A-35 | 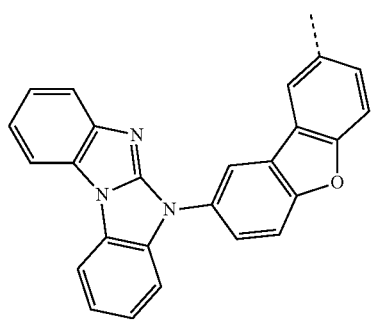 | H |
| A-36 | H | 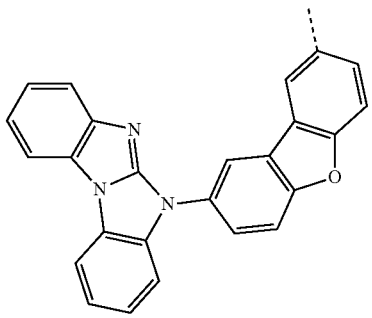 |
| A-37 | 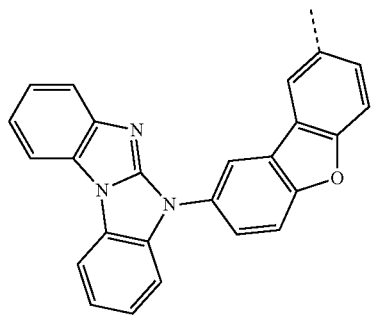 | 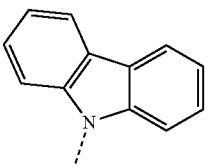 |

-continued
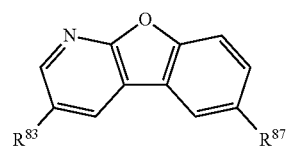
| Compound | R83 | R87 |
|---|---|---|
| A-38 | 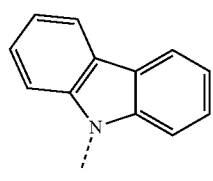 | 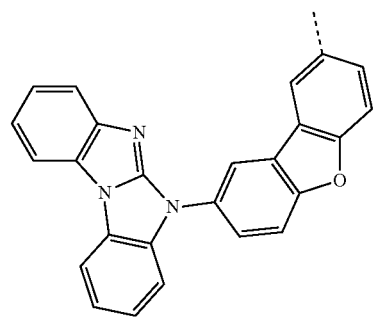 |
| A-39 | 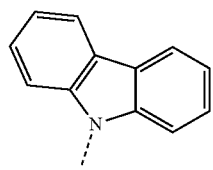 | 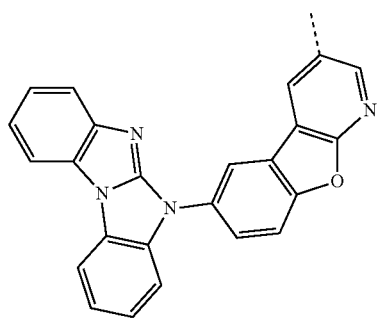 |
| A-40 | 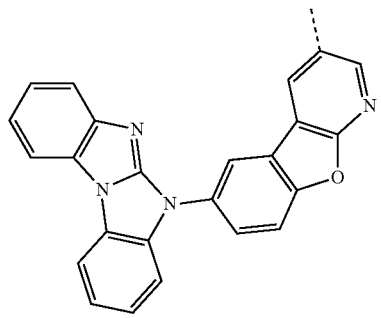 | 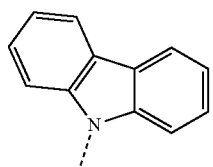 |
| A-41 | 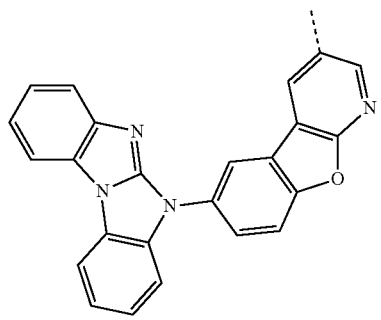 | H |

-continued
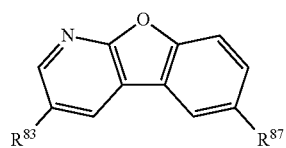
| Compound | R83 | R87 |
|---|---|---|
| A-42 | H | 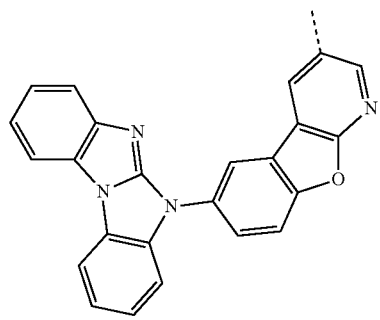 |
| A-43 | 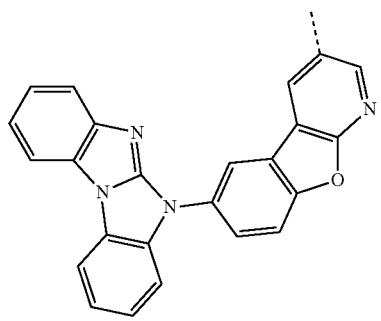 | 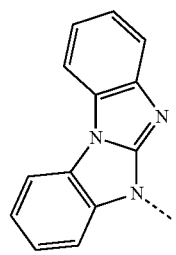 |
| A-44 | 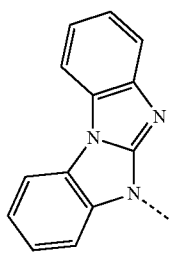 | 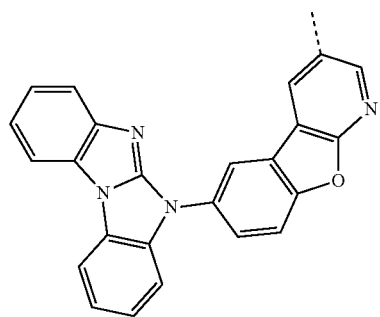 |
| A-45 | 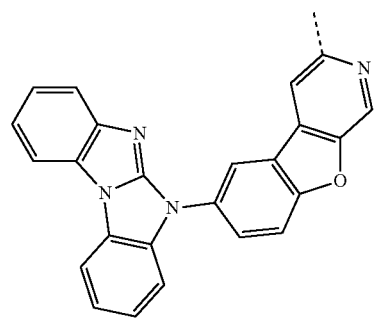 | 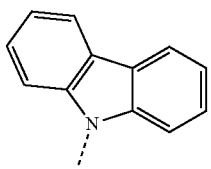 |

-continued
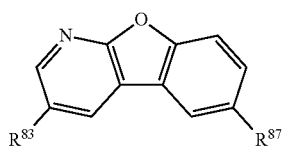
| Compound | R83 | R87 |
|---|---|---|
| A-46 | 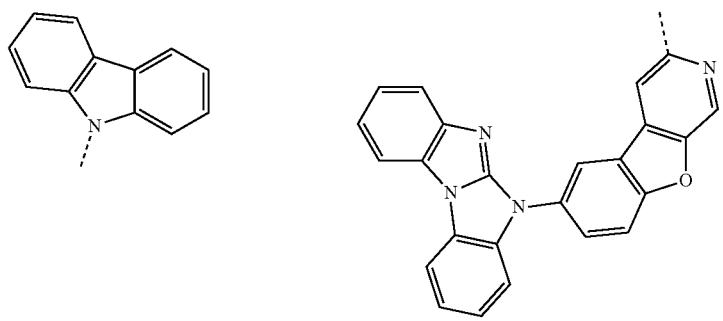 | |
| A-47 | 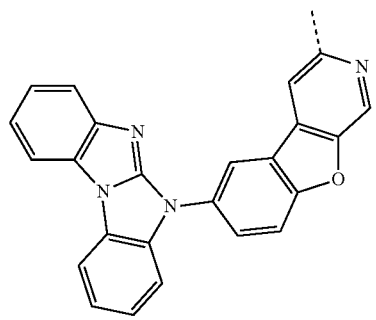 | H |
| A-48 | H | 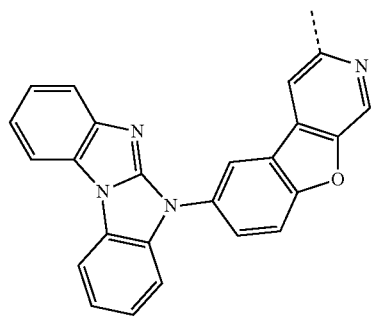 |
| A-49 | 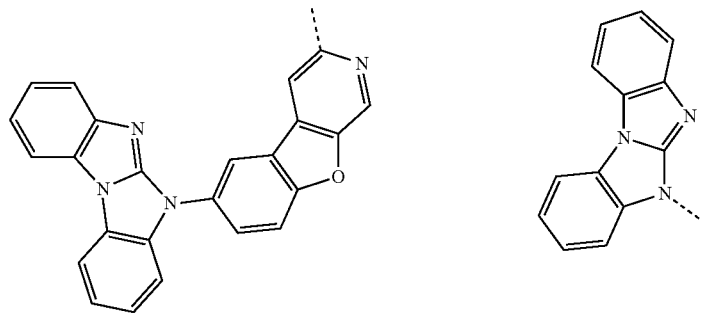 | |

-continued
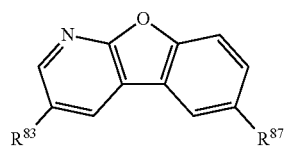
| Compound | R<sup>83</sup> | R<sup>87</sup> |
|---|---|---|
| A-50 | 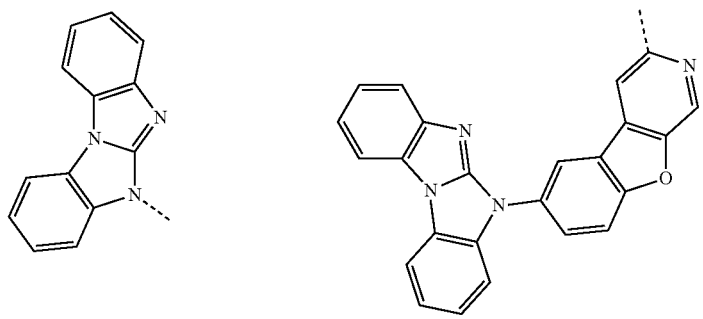 | |
| A-51 | 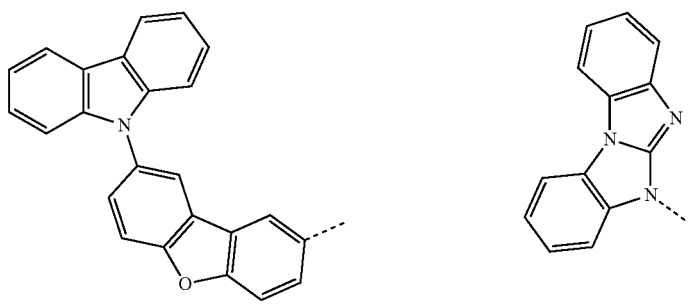 | |
| A-52 | 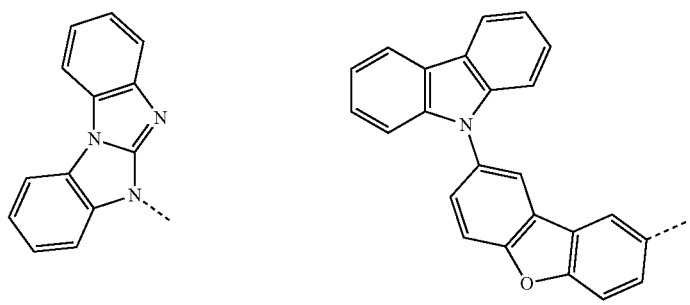 | |
| A-53 | 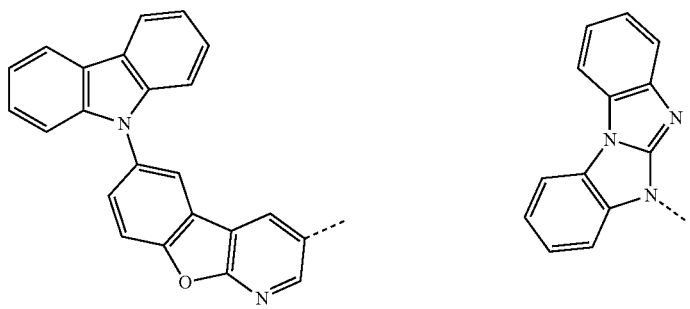 | |

-continued
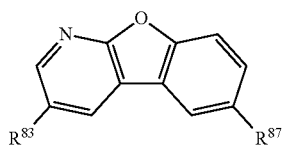
| Compound | R<sup>83</sup> | R<sup>87</sup> |
|---|---|---|
| A-54 | 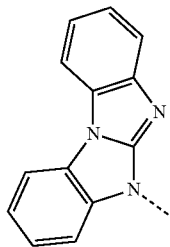 | 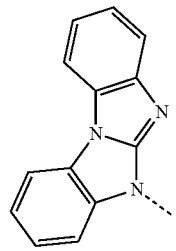 |
| A-55 | 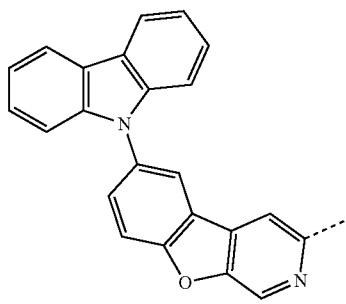 | 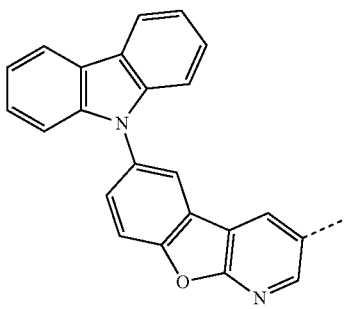 |
| A-56 | 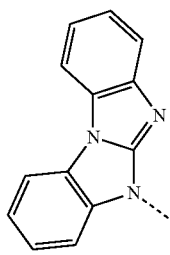 | 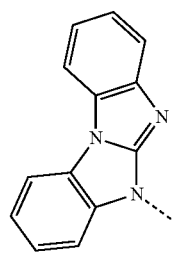 |
| A-57 | H | 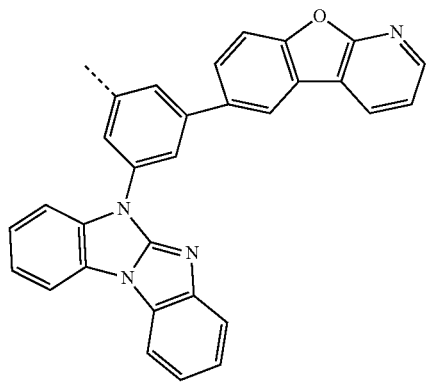 |

-continued
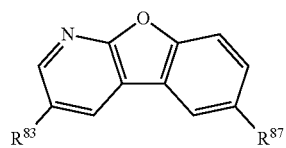
| Compound | R⁸³ | R⁸⁷ |
|---|---|---|
| A-58 | 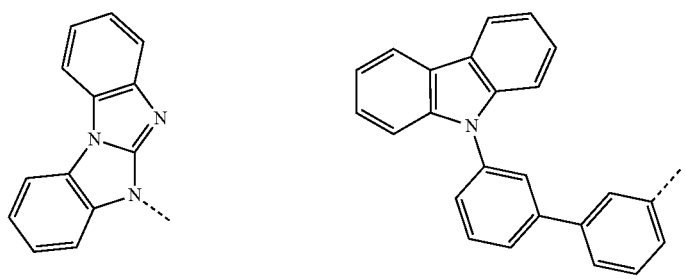 | |
| A-59 | 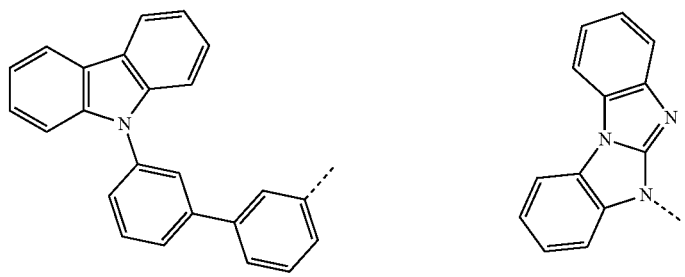 | |
| A-60 | 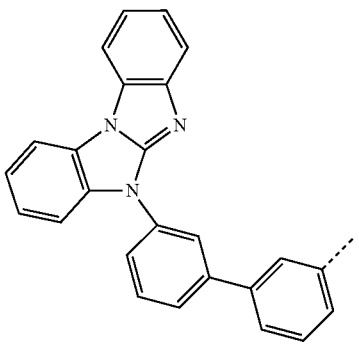 | H |
| A-61 | H | 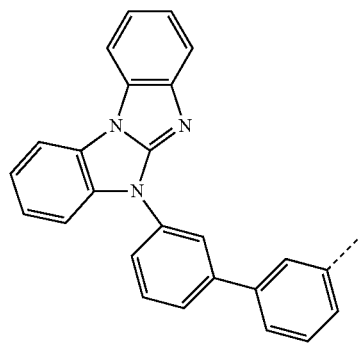 |

-continued
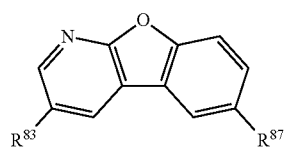
| Compound | R<sup>83</sup> | R<sup>87</sup> |
|---|---|---|
| A-62 | H | 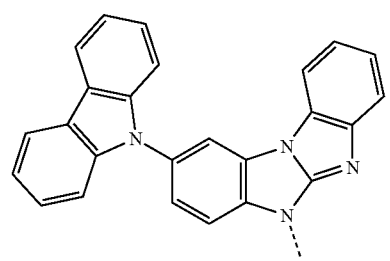 |
| A-63 | H | 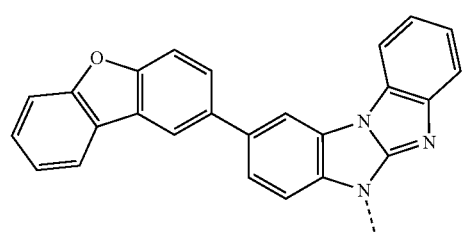 |
| A-64 | H | 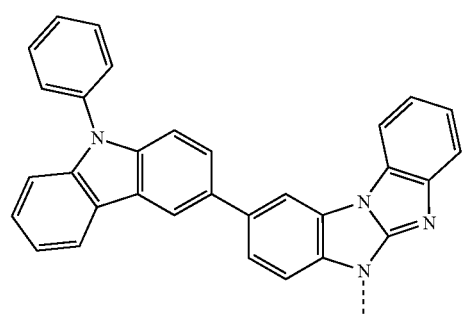 |
| A-65 | H | 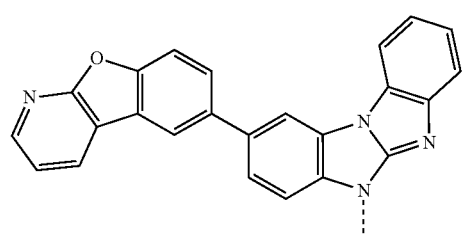 |

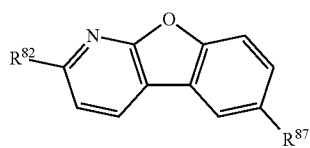
| Compound | R⁸² | R⁸⁷ |
|---|---|---|
| B-1 | 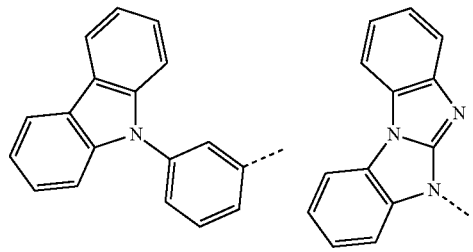 | |
| B-2 | 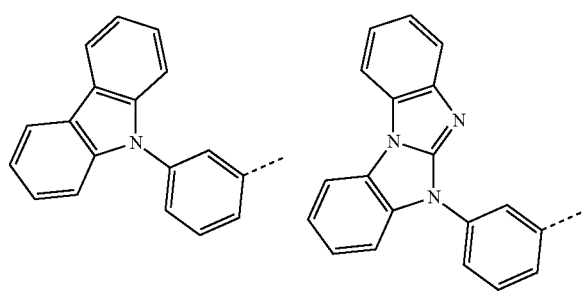 | |
| B-3 | 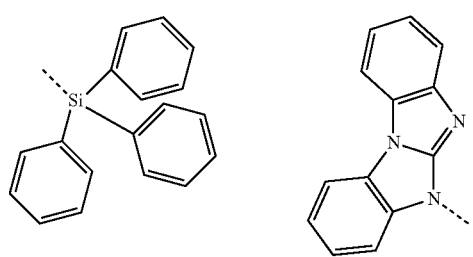 | |
| B-4 | 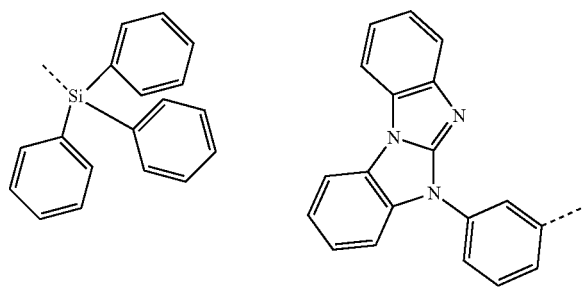 | |
| B-5 | 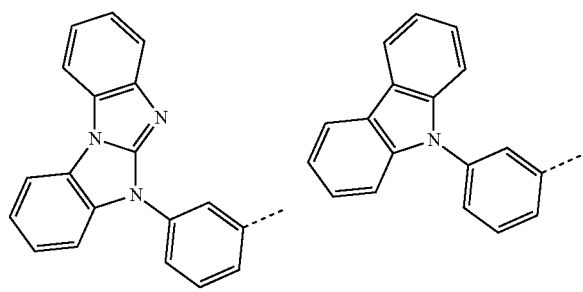 | |

-continued
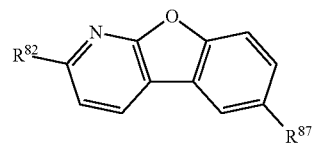
| Compound | R⁸² | R⁸⁷ |
|---|---|---|
| B-6 | 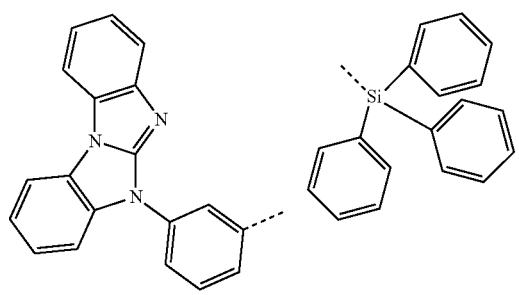 | |
| B-7 | 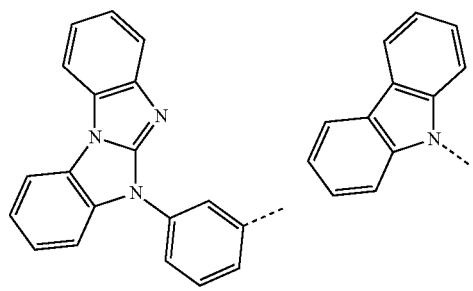 | |
| B-8 | 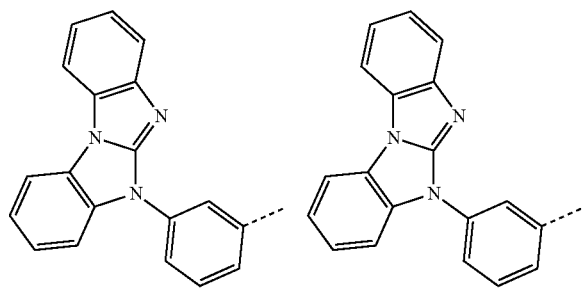 | |
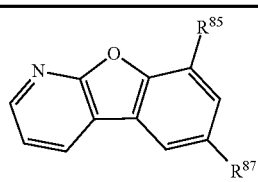
| Compound | R⁸⁵ | R⁸⁷ |
|---|---|---|
| C-1 | 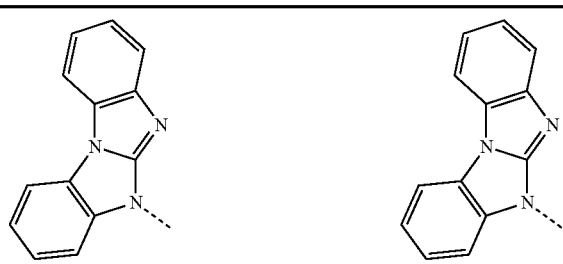 | |

-continued
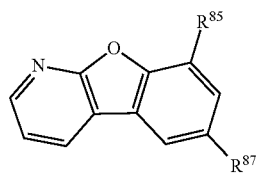
| Compound | R⁸⁵ | R⁸⁷ |
|---|---|---|
| C-2 | 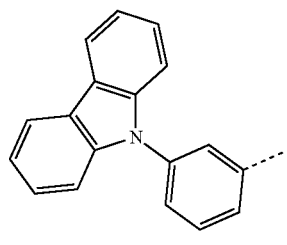 | 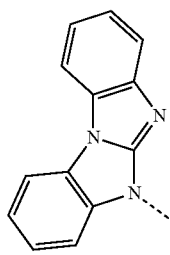 |
| C-3 | 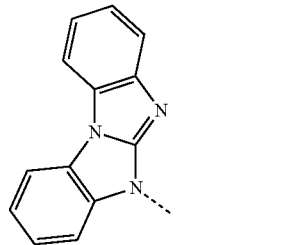 | 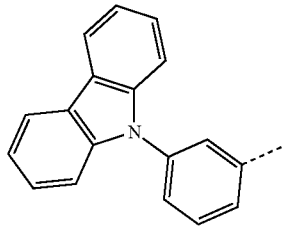 |
| C-4 | 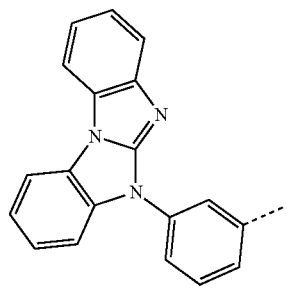 | 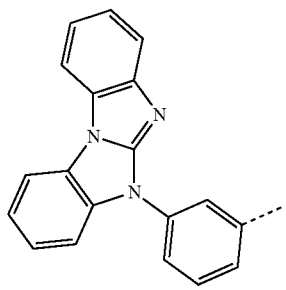 |
| C-5 | H | 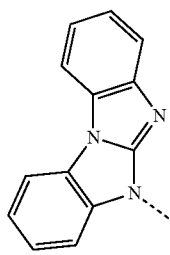 |
| C-6 | 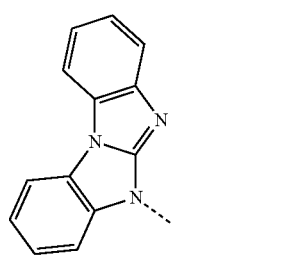 | H |

-continued
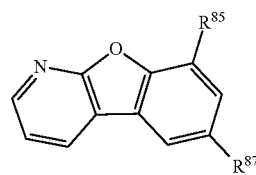
| Compound | R85 | R87 |
|---|---|---|
| C-7 | H | 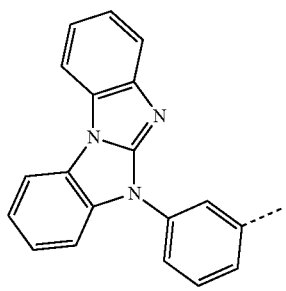 |
| C-8 | 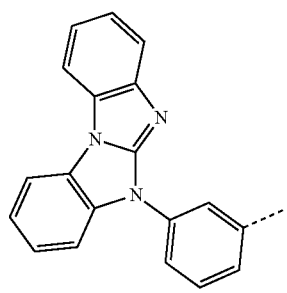 | H |
| C-9 | H | 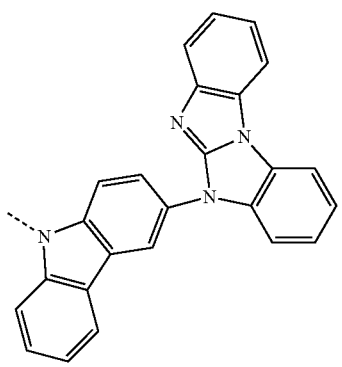 |
| C-10 | 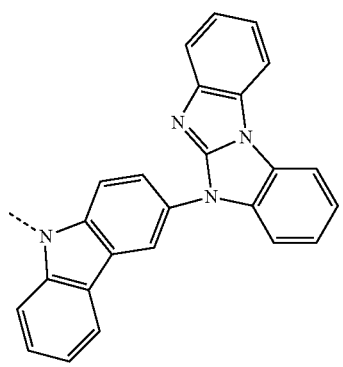 | H |

-continued
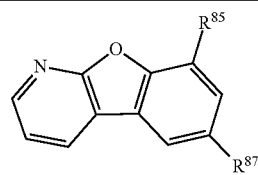
| Compound | R⁸⁵ | R⁸⁷ |
|---|---|---|
| C-11 | 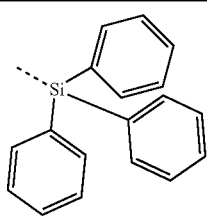 | 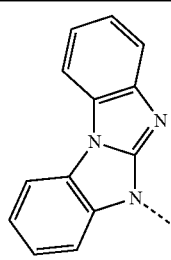 |
| C-12 | 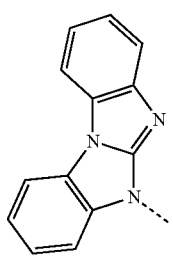 | 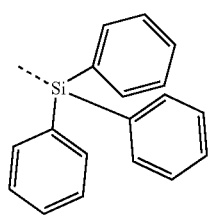 |
| C-13 | 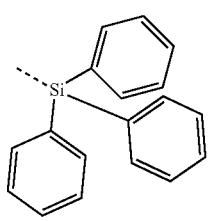 | 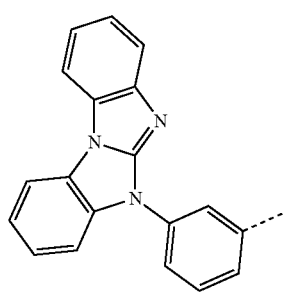 |
| C-14 | 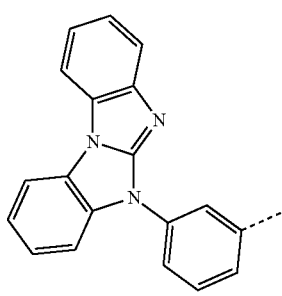 | 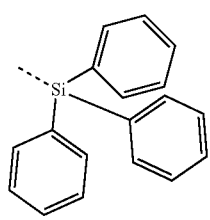 |
| C-15 | 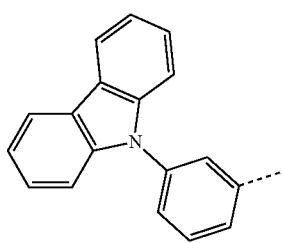 | 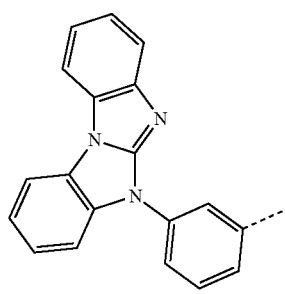 |

-continued
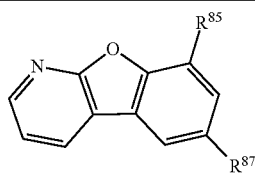
| Compound | R85 | R87 |
|---|---|---|
| C-16 | 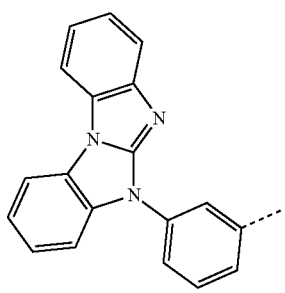 | 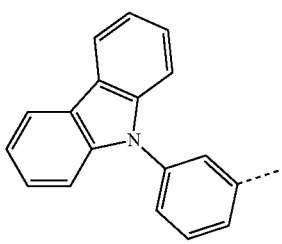 |
| C-17 | 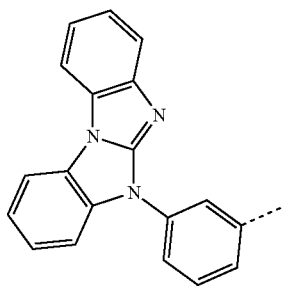 | 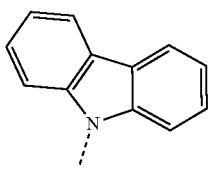 |
| C-18 | 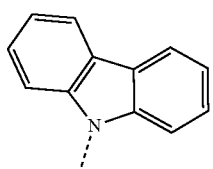 | 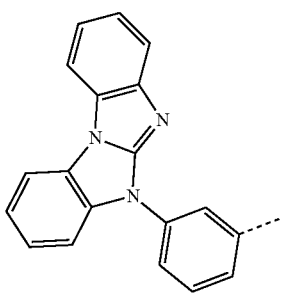 |
| C-19 | 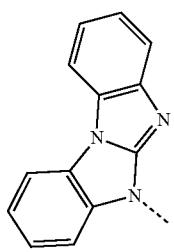 | 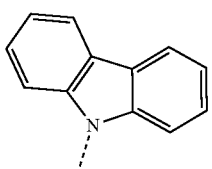 |
| C-20 | 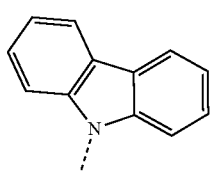 | 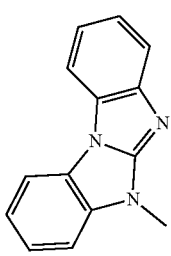 |

-continued
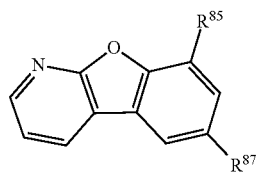
| Compound | R85 | R87 |
|---|---|---|
| C-21 | 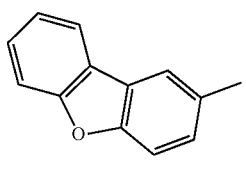 | 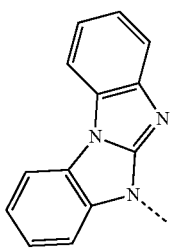 |
| C-22 | 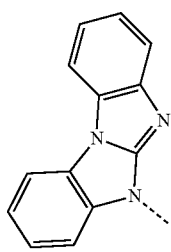 | 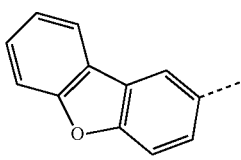 |
| C-23 | 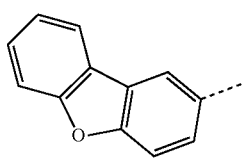 | 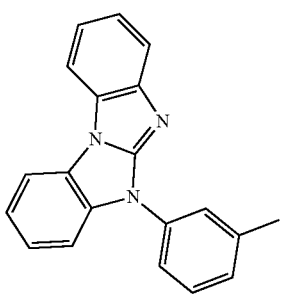 |
| C-24 | 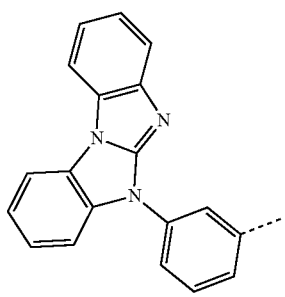 | 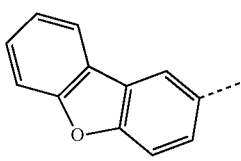 |
| C-25 | 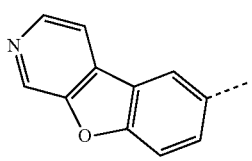 | 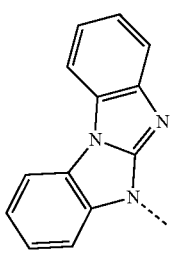 |

-continued
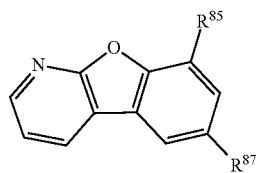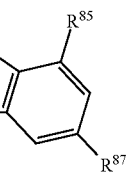
| Compound | R85 | R87 |
|---|---|---|
| C-26 | 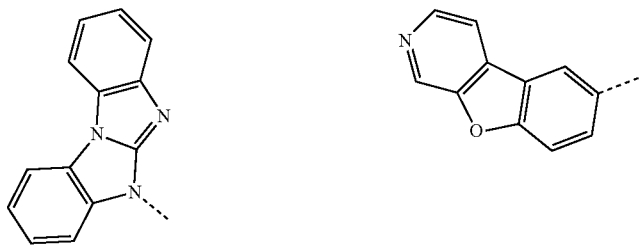 | |
| C-27 | 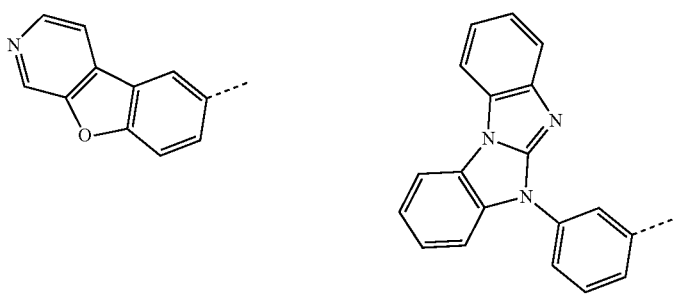 | |
| C-28 | 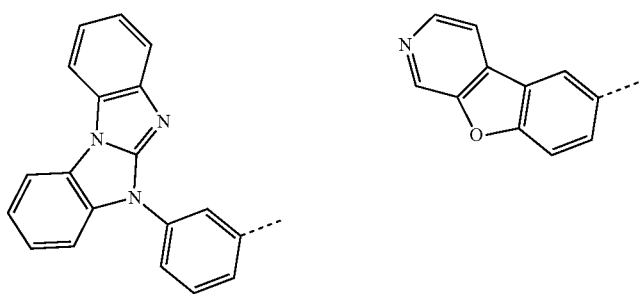 | |
| C-29 | 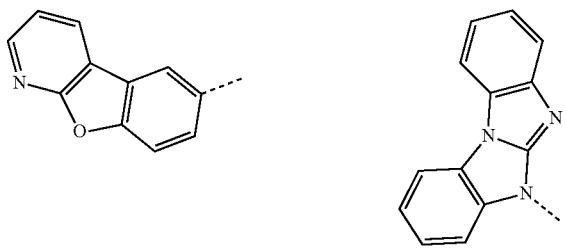 | |
| C-30 | 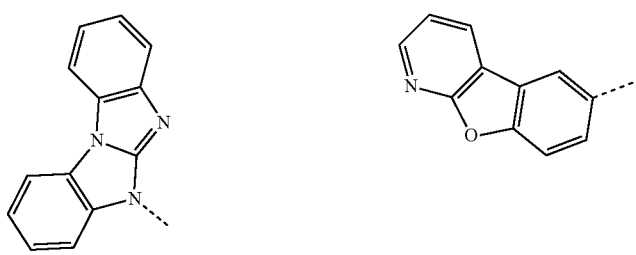 | |

-continued
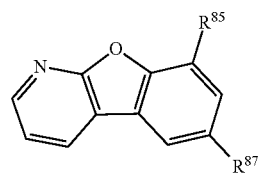
| Compound | R85 | R87 |
|---|---|---|
| C-31 | 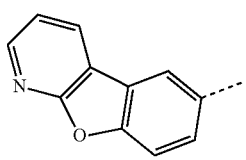 | 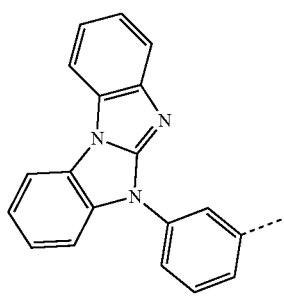 |
| C-32 | 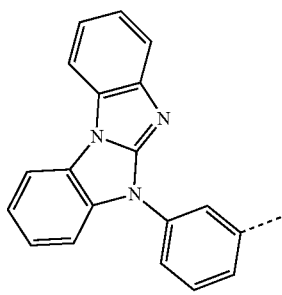 | 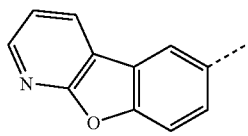 |
| C-33 | 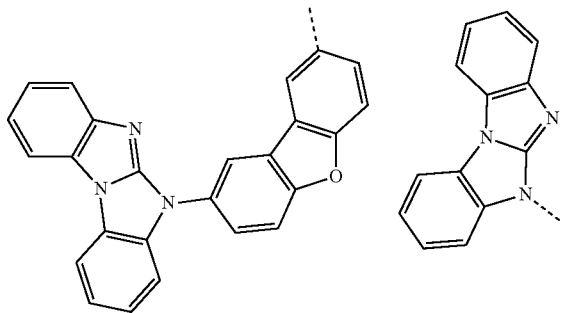 | 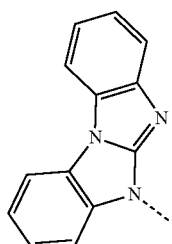 |
| C-34 | 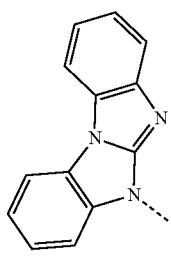 | 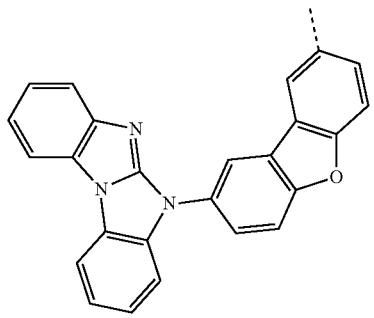 |

-continued
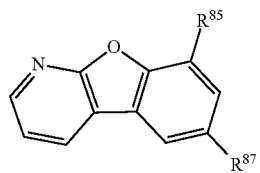
| Compound | R85 | R87 |
|---|---|---|
| C-35 | 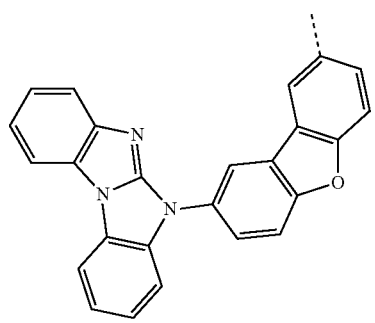 | H |
| C-36 | H | 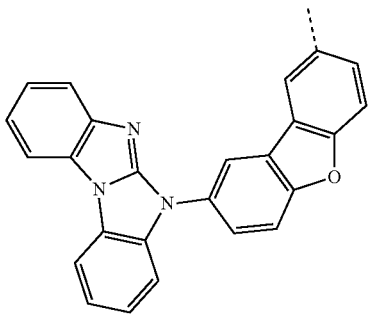 |
| C-37 | 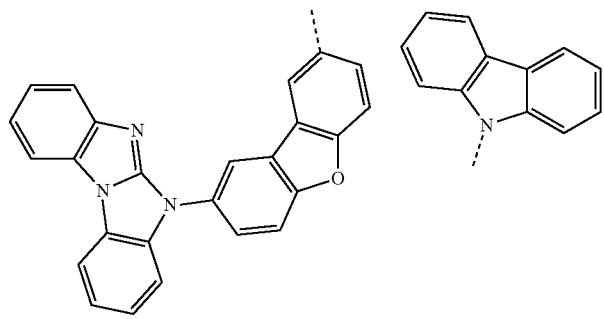 | |
| C-38 | 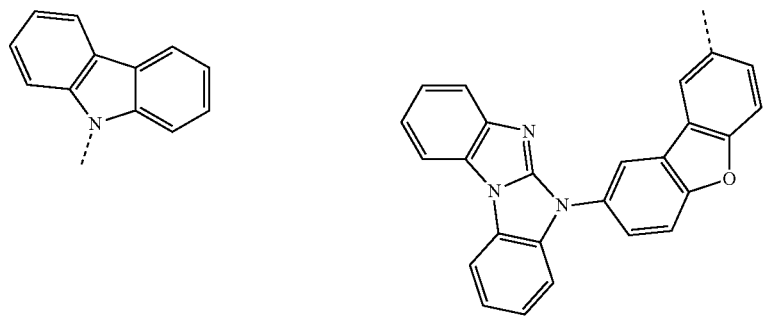 | |

-continued
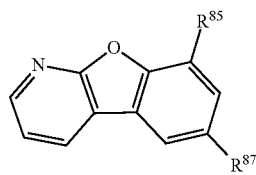
| Compound | R85 | R87 |
|---|---|---|
| C-39 | 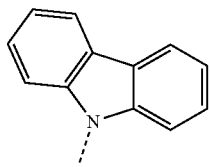 | 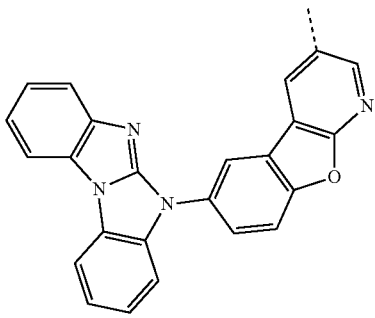 |
| C-40 | 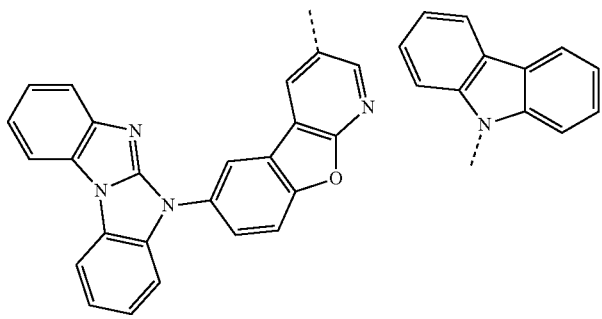 | |
| C-41 | 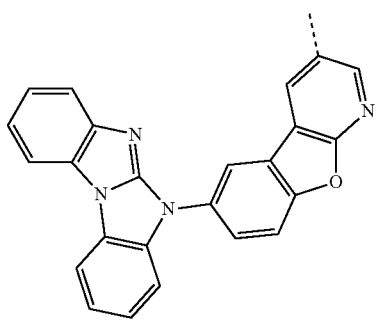 | H |
| C-42 | H | 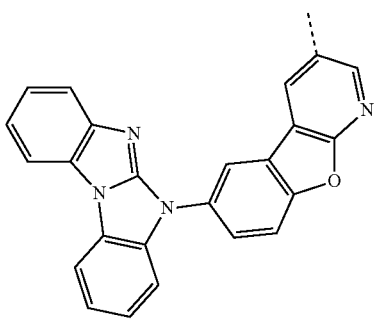 |

-continued
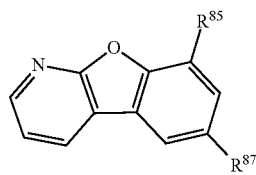
| Compound | R85 | R87 |
|---|---|---|
| C-43 | 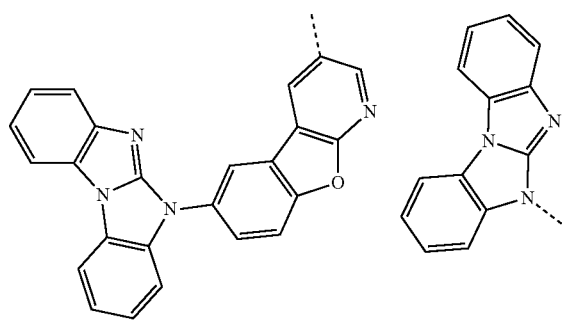 | |
| C-44 | 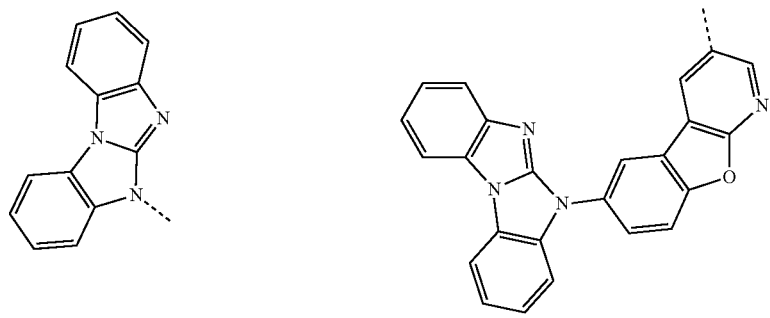 | |
| C-45 | 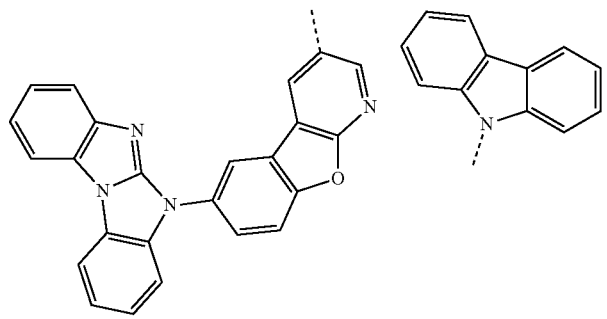 | |
| C-46 | 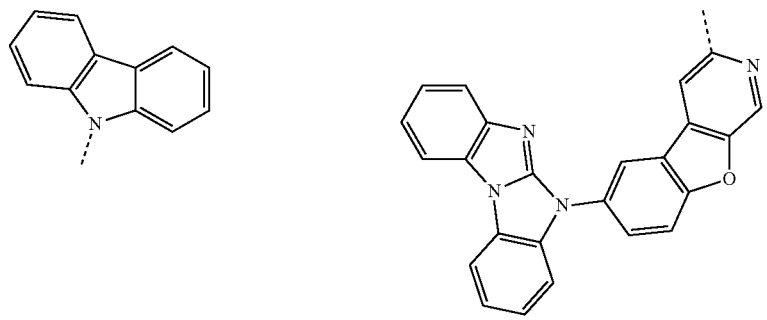 | |

-continued
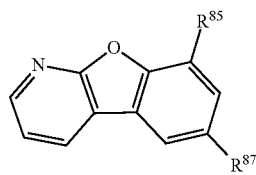
| Compound | R85 | R87 |
|---|---|---|
| C-47 | 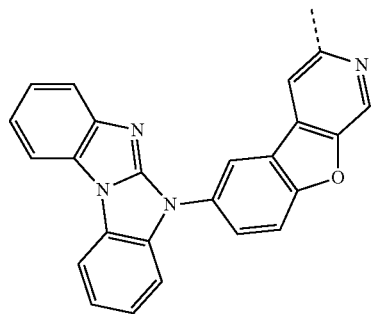 | H |
| C-48 | H | 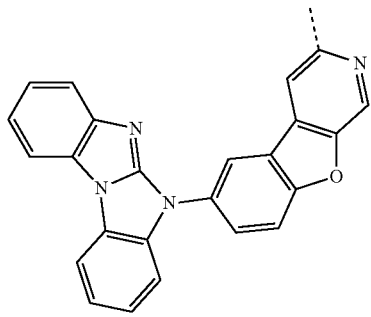 |
| C-49 | 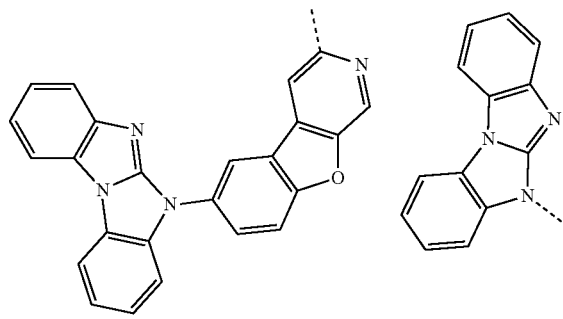 | |
| C-50 | 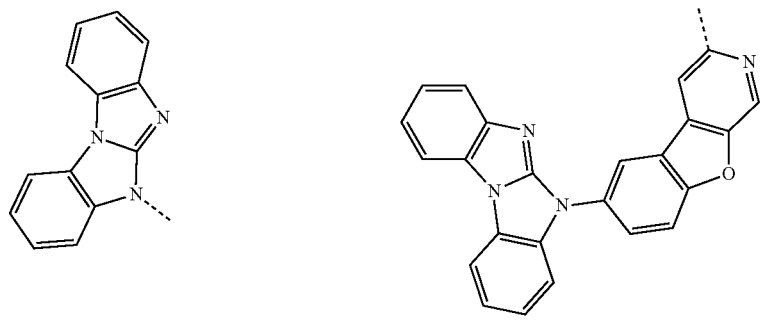 | |

-continued
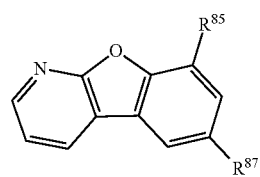
| Compound | R<sup>85</sup> | R<sup>87</sup> |
|---|---|---|
| C-51 | | |
| C-52 | | |
| C-53 | | |
| C-54 | | |
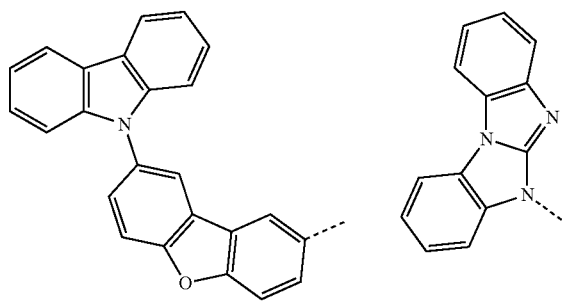
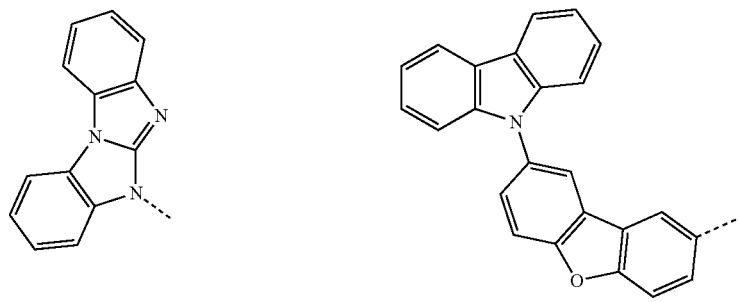
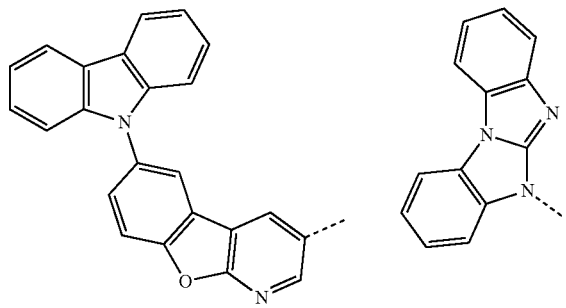
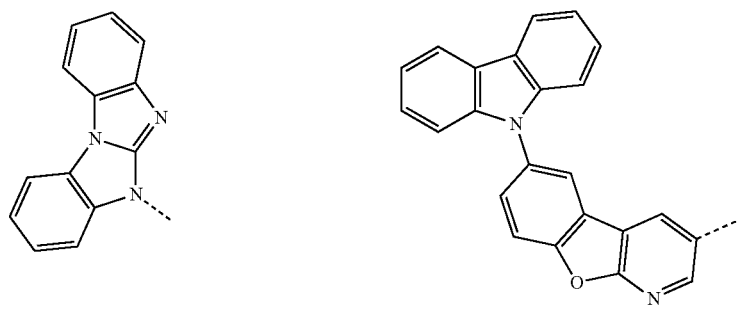

-continued
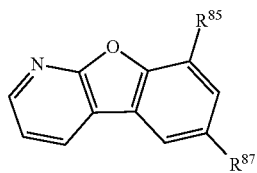
| Compound | R85 | R87 |
|---|---|---|
| C-55 | 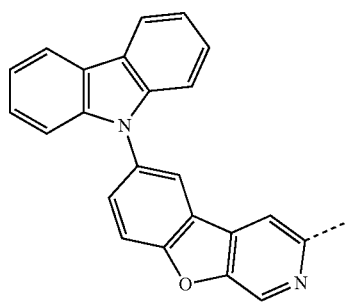 | 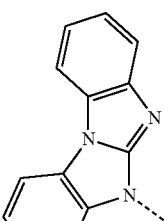 |
| C-56 | 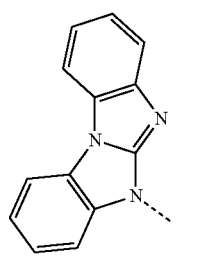 | 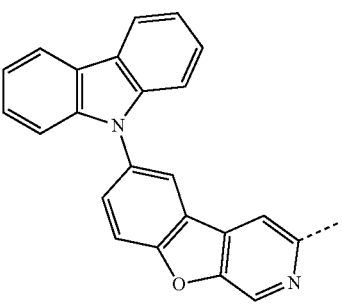 |
| C-57 | H | 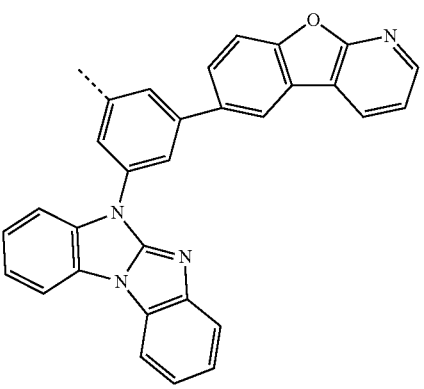 |
| C-58 | 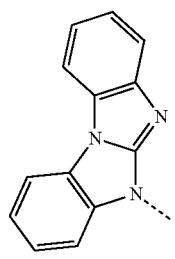 | 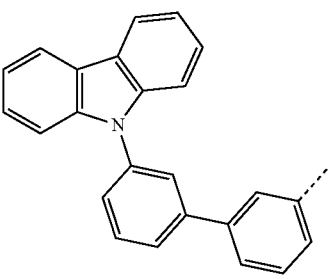 |

-continued
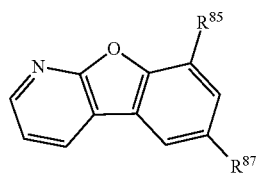
| Compound | R⁸⁵ | R⁸⁷ |
|---|---|---|
| C-59 | 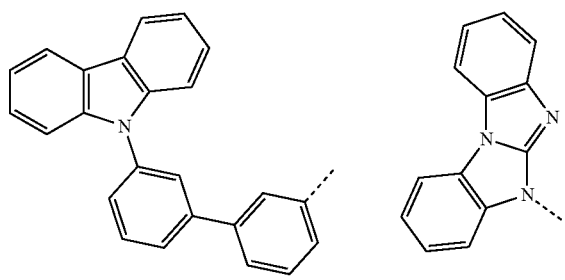 | |
| C-60 | 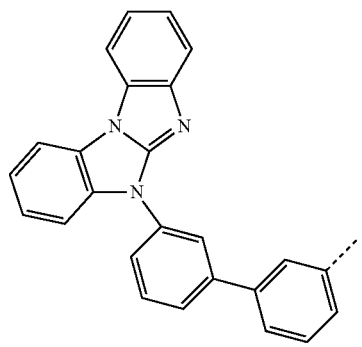 | H |
| C-61 | H | 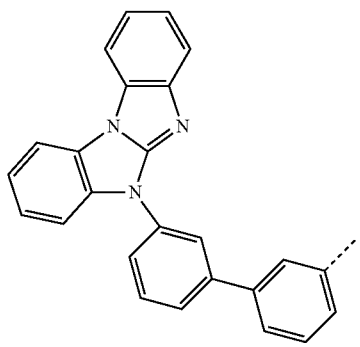 |
| C-62 | H | 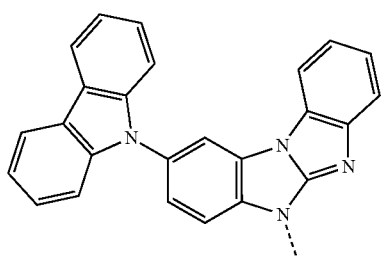 |

-continued
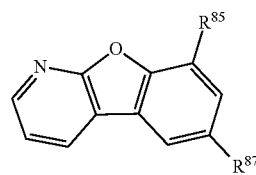
| Compound | R85 | R87 |
|---|---|---|
| C-63 | H | 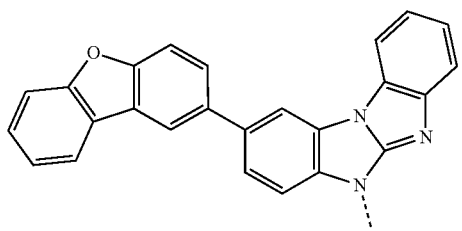 |
| C-64 | H | 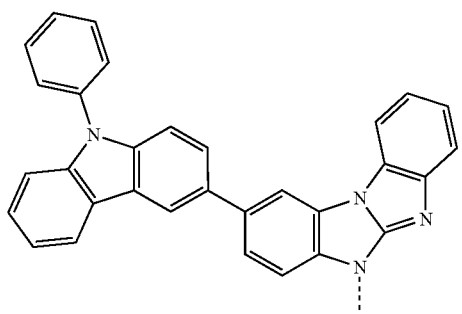 |
| C-65 | H | 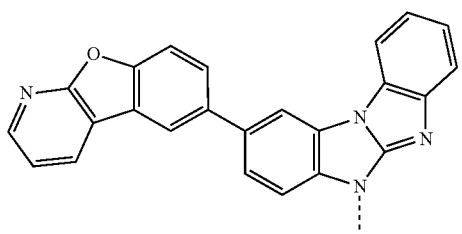 |
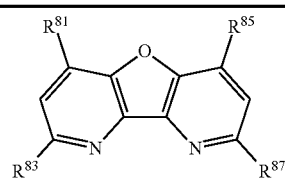
| Cmp. | R81 | R83 | R85 | R87 |
|---|---|---|---|---|
| D-1 | 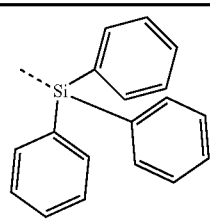 | 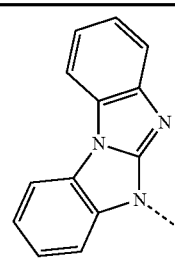 | 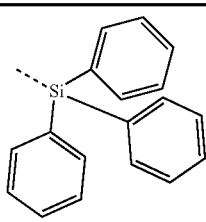 | 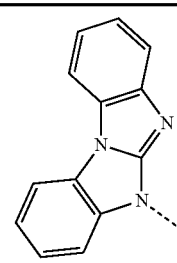 |

-continued

| Cmp. | R⁸¹ | R⁸³ | R⁸⁵ | R⁸⁷ |
|---|---|---|---|---|
| D-2 | H | benzimidazole group | H | benzimidazole group |
| D-3 | H | benzimidazole group | H | |
| D-4 | H | benzimidazole group | triphenylsilyl | benzimidazole group |
| D-5 | triphenylsilyl | N-phenyl-benzimidazole group | triphenylsilyl | N-phenyl-benzimidazole group |
| D-6 | H | N-phenyl-benzimidazole group | H | N-phenyl-benzimidazole group |

-continued
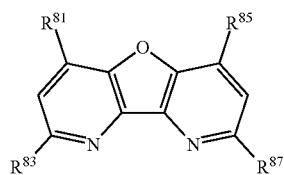
| Cmp. | R⁸¹ | R⁸³ | R⁸⁵ | R⁸⁷ |
|---|---|---|---|---|
| D-7 | H | (benzimidazole-phenyl) | H | |
| D-8 | H | (benzimidazole-phenyl) | (triphenylsilyl) | (benzimidazole-phenyl) |
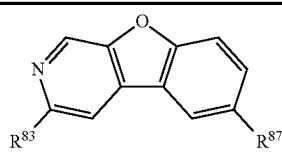
| Compound | R⁸³ | R⁸⁷ |
|---|---|---|
| E-1 | (benzimidazole) | (benzimidazole) |
| E-2 | (carbazole-phenyl) | (benzimidazole) |

-continued
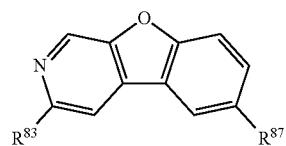
| Compound | R⁸³ | R⁸⁷ |
|---|---|---|
| E-3 | 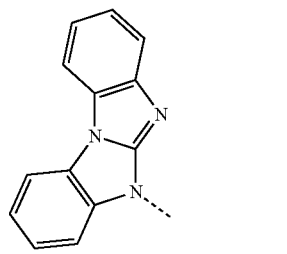 | 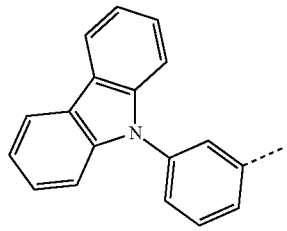 |
| E-4 | 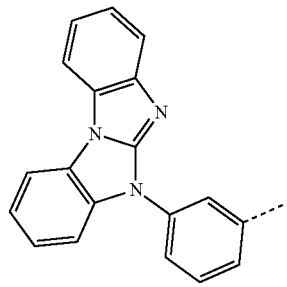 | 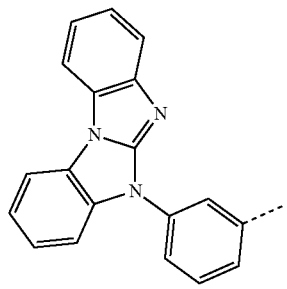 |
| E-5 | H | 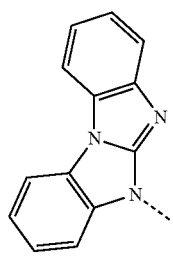 |
| E-6 | 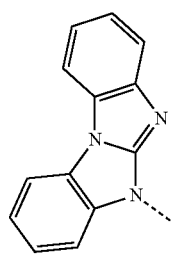 | H |
| E-7 | H | 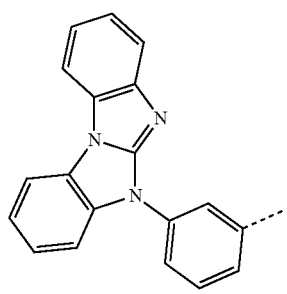 |

-continued
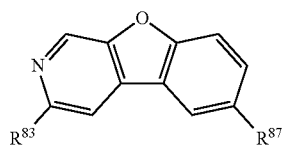
| Compound | R83 | R87 |
|---|---|---|
| E-8 | 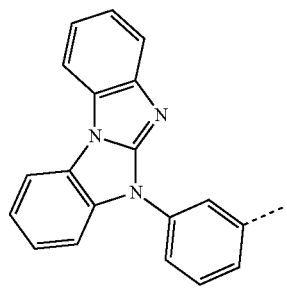 | H |
| E-9 | H | 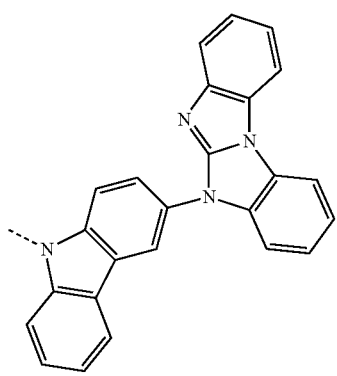 |
| E-10 | 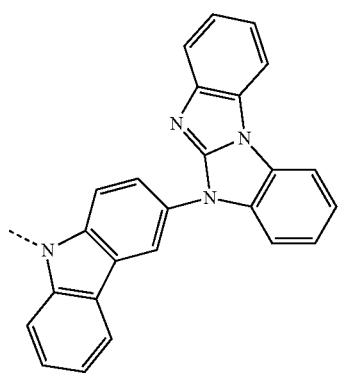 | H |
| E-11 | 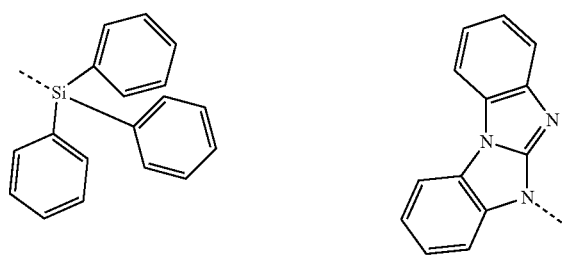 | |

-continued
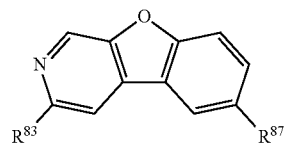
| Compound | R⁸³ | R⁸⁷ |
|---|---|---|
| E-12 | 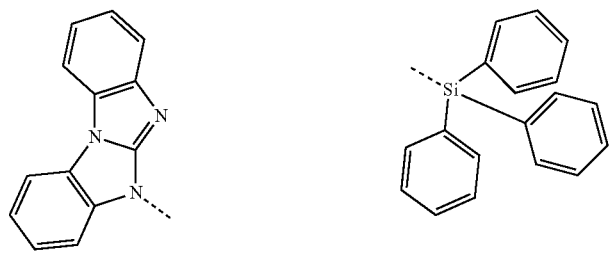 | |
| E-13 | 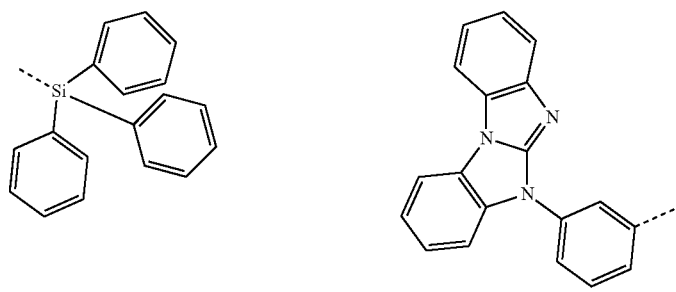 | |
| E-14 | 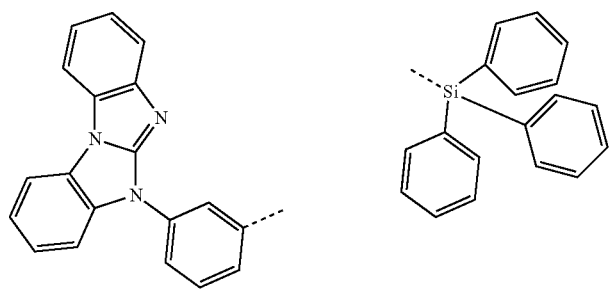 | |
| E-15 | 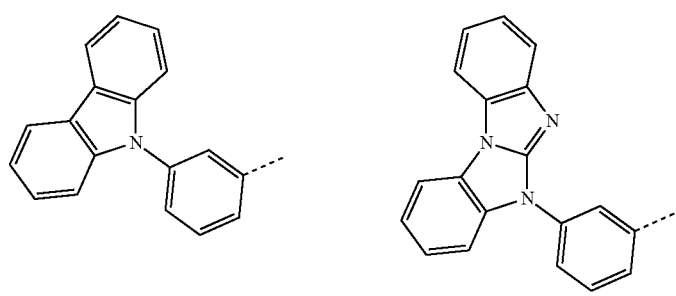 | |
| E-16 | 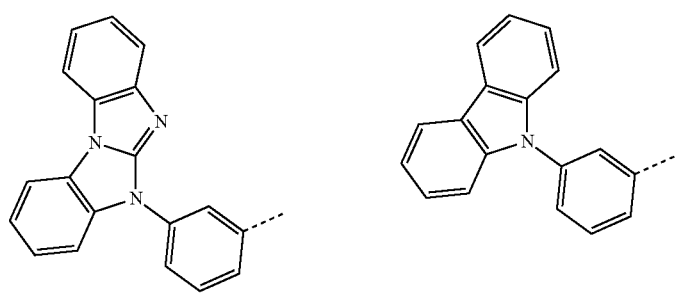 | |

-continued
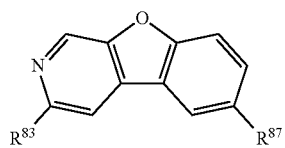
| Compound | R<sup>83</sup> | R<sup>87</sup> |
|---|---|---|
| E-17 | 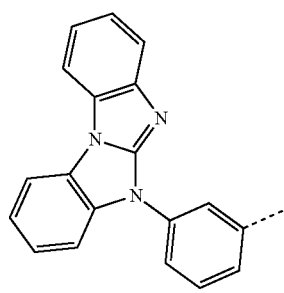 | 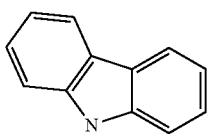 |
| E-18 | 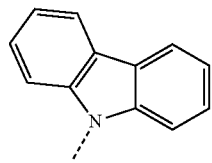 | 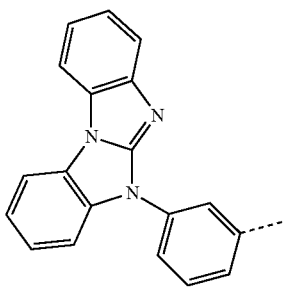 |
| E-19 | 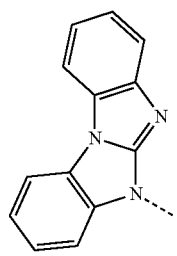 | 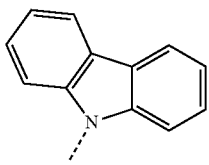 |
| E-20 | 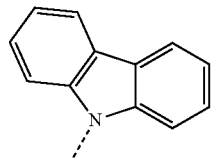 | 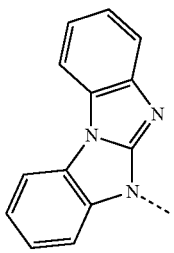 |
| E-21 | 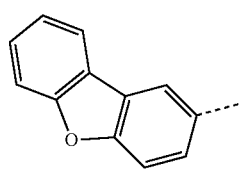 | 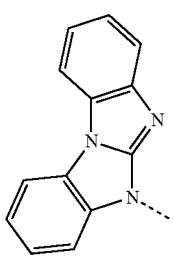 |

-continued
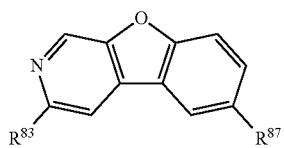
| Compound | R83 | R87 |
|---|---|---|
| E-22 | 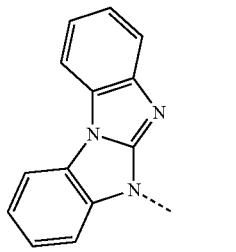 | 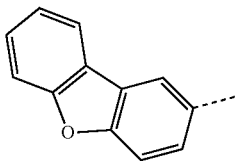 |
| E-23 | 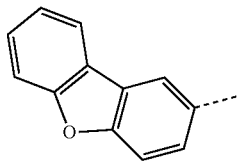 | 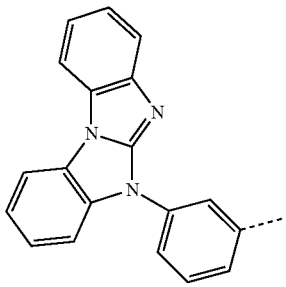 |
| E-24 | 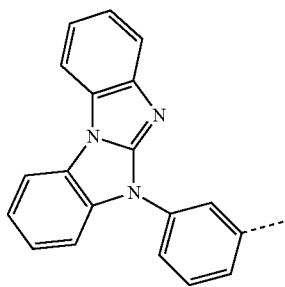 | 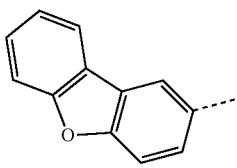 |
| E-25 | 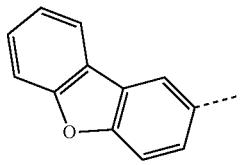 | 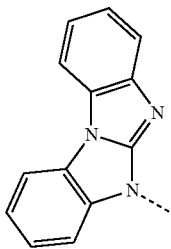 |
| E-26 | 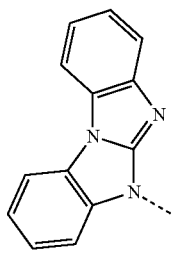 | 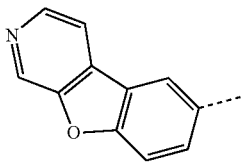 |

-continued
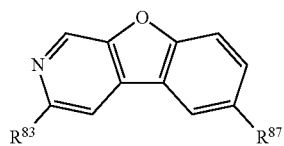
| Compound | R^83 | R^87 |
|---|---|---|
| E-27 | 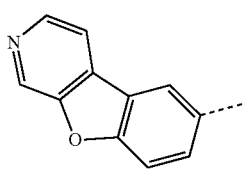 | 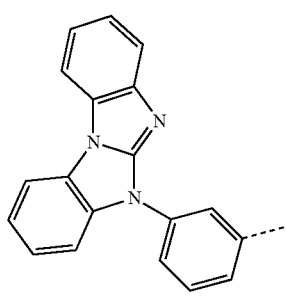 |
| E-28 | 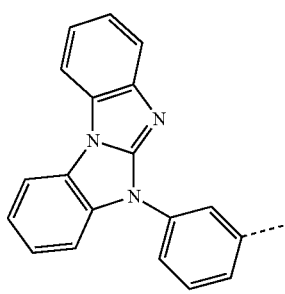 | 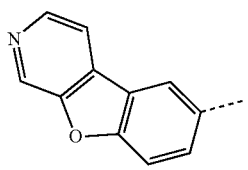 |
| E-29 | 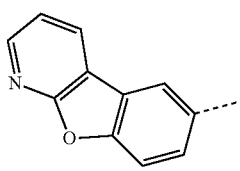 | 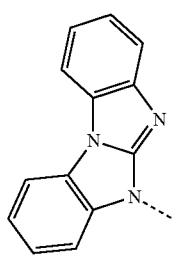 |
| E-30 | 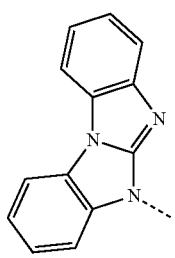 | 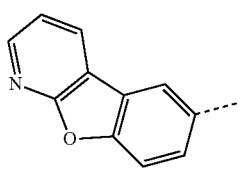 |
| E-31 | 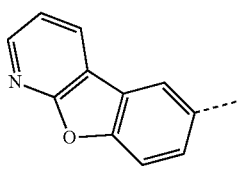 | 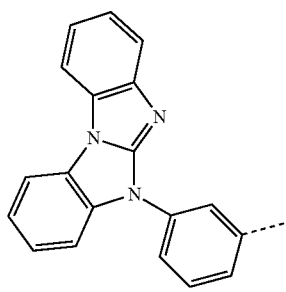 |

-continued
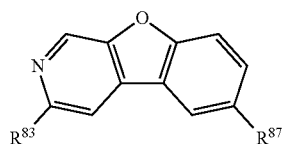
| Compound | R<sup>83</sup> | R<sup>87</sup> |
|---|---|---|
| E-32 | 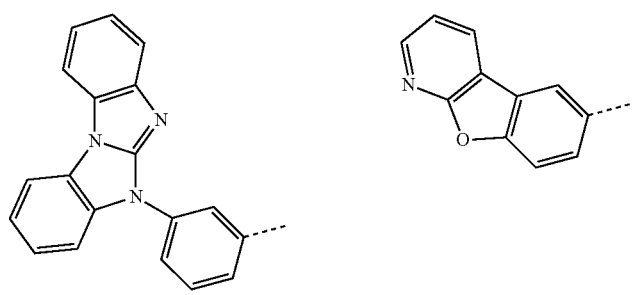 | |
| E-33 | 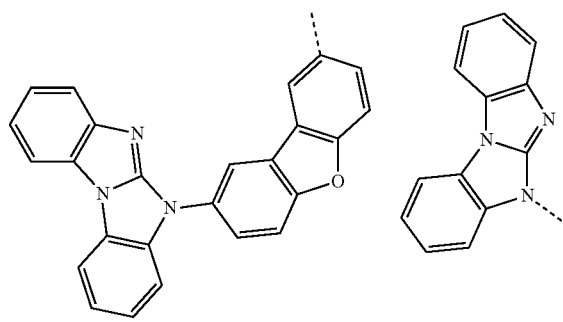 | |
| E-34 | 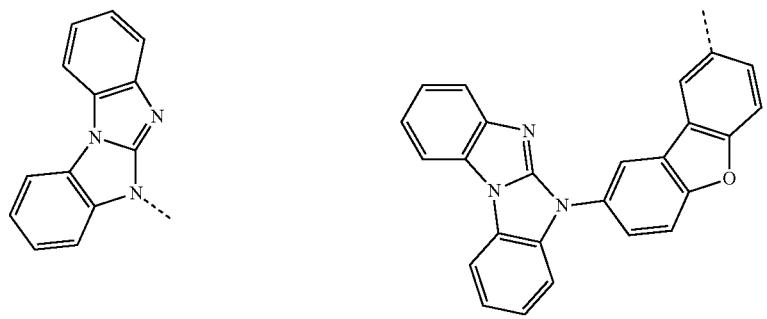 | |
| E-35 | 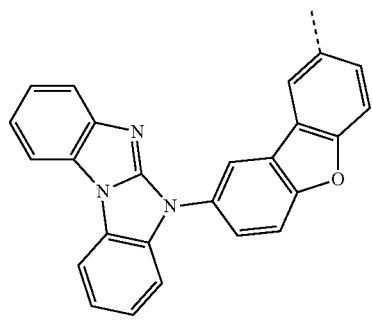 | H |

-continued
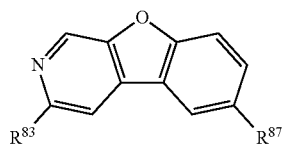
| Compound | R<sup>83</sup> | R<sup>87</sup> |
|---|---|---|
| E-36 | H | 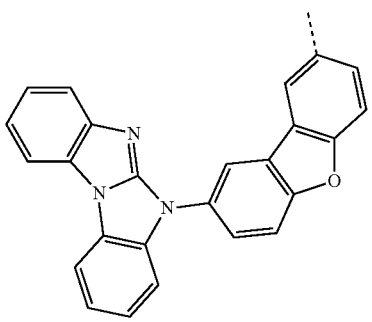 |
| E-37 | 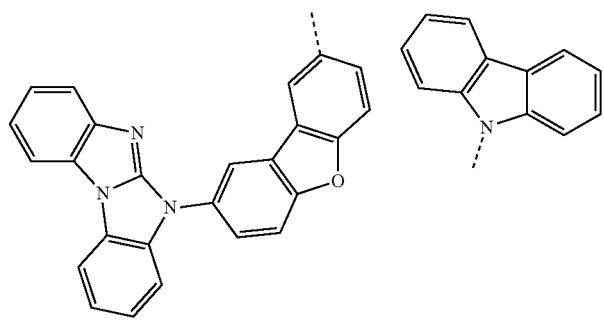 | |
| E-38 | 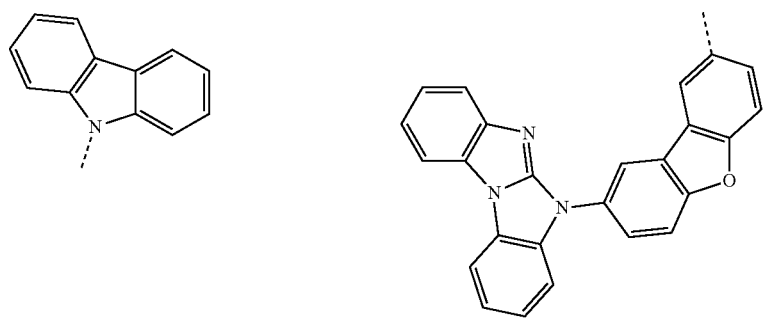 | |
| E-39 | 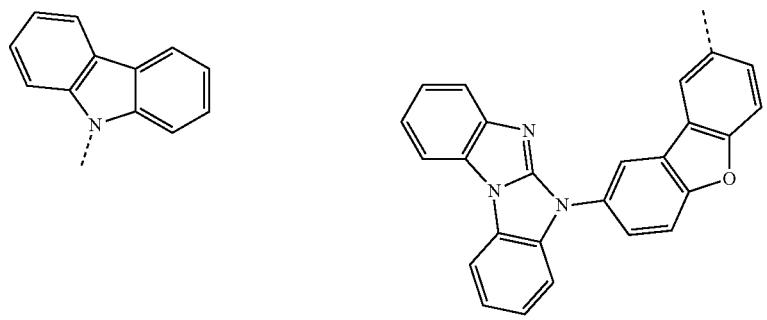 | |

-continued
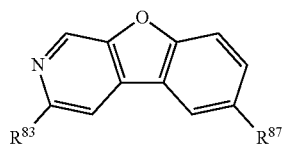
| Compound | R<sup>83</sup> | R<sup>87</sup> |
|---|---|---|
| E-40 | 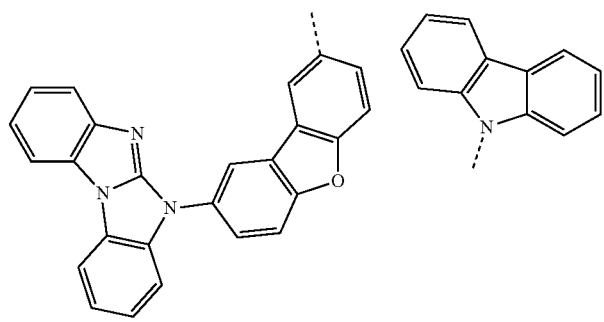 | |
| E-41 | 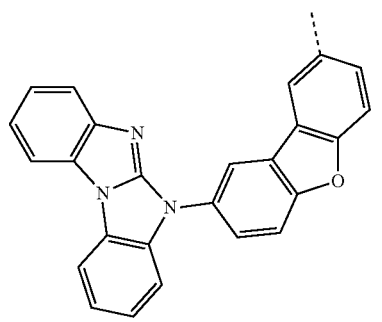 | H |
| E-42 | H | 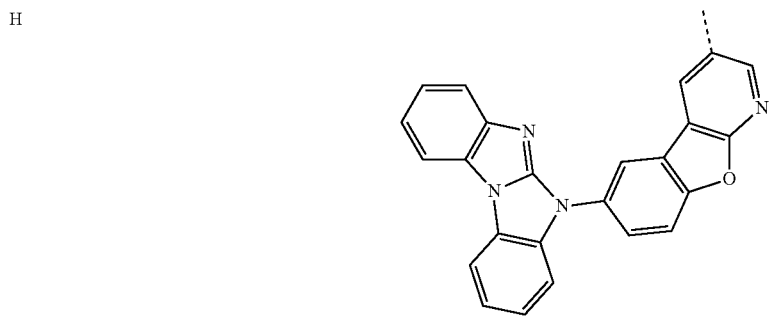 |
| E-43 | 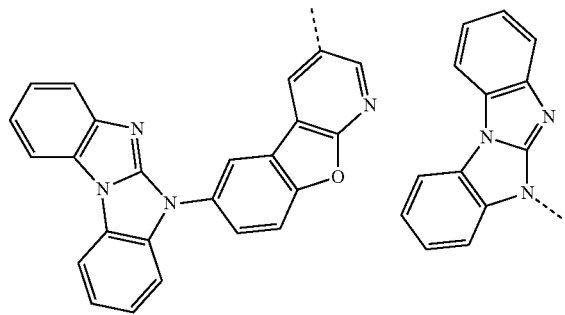 | |

-continued
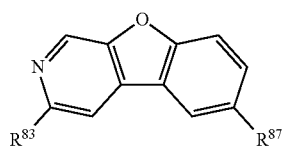
| Compound | R$^{83}$ | R$^{87}$ |
|---|---|---|
| E-44 | 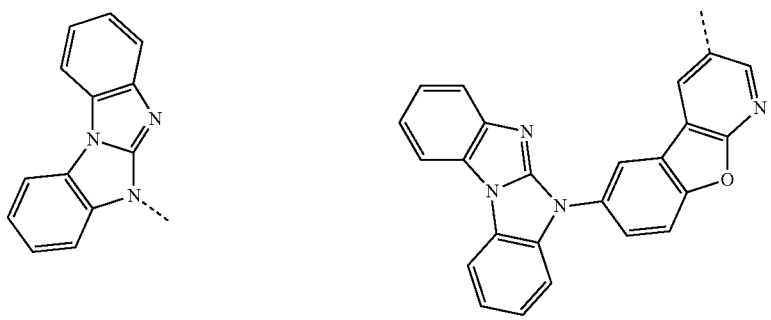 | |
| E-45 | 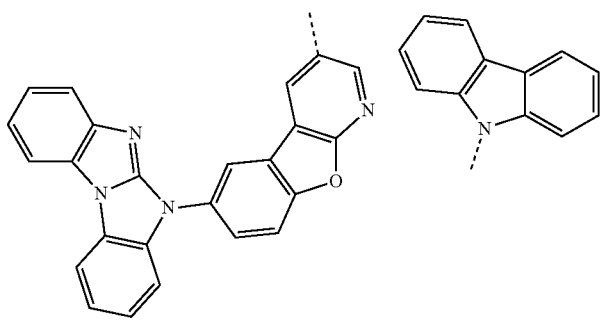 | |
| E-46 | 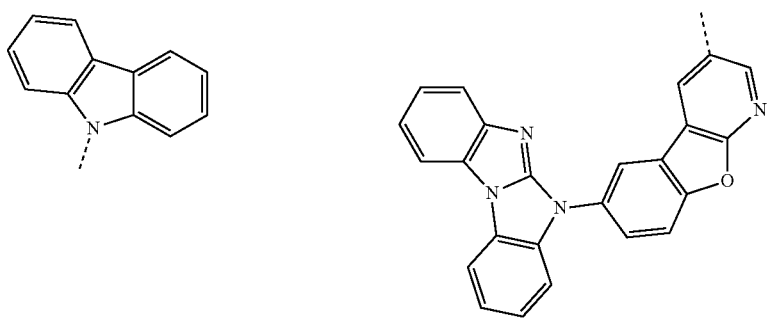 | |
| E-47 | 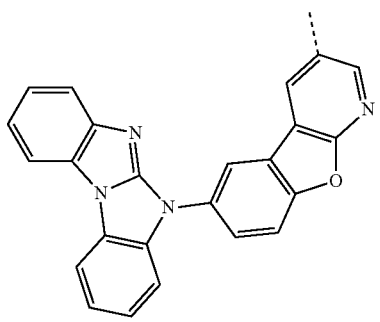 | H |

-continued
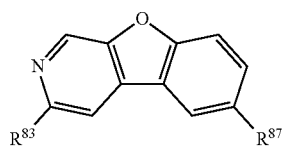
| Compound | R83 | R87 |
|---|---|---|
| E-48 | H | 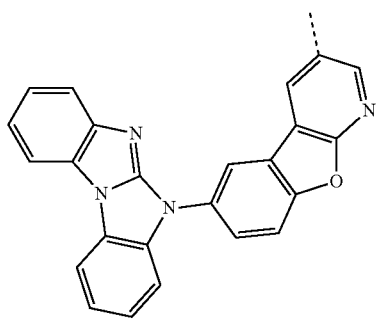 |
| E-49 | 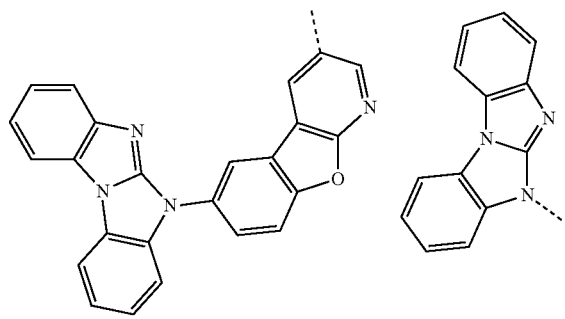 | |
| E-50 | 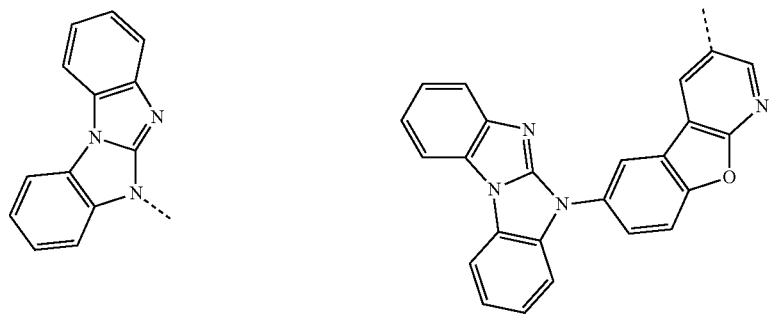 | |
| E-51 | 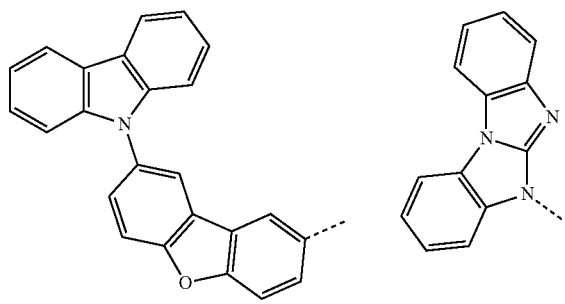 | |

-continued
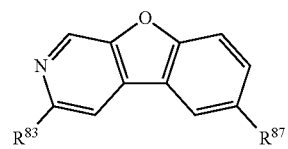
| Compound | R⁸³ | R⁸⁷ |
|---|---|---|
| E-52 | 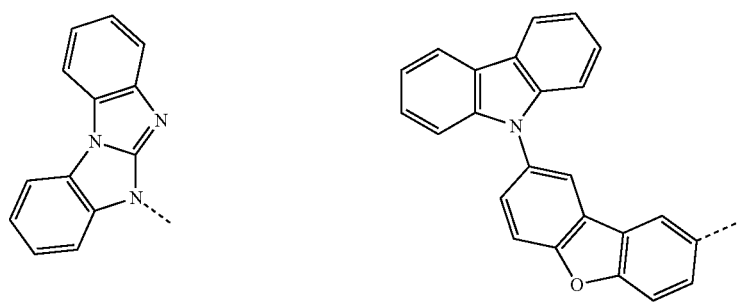 | |
| E-53 | 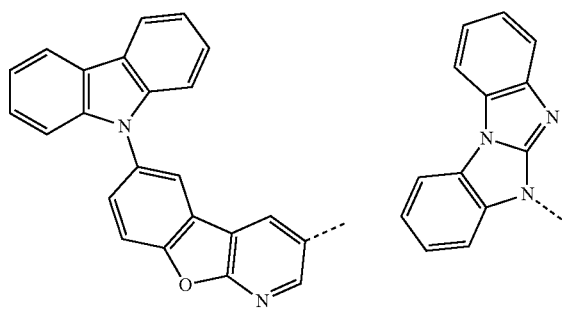 | |
| E-54 | 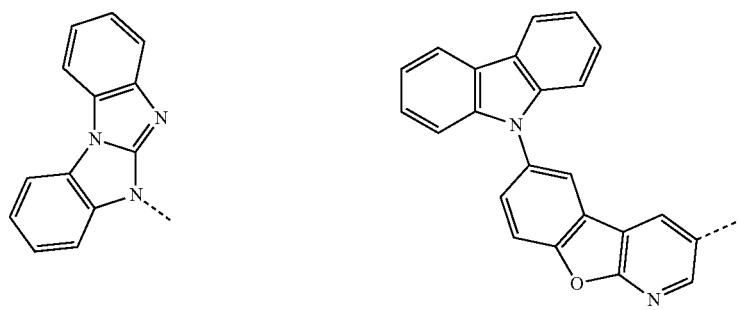 | |
| E-55 | 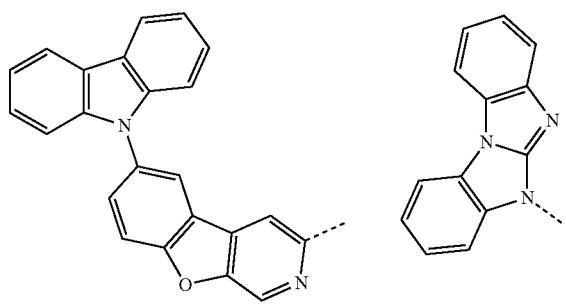 | |

-continued
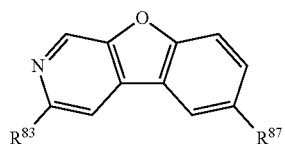
| Compound | R^83 | R^87 |
|---|---|---|
| E-56 | | |
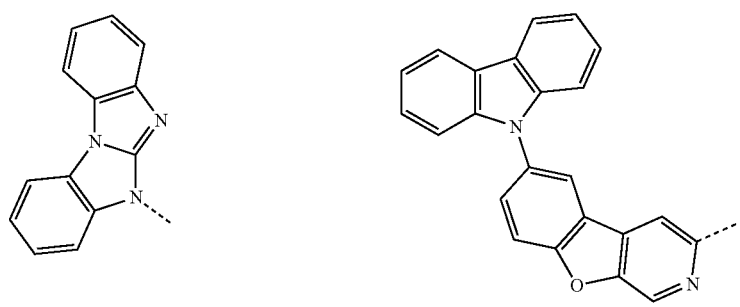
| E-57 | H | |
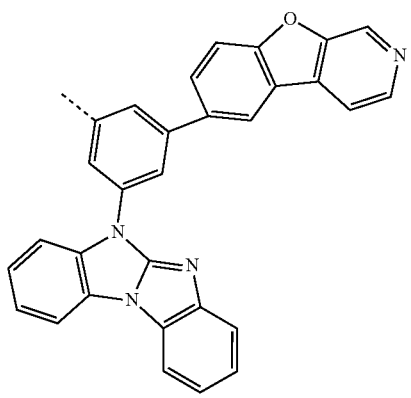
| E-58 | | |
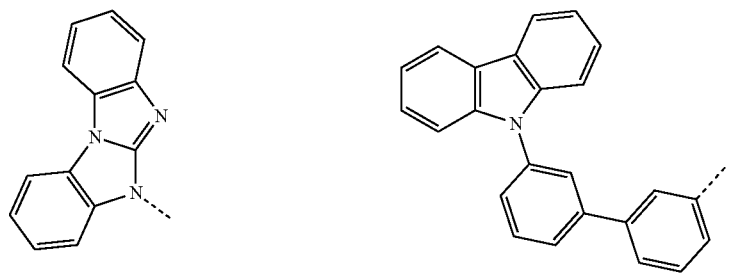
| E-59 | | |
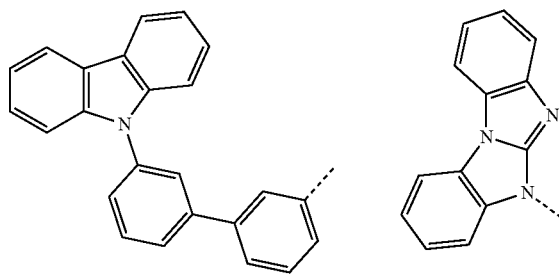

-continued
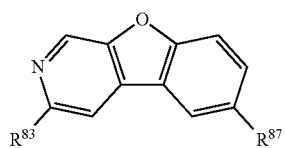
| Compound | R^{83} | R^{87} |
|---|---|---|
| E-60 | 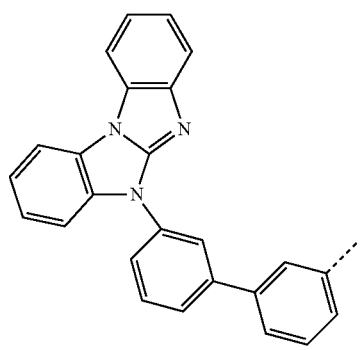 | H |
| E-61 | H | 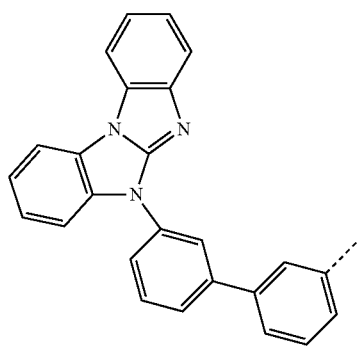 |
| E-62 | H | 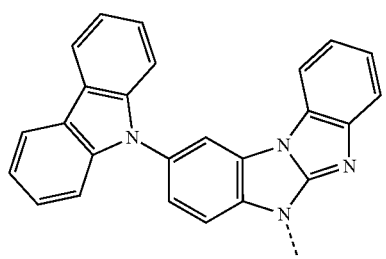 |
| E-63 | H | 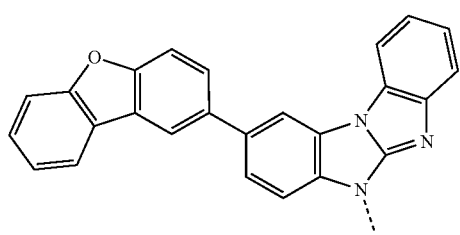 |

-continued
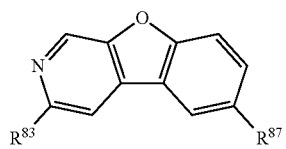
| Compound | R83 | R87 |
|---|---|---|
| E-64 | H | 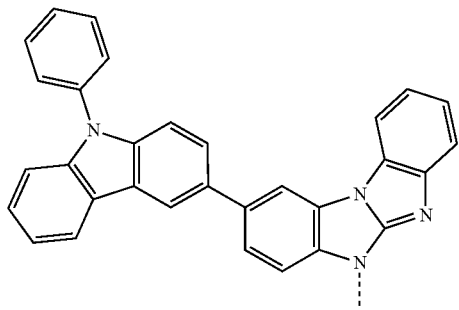 |
| E-65 | H | 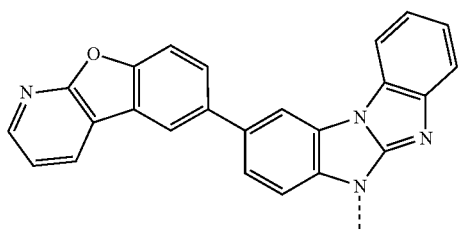 |
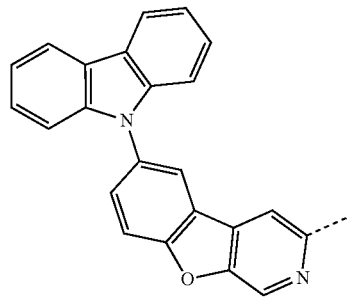
| Compound | R83 | R85 |
|---|---|---|
| F-1 | 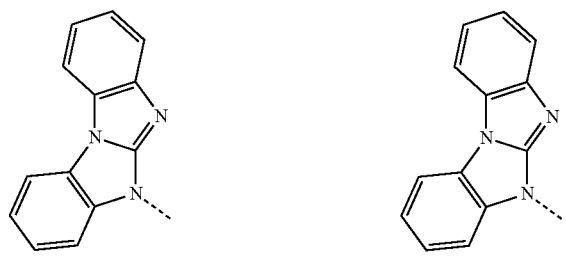 | |

-continued
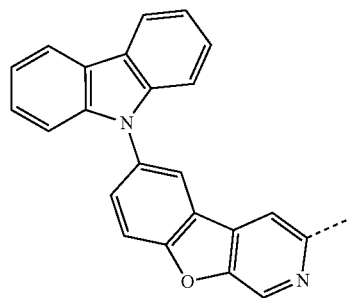
| Compound | R83 | R85 |
|---|---|---|
| F-2 | 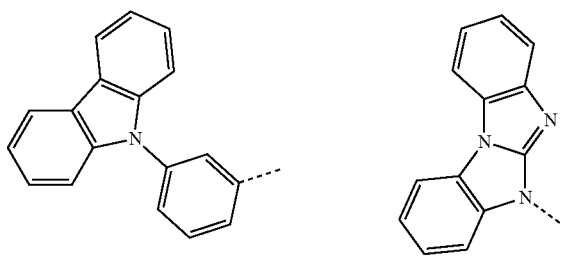 | |
| F-3 | 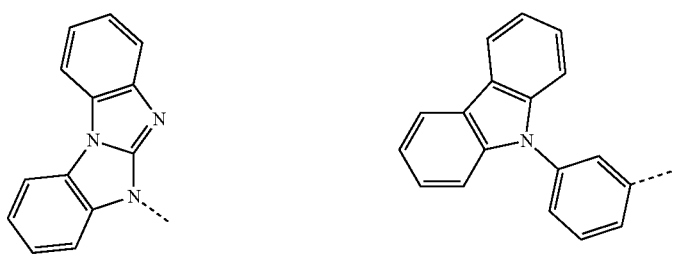 | |
| F-4 | 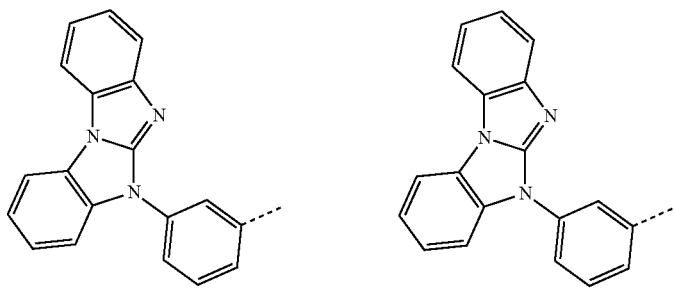 | |
| F-5 | H |  |

-continued
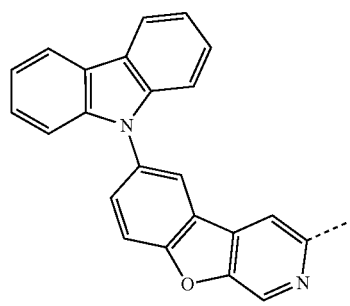
| Compound | R83 | R85 |
|---|---|---|
| F-6 | 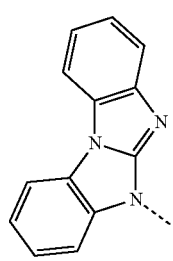 | H |
| F-7 | H | 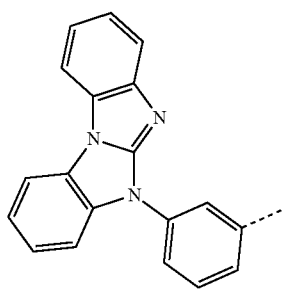 |
| F-8 | 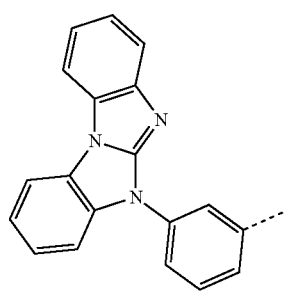 | H |
| F-9 | H | 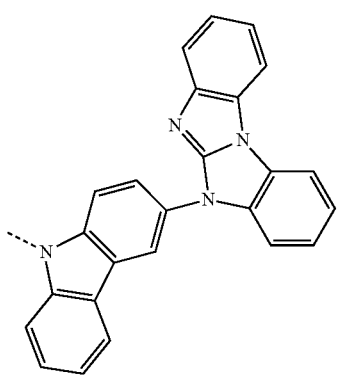 |

-continued
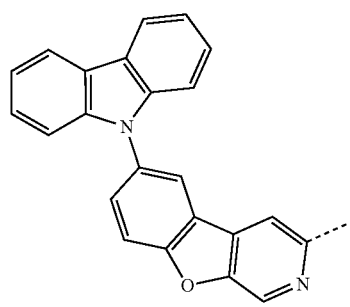
| Compound | R83 | R85 |
|---|---|---|
| F-10 | 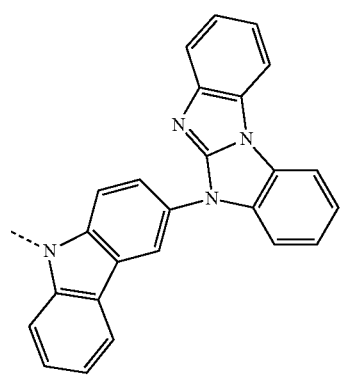 | H |
| F-11 | 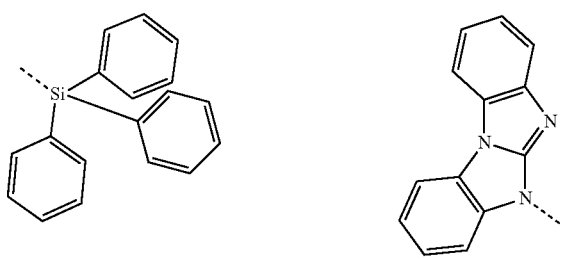 | |
| F-12 | 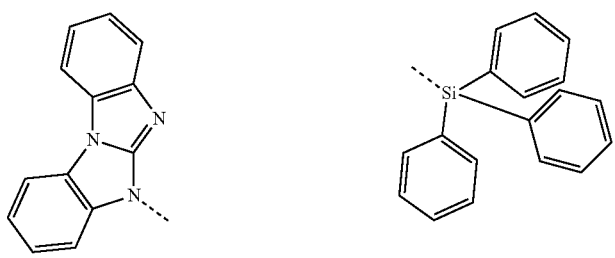 | |
| F-13 | 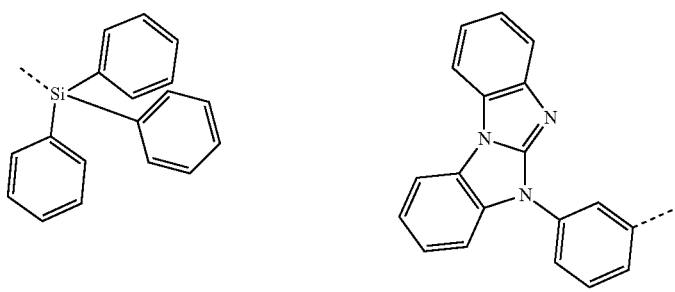 | |

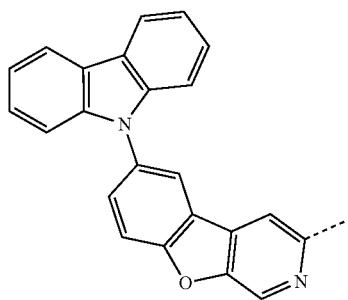
| Compound | R83 | R85 |
|---|---|---|
| F-14 | 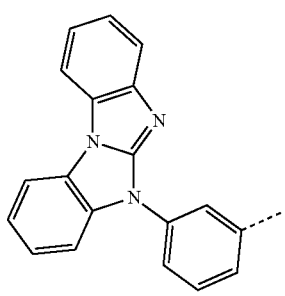 | 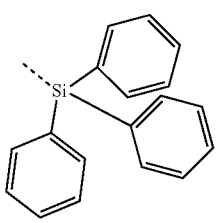 |
| F-15 | 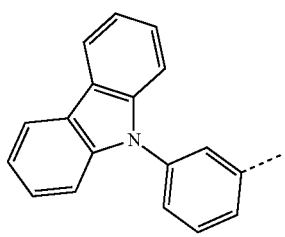 | 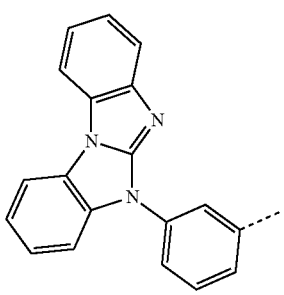 |
| F-16 | 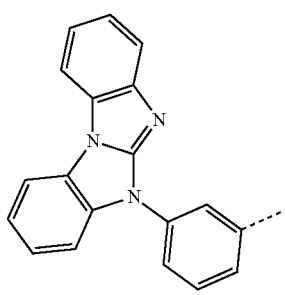 | 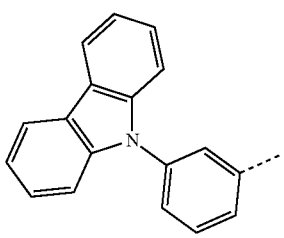 |
| F-17 | 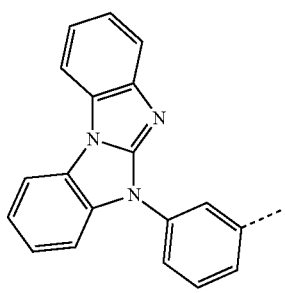 | 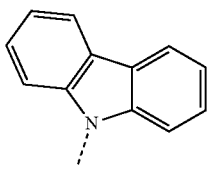 |

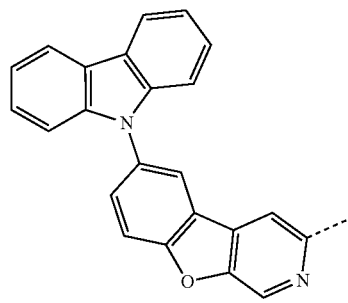
| Compound | R⁸³ | R⁸⁵ |
|---|---|---|
| F-18 | 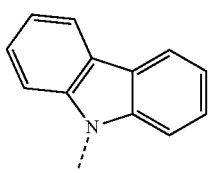 | 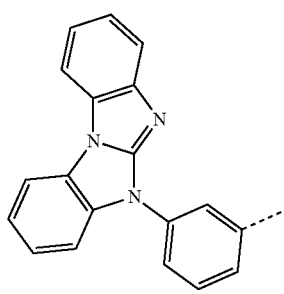 |
| F-19 | 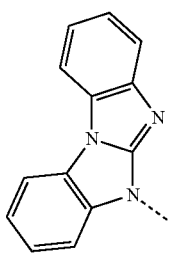 | 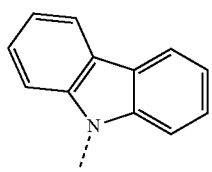 |
| F-20 | 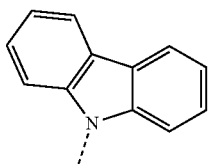 | 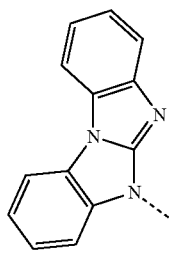 |
| F-21 | 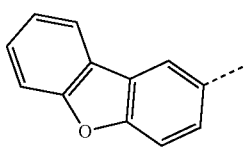 | 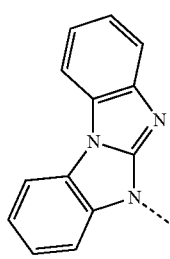 |

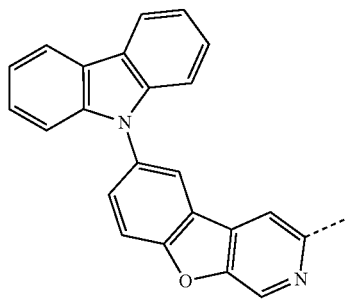
| Compound | R83 | R85 |
|---|---|---|
| F-22 | 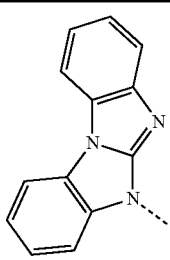 | |
| F-23 | 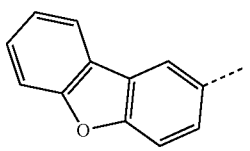 | 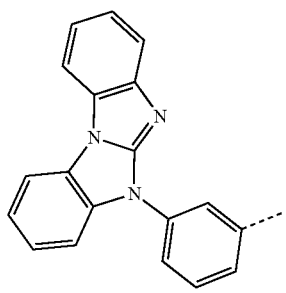 |
| F-24 | 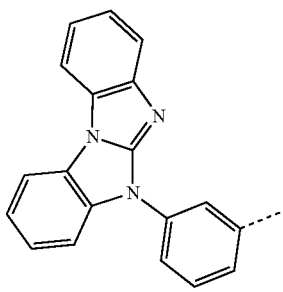 | 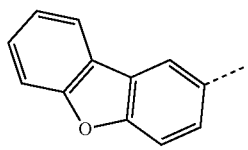 |
| F-25 | 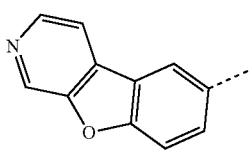 | 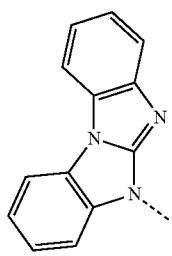 |

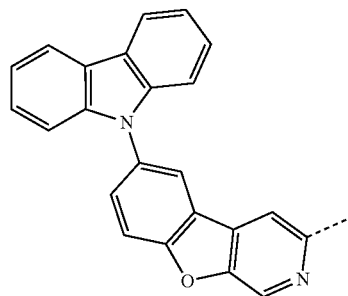
| Compound | R83 | R85 |
|---|---|---|
| F-26 | 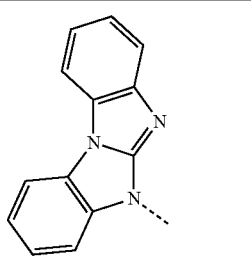 | 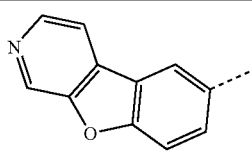 |
| F-27 | 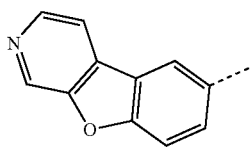 | 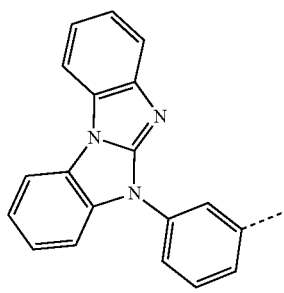 |
| F-28 | 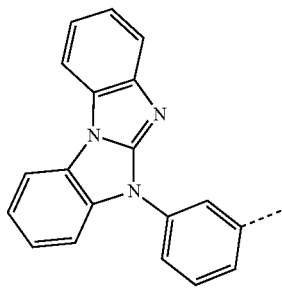 | 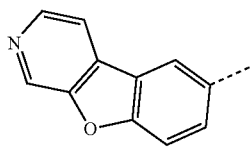 |
| F-29 | 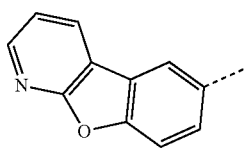 | 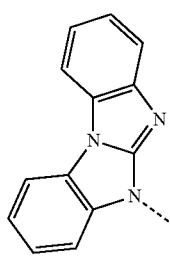 |

-continued
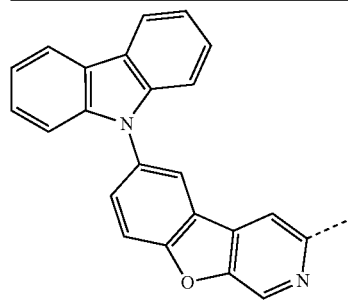
| Compound | R⁸³ | R⁸⁵ |
|---|---|---|
| F-30 | 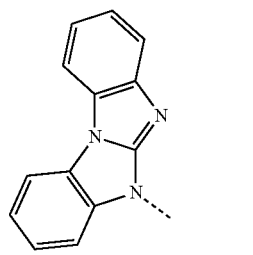 | 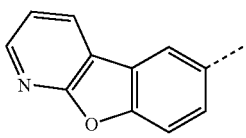 |
| F-31 | 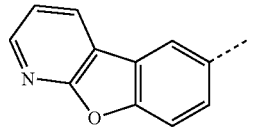 | 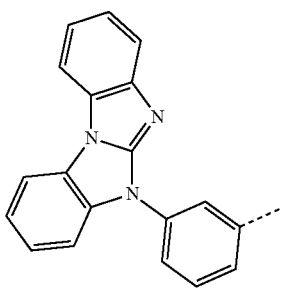 |
| F-32 | 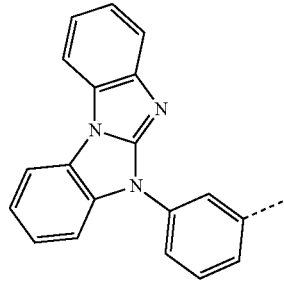 | 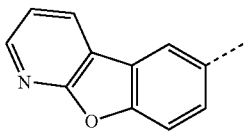 |
| F-33 | 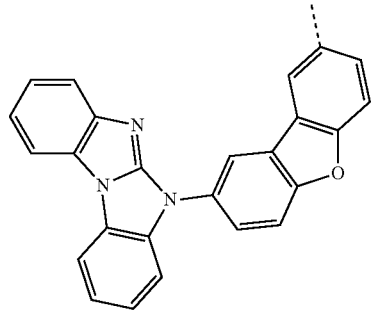 | 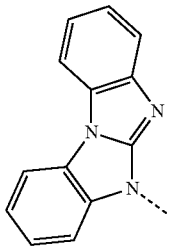 |

-continued
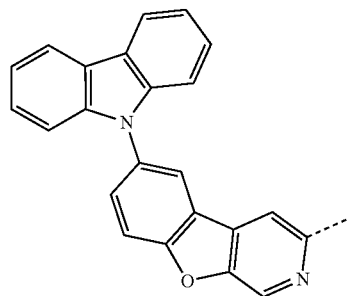
| Compound | R⁸³ | R⁸⁵ |
|---|---|---|
| F-34 | 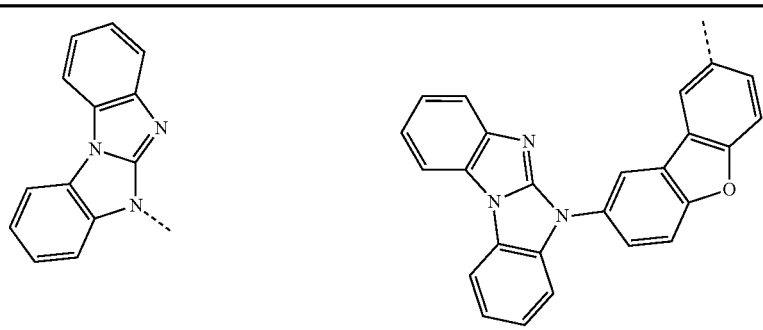 | |
| F-35 | 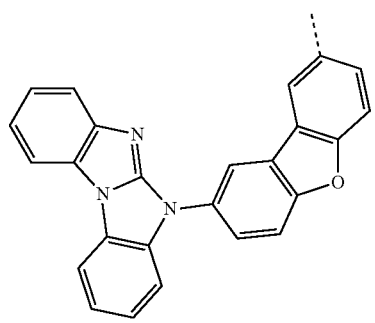 | H |
| F-36 | H | 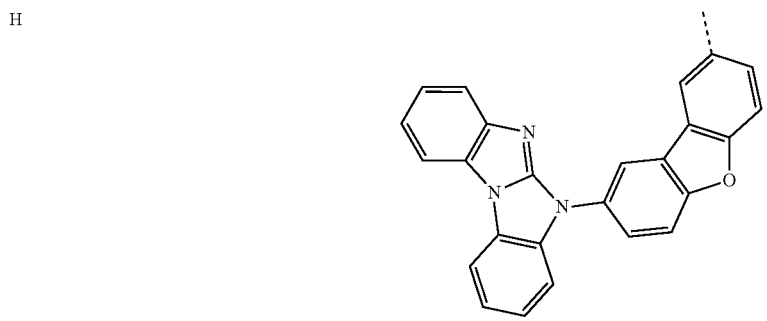 |
| F-37 | 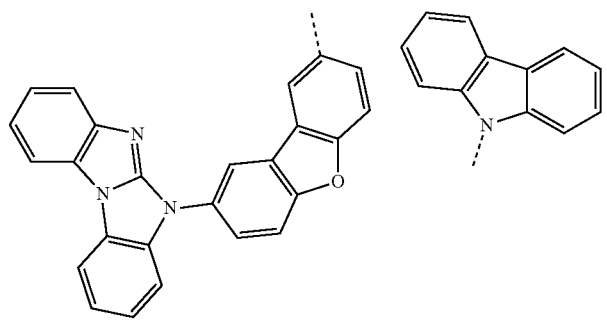 | |

-continued
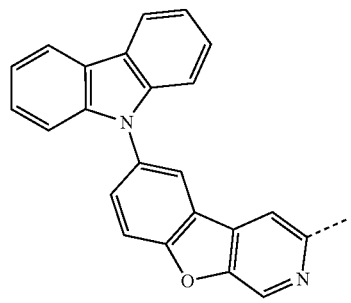
| Compound | R$^{83}$ | R$^{85}$ |
|---|---|---|
| F-38 | 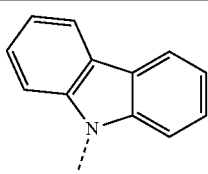 | 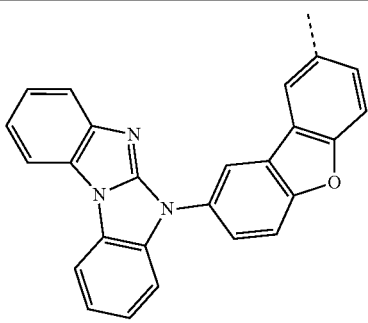 |
| F-39 | 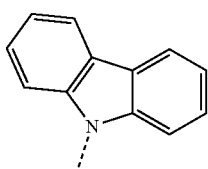 | 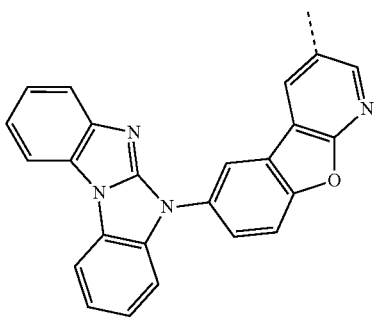 |
| F-40 | 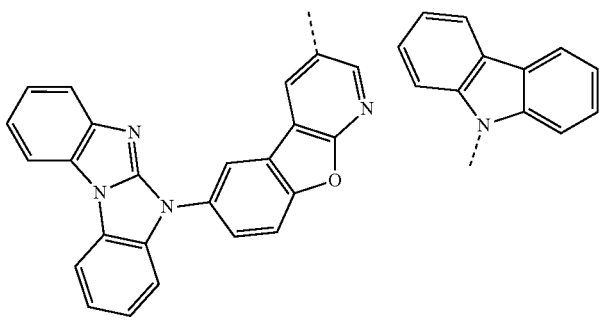 | |
| F-41 | 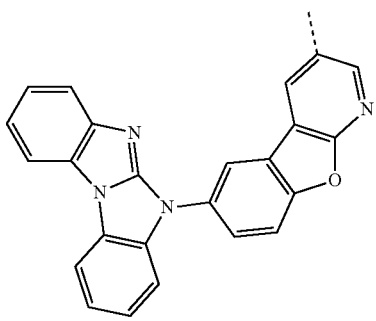 | H |

-continued
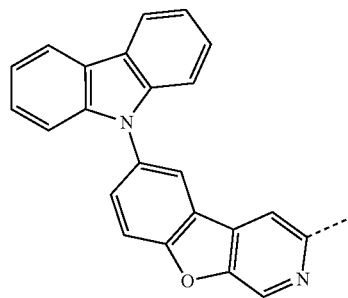
| Compound | R83 | R85 |
|---|---|---|
| F-42 | H | 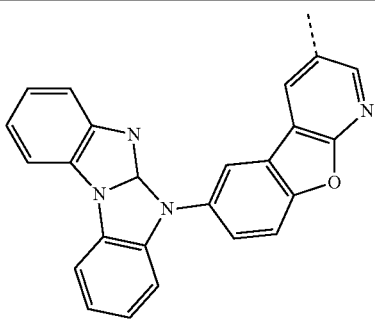 |
| F-43 | 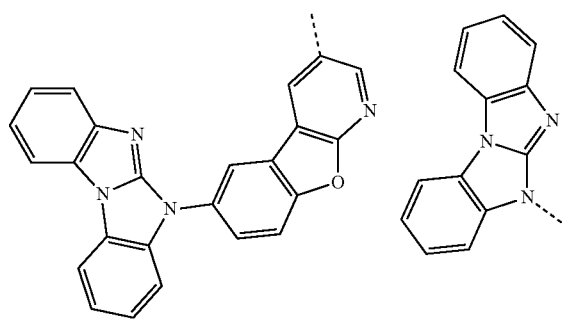 | |
| F-44 | 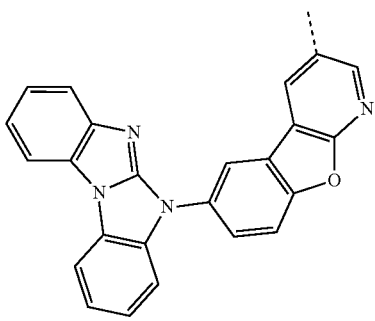 | |
| F-45 | 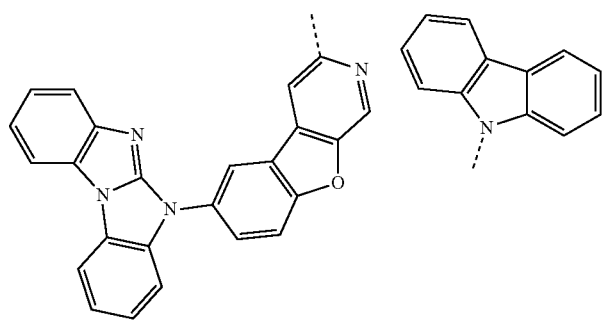 | |

-continued
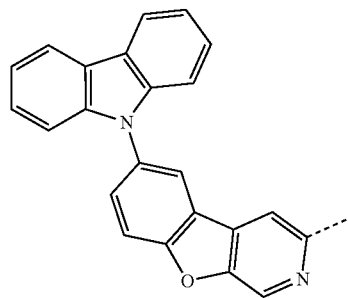
| Compound | R[83] | R[85] |
|---|---|---|
| F-46 | 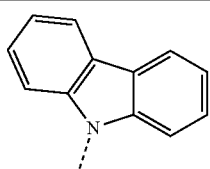 | 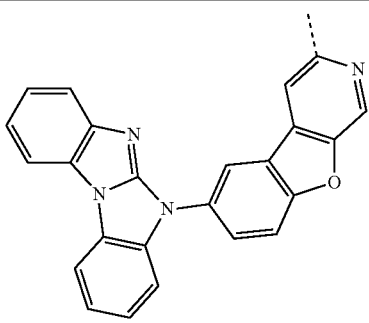 |
| F-47 | 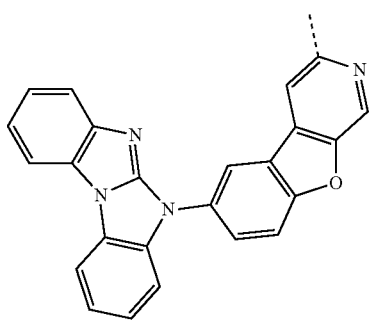 | H |
| F-48 | H | 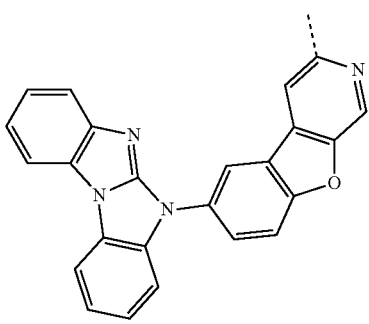 |
| F-49 | 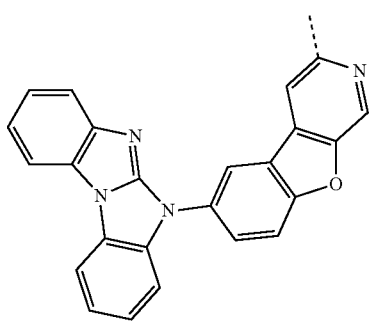 | 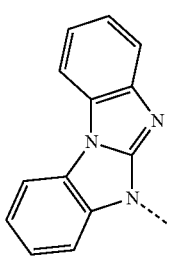 |

-continued
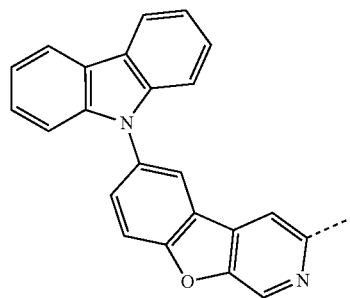
| Compound | R83 | R85 |
|---|---|---|
| F-50 | 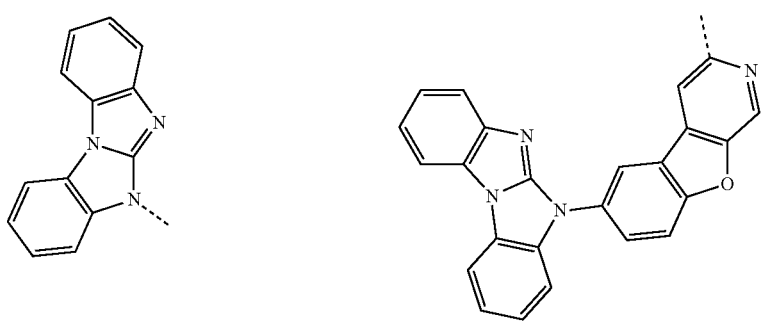 | |
| F-51 | 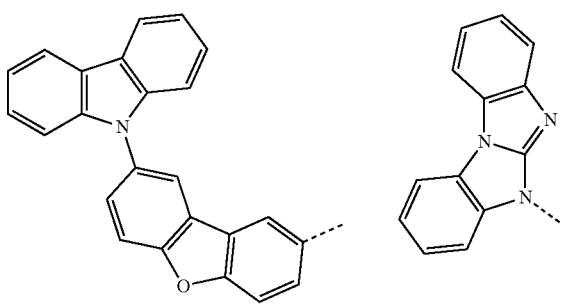 | |
| F-52 | 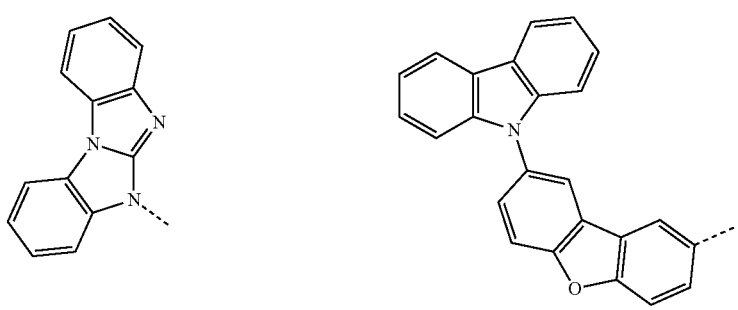 | |
| F-53 | 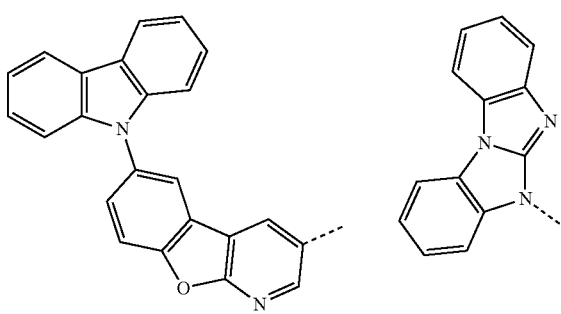 | |

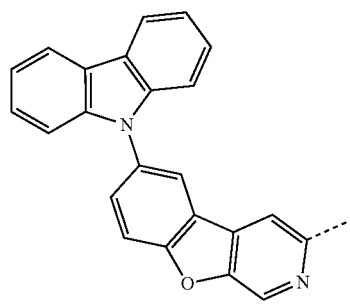
| Compound | $R^{83}$ | $R^{85}$ |
|---|---|---|
| F-54 | | |
| F-55 | | |
| F-56 | | |
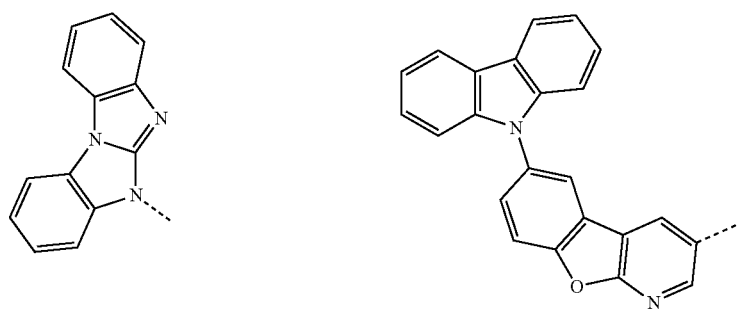
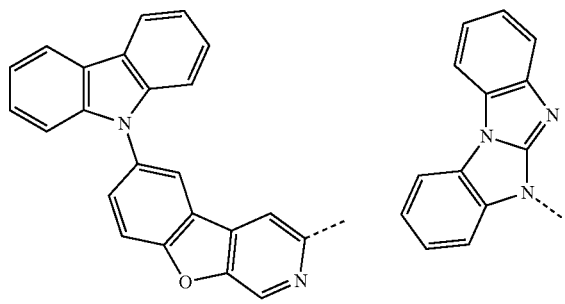
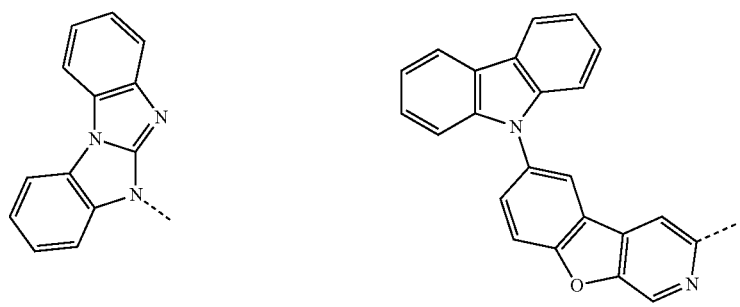

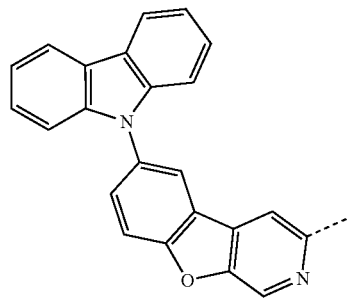
| Compound | R[83] | R[85] |
|---|---|---|
| F-57 | H | 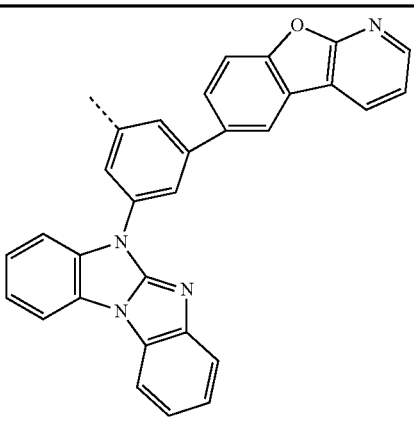 |
| F-58 | 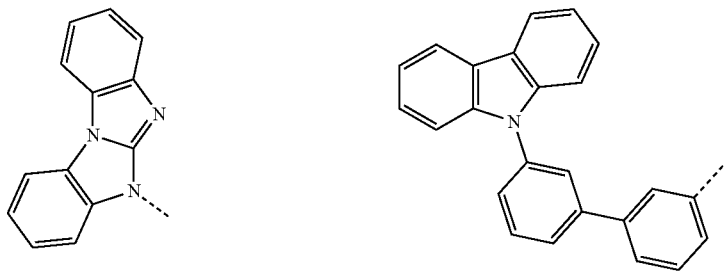 | |
| F-59 | 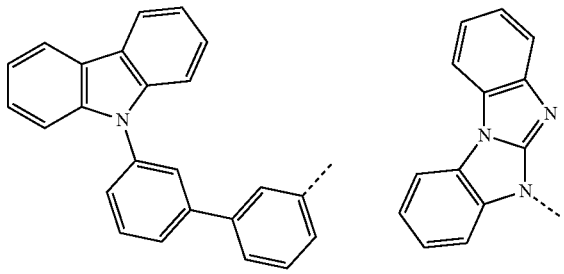 | |
| F-60 | 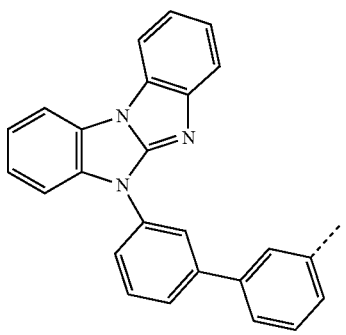 | H |

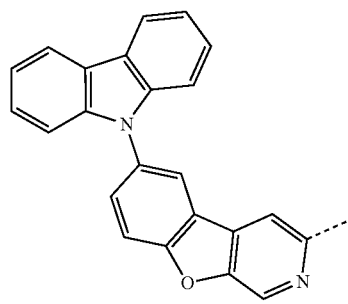
| Compound | R83 | R85 |
|---|---|---|
| F-61 | H | 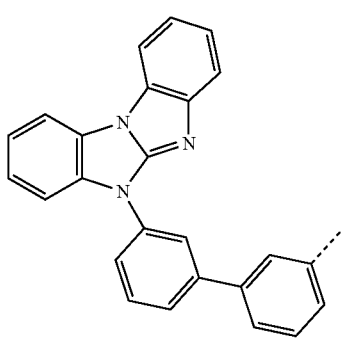 |
| F-62 | H | 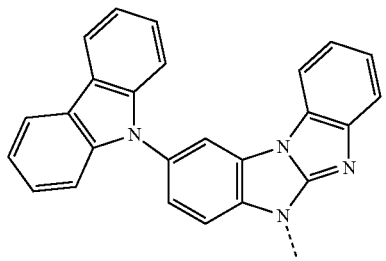 |
| F-63 | H | 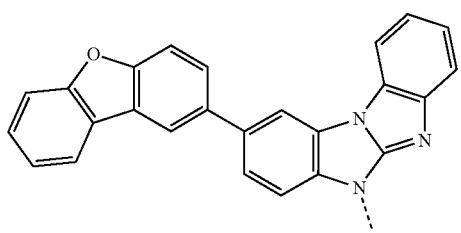 |
| F-64 | H | 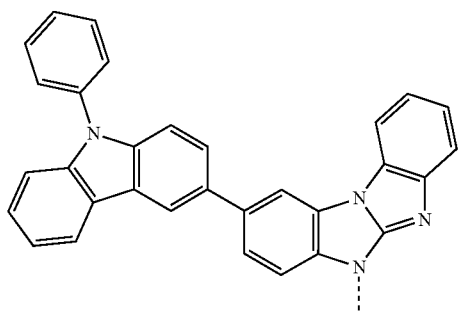 |

-continued
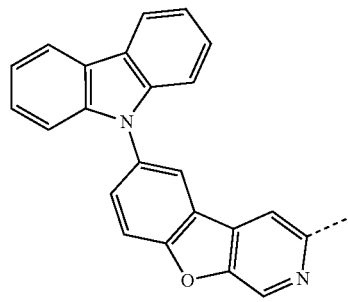
| Compound | R83 | R85 |
|---|---|---|
| F-65 | H | 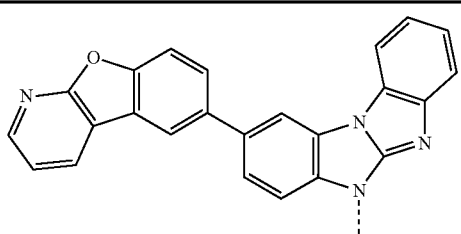 |
and
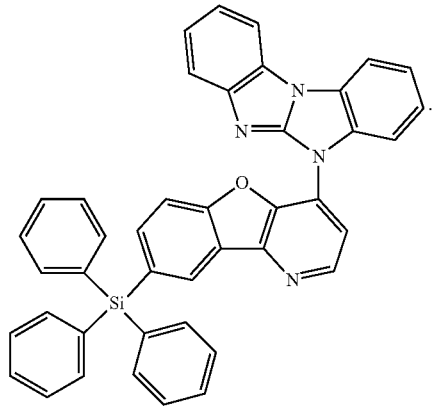  (G-1)
* * * * *

UNITED STATES PATENT AND TRADEMARK OFFICE
CERTIFICATE OF CORRECTION

PATENT NO. : 10,249,827 B2
APPLICATION NO. : 14/427134
DATED : April 2, 2019
INVENTOR(S) : Annemarie Wolleb et al.

It is certified that error appears in the above-identified patent and that said Letters Patent is hereby corrected as shown below:

In the Claims

Please replace C6-C24 alkyl in Claim 1 (Column 145, Line 13) with C6-C24 aryl.

Please replace fonn in Claim 1 (Column 145, Line 56) with from.

Please delete the text "are excluded" from the last line of Claim 16 (Column 314, Line 65).

Signed and Sealed this
Thirtieth Day of June, 2020

Andrei Iancu
*Director of the United States Patent and Trademark Office*